(12) United States Patent
Koshio et al.

(10) Patent No.: US 9,598,434 B2
(45) Date of Patent: *Mar. 21, 2017

(54) BENZAZEPINE COMPOUND

(71) Applicant: Astellas Pharma Inc., Tokyo (JP)

(72) Inventors: Hiroyuki Koshio, Tokyo (JP); Norio Asai, Tokyo (JP); Taisuke Takahashi, Tokyo (JP); Takafumi Shimizu, Tokyo (JP); Yasuhito Nagai, Tokyo (JP); Keiko Kawabata, Tokyo (JP); Karl Bruce Thor, Durham, NC (US)

(73) Assignee: ASTELLAS PHARMA INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/797,277

(22) Filed: Jul. 13, 2015

(65) Prior Publication Data
US 2015/0315208 A1 Nov. 5, 2015

Related U.S. Application Data

(63) Continuation of application No. 13/613,948, filed on Sep. 13, 2012, now Pat. No. 9,108,977, which is a continuation-in-part of application No. 13/044,080, filed on Mar. 9, 2011, now abandoned, application No. 14/797,277, which is a continuation of application No. 13/613,948, which is a continuation-in-part of application No. 13/583,410, filed as application No. PCT/JP2011/055759 on Mar. 11, 2011, now abandoned.

(60) Provisional application No. 61/313,133, filed on Mar. 12, 2010.

(51) Int. Cl.
*A61K 31/55* (2006.01)
*C07D 487/04* (2006.01)
*C07D 498/04* (2006.01)
*C07D 471/04* (2006.01)

(52) U.S. Cl.
CPC ......... *C07D 498/04* (2013.01); *C07D 471/04* (2013.01)

(58) Field of Classification Search
CPC ..... A61K 31/55; C07D 487/04; C07D 498/04
USPC .................. 514/215; 540/578, 580
See application file for complete search history.

(56) References Cited

U.S. PATENT DOCUMENTS

| 2003/0225057 A1 | 12/2003 | Smith et al. |
| 2007/0142357 A1 | 6/2007 | Smith et al. |
| 2007/0275949 A1 | 11/2007 | Smith et al. |
| 2008/0009478 A1 | 1/2008 | Smith et al. |
| 2009/0099155 A1 | 4/2009 | Allen et al. |
| 2010/0016287 A1 | 1/2010 | Bonanomi et al. |
| 2012/0053168 A1 | 3/2012 | Bhatti et al. |

FOREIGN PATENT DOCUMENTS

| WO | 02/074746 | 9/2002 |
| WO | 03/086306 | 10/2003 |
| WO | 2005/003096 | 1/2005 |
| WO | 2005/042490 | 5/2005 |
| WO | 2005/042491 | 5/2005 |
| WO | 2005/082859 | 9/2005 |
| WO | 2005/118549 | 12/2005 |
| WO | 2010/096384 | 8/2010 |

OTHER PUBLICATIONS

Micheli, F. et al., New fused benzazepine as selective D3 receptor antagonists. Synthesis and biological evaluation. Part one: [h]-fused tricyclic systems, Bioorganic & Medicinal Chemistry Letters, 2008, vol. 18, pp. 901-907.
Trani, G. et al., Tricyclic azepine derivatives as selective brain penetrant 5-HT6 receptor antagonists, Bioorganic & Medicinal Chemistry Letters, 2008, vol. 18, pp. 5698-5700.
Smith, S. et al., Lorcaserin (APD356), a selective 5-HT2c agonist, reduces body weight in obese men and women, Obesity, 2008, vol. 17, pp. 494-503.
Schreiber, R. et al., Role of 5-HT2c receptors in the hypophagic effect of m-CPP, ORG 37684 and CP-94,253 in the rat, Progress in Neuro-Psychopharmacology and Biological Psychiatry, 2002, vol. 26, pp. 441-449.
Thomsen, W. et al., Lorcaserin, a novel selective human 5-hydroxytryptamine2c agonist: in vitro and in vivo pharmacological characterization, Journal of Pharmacology and Experimental Therapeutics, 2008, vol. 325, No. 2, pp. 577-587.
Kimura, Y. et al., Pharmacological profile of YM348, a novel, potent and orally active 5-HT2c receptor agonist, European Journal of Pharmacology, 2004, vol. 483, pp. 37-43.

(Continued)

*Primary Examiner* — Brenda Coleman
(74) *Attorney, Agent, or Firm* — Wenderoth, Lind & Ponack, L.L.P.

(57) ABSTRACT

Provided is a compound which is useful as an agent for treating or preventing 5-HT$_{2C}$ receptor-related diseases, particularly incontinence such as stress urinary incontinence, urge urinary incontinence, mixed urinary incontinence, and the like, sexual dysfunction such as erectile dysfunction syndrome and the like, obesity, and the like. The present inventors have investigated compounds having a 5-HT$_{2C}$ receptor agonist activity and have found that the benzazepine compounds of the present invention have an excellent 5-HT$_{2C}$ receptor agonist activity, thereby completing the present invention. That is, the benzazepine compounds of the present invention have a 5-HT$_{2C}$ receptor agonist activity and can be used as an agent for treating or preventing 5-HT$_{2C}$ receptor-related diseases, particularly incontinence such as stress urinary incontinence, urge urinary incontinence, mixed urinary incontinence, and the like, sexual dysfunction such as erectile dysfunction syndrome and the like, obesity, and the like.

9 Claims, No Drawings

(56) References Cited

OTHER PUBLICATIONS

Pomerantz, S. et al., Serotonergic influences on male sexual behavior of rhesus monkeys: effects of serotonin agonists, Psychopharmacology, 1993, vol. 111, pp. 47-54.

Miyazato, M. et al., Role of spinal serotonergic pathways in sneeze-induced urethral continence reflex in rats, American Journal of Physiology: Renal Physiology, 2009, vol. 297, pp. 1024-1031.

Obata, H. et al., Antiallodynic effects of intrathecally administered 5-HT2c receptor agonists in rats with nerve injury, Pain, 2004, vol. 108, pp. 163-169.

Sasaki, M. et al., Antinociception with intrathecal alpha-methyl-5-hydroxytryptamine, a 5-hydroxytryptamine2A/2c receptor agonist, in two rat models of sustained pain, Anesthesia and Analgesia, 2003, vol. 96, pp. 1072-1078.

International Search Report for PCT/JP2011/055759, dated Apr. 5, 2011.

Office Action dated Jan. 14, 2014 in corresponding Australian Patent Application No. 2011225108.

Office Action, dated Aug. 18, 2014, in corresponding IL Patent Application No. 221737, and English translation thereof.

Office Action, dated Sep. 12, 2014, in corresponding PH Patent Application No. 1/2012/501735.

Extended European Search Report, dated Aug. 5, 2014, in corresponding European Patent Application No. 11753475.0.

Chinese Office Action, dated Jan. 30, 2014, in corresponding CN Application No. 201180013703.2, and English language translation thereof.

Chinese Office Action, dated Jun. 27, 2014, in corresponding CN Application No. 201180013703.2, and English language translation thereof.

Taiwanese Office Action, dated Sep. 3, 2014, in corresponding TW Application No. 100108310, and English language translation thereof.

Office Action dated Dec. 14, 2012 in U.S. Appl. No. 13/044,080.

Office Action dated Aug. 20, 2013 in corresponding Eurasian Patent Application No. 201290905, and English translation thereof.

BENZAZEPINE COMPOUND

CROSS REFERENCE TO RELATED APPLICATIONS

This application is a continuation of U.S. application Ser. No. 13/613,948 filed on Sep. 13, 2012, which is a continuation-in-part of U.S. application Ser. No. 13/044,080 filed on Mar. 9, 2011, which claims the benefit of U.S. Provisional Application No. 61/313,133 filed on Mar. 12, 2010. U.S. application Ser. No. 13/613,948 is also a continuation-in-part of U.S. application Ser. No. 13/583,410 filed on Sep. 7, 2012, which is a U.S. national-stage of International Application No. PCT/JP2011/055759 filed on Mar. 11, 2011, which claims the benefit of U.S. Provisional Application No. 61/313,133 filed on Mar. 12, 2010. The entire disclosures of U.S. application Ser. No. 13/044,080 and U.S. application Ser. No. 13/583,410 are incorporated by reference herein.

TECHNICAL FIELD

The present invention relates to a benzazepine compound which is useful as an active ingredient of a pharmaceutical composition, particularly a pharmaceutical composition for treating or preventing $5\text{-}HT_{2C}$ receptor-related diseases, particularly incontinence such as stress urinary incontinence, urge urinary incontinence, mixed urinary incontinence, and the like, sexual dysfunction such as erectile dysfunction syndrome and the like, obesity, and the like.

BACKGROUND ART

A serotonin 2C ($5\text{-}HT_{2C}$) receptor is one of the receptors for serotonin, a transmitter related to various physiological functions in the biological body. Its expression has been recognized mainly in the central nervous system (brain/spinal cord).

An anorectic action is known as a physiological function of the central $5\text{-}HT_2$ receptor, and the lowering action of various $5\text{-}HT_2$ receptor agonists on food intake has been reported in rats (Non-Patent Documents 1 and 2). Further, it has been confirmed that an anti-obesity action in humans is exhibited due to the anorectic action of the $5\text{-}HT_{2C}$ receptor agonist (Non-Patent Document 3).

The central $5\text{-}HT_{2C}$ receptor is involved in the control of peripheral nerve functions and it has been reported that the rat penile erection is induced by a $5\text{-}HT_{2C}$ receptor agonist (Non-Patent Document 4) and that the time taken from insertion to ejaculation in the experiment for mating behavior of monkeys is prolonged (Non-Patent Document 5). Moreover, it has been reported that a $5\text{-}HT_{2C}$ receptor agonist increases the urethral resistance when the abdominal pressure is increased in rats (Non-Patent Document 6). In addition, it has been reported that in disease models with neuropathic/inflammatory pain in rats, efficacy is exhibited by intraspinal administration of a $5\text{-}HT_{2C}$ receptor agonist (Non-Patent Documents 7 and 8). Various clinical applications are considered for $5\text{-}HT_{2C}$ receptor agonists, particularly as anti-obesity drugs, drugs for treating male erectile dysfunction, drugs for treating premature ejaculation, drugs for treating stress urinary incontinence, drugs for treating neuropathic/inflammatory pain, or the like.

As the $5\text{-}HT_{2C}$ receptor agonist, a benzazepine derivative has been reported, and as a tricyclic benzazepine derivative, for example, Compound A (Patent Document 1) and Compound B (Patent Document 2) are known.

[Chem. 1]

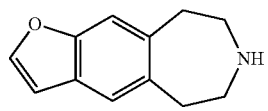

Compound A

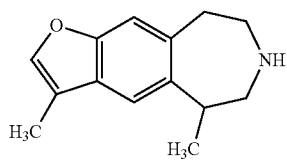

Compound B

As other $5\text{-}HT_{2C}$ receptor agonists, bicyclic benzazepine derivatives have been reported (Patent Document 3, Patent Document 4, and Patent Document 5).

As a 2,3,4,6,7,8,9,10-octahydro-1H-azepino[4,5-g]quinoline derivative or a 3,4,6,7,9,10-hexahydro[1,4]oxazino[2,3-h][3]benzazepine derivative, which is a tricyclic benzazepine derivative, a compound of the formula (AA) is known to be a Dopamine D3 modulator and be useful for central drug abuse and drug dependence (Patent Document 6).

[Chem. 2]

(AA)

In addition, in this document, the following compounds are disclosed as a synthetic intermediate for the formula (AA).

[Chem. 3]

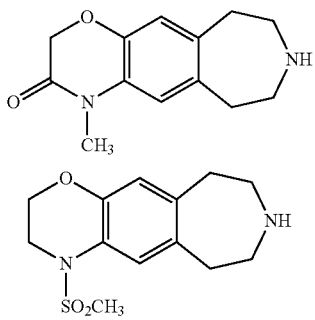

Furthermore, there is a report on the structure-activity relationship of a specific compound of the formula (AA) (Non-Patent Document 9), and in this report, it is described that the following compound was used in the preparation of the compound of the formula (AA).

[Chem. 4]

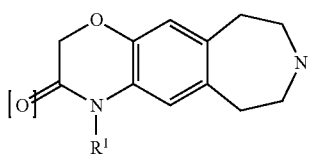

Moreover, there is a report on a 5-HT$_6$ receptor antagonist (Non-Patent Document 10), and it is disclosed that for the compound below, potency on the 5-HT$_6$ receptor is lost by changing a ring condensed with benzazepine from a 5-membered ring to a 6-membered ring.

[Chem. 5]

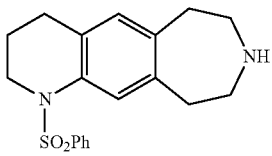

However, in the documents which disclose such tricyclic benzazepine derivatives, there is no disclosure on the 5-HT$_{2C}$ receptor agonist activity of the 2,3,4,6,7,8,9,10-octahydro-1H-azepino[4,5-g]quinoline derivative or the 3,4,6,7,9,10-hexahydro[1,4]oxazino[2,3-h][3]benzazepine derivative.

PRIOR ART DOCUMENT

Patent Document

[Patent Document 1] WO 2002/074746
[Patent Document 2] WO 2003/086306
[Patent Document 3] WO 2005/042490
[Patent Document 4] WO 2005/042491
[Patent Document 5] WO 2005/003096
[Patent Document 6] WO 2005/118549

Non-Patent Document

[Non-Patent Document 1] Obesity, 2008, vol. 17, pp. 494-503
[Non-Patent Document 2] Progress in Neuro-Psychopharmacology and Biological Psychiatry, 2002, vol. 26, pp. 441-449
[Non-Patent Document 3] Journal of Pharmacology and Experimental Therapeutics, 2008, vol. 325, pp. 577-587
[Non-Patent Document 4] European Journal of Pharmacology, 2004, vol. 483, pp. 37-43
[Non-Patent Document 5] Psychopharmacology, 1993, vol. 111, pp. 47-54
[Non-Patent Document 6] American Journal of Physiology: Renal Physiology, 2009, vol. 297, pp. 1024-1031
[Non-Patent Document 7] Pain, 2004, vol. 108, pp. 163-169
[Non-Patent Document 8] Anesthesia and Analgesia, 2003, vol. 96, pp. 1072-1078
[Non-Patent Document 9] Bioorganic & Medicinal Chemistry Letters, 2008, vol. 18, pp. 901-907
[Non-Patent Document 10] Bioorganic & Medicinal Chemistry Letters, 2008, vol. 18, pp. 5698-5700

SUMMARY OF THE INVENTION

Problems to be Solved by the Invention

A benzazepine compound which is useful as an active ingredient for a pharmaceutical composition, particularly a pharmaceutical composition for treating or preventing 5-HT$_{2C}$ receptor-related diseases, particularly incontinence such as stress urinary incontinence, urge urinary incontinence, mixed urinary incontinence, and the like, sexual dysfunction such as erectile dysfunction syndrome and the like, obesity, and the like is provided.

Means for Solving the Problem

The present inventors have extensively studied compounds having a 5-HT$_{2C}$ receptor agonist activity, and as a result, they have found that the benzazepine compound of the present invention has a 5-HT$_{2C}$ receptor agonist activity, thereby completing the present invention.

That is, the present invention relates to a pharmaceutical composition including the compound of the formula (I) or a salt thereof and a pharmaceutically acceptable excipient.

[Chem. 6]

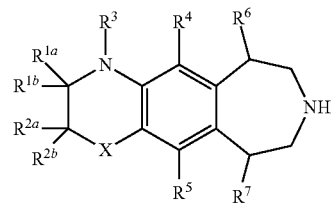

(wherein $R^{1a}$ and $R^{1b}$ are the same or different and each represents —H or $C_{1-6}$ alkyl, or are combined to form oxo, $R^{2a}$ and $R^{2b}$ are the same or different and each represents —H or $C_{1-6}$ alkyl which may be substituted with —O—$C_{1-6}$ alkyl, $R^3$ represents —H, $C_{1-6}$ alkyl which may be substituted, $C_{3-8}$ cycloalkyl, aryl which may be substituted, —SO$_2$—$C_{1-6}$ alkyl, or a hetero ring which may be substituted, $R^4$ represents —H, halogen, cyano, $C_{1-6}$ alkyl which may be substituted, $C_{2-6}$ alkenyl, aryl which may be substituted, $C_{3-8}$ cycloalkyl which may be substituted, an aromatic hetero ring, or an oxygen-containing hetero ring, $R^5$ represents —H, halogen, $C_{1-6}$ alkyl, $C_{3-8}$ cycloalkyl, aryl, or an aromatic hetero ring, $R^6$ and $R^7$ are the same or different and each represents —H or $C_{1-6}$ alkyl, X represents —C($R^A$)($R^B$)— or —O—, and $R^A$ and $R^B$ are the same or different and each represents —H or $C_{1-6}$ alkyl.)

Furthermore, the present invention relates to a compound of the formula (II) or a salt thereof.

[Chem. 7]

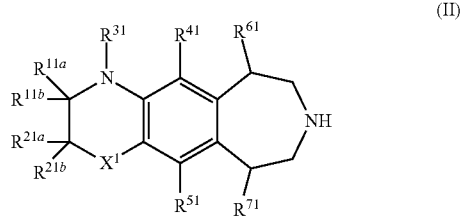

(II)

(wherein $R^{11a}$ and $R^{11b}$ are the same or different and each represents —H or $C_{1-6}$ alkyl, or are combined to form oxo, $R^{21a}$ and $R^{21b}$ are the same or different and each represents —H or $C_{1-6}$ alkyl which may be substituted with —O—$C_{1-6}$ alkyl, $R^{31}$ represents —H, $C_{1-6}$ alkyl which may be substituted, $C_{3-8}$ cycloalkyl, aryl which may be substituted, —SO$_2$—$C_{1-6}$ alkyl, or a hetero ring which may be substituted, $R^{41}$ represents —H, halogen, cyano, $C_{1-6}$ alkyl which may be substituted, $C_{2-6}$ alkenyl, aryl which may be substituted, $C_{3-8}$ cycloalkyl which may be substituted, an aromatic hetero ring, or an oxygen-containing hetero ring, $R^{51}$ represents —H, halogen, $C_{1-6}$ alkyl, $C_{3-8}$ cycloalkyl, aryl, or an aromatic hetero ring, $R^{61}$ and $R^{71}$ are the same or different and each represents —H or $C_{1-6}$ alkyl, $X^1$ represents —C($R^{A1}$)($R^{B1}$)— or —O—, and $R^{A1}$ and $R^{B1}$ are the same or different and each represents —H or $C_{1-6}$ alkyl, provided that (i) in the case where $R^{11a}$, $R^{11b}$, $R^{21a}$, $R^{21b}$, $R^{41}$, $R^{51}$, $R^{61}$, and $R^{71}$ are respectively —H and $X^1$ is —O—, $R^{31}$ is a group other than —H, —CO-methyl, or —SO$_2$-methyl, and (ii) in the case where $R^{11a}$ and $R^{11b}$ are combined to form oxo, $R^{21a}$, $R^{21b}$, $R^{41}$, $R^{51}$, $R^{61}$, and $R^{71}$ are respectively —H, and $X^1$ is —O—, $R^{31}$ is a group other than or methyl.)

Furthermore, in the case where the symbols in any of the formulas in the present specification are also used in other formulas, the same symbols denote the same meanings, unless specifically described otherwise.

Furthermore, the present invention relates to a pharmaceutical composition for preventing or treating 5-HT$_{2C}$ receptor-related diseases, including the compound of the formula (I) or a salt thereof, or the compound of the formula (II) or a salt thereof. In this connection, the pharmaceutical composition includes an agent for preventing or treating 5-HT$_{2C}$ receptor-related diseases, including the compound of the formula (I) or a salt thereof, or the compound of the formula (II) or a salt thereof.

Moreover, the present invention relates to use of the compound of the formula (I) or a salt thereof, or the compound of the formula (II) or a salt thereof for preparation of a pharmaceutical composition for preventing or treating 5-HT$_{2C}$ receptor-related diseases; the compound of the formula (I) or a salt thereof, or the compound of the formula (II) or a salt thereof for prevention or treatment of 5-HT$_{2C}$ receptor-related diseases; and a method for preventing or treating 5-HT$_{2C}$ receptor-related diseases, including administering to a subject an effective amount of the compound of the formula (I) or a salt thereof, or the compound of the formula (II) or a salt thereof. In addition, the "subject" is human or other animals in need of the prevention or treatment, and in a certain embodiment, human in need of the prevention or treatment.

In addition, the compound of the formula (II) or a salt thereof is included in the compound of the formula (I) or a salt thereof. Accordingly, in the present specification, the explanation of the compound of the formula (I) includes that of the compound of the formula (II).

Effects of the Invention

The compound of the formula (I) or a salt thereof, or the compound of the formula (II) or a salt thereof has a 5-HT$_{2C}$ receptor agonist activity and can be used as an agent for preventing or treating 5-HT$_{2C}$ receptor-related diseases.

Here, examples of the 5-HT$_{2C}$ receptor-related diseases include incontinence such as stress urinary incontinence, urge urinary incontinence, mixed urinary incontinence, and the like, sexual dysfunction such as erectile dysfunction syndrome and the like, obesity, and the like.

EMBODIMENTS FOR CARRYING OUT THE INVENTION

Hereinafter, the present invention will be described in detail.

In the present specification, the "alkyl" includes straight alkyl and branched alkyl. Accordingly, the "$C_{1-6}$ alkyl" is a straight or branched alkyl having 1 to 6 carbon atoms, and specific examples thereof include methyl, ethyl, propyl, isopropyl, butyl, tert-butyl, pentyl, hexyl, and the like, in another embodiment, methyl, ethyl, propyl, isopropyl, in a further embodiment, methyl, ethyl, in a still further embodiment, methyl, and in a still further embodiment, ethyl.

The "alkylene" is a divalent group formed by the removal of any one hydrogen atom of the "alkyl" above. Accordingly, the "$C_{1-6}$ alkylene" is straight or branched alkylene having 1 to 6 carbon atoms, and specific examples thereof include methylene, ethylene, trimethylene, tetramethylene, pentamethylene, hexamethylene, methylmethylene, dimethylmethylene, ethylmethylene, methylethylene, dimethylethylene, ethylethylene, and the like, in another embodiment, methylene, ethylene, and in a further embodiment methylene.

The "aryl" is a monocyclic to tricyclic aromatic hydrocarbon ring group having 6 to 14 carbon atoms. Specific examples thereof include phenyl and naphthyl, in another embodiment, phenyl, and in a further embodiment, naphthyl.

The "cycloalkyl" is a saturated hydrocarbon ring group, the cycloalkyl may have a bridge and may be condensed with a benzene ring, and a part of the bonds may be unsaturated. Accordingly, specific examples of the "$C_{3-8}$ cycloalkyl" include cyclopropyl, cyclobutyl, cyclopentyl, cyclohexyl, cyclohexenyl, cycloheptyl, cyclooctyl, cyclooctadienyl, norbornyl, bicyclo[2.2.2]octyl, indanyl, indenyl, 1,2-dihydronaphthyl, 1,2,3,4-tetrahydronaphthyl, and the like.

The "hetero ring" is a monovalent group of a 3- to 15-membered, in another embodiment, a 5- to 10-membered, monocyclic to tricyclic heterocyclic group containing 1 to 4 hetero atoms selected from oxygen, sulfur, and nitrogen, and includes a saturated ring, an aromatic ring, and a partially hydrogenated ring group thereof. The ring atom, sulfur or nitrogen, may be oxidized to form an oxide or a dioxide. Specific examples thereof include monocyclic aromatic hetero rings such as pyrrolyl, furyl, thienyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, triazinyl, and the like, bicyclic aromatic hetero rings such as indolyl, isoindolyl, benzofuranyl, benzothienyl, indazolyl, benzimidazolyl, benzoxazolyl, benzoisoxazolyl, benzothiazolyl, benzoisothiazolyl, quinolyl, isoquinolyl, quinoxalinyl, quinazolinyl, phthalazinyl, benzothiadiazolyl, and the like, tricyclic aromatic hetero rings such as carbazolyl, dibenzo[b,d]furanyl, dibenzo[b,d]thienyl, and the like, monocyclic non-aromatic hetero rings such as azetidinyl, pyrrolidinyl, piperidyl, piperazinyl, azepanyl, diazepanyl, morpholinyl, thiomorpholinyl, tetrahydropyridinyl, oxetanyl, tetrahydrofuranyl, tetrahydropyranyl, dioxolanyl, dioxanyl, tetrahydrothiopyranyl, and the like, bicyclic non-aromatic hetero rings such as indolinyl, tetrahydroquinolyl, tetrahydroisoquinolyl, dihydrobenzimidazolyl, tetrahydrobenzimidazolyl, tetrahydroquinoxalinyl, dihydroquinoxalinyl, dihydrobenzoxazolyl, dihydrobenzoxazinyl, dihydrobenzofuryl, chromanyl, chromenyl, methylenedioxyphenyl, ethylenedioxyphenyl, and the like, bridged hetero rings such as quinuclidinyl and the like, in another embodiment, a 5- to 10-membered monocyclic to bicyclic hetero ring, in a further embodiment, a 5- to 6-membered monocyclic hetero ring, and in a still further embodiment, a 5- to 6-membered monocyclic aromatic hetero ring.

The "aromatic hetero ring" is a 5- to 10-membered monocyclic to bicyclic aromatic hetero ring among the "hetero rings" above, and specific examples thereof include pyrrolyl, furyl, thienyl, pyrazolyl, imidazolyl, oxazolyl, thiazolyl, triazolyl, oxadiazolyl, thiadiazolyl, tetrazolyl, pyridyl, pyridazinyl, pyrimidinyl, pyrazinyl, triazinyl, indolyl, isoindolyl, benzofuranyl, benzothienyl, indazolyl, benzimidazolyl, benzoxazolyl, benzoisoxazolyl, benzothiazolyl, benzoisothiazolyl, quinolyl, isoquinolyl, quinoxalinyl, quinazolinyl, phthalazinyl, and the like, and in another embodiment, furyl, thienyl, pyrazolyl, thiazolyl, pyridyl, pyrimidinyl, and pyrazyl.

The "cyclic amino" is a 5- to 7-membered non-aromatic hetero ring having a binding position at a nitrogen atom among the "hetero rings" above, and specific examples thereof include pyrrolidinyl, piperidyl, piperazinyl, azepanyl, diazepanyl, morpholinyl, and thiomorpholinyl.

The "oxygen-containing hetero ring" is a monovalent group of a non-aromatic 5- to 6-membered ring which may be condensed with a benzene ring having one or two oxygen atoms as ring-constituting atoms. Specific examples thereof include tetrahydrofuranyl, tetrahydropyranyl, dioxolanyl, dioxanyl, dihydrobenzofuranyl, dihydrochromenyl, benzodioxolyl, benzodioxinyl, dihydrodioxinyl, dihydrobenzodioxinyl, dihydropyranyl, dioxinyl, chromenyl, and benzodioxinyl.

The "halogen" means —F, —Cl, —Br, or —I, and in another embodiment, —F, —Cl, or —Br.

The "halogeno-$C_{1-6}$ alkyl" is $C_{1-6}$ alkyl substituted with one or more halogen atoms, and specific examples thereof include fluoromethyl, difluoromethyl, trifluoromethyl, trifluoroethyl, fluoroethyl, chloroethyl, bromoethyl, fluoropropyl, dichloropropyl, fluorochloropropyl, and the like, and in another embodiment, difluoromethyl, trifluoromethyl, difluoroethyl, trifluoroethyl, and fluoropropyl.

In the present specification, the expression "which may be substituted" means unsubstituted or substituted with 1 to 5 substituents. Further, if it has a plurality of substituents, the substituents may be the same as or different from each other.

Specific examples of the substituent for the "$C_{1-6}$ alkyl which may be substituted", "$C_{1-6}$ alkylene which may be substituted", "($C_{3-8}$)cycloalkyl which may be substituted", "aryl which may be substituted", or "hetero ring which may be substituted" of $R^3$ and $R^4$ include amino, nitro, cyano, halogen, $C_{1-6}$ alkyl, halogeno-$C_{1-6}$ alkyl, —OH, —$C_{1-6}$ alkylene-OH, —O—$C_{1-6}$ alkyl, —$C_{1-6}$ alkylene-O—$C_{1-6}$ alkyl, —$C_{1-6}$ alkylene-cycloalkyl, —$C_{1-6}$ alkylene-aryl, —$C_{1-6}$ alkylene-hetero ring, —CO—$C_{1-6}$ alkyl, —CO—$C_{1-6}$ alkylene-O—$C_{1-6}$ alkyl, —CO— cycloalkyl, —CO-aryl, —CO—NR$^8$R$^9$, —CO—O—$C_{1-6}$ alkyl, —CO—O—$C_{1-6}$ alkylene-aryl, —SO$_2$—$C_{1-6}$ alkyl, aryl, a hetero ring, and the like.

Here, $R^8$ and $R^9$ are the same or different and each represents —H or $C_{1-6}$ alkyl.

In another embodiment, examples of the substituent for "$C_{1-6}$ alkyl which may be substituted" in $R^3$ include:
(1) halogen,
(2) oxo, —OH, and —O—$R^Z$,
(3) —O-(phenyl which may be substituted with one or more groups selected from the group consisting of $R^Z$, —O—$R^Z$, halogen, and cyano),
(4) —O-aromatic hetero ring,
(5) amino which may be substituted with one or two $R^Z$,
(6) phenyl which may be substituted with one or more groups selected from the group consisting of $R^Z$, —O—$R^Z$, halogen, and cyano,
(7) $C_{34}$ cycloalkyl which may be substituted with $R^Z$,
(8) an oxygen-containing hetero ring which may be substituted with halogen,
(9) a cyclic amino which may be substituted with $R^Z$, and
(10) an aromatic hetero ring,
in which the $C_{1-6}$ alkyl may be substituted with one or more substituents.

Furthermore, $R^Z$ herein represents $C_{1-6}$ alkyl which may be substituted with one or more groups selected from the group consisting of halogen, —O—$C_{1-6}$ alkyl, $C_{34}$ cycloalkyl, and phenyl (in which the phenyl may be substituted with one or more groups selected from the group consisting of halogen and —O—$C_{1-6}$ alkyl).

In another embodiment, examples of the substituent for the "aryl which may be substituted" in $R^3$ include halogen, and the aryl may be substituted with one or more substituents.

In a further embodiment, examples of the substituent for the "$C_{1-6}$ alkyl which may be substituted" in $R^4$ include halogen and aryl, and the $C_{1-6}$ alkyl may be substituted with one or more substituents.

In a still further embodiment, examples of the substituent of the "aryl which may be substituted" in $R^4$ include halogen, $C_{1-6}$ alkyl, and —O—$C_{1-6}$ alkyl, and the aryl may be substituted with one or more substituents.

Some embodiments of the compound of the formula (I) or a salt thereof are presented below.

(1) The compound or a salt thereof, wherein $R^{1a}$ and $R^{1b}$ are the same or different and each represents —H or methyl. In another embodiment, the compound or a salt thereof, wherein $R^{1a}$ and $R^{1b}$ are respectively —H. In a further embodiment, the compound or a salt thereof, wherein $R^{1a}$ is —H and $R^{1b}$ is methyl. In a still further embodiment, the compound or a salt thereof, wherein $R^{1a}$ and $R^{1b}$ are combined to form oxo.

(2) The compound or a salt thereof, wherein $R^{2a}$ is —H and $R^{2b}$ is —H or $C_{1-6}$ alkyl. In another embodiment, the compound or a salt thereof, wherein $R^{2a}$ is —H and $R^{2b}$ is —H or methyl. In a further embodiment, the compound or a salt thereof, wherein $R^{2a}$ and $R^{2b}$ are respectively —H.

(3) The compound or a salt thereof, wherein $R^3$ is $C_{1-6}$ alkyl which may be substituted with one or more groups selected from the group consisting of (a) to (e) below:

(a) halogen, (b) —O—$C_{1-6}$ alkyl, (c) phenoxy which may be substituted with one or more groups selected from the group consisting of halogen and cyano, (d) an oxygen-containing hetero ring, and (e) phenyl which may be substituted with one or more groups selected from the group consisting of $C_{1-6}$ alkyl which may be substituted with —O—$C_{1-6}$ alkyl, halogen, and —O—$C_{1-6}$ alkyl.

In another embodiment, the compound or a salt thereof, wherein $R^3$ is $C_{1-6}$ alkyl which may be substituted with one or more groups selected from the group consisting of (f) to (j) below:

(f) fluoro, (g) methoxy, ethoxy, (h) phenoxy which may be substituted with one or more groups selected from the group consisting of fluoro and cyano, (i) tetrahydrofuranyl, tetrahydropyranyl, or dihydrobenzodioxinyl, and (j) phenyl which may be substituted with one or more groups selected from the group consisting of fluoro, chloro, methyl, and methoxymethyl.

In another embodiment, the compound or a salt thereof, wherein $R^3$ is isobutyl. In another embodiment, the compound or a salt thereof, wherein $R^3$ is ethyl or propyl, which respectively is substituted with one or more groups selected from the group consisting of fluoro, methoxy, and ethoxy. In a further embodiment, the compound or a salt thereof, wherein $R^3$ is ethyl substituted with phenoxy which may be substituted with one or more groups selected from the group consisting of fluoro and cyano. In a still further embodiment, the compound or a salt thereof, wherein $R^3$ is methyl substituted with a group selected from the group consisting of tetrahydrofuranyl, tetrahydropyranyl and dihydrobenzodioxinyl. In a still further embodiment, the compound or a salt thereof, wherein $R^3$ is methyl substituted with phenyl which may be substituted with one or more groups selected from the group consisting of fluoro, chloro, methyl, and methoxymethyl.

(4) The compound or a salt thereof, wherein $R^4$ is —H, halogen, or $C_{3-8}$ cycloalkyl. In another embodiment, the compound or a salt thereof, wherein $R^4$ is —H, bromo, or cyclopropyl. In a further embodiment, the compound or a salt thereof, wherein $R^4$ is —H. In a further embodiment, the compound or a salt thereof, wherein $R^4$ is bromo. In a still further embodiment, the compound or a salt thereof, wherein $R^4$ is cyclopropyl.

(5) The compound or a salt thereof, wherein $R^5$ is —H or $C_{1-6}$ alkyl. In another embodiment, the compound or a salt thereof, wherein $R^5$ is —H or methyl. In a further embodiment, the compound or a salt thereof, wherein $R^5$ is —H.

(6) The compound or a salt thereof, wherein $R^6$ and $R^7$ are the same or different and each represents —H or methyl. In another embodiment, the compound or a salt thereof, wherein $R^6$ is methyl and $R^7$ is —H. In a further embodiment, the compound or a salt thereof, wherein $R^6$ is —H and $R^7$ is methyl. In a still further embodiment, the compound or a salt thereof, wherein $R^6$ and $R^7$ are respectively —H.

(7) The compound or a salt thereof, wherein X is —$CH_2$— or —O—. In another embodiment, the compound or a salt thereof, wherein X is —$CH_2$—. In a further embodiment, the compound or a salt thereof, wherein X is —O—.

(8) The compound or a salt thereof, which is a combination of two or more of (1) to (7) as described above.

The compound or a salt thereof as described above in (8), which is a combination of two or more of (1) to (7) as described above, is included in the present invention, and the following embodiments including the specific examples thereof can be exemplified as below.

(9) The compound or a salt thereof, wherein $R^3$ is —H, $C_{1-6}$ alkyl which may be substituted, $C_{3-8}$ cycloalkyl, aryl which may be substituted, —$SO_2$—$C_{1-6}$ alkyl, or an oxygen-containing hetero ring, and $R^4$ is —H, halogen, cyano, $C_{1-6}$ alkyl which may be substituted, $C_{2-6}$ alkenyl, aryl which may be substituted, $C_{3-8}$ cycloalkyl, an aromatic hetero ring, or an oxygen-containing hetero ring.

(10) The compound or a salt thereof as described in (9), wherein $R^3$ is a group other than —H, methyl, —CO-methyl, or —$SO_2$-methyl.

(11) The compound or a salt thereof as described in (10), wherein $R^{1a}$ is —H or methyl, and $R^{1b}$, $R^{2a}$, $R^{2b}$, $R^5$, $R^6$, and $R^7$ are respectively —H.

(12) The compound or a salt thereof as described in (11), wherein $R^4$ is —H, halogen, or $C_{3-8}$ cycloalkyl.

(13) The compound or a salt thereof as described in (12), wherein $R^4$ is cyclopropyl.

(14) The compound or a salt thereof as described in (13), wherein $R^3$ is $C_{1-6}$ alkyl which may be substituted with one or more groups selected from the group consisting of (a) halogen, (b) —O—$C_{1-6}$ alkyl, (c) phenoxy which may be substituted with one or more groups selected from the group consisting of halogen and cyano, (d) an oxygen-containing hetero ring, and (e) phenyl which may be substituted with one or more groups selected from the group consisting of $C_{1-6}$ alkyl which may be substituted with —O—$C_{1-6}$ alkyl, halogen, and —O—$C_{1-6}$ alkyl.

(15) The compound or a salt thereof as described in any one of (1) to (14), wherein X is —$CH_2$— or —O—. In another embodiment, the compound or a salt thereof as described in any one of (1) to (14), wherein X is —O—. In a still further embodiment, the compound or a salt thereof as described in any one of (1) to (14), wherein X is —$CH_2$—.

Examples of the specific compounds included in the compound of the formula (I) or a salt thereof include:

11-cyclopropyl-1-(2-methoxyethyl)-2,3,4,6,7,8,9,10-octahydro-1H-azepino[4,5-g]quinoline, 4-(3-methoxypropyl)-2,3,4,6,7,8,9,10-octahydro[1,4]oxazino[2,3-h][3]benzazepine, 5-cyclopropyl-4-(2-methoxyethyl)-2,3,4,6,7,8,9,10-octahydro[1,4]oxazino[2,3-h][3]benzazepine, 5-cyclopropyl-4-(2-ethoxyethyl)-2,3,4,6,7,8,9,10-octahydro[1,4]oxazino[2,3-h][3]benzazepine, 5-cyclopropyl-4-(3-methoxypropyl)-2,3,4,6,7,8,9,10-octahydro[1,4]oxazino[2,3-h][3]benzazepine, 5-cyclopropyl-4-(3-fluoropropyl)-2,3,4,6,7,8,9,10-octahydro[1,4]oxazino[2,3-h][3]benzazepine, 1-isobutyl-2,3,4,6,7,8,9,10-octahydro-1H-azepino[4,5-g]quinoline, 5-bromo-4-(2-methoxyethyl)-2,3,4,6,7,8,9,10-octahydro[1,4]oxazino[2,3-h][3]benzazepine, 5-cyclopropyl-4-[(2S)-tetrahydrofuran-2-ylmethyl]-2,3,4,6,7,8,9,10-octahydro[1,4]oxazino[2,3-h][3]benzazepine, 5-cyclopropyl-4-[(2R)-2-methoxypropyl]-2,3,4,6,7,8,9,10-octahydro[1,4]oxazino[2,3-h][3]benzazepine, 5-cyclopropyl-4-(2-fluorobenzyl)-2,3,4,6,7,8,9,10-octahydro[1,4]oxazino[2,3-h][3]benzazepine, 5-cyclopropyl-4-[(2S)-3-fluoro-2-methoxypropyl]-2,3,4,6,7,8,9,10-octahydro[1,4]oxazino[2,3-h][3]benzazepine, 4-(3-chlorobenzyl)-5-cyclopropyl-2,3,4,6,7,8,9,10-octahydro[1,4]oxazino[2,3-h][3]benzazepine, 5-cyclopropyl-4-(tetrahydro-2H-pyran-3-ylmethyl)-2,3,4,6,7,8,9,10-octahydro[1,4]oxazino[2,3-h][3]benzazepine, 5-cyclopropyl-4-(2,3-dihydro-1,4-benzodioxin-2-ylmethyl)-2,3,4,6,7,8,9,10-octahydro[1,4]oxazino[2,3-h][3]benzazepine, 5-cyclopropyl-4-(2-phenoxyethyl)-2,3,4,6,7,8,9,10-octahydro[1,4]oxazino[2,3-h][3]benzazepine,
5-cyclopropyl-4-(2-methylbenzyl)-2,3,4,6,7,8,9,10-octahydro[1,4]oxazino[2,3-h][3]benzazepine,
5-cyclopropyl-4-(3-methylbenzyl)-2,3,4,6,7,8,9,10-octahydro[1,4]oxazino[2,3-h][3]benzazepine,
5-cyclopropyl-4-(2,5-difluorobenzyl)-2,3,4,6,7,8,9,10-octahydro[1,4]oxazino[2,3-h][3]benzazepine,
5-cyclopropyl-4-[3-(methoxymethyl)benzyl]-2,3,4,6,7,8,9,10-octahydro[1,4]oxazino[2,3-h][3]benzazepine,
4-(5-chloro-2-fluorobenzyl)-5-cyclopropyl-2,3,4,6,7,8,9,10-octahydro[1,4]oxazino[2,3-h][3]benzazepine,
5-cyclopropyl-4-(2,3-dihydro-1,4-benzodioxin-6-ylmethyl)-2,3,4,6,7,8,9,10-octahydro[1,4]oxazino[2,3-h][3]benzazepine,
(3S)-5-cyclopropyl-4-(2-methoxyethyl)-3-methyl-2,3,4,6,7,8,9,10-octahydro[1,4]oxazino[2,3-h][3]benzazepine,
4-[2-(5-cyclopropyl-2,3,7,8,9,10-hexahydro[1,4]oxazino[2,3-h][3]benzazepin-4(6H)-yl)ethoxy]-3,5-difluorobenzonitrile,
5-cyclopropyl-4-(3-methoxybenzyl)-2,3,4,6,7,8,9,10-octahydro[1,4]oxazino[2,3-h][3]benzazepine,
5-cyclopropyl-4-(3,5-difluorobenzyl)-2,3,4,6,7,8,9,10-octahydro[1,4]oxazino[2,3-h][3]benzazepine, and
5-cyclopropyl-4-[(2R)-2-ethoxypropyl]-2,3,4,6,7,8,9,10-octahydro[1,4]oxazino[2,3-h][3]benzazepine, and salts thereof.

The compound of the formula (I) may exist in the form of tautomers or geometrical isomers depending on the kind of substituents. In the present specification, the compound of the formula (I) shall be described in only one form of isomer, yet the present invention includes other isomer, such as an isolated forms of the isomers, or a mixture thereof.

In addition, the compound of the formula (I) may have asymmetric carbon atoms or axial asymmetry in some cases, and correspondingly, it may exist in the form of optical isomers. The present invention includes both an isolated form of the optical isomers of the compound of the formula (I) or a mixture thereof.

Moreover, the present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the functional group) at the stage from starting material to an intermediate may be effective depending on the type of the functional group in production technology in some cases. The protective group for such a functional group may include, for example, the protective groups described in "Greene's Protective Groups in Organic Synthesis (4$^{th}$ Ed., 2006)" written by P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

[Chem. 8]

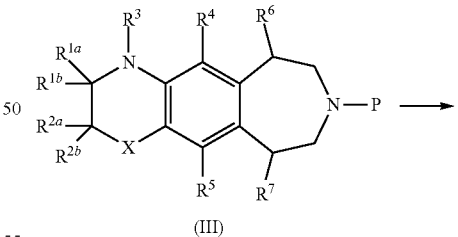

(III)

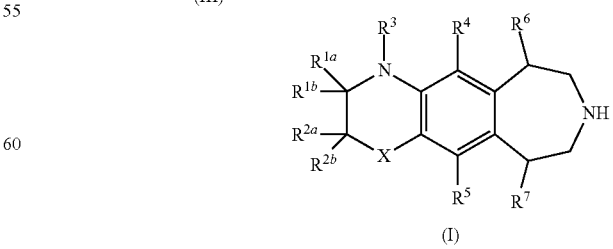

(I)

The compound of the formula (I) can be obtained by removing P which is a protective group for an amino group.

The protective group for P may be any protective group for an amino group which is usually used by a person skilled in the art, and carbonyl such as trifluoroacetyl and the like; oxycarbonyl such as t-butoxycarbonyl, ethoxycarbonyl, benzyloxycarbonyl, and the like; or sulfonyl such as methanesulfonyl, p-toluenesulfonyl, trifluoromethanesulfonyl, p-nitrophenylsulfonyl, 2,4-dinitrophenylsulfonyl, and the like is suitably used.

For the deprotection in the present step, the conditions for deprotection usually used by a person skilled in the art can be employed. For example, preparation can be performed by acid treatment, hydrolysis, hydrogenolysis, or the like. For acid treatment, for example, trifluoroacetic acid, hydrochloric acid, sulfuric acid, or the like can be used. In the case of alkali hydrolysis, inorganic bases (for example NaOH, KOH, $NaHCO_3$, $Cs_2CO_3$, and the like) can be used. In the case of acid hydrolysis, hydrochloric acid and the like can be used. For any reaction temperature, the reaction can be performed under the condition from under ice-cooling to under refluxing and under the condition which does not allow the substrate to be decomposed. As the solvent, dioxane, tetrahydrofuran, dichloromethane, chloroform, ethyl acetate, alcohols (MeOH, EtOH, and the like), N,N-dimethylformamide (DMF), dimethylsulfoxide (DMSO), water, or a mixed solvent thereof, and the like may be used, but are not limited thereto. In the case of hydrogenolysis, the reaction can usually be performed under a hydrogen atmosphere in the presence of a palladium catalyst. Usually, the reaction can be performed under the condition of from room temperature to under refluxing and under the condition which does not allow the substrate to be decomposed. As the solvent, DMF or alcohols (MeOH, EtOH, and the like) may be used, but are not limited thereto. Further, the conditions for the de-carboxamide reaction, the de-carbamate reaction, the de-sulfonamide reaction described in "Green's Protective Groups in Organic Synthesis ($4^{th}$ Ed., 2006)" above can be employed.

Various substituents defined as the groups in the compound of the formula (I), $R^{1a}$, $R^{1b}$, $R^{2a}$, $R^{2b}$, $R^3$, $R^4$, $R^5$, $R^6$, and $R^7$ can be easily converted to other functional groups by using the compound of the formula (I) as a starting material or using the synthetic intermediate of the compound of the formula (I) as a starting material by means of the reaction described in Examples as described later, the reaction apparent to a person skilled in the art, or modified methods thereof. For example, the step that can be usually employed by a person skilled in the art, such as O-alkylation, N-alkylation, reduction, hydrolysis, amidation, and the like can be arbitrarily combined and performed.

(Preparation of Starting Compound)

The starting compound in the preparation method above can be prepared by, for example, the following method, the method described in Preparation Examples as described later, known methods, or modified methods thereof.

(Starting Material Synthesis 1)

[Chem. 9]

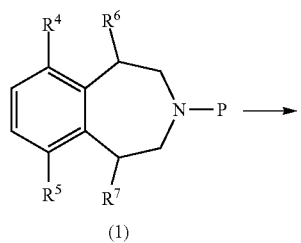

(1)

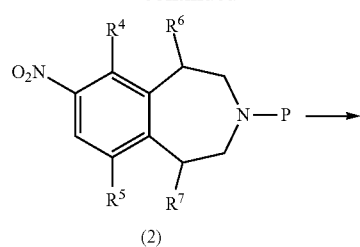

(2)

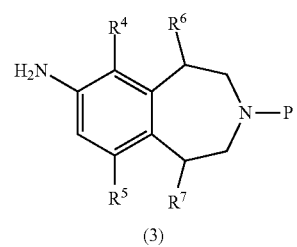

(3)

A compound represented by the general formula (1) which is a starting material for synthesizing a compound of the general formula (2) is commercially available or prepared by a means known to a person skilled in the art. Then, the compound of the general formula (2) can be prepared by nitrating the compound of the general formula (1). For example, a number of known nitration reactions can be used, examples of which include a method using nitric acid, fumed nitric acid, potassium nitrate, or the like in an acid solvent, a method using nitronium tetrafluoroborate, and the like. Then, the compound of the general formula (3) can be prepared by reducing a nitro group of the compound of the general formula (2) to an amino group. For example, a number of known reduction methods can be used, examples of which include a method using metal hydrides such as lithium aluminum hydride and the like, a method using reduced iron or the like, and the like. Further, catalytic hydrogenation using noble metal catalysts such as Raney nickel, palladium, ruthenium, rhodium, platinum, and the like can also be used.

(Starting Material Synthesis 2)

[Chem. 10]

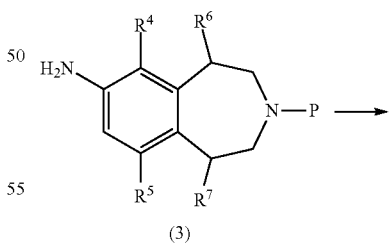

(3)

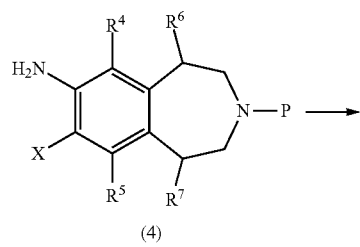

(4)

-continued

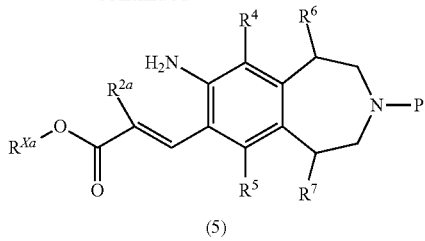

(5)

(wherein $R^{Xa}$ is $C_{1-6}$ alkyl).

A compound of the general formula (4) can be prepared by halogenating the compound of the general formula (3). For example, a number of known halogenation reactions can be used, examples of which include a method using N-bromosuccinimide or N-chlorosuccinimide, and the like. Then, the compound of the general formula (5) can be prepared from the compound of the general formula (4) by a coupling reaction using a transition metal catalyst. Examples of the coupling reaction include a Heck reaction. The reaction conditions for the Heck reaction vary depending on the starting materials, solvents, and transition metal catalysts used, and techniques known to a person skilled in the art can be used. Examples of the preferred solvent include acetonitrile, tetrahydrofuran, 1,4-dioxane or DMF, and the like, but are not limited thereto. The transition metal catalyst is preferably a palladium complex, and more preferably known palladium complexes such as palladium(II) acetate, dichlorobis(triphenylphosphine)palladium(II), tetrakis(triphenylphosphine)palladium(0), and the like. Further, for the present reaction, a phosphorous ligand (preferably, triphenylphosphine, tri-o-tolylphosphine, tri-tert-butylphosphine, 2-(di-tert-butylphosphino)biphenyl, or the like) may be added in order to obtain excellent results. Also, the present reaction can yield preferable results in the presence of a base, and the base used herein is not particularly limited as long as it is used for the coupling reaction of the present reaction, but it is preferably triethylamine, N,N-diisopropylethylamine, or the like.

(Starting Material Synthesis 3)

[Chem. 11]

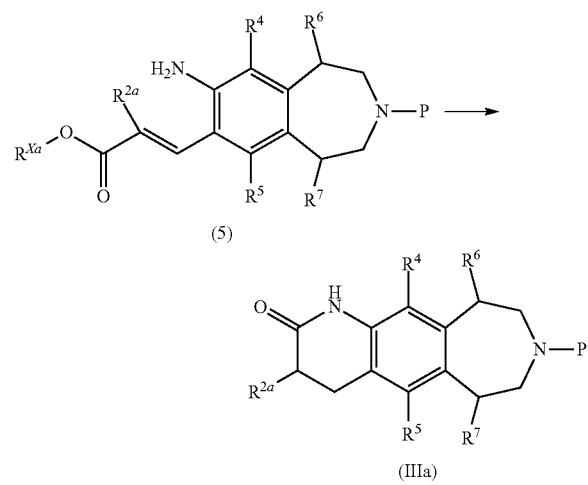

The compound of the general formula (IIIa) can be obtained by allowing an intramolecular amide condensation cyclization reaction to proceed by carrying out a hydrogenation reaction of the double bond of the α,β-unsaturated esters of the compound of the general formula (5). In this reaction, the compound of the general formula (5) is stirred in the presence of a metal catalyst, usually for 1 hour to 5 days, in a solvent inert to the reaction, under a hydrogen atmosphere. This reaction is usually carried out in the range from cooling to heating, preferably at room temperature. Examples of the solvent used herein are not particularly limited, but include alcohols such as methanol, ethanol, 2-propanol, and the like, ethers such as diethylether, tetrahydrofuran, dioxane, dimethoxyethane, and the like, water, ethyl acetate, DMF, DMSO and a mixture thereof. As the metal catalyst, palladium catalysts such as palladium on carbon, palladium black, palladium hydroxide, and the like, platinum catalysts such as a platinum plate, platinum oxide, and the like, nickel catalysts such as reduced nickel, Raney nickel, and the like, rhodium catalysts such as tetrakistriphenylphosphine chlororhodium, and the like, iron catalysts such as reduced iron and the like, etc. are preferably used. Instead of hydrogen gas, formic acid or ammonium formate in an equivalent amount or in an excess amount to the compound of the general formula (5) can be used as a hydrogen source.

Furthermore, for the compound in which $R^{2b}$ is other than —H, an $R^{2b}$ group other than —H can be introduced to a desired position by using an electrophilic substitution reaction to the α-position of carbonyl by the use of a base or by a method which can be usually employed by a person skilled in the art for the compound (IIIa).

REFERENCES

"Reductions in Organic Chemistry, $2^{nd}$ Ed. (ACS Monograph: 188)" written by M. Hudlicky, ACS, 1996

(Starting Material Synthesis 4)

[Chem. 12]

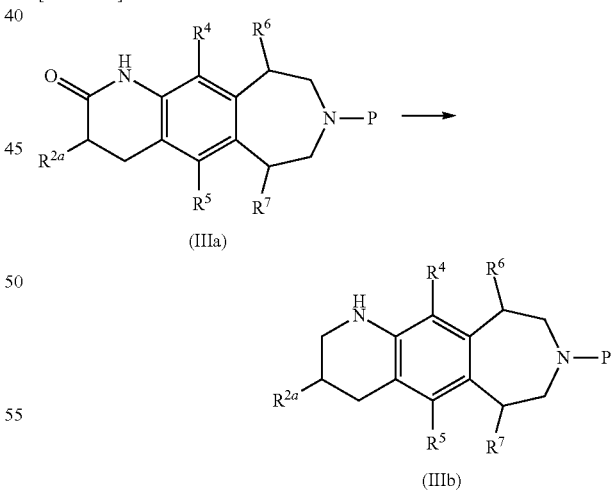

A compound of the general formula (IIIb) can be obtained by carrying out reduction of a carbonyl group of the compound of the general formula (IIIa). This reaction is usually carried out in the presence of a reducing agent in a solvent. Examples of the solvent used herein are not particularly limited, but include ethers such as diethylether, tetrahydrofuran, dioxane, dimethoxyethane, and the like, and aromatic hydrocarbons such as benzene, toluene, xylene, and the like.

Examples of the reducing agent include aluminum hydride compounds such as lithium aluminum hydride, sodium bis(2-methoxyethoxy)aluminum hydride, and the like, and borohydride compounds such as sodium borohydride, diborane, a borane-tetrahydrofuran complex, and the like.

(Starting Material Synthesis 5)

[Chem. 13]

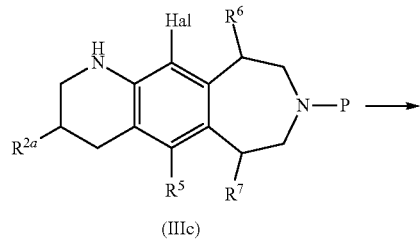

(IIIc)

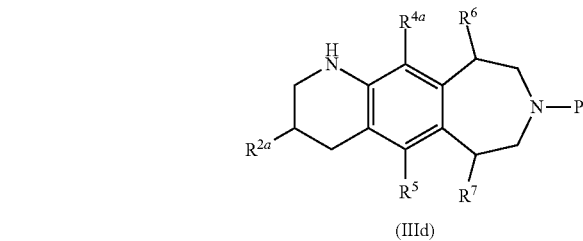

(IIId)

(wherein $R^{4a}$ represents $C_{1-6}$ alkyl, halogeno-$C_{1-6}$ alkyl, cycloalkyl which may be substituted, or aryl which may be substituted, and Hal represents halogen).

A compound of the general formula (IIId) can be obtained by a coupling reaction of a compound of the general formula (IIIc). For example, the Suzuki coupling described in the following references, the Heck reaction described for the Starting Material Synthesis 2 above, or the like can be employed.

REFERENCES

Chemical Reviews, vol. 95, No. 7, p. 2457 (1995), Journal of American Chemical Society, vol. 127, p. 4685 (2005), Synlett, No. 13, p. 2327 (2004), Tetrahedron letters, No. 41, p. 4363 (2000), or Tetrahedron letters, No. 43, p. 2695 (2002)

The compound of the general formula (IIId) can also be obtained by the method described in Examples as described later.

(Starting Material Synthesis 6)

[Chem. 14]

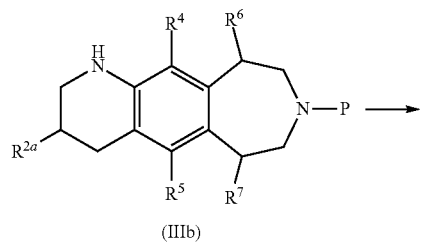

(IIIb)

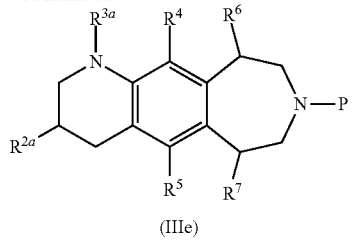

(IIIe)

(wherein $R^{3a}$ represents a group other than —H among the groups defined as $R^3$).

A compound of the general formula (IIIe) can be obtained by alkylation, acylation, or the like of the compound of the general formula (IIIb). For the specific reaction conditions, the conditions described in the following references can be employed.

REFERENCES

"Organic Functional Group Preparations" written by S. R. Sandler and W. Karo, $2^{nd}$ Ed., vol. 1, Academic Press Inc., 1991

"Courses in Experimental Chemistry ($5^{th}$ Ed.)", edited by The Chemical Society of Japan, vol. 14 (2005) (Maruzen)

The compound of the general formula (IIIe) can also be obtained by the method described in the Examples as described later and the method described for the Starting Material Synthesis 4 above.

(Starting Material Synthesis 7)

[Chem. 15]

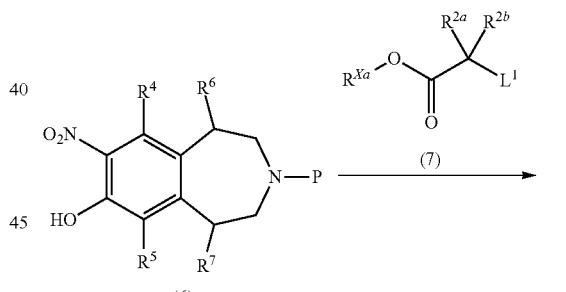

(6)

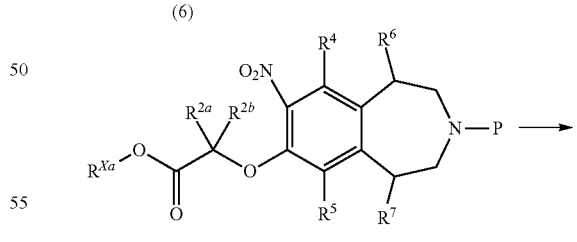

(8)

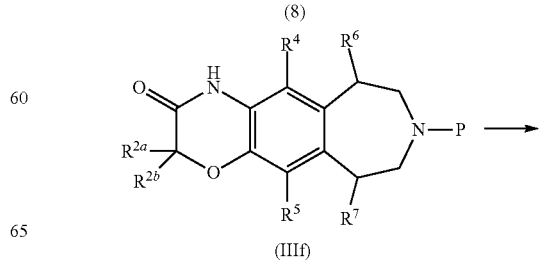

(IIIf)

-continued

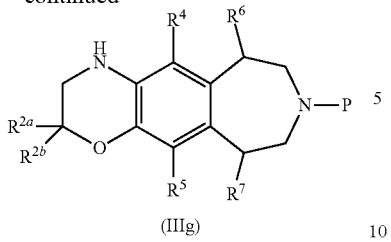

(IIIg)

A compound of the general formula (8) can be obtained by the reaction of a compound of the general formula (6) with a compound of the general formula (7). In this regard, examples of the leaving group of $L^1$ include halogen, methanesulfonyloxy, p-toluenesulfonyloxy groups, and the like.

In this reaction, the compound of the general formula (6) and the compound of the general formula (7) are used in equivalent amounts, or with either one of them in an excess amount, and a mixture thereof is stirred under a temperature condition from cooling to heating and refluxing, preferably at 0° C. to 80° C., usually for 0.1 hours to 5 days, in a solvent inert to the reaction in the presence of a base. Examples of the solvent used herein are not particularly limited, but include aromatic hydrocarbons such as benzene, toluene, xylene, and the like, ethers such as diethylether, tetrahydrofuran, dioxane, dimethoxyethane, and the like, halogenated hydrocarbons such as dichloromethane, 1,2-dichloroethane, chloroform, and the like, DMF, DMSO, ethyl acetate, acetonitrile, and a mixture thereof. Examples of the base include organic bases such as triethylamine, N,N-diisopropylethylamine, 1,8-diazabicyclo[5.4.0]-7-undecene, n-butyllithium, and the like, and inorganic bases such as sodium carbonate, potassium carbonate, sodium hydride, potassium tert-butoxide, and the like. It may be advantageous to carry out a reaction in the presence of a phase transfer catalyst such as tetra-n-butylammonium chloride and the like in some cases.

A compound of the general formula (IIIf) can be obtained by the method described in the Starting Material Synthesis 3 above and a compound of the general formula (IIIg) can be obtained by the method described in the Starting Material Synthesis 4 above.

REFERENCES

"Organic Functional Group Preparations" written by S. R. Sandler and W. Karo, 2$^{nd}$ Ed., vol. 1, Academic Press Inc., 1991

"Courses in Experimental Chemistry (5$^{th}$ Ed.)", edited by The Chemical Society of Japan, vol. 14 (2005) (Maruzen) (Starting Material Synthesis 8)

[Chem. 16]

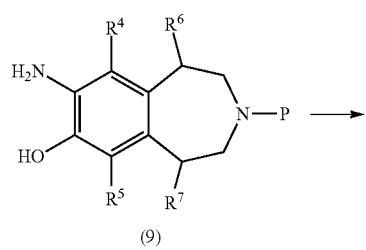

(9)

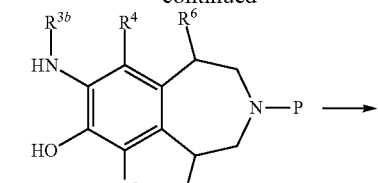

(10)

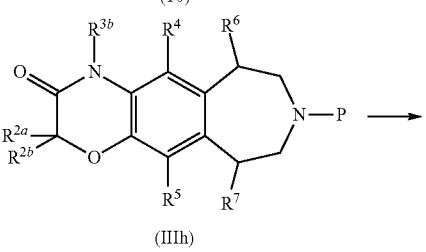

(IIIh)

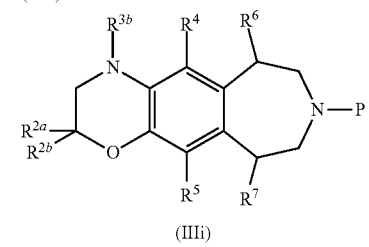

(IIIi)

(wherein $R^{3b}$ represents $C_{1-6}$ alkyl which may be substituted, $C_{3-8}$ cycloalkyl, aryl which may be substituted, or a hetero ring which may be substituted, among the groups defined as $R^3$. Further, among the $C_{1-6}$ alkyl which may be substituted, one having oxo substituted on a carbon atom directly bonded to a nitrogen atom connected with $R^{3b}$ is excluded).

The compound of the general formula (10) can be obtained by using the compound of the general formula (9) and a suitable aldehyde or ketone compound in equivalent amounts, and stirring a mixture thereof under a temperature condition from −45° C. to heating and refluxing, preferably at 0° C. to room temperature, usually for 0.1 hours to 5 days, in a solvent inert to the reaction in the presence of a reducing agent. Examples of the solvent used herein are not particularly limited, but include alcohols such as methanol, ethanol, and the like, ethers such as diethylether, tetrahydrofuran, dioxane, dimethoxyethane, and the like, and a mixture thereof. Examples of the reducing agent include sodium cyanoborohydride, sodium triacetoxyborohydride, sodium borohydride, and the like. It is preferable in some cases to carry out the reaction in the presence of a dehydrating agent such as molecular sieves, and the like or an acid such as acetic acid, hydrochloric acid, a titanium(IV) isopropoxide complex, and the like. Further, the reaction can be carried out in a solvent such as methanol, ethanol, ethyl acetate, and the like, in the presence or absence of an acid such as acetic acid, hydrochloric acid, and the like, using a reduction catalyst (for example, palladium on carbon, Raney nickel, and the like), instead of treatment with the reducing agent. In this case, it is preferable to carry out the reaction under a hydrogen atmosphere from normal pressure to 50 atmospheres under a temperature condition ranging from cooling to heating.

A compound of the general formula (IIIh) can be obtained by using the compound of the general formula (10) and a suitable halogenocarboxylic ester and reacting them in the presence of a base.

The compound of the general formula (IIIi) can be obtained by using the method described in the Starting Material Synthesis 4 above and carrying out reduction of a carbonyl group of the compound of the general formula (IIIh).

REFERENCES

"Comprehensive Organic Functional Group Transformations II" written by A. R. Katritzky and R. J. K. Taylor, vol. 2, Elsevier Pergamon, 2005
"Courses in Experimental Chemistry ($5^{th}$ Ed.)", edited by The Chemical Society of Japan, vol. 14 (2005) (Maruzen)

The compounds of the formula (I) can be isolated and purified as their free compounds, salts, hydrates, solvates, or polymorphic crystal substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting material.

The pharmacological activity of the compound of the formula (I) was confirmed by the tests shown below.

Test Example 1

Evaluation of $5-HT_{2C}$ Receptor Agonist Activity

The agonist activity of the compound of the formula (I) on the $5-HT_{2C}$ receptor was confirmed by the method shown below.

The human $5-HT_{2C}$ receptor agonist activity was evaluated by measuring the increase of the ligand-dependent intracellular calcium concentration. CHO cells which stably expressing a human $5-HT_{2C}$ receptor were used. The receptor-expressing cells were prepared by transfecting the genes of the human $5-HT_{2C}$ receptor (Accession numbers: AF498983 ($5-HT_{2C}$)) into CHO cells (dihydrofolic acid-deficient strain, DS Pharma Biomedical Co., Ltd.)) using a pEF-BOS vector (Nucleic Acids Research, vol. 18, No. 17). After transcription, the $5-HT_{2C}$ is known to be subjected to RNA editing to cause differences in three kinds of amino acids, resulting in fourteen receptor isoforms. Among them, cells stably expressing an INI type of $5-HT_{2C}$ receptor which had not been subjected to editing were used. Cells used for evaluation were cultured in a 10% fetal bovine serum (FBS)-containing medium (trade name: α-MEM, Invitrogen) at 37° C. and 5% carbon dioxide. On the day before the evaluation, the cells were suspended in a serum-free medium (trade name: CD-CHO, Invitrogen) containing 8 mM L-glutamine (trade name: L-glutamine 200 mM, Invitrogen, added to the medium at a final concentration of 8 mM) and dispensed into a 96-well poly-D-lysine-coated plate (trade name: Biocoat PDL96W Black/Clear, Japan Becton, Dickinson and Company)) at $4\times10^4$ cells/well and cultured at 37° C. and 5% carbon dioxide overnight. A solution including a washing solution (mixture of Hank's Balanced Salt Solution (HBSS)-sodium hydroxide (NaOH), 20 mM 2-[4-(2-hydroxyethyl)-1-piperazinyl]ethanesulfonic acid (HEPES)-sodium hydroxide (NaOH), 2.5 mM probenecid, and 0.1% bovine serum albumin (BSA)), and a 4 μM fluorescent reagent (trade name: Fluo4-AM, Dojindo Co., Ltd.) was used as a loading buffer and the medium of the 96-well plate which had been cultured overnight was replaced with a loading buffer. After leaving to stand (with light-shielding) at room temperature for 3 hours, the cells were washed with a plate washer (trade name: ELx405, BioTek Instruments, Inc.) in which a washing solution had been set up. The plates of the washed cells were set up in a system for measuring a calcium (Ca) concentration in a cell (trade name: FLIPR, Molecular Devices, Inc.). In this device, a test compound that had been dissolved in dimethyl sulfoxide and diluted in the washing solution at a predetermined concentration was added and set up to measure a change in the Ca concentrations in a cell. The difference between a maximum value and a minimum value in the change of the intracellular Ca concentration was determined and kept as measurement data.

Taking the maximum reaction of the 5-HT (agonist action with addition of 5-HT 10 μM) as 100% and the reaction of a solvent alone as 0%, the efficacy (Emax (%)) and potency (EC50 (nM)) of the present invention compound to the maximum reaction of the 5-HT were calculated with a logistic regression method.

The results of several compounds are shown in Table 1. In the Table, Ex represents Example Compound No. below.

TABLE 1

| | $5-HT_{2C}$ agonist activity | |
|---|---|---|
| Ex | EC50 (nM) | Emax (%) |
| 2 | 0.64 | 99 |
| 16 | 1.5 | 109 |
| 21 | 0.81 | 101 |
| 33 | 32.9 | 94 |
| 35 | 0.42 | 100 |
| 36 | 12 | 97 |
| 38 | 2.1 | 94 |
| 42 | 1.9 | 97 |
| 45 | 3.9 | 107 |
| 50 | 68 | 98 |
| 56 | 3.2 | 112 |
| 58 | 4.0 | 117 |
| 59 | 7.1 | 108 |
| 76 | 1.9 | 116 |
| 78 | 36 | 98 |
| 81 | 0.84 | 114 |
| 88 | 1.1 | 105 |
| 90 | 8.3 | 113 |
| 92 | 79 | 84 |
| 98 | 4.4 | 107 |
| 104 | 1.1 | 107 |
| 105 | 8.0 | 111 |
| 106 | 1.1 | 112 |
| 108 | 5.9 | 106 |
| 135 | 2.9 | 112 |
| 141 | 0.36 | 100 |
| 215 | 1.0 | 96 |
| 243 | 0.53 | 96 |
| 258 | 1.9 | 97 |
| 263 | 2.8 | 96 |
| 265 | 1.3 | 97 |
| 267 | 0.51 | 99 |
| 268 | 0.92 | 99 |
| 276 | 6.4 | 104 |
| 277 | 2.3 | 95 |
| 283 | 1.7 | 90 |

TABLE 1-continued

| Ex | 5-HT$_{2C}$ agonist activity | |
|---|---|---|
|  | EC50 (nM) | Emax (%) |
| 287 | 1.0 | 97 |
| 288 | 0.64 | 90 |
| 290 | 3.8 | 93 |
| 291 | 1.2 | 93 |
| 292 | 0.65 | 93 |
| 297 | 0.71 | 96 |
| 299 | 1.0 | 98 |
| 313 | 4.2 | 97 |
| 315 | 2.8 | 108 |

Test Example 2

Measurement of External Urethral Sphincter Electromyography

The activating action of the compound of the formula (I) on the urethral sphincter electromyography was confirmed with the method shown below.

Hartley female guinea pigs with a body weight of 250 to 350 g were anesthetized with urethane (Sigma). The guinea pigs were fixed in a supine position and catheters (PE-50; Clay Adams) for administration of test compounds were inserted into the jugular vein. Further, a catheters (PE-160; Clay Adams), for an infusion of physiological saline into bladder and measurement of the intravesical pressure, were inserted through an incision into the dome of the bladder. Further, in order to measure the external urethral sphincter electromyography, two electrodes were inserted into both the left and right sides of the urethral opening to the urethral sphincter. The electrodes for measuring base voltages were placed under the skin of the hind part. The bladder catheter was branched over a three-way stopcock, and one was connected with a 50 mL syringe (Terumo) fixed to an infusion pump (Terumo). The other was connected to a pressure transducer (DX-100; Nihon Kohden Corporation) to transfer the signal of the transducer through an amplifier (AP-630G; Nihon Kohden Corporation) and a data acquisition system (PowerLab; AD Instruments) to a computer and record on a hard disk. The electrodes for electromyography measurement were connected to a control unit (JB-101J; Nihon Kohden Corporation) to transfer the signal through an amplifier (AP-651J; Nihon Kohden Corporation) and a data acquisition system (PowerLab; AD Instruments) to a computer and record on a hard disk. Further, the data were analyzed on the computer using a software (Chart; AD Instruments). Physiological saline was continuously injected into the bladder using an infusion pump at a rate of 18 mL/hour and it was confirmed that a micturition reflexes were stably induced. The electromyography activity was analyzed by taking the lowest potential amplitude as a standard during the stabilization period and using the firing frequency over the standard amplitude as an indicator. At internals between the respective urinations (urine filling phase), the activity of the urethral sphincter electromyography was analyzed and its average value was calculated. After the stabilization period, the solvent and the test compound were administered at an increased dose at an interval of 40 minutes through the catheter placed into the jugular vein. The urethral sphincter electromyography activity after the administration of the solvent was taken as 100% and the urethral sphincter electromyography activity after the administration of the test compound was denoted as a percentage (%) of the electromyography activity after the administration of the solvent.

As a result, the compounds of Example 81, Example 59, Example 88, Example 104, Example 106, Example 141, Example 38, Example 135, Example 215, Example 243, Example 265, Example 287, Example 258, Example 263, Example 267, Example 268, Example 276, Example 277, Example 283, Example 288, Example 290, Example 291, Example 292, Example 297, Example 299, Example 313, and Example 315 as shown later showed an external urethral sphincter electromyography activity of 200% or more with intravenous administration at 3 mg/kg.

As a result of each test above, it was confirmed that the compound of the formula (I) has a 5-HT$_{2C}$ receptor agonist activity, and the compound of the formula (I) can be used for treatment or prevention of 5-HT$_{2C}$ receptor-related diseases, particularly incontinence such as stress urinary incontinence, urge urinary incontinence, mixed urinary incontinence, and the like, sexual dysfunction such as erectile dysfunction syndrome and the like, obesity, and the like as a pharmaceutical.

According to the results obtained by the tests above, it is considered that the compound has a 5-HT$_{2C}$ receptor agonist activity and thus has substantially the same or a higher activity value than Lorcaserin under development as an anti-obesity drug (The Journal of Pharmacology and Experimental Therapeutics vol. 325, No. 2 p. 577-587 (2008)).

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalations, and the like.

The solid composition for oral administration is used in the form of tablets, powders, granules, or the like. In such a solid composition, one or more active ingredient(s) are mixed with at least one inactive excipient. According to a usual method, the composition may contain inactive additives, such as lubricants, disintegrating agents, stabilizing agents, and solubilization assisting agents. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, as well as sweeteners, flavors, aromatics, and antiseptics.

The injections for parenteral administration contain sterile aqueous or non-aqueous solutions, suspensions, or emulsions. Examples of the aqueous solvent include distilled water for injection use and physiological saline. Examples of the non-aqueous solvent include alcohols such as ethanol. Such a composition may further contain a tonicity agent, an antiseptic, a moistening agent, an emulsifying agent, a dispersing agent, a stabilizing agent, and a solubilization assisting agent. These are sterilized by filtration through a bacteria retaining filter, blending of a germicide, or irradiation. Furthermore, they may also be prepared in the form of sterile solid compositions and dissolved or suspended in sterile water or a sterile solvent for injecting prior to their use.

Examples of the formulation for external use include ointments, plasters, creams, jellies, patches, sprays, lotions, eye-drops, eye ointments, and the like. The drug contains generally used ointment bases, lotion bases, aqueous or non-aqueous liquid preparations, suspensions, emulsions, or the like.

Transmucosal agents such as inhalers, transnasal agents, and the like are used in the form of solids, liquids, or semisolids and can be prepared according to conventional known methods. For example, known excipients, and further, pH adjusters, antiseptics, surfactants, lubricants, stabilizing agents, thickeners, or the like may also be added where appropriate. For administration, suitable devices for inhalation or insufflation can be used. For example, using known devices and sprayers such as a metered dose inhaler, the compound can be administered independently or in the form of prescribed mixture powders. Furthermore, the compound combined with pharmaceutically acceptable carriers can also be administered in the form of solutions or suspensions. Dry powder inhalers and the like may be devices for single or multiple administrations, and dry powders or capsules containing powders can also be used. Still further, the devices may be in the form of a pressure aerosol spray or the like that use suitable ejection agents, for example, chlorofluoroalkane, hydrofluoroalkane, or a suitable gas such as carbon dioxide and the like.

Usually, in the case of oral administration, the daily dose is suitably from 0.001 to 100 mg/kg per body weight, preferably from 0.1 to 30 mg/kg, and more preferably from 0.1 to 10 mg/kg, and this is administered in one portion or dividing it into 2 to 4 portions. In the case of intravenous administration, the daily dose is suitably from about 0.0001 to 10 mg/kg per body weight, and this is administered once a day or two or more times a day. In addition, a transmucosal agent is administered at a dose from about 0.001 to 100 mg/kg per body weight, and this is administered once a day or two or more times a day. The dose is appropriately decided in response to an individual case by taking the symptoms, the age, the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing the diseases, in which the compound of the formula (I) is considered effective, as described above. The combined preparation may be administered simultaneously or separately and continuously, or at a desired time interval. The preparations to be co-administered may be prepared individually or may be a pharmaceutical composition including various agents for treating or preventing the diseases, in which the compound of the formula (I) is considered effective, as described above, and the compound of the formula (I).

EXAMPLES

Hereinbelow, the preparation methods for the compound of the formula (I) and the starting compounds thereof will be described in more detail with reference to Examples. The present invention is not limited to the compounds described in the Examples described below. Furthermore, the production processes for the starting compounds will be described in Preparation Examples. The preparation methods for the compound of the formula (I) are not limited to the preparation methods of the specific Examples as below, but the compound of the formula (I) can be prepared by any combination of the preparation methods or the methods that are apparent to a person skilled in the art.

Furthermore, the following abbreviations may be used in some cases in the Preparation Examples, Examples, and Tables below.

PEx: Preparation Example No., Ex: Example No., PSyn: Preparation Example No. prepared by the same method, Syn: Example No. prepared by the same method, No: Compound No., Str: Structural formula, Dat: Physicochemical Data, EI: m/z values in mass spectroscopy (Ionization EI, representing (M)$^+$ unless otherwise specified), ESI+: m/z values in mass spectroscopy (Ionization ESI, representing (M+H)$^+$ unless otherwise specified), ESI−: m/z values in mass spectroscopy (Ionization ESI, representing (M−H)$^−$ unless otherwise specified), FAB+: m/z values in mass spectroscopy (Ionization FAB, representing (M+H)$^+$ unless otherwise specified), FAB−: m/z values in mass spectroscopy (Ionization FAB, representing (M−H)$^−$ unless otherwise specified), APCI+: m/z values in mass spectroscopy (Ionization APCI, representing (M+H)$^+$ unless otherwise specified), NMR: δ (ppm) in $^1$H NMR in DMSO-d$_6$, NMR-A: δ (ppm) in $^1$H NMR in DMSO-d$_6$ (with addition of trifluoroacetic acid), NMR-C: δ (ppm) in $^1$H NMR in CDCl$_3$, s: singlet (spectrum), d: doublet (spectrum), t: triplet (spectrum), q: quartet (spectrum), br: broad line (spectrum) (e.g.: br-s), mp: melting point (° C.).

Me: methyl, Et: ethyl, nPr: normal propyl, iPr: isopropyl, nBu: normal butyl, iBu: isobutyl, t-Bu: tert-butyl, cyclopropyl, cBu: cyclobutyl, cPen: cyclopentyl, cHex: cyclohexyl, Bz: benzyl, Boc: t-butoxycarbonyl, MeOH: methanol, EtOH: ethanol, EtOAc: ethyl acetate, HEX: n-hexane, DMF: N,N-dimethylformamide, TFA: trifluoroacetic acid, THF: tetrahydrofuran, DPPA: diphenylphosphorylazide, HOBt: 1-hydroxybenzotriazole.

HCl in the structural formula indicates that the Example compound is isolated as a hydrochloride. Further, a case where the structural formula of fumaric acid is described together in the structural formula indicates that the Example compound is isolated as fumarate. Also, a case where the structural formula of oxalic acid is described together in the structural formula indicates that the Example compound is isolated as an oxalate. In addition, a case where the structural formula of succinic acid is described together in the structural formula indicates that the Example compound is isolated as a succinate.

Furthermore, in the case where a numeral is prefixed to HCl, the numeral means a molar ratio of the compound to hydrochloric acid. For example, 2HCl represents dihydrochloride. Further, in the Example Compounds in which the structural formula of fumaric acid is described together in the structural formula, "M" described under the Example No. indicates that the Example Compound is isolated as monofumarate, "H" described as such indicates that the Example Compound is isolated as hemifumarate, and "S" described as such indicates that the Example Compound is isolated as sesquifumarate. Also, "T" of Example 267 indicates that the compound is isolated as 0.75 fumarate. Further, description of these "M", "H", and "S" has the same meanings in the Example Compound in which the structural formula of oxalic acid is described together in the structural formula and the Example Compound in which where the structural formula of succinic acid is described together in the structural formula.

Furthermore, for the sake of convenience, a concentration mol/l is expressed as M. For example, a 1 M aqueous sodium hydroxide solution means a 1 mol/l aqueous sodium hydroxide solution.

Preparation Example 1

To a solution of 27.11 g of 3-chloro-o-xylene in 300 ml of carbon tetrachloride were added 75 g of N-bromosuccinimide and 0.81 g of 2,2'-azobis(isobutyronitrile), followed by heating and refluxing for 2 hours. The reaction mixture was washed with water and saturated sodium hydrogen carbonate, the organic layer was dried over anhydrous magnesium sulfate and then filtered, and the filtrate was concentrated under reduced pressure to obtain 63.297 g of 1,2-bis(bromomethyl)-3-chlorobenzene as a reddish orange oily substance.

Preparation Example 2

To a solution of 20.5 g of sodium cyanide in 120 ml of water was added a solution of 57.533 g of 1,2-bis(bromomethyl)-3-chlorobenzene in 120 ml of EtOH, followed by heating and refluxing for 30 minutes. The reaction mixture was poured into ice, followed by stirring, and the precipitated solid was collected by filtration to obtain 32.941 g of 2,2'-(3-chloro-1,2-phenylene)diacetonitrile as a yellowish brown solid.

Preparation Example 3

To a suspension of 32.94 g of 2,2'-(3-chloro-1,2-phenylene)diacetonitrile in 100 ml of acetic acid was added dropwise 100 ml of a 33% hydrogen bromide-acetic acid solution over 1.5 hours while keeping the inner temperature at 20° C. or lower. The reaction mixture was stirred at room temperature for 3 hours, and then to the reaction mixture were added diethylether and acetone. The resulting candy-like dark brown solid substance and the suspension were separated, the suspension was concentrated under reduced pressure, and the candy-like substance was pulverized in acetone to obtain a suspension. The concentrated residue and the acetone suspension were combined and concentrated under reduced pressure, and to the residue was added EtOAc, followed by stirring. The solid was collected by filtration. The resulting solid was suspended in 400 ml of water which had been heated to 80° C., and 31.2 g of sodium acetate was added thereto, followed by stirring at 90° C. for 3 hours. The reaction mixture was cooled to room temperature and then the solid was collected by filtration to obtain 22.506 g of 6-chloro-1H-3-benzazepine-2,4(3H,5H)-dione as a brown solid.

Preparation Example 4

To a solution of 22.5 g of 6-chloro-1H-3-benzazepine-2,4(3H,5H)-dione in 200 ml of THF were added dropwise 38 ml of a 10 M borane-dimethyl sulfide complex at 0° C. for 20 minutes, followed by stirring for 2.5 hours. The reaction mixture was heated and refluxed, and further stirred. To the reaction mixture was added dropwise 30 ml of MeOH under ice-cooling, followed by stirring, and then 30 ml of 4 M hydrochloric acid was added dropwise thereto, followed by heating and refluxing for 1 hour after generation of bubbles substantially settled. The mixture was alkalified by the addition of aqueous ammonia and a 1 M aqueous sodium hydroxide solution, followed by extraction with chloroform. The organic layer was dried over anhydrous sodium sulfate and then filtered. The filtrate was concentrated under reduced pressure, the residue was dissolved in EtOH, and activated carbon was added thereto, followed by heating and refluxing, and then filtering on amino silica gel, and the filtrate was concentrated under reduced pressure. To a solution of 18.7 g of the resulting residue in 180 ml of dichloromethane was added 17 ml of pyridine, followed by ice-cooling, and 13 ml of ethyl chlorocarbonate was added dropwise thereto, followed by stirring for 1.5 hours. The reaction mixture was concentrated under reduced pressure, the residue was diluted with EtOAc, then washed with 1 M hydrochloric acid and water, dried over anhydrous sodium sulfate, and then filtered, and the filtrate was concentrated under reduced pressure. The residue was purified by silica gel chromatography (elution solvent: HEX-EtOAc) to obtain 9.653 g of ethyl 6-chloro-1,2,4,5-tetrahydro-3H-3-benzazepine-3-carboxylate as a reddish brown oily substance.

Preparation Example 5

A solution of 11.86 g of ethyl 6-chloro-1,2,4,5-tetrahydro-3H-3-benzazepine-3-carboxylate in 30 ml of chloroform was ice-cooled, and while maintaining the inner temperature at 10° C. or lower, 60 ml of concentrated sulfuric acid was added thereto. Then, 3.2 ml of concentrated nitric acid was added dropwise thereto, followed by stirring for 30 minutes. The reaction mixture was poured into ice, followed by extraction with chloroform, the organic layer was dried over anhydrous sodium sulfate and then filtered, and the filtrate was concentrated under reduced pressure. The residue was purified by silica gel chromatography (elution solvent: HEX-EtOAc) to obtain 6.442 g of ethyl 6-chloro-7-nitro-1,2,4,5-tetrahydro-3H-3-benzazepine-3-carboxylate as a reddish orange viscous substance and 5.201 g of ethyl 6-chloro-9-nitro-1,2,4,5-tetrahydro-3H-3-benzazepine-3-carboxylate as a pale yellow solid.

Preparation Example 6

To 6.431 g of ethyl 6-chloro-7-nitro-1,2,4,5-tetrahydro-3H-3-benzazepine-3-carboxylate was added 120 ml of EtOH, followed by stirring at 60° C. for dissolution, and 12.15 g of reduced iron and 60 ml of 1 M hydrochloric acid were added thereto, followed by heating and refluxing for 1 hour. The reaction mixture was alkalified by the addition of a 1 M aqueous sodium hydroxide solution and then filtered through celite, and then the organic solvent was evaporated under reduced pressure. The residue was extracted with chloroform, the organic layer was dried over anhydrous sodium sulfate and then filtered, and the filtrate was concentrated under reduced pressure to obtain 5.743 g of ethyl 7-amino-6-chloro-1,2,4,5-tetrahydro-3H-3-benzazepine-3-carboxylate as a reddish orange viscous substance.

Preparation Example 7

To a solution of 5.74 g of ethyl 7-amino-6-chloro-1,2,4,5-tetrahydro-3H-3-benzazepine-3-carboxylate in 100 ml of dichloromethane was added portionwise 3.9 g of N-bromosuccinimide under ice-cooling, followed by stirring for 40 minutes. The reaction mixture was concentrated under reduced pressure and the residue was purified by silica gel chromatography (elution solvent: HEX-EtOAc) to obtain 5.769 g of ethyl 7-amino-8-bromo-6-chloro-1,2,4,5-tetrahydro-3H-3-benzazepine-3-carboxylate as a brown solid.

Preparation Example 8

To a solution of 4.37 g of ethyl 7-amino-8-bromo-6-chloro-1,2,4,5-tetrahydro-3H-3-benzazepine-3-carboxylate in 40 ml of DMF were added 2.1 ml of ethyl acrylate, 230 mg of tris-o-tolylphosphine, 85 mg of palladium(II) acetate, and 3.6 ml of triethylamine, followed by stirring at 120° C. for 3 hours. The reaction mixture was diluted with EtOAc, washed with water and saturated brine, dried over anhydrous sodium sulfate, and then filtered, and the filtrate was concentrated under reduced pressure. The resulting yellow solid was stirred and washed in diisopropylether to obtain 3.125 g of ethyl 7-amino-6-chloro-8-[(1E)-3-ethoxy-3-oxoprop-1-en-1-yl]-1,2,4,5-tetrahydro-3H-3-benzazepine-3-carboxylate as a pale yellow solid.

Preparation Example 9

To a solution of 2.12 g of ethyl 7-amino-6-chloro-8-[(1E)-3-ethoxy-3-oxoprop-1-en-1-yl]-1,2,4,5-tetrahydro-3H-3-benzazepine-3-carboxylate in 20 ml of chloroform and 20 ml of MeOH was added 65 mg of platinum(IV) oxide, followed by stirring for 20 hours at 1 atm under a hydrogen atmosphere. The reaction mixture was filtered through celite and the filtrate was concentrated under reduced pressure to obtain 2.256 g of ethyl 11-chloro-2-oxo-1,2,3,4,6,7,9,10-octahydro-8H-azepino[4,5-g]quinoline-8-carboxylate as a milky white solid.

Preparation Example 10

To a suspension of 1.403 g of 11-chloro-1,3,4,6,7,8,9,10-octahydro-2H-azepino[4,5-g]quinolin-2-one in 15 ml of dioxane were added 1.2 ml of triethylamine and 1.5 g of di-t-butyl dicarbonate, followed by stirring at room temperature for 2 hours. The reaction mixture was concentrated under reduced pressure and the residue was purified by silica gel chromatography (elution solvent: HEX-EtOAc) to obtain 1.779 g of t-butyl 11-chloro-2-oxo-1,2,3,4,6,7,9,10-octahydro-8H-azepino[4,5-g]quinoline-8-carboxylate as a milky white solid.

Preparation Example 11

To a solution of 1.772 g of t-butyl 11-chloro-2-oxo-1,2,3,4,6,7,9,10-octahydro-8H-azepino[4,5-g]quinoline-8-carboxylate in 10 ml of THF was added 10.1 ml of a 1 M solution of a borane-THF complex in THF under ice-cooling, followed by elevating to room temperature and stirring for 3 hours. To the reaction mixture was added dropwise 10 ml of EtOH, and subsequently 10 ml of a 1 M aqueous sodium hydroxide solution was added dropwise thereto, followed by stirring. The mixed solution was diluted with water, followed by extraction with EtOAc. The organic layer was dried over anhydrous sodium sulfate and then filtered, and the filtrate was concentrated under reduced pressure. The residue was purified by silica gel chromatography (elution solvent: HEX-EtOAc) to obtain 2.007 g of t-butyl 11-chloro-1,2,3,4,6,7,9,10-octahydro-8H-azepino[4,5-g]quinoline-8-carboxylate as a colorless viscous substance.

Preparation Example 12

To a solution of 205 mg of t-butyl 11-chloro-1,2,3,4,6,7,9,10-octahydro-8H-azepino[4,5-g]quinoline-8-carboxylate in 3 ml of acetonitrile were added 0.077 ml of 36% formalin, 58 mg of sodium cyanoborohydride, and 0.5 ml of acetic acid, followed by stirring at room temperature. To the reaction mixture was added water, followed by extraction with EtOAc, the organic layer was dried over anhydrous sodium sulfate and then filtered, and the filtrate was concentrated under reduced pressure. The residue was purified by silica gel chromatography (elution solvent: HEX-EtOAc) to obtain 96 mg of t-butyl 11-chloro-1-methyl-1,2,3,4,6,7,9,10-octahydro-8H-azepino[4,5-g]quinoline-8-carboxylate as an orange viscous substance.

Preparation Example 13

To a solution of 193 mg of t-butyl 11-chloro-1,2,3,4,6,7,9,10-octahydro-8H-azepino[4,5-g]quinoline-8-carboxylate in 2 ml of toluene was added 0.121 ml of isobutyric chloride, followed by stirring at 60° C. The reaction mixture was purified by silica gel chromatography (elution solvent: HEX-EtOAc) to obtain 80 mg of t-butyl 11-chloro-1-isobutyryl-1,2,3,4,6,7,9,10-octahydro-8H-azepino[4,5-g]quinoline-8-carboxylate as a colorless solid.

Preparation Example 14

To a solution of 1.75 g of 2,3,4,5-tetrahydro-1H-3-benzazepine in 20 ml of dichloromethane was added 2.884 ml of pyridine. The reaction mixture was ice-cooled, and 1.705 ml of ethyl chloroformate which had been dissolved in 5 ml of dichloromethane was added dropwise thereto, followed by stirring overnight. The reaction mixture was concentrated under reduced pressure and the residue was purified by silica gel chromatography (elution solvent: HEX-EtOAc) to obtain 2.15 g of ethyl 1,2,4,5-tetrahydro-3H-3-benzazepine-3-carboxylate as a pale yellow oily substance.

Preparation Example 15

287 mg of ethyl 2-oxo-1,2,3,4,6,7,9,10-octahydro-8H-azepino[4,5-g]quinoline-8-carboxylate was dissolved in 5 ml of DMF, and 65 mg of 60% sodium hydride was added thereto in an ice-bath, followed by stirring for 1 hour. 0.3 ml of methyl iodide was added thereto, followed by stirring at room temperature for 3 hours. Then, a saturated aqueous sodium hydrogen carbonate solution was added thereto, followed by extraction with chloroform. The solvent was concentrated under reduced pressure and the residue was purified by silica gel chromatography (elution solvent: HEX-EtOAc) to obtain 94 mg of ethyl 1-methyl-2-oxo-1,2,3,4,6,7,9,10-octahydro-8H-azepino[4,5-g]quinoline-8-carboxylase as a colorless solid.

Preparation Example 71

To 5 g of ethyl 2-oxo-1,2,3,4,6,7,9,10-octahydro-8H-azepino[4,5-g]quinoline-8-carboxylate were added 40 ml of ethylene glycol and 28 ml of a 4 M aqueous sodium hydroxide solution, followed by stirring at 150° C. After stirring overnight, the reaction mixture was ice-cooled, then acidified by the addition of concentrated hydrochloric acid, and stirred at room temperature for 1 hour. The reaction mixture was concentrated under reduced pressure, and then the residue was alkalified by the addition of a 1 M aqueous sodium hydroxide solution, followed by extraction with chloroform. The solvent was concentrated under reduced pressure and then the resulting dark brown residue was dissolved in dichloromethane, followed by addition of 4 g of di-t-butyl dicarbonate and 3.5 ml of triethylamine. The reaction mixture was stirred at room temperature overnight and concentrated under reduced pressure, and the residue was purified by silica gel chromatography (elution solvent: chloroform-MeOH) to obtain 3.39 g of t-butyl 2-oxo-1,2,3,4,6,7,9,10-octahydro-8H-azepino[4,5-g]quinoline-8-carboxylate.

Preparation Example 17

To a solution of 250 mg of t-butyl 1,2,3,4,6,7,9,10-octahydro-8H-azepino[4,5-g]quinoline-8-carboxylate in 2.5 ml of dichloroethane were added 0.175 ml of isobutyryl chloride and 0.4 ml of triethylamine, followed by elevating the temperature to 60° C. and stirring for 30 minutes. The reaction mixture was diluted with EtOAc and washed with 1 M hydrochloric acid, water, a 1 M aqueous sodium hydroxide solution, and saturated brine, and the solvent was concentrated. To the resulting residue was added 2 ml of THF and 3.5 ml of a 1 M solution of a borane-THF complex in THF was added thereto in an ice-bath, followed by stirring at room temperature overnight. The reaction mixture was ice-cooled, and EtOH was added thereto, followed by stirring at room temperature for 30 minutes. The reaction mixture was concentrated and the resulting residue was purified by silica gel chromatography (elution solvent: HEX-EtOAc) to obtain 213 mg of t-butyl 1-isobutyl-1,2,3,4,6,7,9,10-octahydro-8H-azepino[4,5-g]quinoline-8-carboxylate.

Preparation Example 18

To a solution of 460 mg of t-butyl 11-bromo-1,2,3,4,6,7,9,10-octahydro-8H-azepino[4,5-g]quinoline-8-carboxylate in 9 ml of dioxane were added 1.6 ml of a 2 M aqueous potassium carbonate solution under an argon atmosphere, and subsequently 449 mg of trimethylboroxine and 70 mg of tetrakistriphenylphosphine palladium, followed by stirring at 90° C. for 13 hours. The reaction mixture was allowed to cool, filtered, and then concentrated under reduced pressure, the resulting residue was diluted with EtOAc, and the organic layer was washed with water and saturated brine. The solvent was evaporated under reduced pressure and the resulting residue was purified by silica gel chromatography (elution solvent: HEX-EtOAc) to obtain 380 mg of t-butyl 11-methyl-1,2,3,4,6,7,9,10-octahydro-8H-azepino[4,5-g]quinoline-8-carboxylate.

Preparation Example 19

To a solution of 670 mg of t-butyl 11-isopropenyl-1,2,3,4,6,7,9,10-octahydro-8H-azepino[4,5-g]quinoline-8-carboxylate in 10 ml of MeOH was added 200 mg of palladium on carbon, followed by stirring at room temperature for 3.5 hours at normal pressure under a hydrogen atmosphere. Further, after stirring overnight at 4.5 atm under a hydrogen atmosphere, the reaction mixture was filtered through celite, and the solvent was evaporated under reduced pressure. The resulting residue was purified by silica gel chromatography (elution solvent: HEX-EtOAc) to obtain 512 mg of t-butyl 11-isopropyl-1,2,3,4,6,7,9,10-octahydro-8H-azepino[4,5-g]quinoline-8-carboxylate.

Preparation Example 20

To a solution of 140 mg of t-butyl 11-ethyl-1,2,3,4,6,7,9,10-octahydro-8H-azepino[4,5-g]quinoline-8-carboxylate in 1.86 ml of acetonitrile was added 0.12 ml of glycidylmethylether, followed by substitution with argon. In an ice-bath, 9 mg of ytterbium(III) trifluoromethanesulfonate was added thereto, followed by stirring at room temperature for 2 hours, then elevating the temperature to 50° C., and stirring overnight. To the reaction mixture were added EtOAc and aqueous sodium bicarbonate, and the organic layer was washed with water and saturated brine. The solvent was evaporated under reduced pressure and the resulting residue was purified by silica gel chromatography (elution solvent: HEX-EtOAc) to obtain 147 mg of t-butyl 1-ethyl-1-(2-hydroxy-3-methoxypropyl)-1,2,3,4,6,7,9,10-octahydro-8H-azepino[4,5-g]quinoline-8-carboxylate.

Preparation Example 21

To a solution of 215 mg of t-butyl 7-hydroxy-8-(tetrahydro-2H-pyran-4-ylamino)-1,2,4,5-tetrahydro-3H-3-benzazepine-3-carboxylate in 4 ml of DMF were added 98 mg of potassium carbonate and 0.062 ml of methyl bromoacetate, followed by stirring at room temperature for 6 hours. To the reaction mixture was added water, followed by extraction with EtOAc twice. The combined organic layer was washed with saturated brine three times, dried over anhydrous sodium sulfate, and then filtered, and the solvent was evaporated under reduced pressure. To a solution of 259 mg of the resulting residue in 7 ml of EtOH was added 1.2 ml of a 1 M aqueous sodium hydroxide solution, followed by stirring at 50° C. overnight. Further, 1.2 ml of a 1 M aqueous hydrochloric acid solution was added thereto under ice-cooling, followed by extraction with chloroform twice, and the combined organic layer was dried over anhydrous sodium sulfate and then filtered. The solvent was evaporated under reduced pressure. To a solution of 239 mg of the resulting residue in 4 ml of DMF were added 120 mg of 1-ethyl-3-(3-dimethylaminopropyl)carbodiimide hydrochloride and 84 mg of HOBt at room temperature, followed by stirring at room temperature overnight. Water was added thereto, followed by extraction with EtOAc twice. The combined organic layer was washed with saturated brine, dried over anhydrous sodium sulfate, and then filtered, and the solvent was evaporated under reduced pressure. The residue was purified by silica gel chromatography (elution solvent: HEX-EtOAc) to obtain 153 mg of t-butyl 3-oxo-4-(tetrahydro-2H-pyran-4-yl)-3,4,6,7,9,10-hexahydro[1,4]oxazino[2,3-h][3]benzazepine-8(2H)-carboxylate as a white solid.

Preparation Example 22

To a solution of 828 mg of t-butyl 7-hydroxy-6-methyl-8-nitro-1,2,4,5-tetrahydro-3H-3-benzazepine-3-carboxylate in 25 ml of DMF were added 0.268 ml of methyl bromoacetate and 390 mg of potassium carbonate, followed by stirring at 55° C. for 13 hours. The reaction mixture was allowed to cool, and water added, followed by extraction with EtOAc twice. The combined organic layer was washed with saturated brine, the organic layer was dried over anhydrous sodium sulfate and then filtered, and the solvent was evaporated under reduced pressure. The residue was purified by silica gel chromatography (elution solvent: HEX-EtOAc) to obtain 1.076 g of t-butyl 7-(2-methoxy-2-oxoethoxy)-6-methyl-8-nitro-1,2,4,5-tetrahydro-3H-3-benzazepine-3-carboxylate as a yellowish white solid.

Preparation Example 23

To a mixture of 967 mg of t-butyl 7-(2-methoxy-2-oxoethoxy)-6-methyl-8-nitro-1,2,4,5-tetrahydro-3H-3-benzazepine-3-carboxylate in 25 ml of EtOH was added 97 mg of 10% palladium on carbon under an argon atmosphere, followed by stirring for 2 hours at normal pressure under a hydrogen atmosphere. To the reaction mixture was added 200 ml of THF, then the catalyst was removed using celite, and the solvent was evaporated under reduced pressure. The residue was purified by silica gel chromatography (elution solvent: HEX-EtOAc) to obtain 629 mg of t-butyl 11-methyl-3-oxo-3,4,6,7,9,10-hexahydro[1,4]oxazino[2,3-h][3]benzazepine-8(2H)-carboxylate as a white solid.

Preparation Example 24

To a solution of 120 mg of t-butyl 2-methyl-3,4,6,7,9,10-hexahydro[1,4]oxazino[2,3-h][3]benzazepine-8(2H)-carboxylate in 4 ml of DMF were added 0.026 ml of methyl iodide and 104 mg of potassium carbonate at room temperature, followed by stirring for 13 hours. To the reaction mixture were added 0.012 ml of methyl iodide and 26 mg of potassium carbonate, followed by further stirring for 3 hours. To the reaction mixture was added water, followed by extraction with EtOAc twice. The combined organic layer was washed with saturated brine, dried over anhydrous sodium sulfate, and then filtered, and the solvent was evaporated under reduced pressure. The residue was purified by silica gel chromatography (elution solvent: HEX-EtOAc) to obtain 55 mg of t-butyl 2,4-dimethyl-3,4,6,7,9,10-hexahydro[1,4]oxazino[2,3-h][3]benzazepine-8(2H)-carboxylate as a brown solid.

Preparation Example 25

To a solution of 120 mg of t-butyl 2-methyl-3,4,6,7,9,10-hexahydro[1,4]oxazino[2,3-h][3]benzazepine-8(2H)-carboxylate in 4 ml of DMF were added 0.113 ml of isopropyl iodide and 0.197 ml of diisopropylethylamine, followed by stirring at 100° C. for 6.5 hours. Further, to the reaction mixture were added 0.113 ml of isopropyl iodide and 0.197 ml of diisopropylethylamine, followed by stirring at 100° C. for 4 hours. Further, to the reaction mixture were added 0.226 ml of isopropyl iodide and 0.394 ml of diisopropylethylamine, followed by stirring at 100° C. for 19 hours. The reaction mixture was cooled to room temperature, and water added, followed by extraction with EtOAc twice. The combined organic layer was washed with saturated brine, the organic layer was dried over anhydrous sodium sulfate and then filtered, and the solvent was evaporated under reduced pressure. The residue was purified by silica gel chromatography (elution solvent: HEX-EtOAc) to obtain 90 mg of t-butyl 4-isopropyl-2-methyl-3,4,6,7,9,10-hexahydro[1,4]oxazino[2,3-h][3]benzazepine-8(2H)-carboxylate as a pale brown solid.

Preparation Example 26

To a solution of 130 mg of t-butyl 3,4,6,7,9,10-hexahydro[1,4]oxazino[2,3-h][3]benzazepine-8(2H)-carboxylate in 4 ml of dichloromethane were added 0.036 ml of methanesulfonyl chloride and 0.089 ml of diisopropylethylamine under ice-cooling, followed by stirring at room temperature for 16 hours. To the reaction mixture were added 0.036 ml of methanesulfonyl chloride and 0.089 ml of diisopropylethylamine, followed by stirring at room temperature for additional 9 hours. To the reaction mixture was added water, followed by extraction with chloroform. The organic layer was dried over anhydrous sodium sulfate and then filtered, and the solvent was evaporated under reduced pressure. The residue was purified by silica gel chromatography (elution solvent: HEX-EtOAc) to obtain 152 mg of t-butyl 4-(methylsulfonyl)-3,4,6,7,9,10-hexahydro[1,4]oxazino[2,3-h][3]benzazepine-8(2H)-carboxylate as a colorless solid.

Preparation Example 27

To a mixture of 5 g of sodium borohydride and 30 ml of anhydrous THF was added a solution of 10.27 g of 2-methyl-3-nitrophenylacetic acid in 60 ml of anhydrous THF under ice-cooling, and then a solution of 3.5 ml of methanesulfonic acid in 10 ml of anhydrous THF was added dropwise thereto. The reaction mixture was heated to 70° C. and then stirred for 30 minutes, and 80 ml of 3 M hydrochloric acid was then added thereto under ice-cooling, followed by stirring. The mixed liquid was extracted with chloroform, and the organic layer was dried over anhydrous magnesium sulfate and then filtered. The filtrate was concentrated under reduced pressure to obtain 9.701 g of an orange viscous substance. To a solution of 9.53 g of the resulting substance in 100 ml of dichloromethane were added dropwise 22 ml of diisopropylethylamine and 4.75 ml of chloromethylmethylether under ice-cooling, followed by stirring for 24 hours. 1.0 ml of chloromethylmethylether was added thereto, followed by further stirring for 24 hours. The reaction mixture was concentrated under reduced pressure and the residue was purified by silica gel chromatography (elution solvent: HEX-EtOAc) to obtain 11.26 g of a yellow oily substance. To a solution of 11.26 g of the resulting substance in 200 ml of EtOH was added 340 mg of platinum(IV) dioxide, followed by stirring at room temperature for 1 hour under a hydrogen atmosphere of 4 atm. The reaction mixture was removed using celite and the filtrate was concentrated under reduced pressure to obtain 9.21 g of an orange viscous substance. To a solution of the residue in 200 ml of dichloromethane and 40 ml of MeOH were added 14.2 g of calcium carbonate and 36.5 g of benzyl trimethylammonium dichloroiodate, followed by stirring at room temperature for 13 hours. The insoluble materials were removed by filtration and the filtrate was concentrated under reduced pressure. The residue was purified by silica gel chromatography (elution solvent: HEX-EtOAc) to obtain 15.93 g of 4,6-diiodo-3-[2-(methoxymethoxy)ethyl]-2-methylaniline as a dark red viscous substance.

Preparation Example 28

To a mixed liquid of 400 mg of palladium(II) acetate, 934 mg of triphenylphosphine, 9.91 g of tetrabutylammonium chloride, and 7 g of potassium acetate in 150 ml of DMF was added a solution of 15.93 g of 4,6-diiodo-3-[2-(methoxymethoxy)ethyl]-2-methylaniline in 150 ml of DMF, and 16 ml of ethyl acrylate was added thereto, followed by stirring at 80° C. for 3 hours. The reaction mixture was diluted with EtOAc, washed with water and saturated brine, and concentrated under reduced pressure. The residue was purified by silica gel chromatography (elution solvent: HEX-EtOAc) to obtain 12.11 g of a yellow solid. To a solution of 12.11 g of the resulting substance in 250 ml of EtOH and 250 ml of THF was added 701 mg of platinum(IV) oxide, followed by stirring at room temperature for 4 hours under a hydrogen atmosphere of 4 atm. The reaction mixture was removed using celite and the filtrate was concentrated-under reduced pressure to obtain 11.39 g of ethyl 3-{7-[2-(methoxymethoxy)ethyl]-8-methyl-2-oxo-1,2,3,4-tetrahydroquinolin-6-yl}propanoate as a milky white solid.

Preparation Example 29

To a solution of 10.81 g of ethyl 3-{7-[2-(methoxymethoxy)ethyl]-8-methyl-2-oxo-1,2,3,4-tetrahydroquinolin-6-yl}propanoate in 100 ml of EtOH and 100 ml of THF was added 100 ml of a 1 M aqueous sodium hydroxide solution, followed by stirring at room temperature for 1 hour. The reaction mixture was neutralized by the addition of hydrochloric acid and then concentrated under reduced pressure to one third of the liquid amount, and the residue was extracted with chloroform. The organic layer was dried over anhydrous magnesium sulfate and then filtered, and the filtrate was concentrated under reduced pressure. To a solution of the resulting residue in 300 ml of t-butanol were added 9.0 ml of triethylamine and 7.0 ml of DPPA, followed by heating and refluxing for 24 hours. The reaction mixture was concentrated under reduced pressure, the residue was purified by silica gel chromatography (elution solvent: HEX-EtOAc), and then the resulting solid was washed with HEX to obtain 8.006 g of t-butyl(2-{7-[2-(methoxymethoxy)ethyl]-8-methyl-2-oxo-1,2,3,4-tetrahydroquinolin-6-yl}ethyl)carbamate as a milky white solid.

Preparation Example 30

To a suspension of 1.01 g of t-butyl(2-{7-[2-(methoxymethoxy)ethyl]-8-methyl-2-oxo-1,2,3,4-tetrahydroquinolin-6-yl}ethyl)carbamate in 10 ml of THF was added 10 ml of 6 M hydrochloric acid, followed by stirring at 50° C. for 1 hour. The reaction mixture was alkalified by the addition of sodium hydroxide and then 675 mg of di-t-butyl dicarbonate was added thereto, followed by stirring at room temperature for 15 hours. The reaction mixture was extracted with chloroform, and the organic layer was dried over anhydrous magnesium sulfate and then filtered. The filtrate was concentrated under reduced pressure to obtain 1.105 g of t-butyl {2-[7-(2-hydroxyethyl)-8-methyl-2-oxo-1,2,3,4-tetrahydroquinolin-6-yl]ethyl}carbamate as a white foamed substance.

Preparation Example 31

To a solution of 1.793 g of t-butyl {2-[7-(2-hydroxyethyl)-8-methyl-2-oxo-1,2,3,4-tetrahydroquinolin-6-yl]ethyl}carbamate in 30 ml of THF were added 0.48 ml of methanesulfonyl chloride and 1.5 ml of triethylamine under ice-cooling, followed by stirring for 30 minutes. To the reaction mixture was added portionwise 1.8 g of potassium t-butoxide under ice-cooling, followed by stirring for 1.5 hours. To the reaction mixture was added a saturated aqueous ammonium chloride solution, followed by extraction with EtOAc. The organic layer was dried over anhydrous magnesium sulfate and then filtered, and the filtrate was concentrated under reduced pressure. The residue was purified by silica gel chromatography (elution solvent: HEX-EtOAc) to obtain 1.06 g of t-butyl 11-methyl-2-oxo-1,2,3,4,6,7,9,10-octahydro-8H-azepino[4,5-g]quinoline-8-carboxylate as a white foamed substance.

Preparation Example 32

To a solution of 167 mg of t-butyl 11-methyl-1,2,3,4,6,7,9,10-octahydro-8H-azepino[4,5-g]quinoline-8-carboxylate in 2 ml of dichloromethane were added 0.221 ml of triethylamine and 0.062 ml of ethyl isocyanate, followed by stirring at room temperature for 15 hours. To the reaction mixture were added 3 ml of toluene and 0.062 ml of ethyl isocyanate, followed by heating to 60° C. and stirring for 15 hours. Then, the reaction mixture was concentrated under reduced pressure and the residue was purified by silica gel chromatography (elution solvent: HEX-EtOAc) to obtain 200 mg of t-butyl 1-(ethylcarbamoyl)-11-methyl-1,2,3,4,6,7,9,10-octahydro-8H-azepino[4,5-g]quinoline-8-carboxylate as a colorless viscous substance.

Preparation Example 33

To a solution of 201 mg of t-butyl 11-methyl-1,2,3,4,6,7,9,10-octahydro-8H-azepino[4,5-g]quinoline-8-carboxylate in 2 ml of pyridine was added 0.1 ml of ethyl chloroformate, followed by stirring at room temperature for 30 minutes. The reaction mixture was concentrated under reduced pressure and the residue was purified by silica gel chromatography (elution solvent: HEX-EtOAc) to obtain 261 mg of 8-t-butyl 1-ethyl 11-methyl-3,4,6,7,9,10-hexahydro-1H-azepino[4,5-g]quinoline-1,8(2H)-dicarboxylate as a colorless viscous substance.

Preparation Example 34

To a suspension of 2 g of 3-(2-oxo-1,2,3,4-tetrahydroquinolin-7-yl)propionic acid in 40 ml of t-butanol were added 2.1 ml of DPPA and 2.6 ml of triethylamine, followed by heating and refluxing at 100° C. for 18 hours. The reaction mixture was concentrated under reduced pressure and the residue was purified by silica gel chromatography (elution solvent: chloroform-MeOH) to obtain 1.832 g of t-butyl[2-(2-oxo-1,2,3,4-tetrahydroquinolin-7-yl)ethyl]carbamate as an orange solid.

Preparation Example 35

To a mixed solution of 770 mg of t-butyl[2-(1,2,3,4-tetrahydroquinolin-7-yl)ethyl]carbamate in 15 ml of dichloromethane and 3 ml of MeOH were added 420 mg of calcium carbonate and 970 mg of benzyltrimethylammonium dichloroiodate, followed by stirring at room temperature for 2 hours. The insoluble materials were removed by filtration and the filtrate was concentrated under reduced pressure. The residue was purified by silica gel chromatography (elution solvent: HEX-EtOAc) to obtain 595 mg of t-butyl[2-(6-iodo-1,2,3,4-tetrahydroquinolin-7-yl)ethyl]carbamate as a reddish brown viscous substance.

Preparation Example 36

To a solution of 595 mg of t-butyl[2-(6-iodo-1,2,3,4-tetrahydroquinolin-7-yl)ethyl]carbamate in 3 ml of dichloromethane were added 3 ml of water and 376 mg of sodium hydrogen carbonate, and a solution of 0.273 ml of benzyl chloroformate in 3 ml of dichloromethane wad added dropwise under ice-cooling while stirring, followed by stirring for additional 5 hours. The reaction mixture was extracted with EtOAc, the organic layer was dried over anhydrous magnesium sulfate and then filtered, and the filtrate was concentrated under reduced pressure to obtain 877 mg of benzyl 7-{2-[(t-butoxycarbonyl)amino]ethyl}-6-iodo-3,4-dihydroquirolin-1(2H)-carboxylate as a reddish orange solid.

Preparation Example 37

To a solution of 793 mg of benzyl 7-{2-[(t-butoxycarbonyl)amino]ethyl}-6-iodo-3,4-dihydroquirolin-1(2H)-carboxylate in 10 ml of THF was added dropwise 1.8 ml of a 1 M solution of sodium bistrimethylsilylamide in THF under ice-cooling, followed by stirring for 5 minutes. Then, 0.166 ml of allyl bromide was added thereto, followed by stirring for 18 hours while slowly elevating the temperature to room temperature. To the reaction mixture were added a saturated aqueous ammonium chloride solution and water, followed by extraction with EtOAc, the organic layer was dried over anhydrous magnesium sulfate and then filtered, and the filtrate was concentrated under reduced pressure. The residue was purified by silica gel chromatography (elution solvent: HEX-EtOAc) to obtain 788 mg of benzyl 7-{2-[allyl(t-butoxycarbonyl)amino]ethyl}-6-iodo-3,4-dihydroquirolin-1(2H)-carboxylate.

Preparation Example 38

To a mixture of 403 mg of potassium acetate, 441 mg of tetrabutylammonium bromide, 9 mg of triphenylphosphine, and 4 mg of palladium(II) acetate was added a solution of 788 mg of benzyl 7-{2-[allyl(t-butoxycarbonyl)amino]ethyl}-6-iodo-3,4-dihydroquirolin-1(2H)-carboxylate in 25 ml of DMF, followed by substitution with argon and stirring at 80° C. for 4 hours. The reaction mixture was diluted with EtOAc, washed with water and saturated brine, and concentrated under reduced pressure. To 25 ml of a solution of the resulting residue in MeOH was added 36 mg of platinum (IV) oxide, followed by stirring at room temperature overnight under a hydrogen atmosphere of 4 atm. The reaction mixture was filtered through celite and the filtrate was concentrated under reduced pressure to obtain 570 mg of 1-benzyl 8-t-butyl 6-methyl-3,4,6,7,9,10-hexahydro-1H-azepino[4,5-g]quinoline-1,8(2H)-dicarboxylate as an orange foamed substance.

Preparation Example 39

To a mixed liquid of 9.3 g of aluminum chloride in 30 ml of dichloromethane was added dropwise 1.6 ml of acetyl chloride under ice-cooling, followed by stirring. Then, a solution of 5 g of 7-methoxy-1-methyl-3-(trifluoroacetyl)-2,3,4,5-tetrahydro-1H-3-benzazepine in 70 ml of dichloromethane was added thereto, followed by stirring for 13 hours while slowly elevating the temperature to room temperature. The reaction mixture was ice-cooled, and 30 ml of 1 M hydrochloric acid was added dropwise thereto, followed by addition of water and extraction with chloroform. The organic layer was dried over anhydrous magnesium sulfate and then filtered, and the filtrate was concentrated under reduced pressure. The residue was purified by flash chromatography (elution solvent: HEX-EtOAc) to obtain 5.137 g of 1-[8-hydroxy-5-methyl-3-(trifluoroacetyl)-2,3,4,5-tetrahydro-1H-3-benzazepine-7-yl]ethanone as a pale brown solid.

Preparation Example 40

To a suspension of 5.13 g of 1-[8-hydroxy-5-methyl-3-(trifluoroacetyl)-2,3,4,5-tetrahydro-1H-3-benzazepine-7-yl]ethanone in 50 ml of MeOH was added 50 ml of a 1 M aqueous sodium hydroxide solution, followed by stirring at room temperature for 30 minutes. The reaction mixture was concentrated under reduced pressure to a half of the amount, and to the residue were added 50 ml of dioxane and 4.27 g of di-t-butyl dicarbonate, followed by stirring at room temperature for 30 minutes. The reaction mixture was neutralized by the addition of 1 M hydrochloric acid and extracted with chloroform. The organic layer was dried over anhydrous magnesium sulfate and then filtered, and the filtrate was concentrated under reduced pressure. The residue was purified by silica gel chromatography (elution solvent: HEX-EtOAc) to obtain 4.385 g of t-butyl 8-acetyl-7-hydroxy-1-methyl-1,2,4,5-tetrahydro-3H-3-benzazepine-3-carboxylate as a yellow viscous substance.

Preparation Example 41

To a solution of 1.715 g of t-butyl 8-acetyl-7-(2-ethoxy-2-oxoethoxy)-1-methyl-1,2,4,5-tetrahydro-3H-3-benzazepine-3-carboxylate in 20 ml of EtOH was added 325 mg of hydroxylamine hydrochloride, followed by heating and refluxing for 3 hours. 500 mg of hydroxylamine hydrochloride was added thereto, followed by further heating and refluxing for 2 hours. The reaction mixture was concentrated under reduced pressure, and to the residue was added water, followed by extraction with chloroform. The organic layer was dried over anhydrous sodium sulfate and then filtered, and the filtrate was concentrated under reduced pressure. To 10 ml of a solution of the resulting residue in acetonitrile were added 24 mg of cyanuric chloride and 33 mg of zinc(II) chloride, followed by heating and refluxing for 12 hours. The reaction mixture was concentrated under reduced pressure. To the resulting residue were added 10 ml of dioxane, 10 ml of a 1 M aqueous sodium hydroxide solution and 1.2 g of di-t-butyl dicarbonate, followed by stirring at room temperature for 24 hours. The reaction mixture was concentrated under reduced pressure to a half of the amount, made weakly acidic by the addition of 1 M hydrochloric acid, and extracted with chloroform. The organic layer was dried over anhydrous magnesium sulfate and then filtered, and the filtrate was concentrated under reduced pressure. To the resulting residue was added 60 ml of a 17% aqueous sulfuric acid solution, followed by stirring at 100° C. for 1 hour. The reaction mixture was ice-cooled and alkalified by the addition of 15 g of sodium hydroxide, and 50 ml of dioxane and 1.21 g of di-t-butyl dicarbonate were added thereto, followed by stirring at room temperature for 3 hours. The reaction mixture was diluted with water and extracted with EtOAc. The organic layer was dried over anhydrous magnesium sulfate and then filtered, and the filtrate was concentrated under reduced pressure. The residue was purified by silica gel chromatography (elution solvent: HEX-EtOAc) to obtain 735 mg of t-butyl 6-methyl-3-oxo-3,4,6,7,9,10-hexahydro[1,4]oxazino[2,3-h][3]benzazepine-8(2H)-carboxylate as a pale yellow solid.

Preparation Example 42

To a solution of 704 mg of t-butyl 6-methyl-3,4,6,7,9,10-hexahydro[1,4]oxazino[2,3-h][3]benzazepine-8(2H)-carboxylate in 15 ml of dichloromethane was added portionwise 438 mg of N-bromosuccinimide under ice-cooling, followed by stirring for 30 minutes. The reaction mixture was concentrated under reduced pressure and the residue was purified by silica gel chromatography (elution solvent: HEX-EtOAc) to obtain 446 mg of a pale yellow foamed substance. To a mixture of 445 mg of the resulting compound, 144 mg of cyclopropylboric acid, 724 mg of potassium phosphate, 65 mg of tricyclohexylphosphine, and 28 mg of palladium(II) acetate were added 10 ml of toluene and 0.5 ml of water, followed by stirring at 110° C. for 12 hours. The reaction mixture was filtered through celite and the filtrate was concentrated under reduced pressure. The residue was purified by silica gel chromatography (elution solvent: HEX-EtOAc) to obtain 379 mg of t-butyl 5-cyclopropyl-6-methyl-3,4,6,7,9,10-hexahydro[1,4]oxazino[2,3-h][3]benzazepine-8(2H)-carboxylate as a pale brown foamed substance.

Preparation Example 334

To a solution of 500 mg of t-butyl 3-oxo-3,4,6,7,9,10-hexahydro[1,4]oxazino[2,3-h][3]benzazepine-8(2H)-carboxylate in 10 ml of DMF were added 250 μl of 1-(bromomethyl)-3-fluorobenzene and 800 mg of cesium carbonate, followed by stirring at 50° C. for 16 hours under an argon atmosphere. The reaction mixture was cooled to room temperature, and water added, followed by extraction with ethyl acetate twice. The combined organic layer was washed with saturated brine and then dried over anhydrous sodium sulfate. The solvent was evaporated and the residue was purified by silica gel chromatography (elution solvent: HEX-EtOAc) to obtain 609 mg of t-butyl 4-(3-fluorobenzyl)-3-oxo-3,4,6,7,9,10-hexahydro[1,4]oxazino[2,3-h][3]benzazepine-8(2H)-carboxylate.

Preparation Example 339

To a solution of 600 mg of t-butyl 2-oxo-1,2,3,4,6,7,9,10-octahydro-8H-azepino[4,5-g]quinoline-8-carboxylate in 9 ml DMF were added 426 mg of potassium t-butoxide and 451 μl of benzyl bromide in an ice-bath, followed by stirring at room temperature for 3 hours. Water and ethyl acetate were added thereto, and the organic layer was concentrated under reduced pressure. The residue was purified by silica gel chromatography (elution solvent: HEX-EtOAc) to obtain 644 mg of t-butyl 1-benzyl-2-oxo-1,2,3,4,6,7,9,10-octahydro-8H-azepino[4,5-g]quinoline-8-carboxylate as a pale yellow solid.

Preparation Example 344

To a solution of 3.83 g of t-butyl 1,2,3,4,6,7,9,10-octahydro-8H-azepino[4,5-g]quinoline-8-carboxylate in 40 ml of dichloromethane were added 1.3 ml of pyridine and 1.29 g of triphosgene under ice-cooling, followed by stirring for 3 hours. The reaction mixture was concentrated under reduced pressure, diluted with ethyl acetate, washed with water and an aqueous ammonium chloride solution, dried over anhydrous magnesium sulfate, and then filtered, and the filtrate was concentrated under reduced pressure. To the residue was added hexane, followed by stirring, and the solid was collected by filtration and dried to obtain 3.07 g of t-butyl 1-(chlorocarbonyl)-1,2,3,4,6,7,9,10-octahydro-8H-azepino[4,5-g]quinoline-8-carboxylate as a white solid.

Preparation Example 345

To a solution of 200 mg of t-butyl 1-(chlorocarbonyl)-1,2,3,4,6,7,9,10-octahydro-8H-azepino[4,5-g]quinoline-8-carboxylate in 2 ml of pyridine was added 140 μl of phenethyl alcohol, followed by stirring at 100° C. for 5.5 hours. The reaction mixture was concentrated under reduced pressure and the residue was purified by silica gel chromatography (elution solvent: HEX-EtOAc) to obtain 68 mg of 8-t-butyl 1-(2-phenylethyl) 3,4,6,7,9,10-hexahydro-1H-azepino[4,5-g]quinoline-1,8(2H)-dicarboxylate as a yellow viscous substance.

Preparation Example 349

To a solution of 200 mg of t-butyl 1,2,3,4,6,7,9,10-octahydro-8H-azepino[4,5-g]quinoline-8-carboxylate and 318 mg of 2-(2-methoxyphenyl)ethyl 4-nitrophenylcarbonate in 5 ml of dichloroethane was added 0.11 ml of pyridine, followed by stirring at room temperature for 2 days. The reaction mixture was concentrated under reduced pressure and the residue was purified by silica gel chromatography (elution solvent: HEX-EtOAc) and basic silica gel chromatography (elution solvent: HEX-EtOAc) to obtain 243 mg of 8-t-butyl 1-[2-(methoxyphenyl)ethyl]-3,4,6,7,9,10-hexahydro-1H-azepino[4,5-g]quinoline-1,8(2H)-carboxylate as a pale yellow viscous substance.

Preparation Example 367

To a solution of 150 mg of t-butyl 11-chloro-3,4,6,7,9,10-hexahydro[1,4]oxazino[2,3-h][3]benzazepine-8(2H)-carboxylate in 3 ml of tetrahydrofuran was added 1.5 ml of a 1 M aqueous sodium hydrogen carbonate solution, followed by ice-cooling, and 64 μl of ethyl chloroformate was added dropwise thereto followed by stirring. The reaction mixture was diluted with ethyl acetate, washed with water and saturated brine, dried over anhydrous magnesium sulfate, and then filtered, and the filtrate was concentrated under reduced pressure. The residue was purified by silica gel chromatography (elution solvent: HEX-EtOAc) to obtain 149 mg of 8-t-butyl 4-ethyl-11-chloro-2,3,6,7,9,10-hexahydro[1,4]oxazino[2,3-h][3]benzazepine-4,8-dicarboxylate as a colorless foamed substance.

Preparation Example 375

To 500 mg of t-butyl 11-bromo-1-methyl-1,2,3,4,6,7,9,10-octahydro-8H-azepino[4,5-g]quinoline-8-carboxylate, 350 mg of potassium carbonate, 290 mg of copper iodide, 173 mg of 1H-pyrazole, and 313 mg of N,N-dimethylglycine was added 6.25 ml of dimethylsulfoxide under argon, followed by stirring at 135° C. for 36 hours. To the reaction mixture were added water and ethyl acetate, followed by stirring, and then the solid was separated by filtration. The organic layer was washed with aqueous sodium bicarbonate and concentrated under reduced pressure. The residue was purified by silica gel chromatography (elution solvent: HEX-EtOAc) to obtain 43 mg of t-butyl 1-methyl-11-(1H-pyrazol-1-yl)-1,2,3,4,6,7,9,10-octahydro-8H-azepino[4,5-g]quinoline-8-carboxylate as a colorless viscous liquid.

Preparation Example 376

A solution of 200 mg of t-butyl 11-bromo-1-(2-methoxyethyl)-1,2,3,4,6,7,9,10-octahydro-8H-azepino[4,5-g]quinoline-8-carboxylate, 34 mg of zinc cyanide, 13 mg of bis(tri-t-butylphosphine)palladium, and 10 mg of zinc powder in 4 ml of N,N-dimethylacetamide was substituted with argon and then stirred at 100° C. for 15 hours. The reaction mixture was purified by silica gel chromatography (elution solvent: HEX-EtOAc) to obtain 132 mg of t-butyl 11-cyano-1-(2- methoxyethyl)-1,2,3,4,6,7,9,10-octahydro-8H-azepino[4,5-g]quinoline-8-carboxylate as a colorless viscous substance.

Preparation Example 377

1.1946 g of 1-[11-bromo-1-(2-methoxyethyl)-1,2,3,4,6,7,9,10-octahydro-8H-azepino[4,5-g]quinolin-8-yl]-2,2,2-trifluoroethanone, 2.2395 g of sodium trifluoroacetate, and 1.568 g of copper iodide were added to 24 ml of N-methylpyrrolidone under an argon atmosphere, followed by stirring at 170° C. for 18 hours. To the reaction mixture were added water and ethyl acetate, and filtered through celite was performed. The filtrate was subjected to liquid separation, the organic layer was washed with saturated brine, dried over anhydrous magnesium sulfate, and then filtered, and the filtrate was concentrated under reduced pressure. The residue was purified by silica gel chromatography (elution solvent: Hex-AcOEt) to obtain 239 mg of 2,2,2-trifluoro-1-[1-(2-methoxyethyl)-11-(trifluoromethyl)-1,2,3,4,6,7,9,10-octahydro-8H-azepino[4,5-g]quinolin-8-yl]ethanone as a pale yellow solid.

Preparation Example 379

To 7.87 g of 3-(6-iodo-2-oxo-1,2,3,4-tetrahydroquinolin-7-yl)propanoic acid were added 200 ml of t-butanol, 7 ml of triethylamine, and 5 ml of diphenylphosphoryl azide, followed by heating and refluxing for 70 hours. The reaction mixture was cooled to room temperature, then diluted by the addition of water, and stirred, and the solid was collected by filtration and dried to obtain 9.49 g of t-butyl[2-(6-iodo-2-oxo-1,2,3,4-tetrahydroquinolin-7-yl)ethyl]carbamate as a pale brown solid. Further, the solid precipitated from the filtrate was collected by filtration to obtain 665 mg of t-butyl[2-(6-iodo-2-oxo-1,2,3,4-tetrahydroquinolin-7-yl)ethyl]carbamate as a white solid.

Preparation Example 380

670 mg of t-butyl 1-[(benzyloxy)methyl]-6-methyl-2-oxo-1,2,3,4,6,7,9,10-octahydro-8H-azepino[4,5-g]quinoline-8-carboxylate was stirred at room temperature for 3.5 hours in a 48% aqueous hydrobromic acid solution. The reaction mixture was extracted with hexane and a side-product, benzyl bromide, was removed. Then, the aqueous layer was alkalified by the addition of a 1 M aqueous sodium hydroxide solution, and 20 ml of tetrahydrofuran was added thereto. To the mixed liquid was added 500 mg of di-t-butyl dicarbonate, followed by stirring at room temperature for 2 hours. The reaction mixture was extracted with ethyl acetate and the organic layer was washed with saturated brine, dried over anhydrous magnesium sulfate, and then filtered. The filtrate was concentrated under reduced pressure to obtain 513 mg of t-butyl 6-methyl-2-oxo-1,2,3,4,6,7,9,10-octahydro-8H-azepino[4,5-g]quinoline-8-carboxylate as a colorless foamed substance.

Preparation Example 381

Under an argon atmosphere, to a solution of 1.7 g of ethyl 7-bromo-8-hydroxy-1,2,4,5-tetrahydro-3H-3-benzazepine-3-carboxylate in 30 ml of DMF was added 283 mg of sodium hydride under ice-cooling, followed by stirring at the same temperature for 10 minutes. Then, 1.54 g of t-butyl(4R)-4-methyl-2,2-dioxo-[1,2,3]oxathiazolidine-3-carboxylate was added thereto, followed by stirring at room temperature for 18 hours. To the reaction mixture was added water and 1 M aqueous hydrochloric acid sequentially, followed by stirring, and the precipitated solid was collected by filtration. To 20 ml of a suspension of the resulting solid in ethanol was added 10 ml of a 4 M hydrogen chloride-ethyl acetate solution under ice-cooling, followed by stirring at 60° C. for 1 hour. The reaction mixture was evaporated under reduced pressure, and to the residue were added chloroform and saturated aqueous sodium bicarbonate. After extraction with chloroform, the combined organic layer was washed with saturated brine, dried over anhydrous magnesium sulfate, filtered, and concentrated under reduced pressure to obtain 2.26 g of ethyl 7-{[(2R)-2-aminopropyl]oxy}-8-bromo-1,2,4,5-tetrahydro-3H-3-benzazepine-3-carboxylate as an opaque cream-colored oily substance.

Preparation Example 383

Under an argon atmosphere, to a solution of 1.64 g of ethyl 7-{[(2R)-2-aminopropyl]oxy}-8-bromo-1,2,4,5-tetrahydro-3H-3-benzazepine-3-carboxylate in 41 ml of toluene were added 509 mg of sodium t-butoxide, 275 mg of 2,2'-bis(diphenylphosphino)-1,1'-binaphthyl, and 202 mg of tris(dibenzylideneacetone)dipalladium (0) in this order, followed by heating at 100° C. for 24 hours. Further, 509 mg of sodium t-butoxide, 275 mg of 2,2'-bis(diphenylphosphino)-1,1'-binaphthyl, and 202 mg of tris(dibenzylideneacetone)dipalladium (0) were added thereto, followed by stirring at 100° C. for additional 24 hours. The reaction mixture was returned to room temperature, then filtered through celite, and washed with ethyl acetate, and the filtrate was concentrated under reduced pressure. The residue was purified by silica gel chromatography (elution solvent: Hex-AcOEt) to obtain 610 mg of ethyl(3R)-3-methyl-3,4,6,7,9,10-hexahydro[1,4]oxazino[2,3-h][3]benzazepine-8(2H)-carboxylate.

Preparation Example 385

Under an argon atmosphere, to a solution of 1.032 g of ethyl 7-[(3-methylbut-2-enoyl)amino]-1,2,4,5-tetrahydro-3H-3-benzazepine-3-carboxylate in 10.5 ml of dichloromethane was added 870 mg of aluminum chloride at room temperature, followed by stirring at room temperature for 3 hours. Further, 435 mg of aluminum chloride was added thereto, followed by stirring at room temperature for 2 hours. The reaction mixture was poured into ice-water, followed by extraction with chloroform. The combined organic layer was washed with water, a saturated aqueous sodium hydrogen carbonate solution, water, and saturated brine, dried over anhydrous magnesium sulfate, and then filtered, and the filtrate was concentrated under reduced pressure. The residue was purified by silica gel chromatography (elution solvent: Hex-AcOEt) to obtain 431 mg of ethyl 4,4-dimethyl-2-oxo-1,2,3,4,6,7,9,10-octahydro-8H-azepino[4,5-g]quinoline-8-carboxylate as a white solid.

Preparation Example 386

Under an argon atmosphere, to a solution of 1 g of ethyl 7-amino-1,2,4,5-tetrahydro-3H-3-benzazepine-3-carboxylate and 539 mg of 1,1-dimethylprop-2-in-1-yl acetate in 10 ml of tetrahydrofuran was added 43 mg of copper chloride, followed by heating at 90° C. for 5 hours. The reaction mixture was concentrated under reduced pressure, ethyl acetate added, and washed with a saturated aqueous ammonium chloride solution, and saturated brine. The aqueous layer was extracted with ethyl acetate twice, the combined organic layer was washed with saturated brine, dried over anhydrous magnesium sulfate, and then filtered, and the filtrate was concentrated under reduced pressure. The residue was purified by preparative thin layer chromatography to obtain 272 mg of ethyl 2,2-dimethyl-1,2,6,7,9,10-hexahydro-8H-azepine[4,5-g]quinoline-8-carboxylate.

Preparation Example 387

To ethyl 7-amino-1,2,4,5-tetrahydro-3H-3-benzazepine-3-carboxylate was added a 5% aqueous sulfuric acid solution, followed by stirring under ice-cooling. An aqueous solution (30 ml) of 10.22 g of sodium nitrite was added dropwise in portions thereto, and followed by stirring at the same temperature for 0.5 hours and then stirring at 60° C. for 3 hours. The reaction mixture was extracted with ethyl acetate, the organic layer was dried over anhydrous magnesium sulfate and then filtered, and the filtrate was concentrated under reduced pressure. The residue was purified by silica gel chromatography (elution solvent: HEX-EtOAc) to obtain a crude purified product having ethyl 7-hydroxy-1,2,4,5-tetrahydro-3H-3-benzazepine-3-carboxylate as a main component. The crude purified product was recrystallized from ethyl acetate twice to obtain 15.66 g of ethyl 7-hydroxy-1,2,4,5-tetrahydro-3H-3-benzazepine-3-carboxylate.

Preparation Example 388

To a solution of 30 g of ethyl 7-nitro-1,2,4,5-tetrahydro-3H-3-benzazepine-3-carboxylate in 300 ml of ethanol was added 3 g of 10% palladium on carbon, followed by stirring at room temperature for 16 hours under a hydrogen atmosphere of 4 atm. The reaction mixture was filtered through celite, and the filtrate was ice-cooled and then 21.6 ml of anhydrous acetic acid was added dropwise thereto, followed by stirring for 16 hours. The reaction mixture was concentrated under reduced pressure and to the residue was added diethylether to wash the solid, thereby obtaining 26.45 g of ethyl 7-acetamide-1,2,4,5-tetrahydro-3H-3-benzazepine-3-carboxylate as a white solid.

Preparation Example 389

The mixed liquid of 12 g of ethyl 7-acetamide-8-bromo-1,2,4,5-tetrahydro-3H-3-benzazepine-3-carboxylate, 1.93 g of copper iodide, 1.89 g of 1,10-phenanthroline, and 33.12 g of cesium carbonate in 240 ml of dioxane was substituted with argon, followed by stirring at 100° C. for 18 hours. The reaction mixture was diluted with ethyl acetate, the insoluble materials were removed using celite, and the filtrate was concentrated under reduced pressure to obtain a milky white solid. The resulting residue was suspended in 240 ml of dioxane, and 1.93 g of copper iodide, 1.89 g of 1,10-phenanthroline, and 33.1 g of cesium carbonate were added thereto, followed by stirring at 100° C. for 3 days. The reaction mixture was cooled to room temperature, diluted with ethyl acetate, and filtered through celite to remove the solid, and the filtrate was concentrated under reduced pressure to obtain 9.245 g of ethyl 2-methyl-5,6,8,9-tetrahydro-7H-[1,3]oxazolo[4,5-h][3]benzazepine-7-carboxylate as a milky white solid.

Preparation Example 390

To a solution of 7 g of ethyl 2-methyl-5,6,8,9-tetrahydro-7H-[1,3]oxazolo[4,5-h][3]benzazepine-7-carboxylate in 130 ml of ethanol was added 130 ml of 1 M aqueous hydrochloric acid, followed by stirring for 16 hours. Ethanol was evaporated under reduced pressure, dried, dissolved in chloroform, and washed with water. The organic layer was dried over anhydrous sodium sulfate and then the solvent was evaporated under reduced pressure to obtain 6.84 g of ethyl 7-acetamide-8-hydroxy-1,2,4,5-tetrahydro-3H-3-benzazepine-3-carboxylate as a brownish white solid.

Preparation Example 408

To a solution of 860 mg of t-butyl 4-ethyl-3,4,6,7,9,10-hexahydro[1,4]oxazino[2,3-h][3]benzazepine-8(2H)-carboxylate in 25 ml of dichloroethane was added 1.1 g of sodium hydrogen carbonate, and further, a solution of 200 μl of bromine in 5 ml of dichloroethane was added dropwise thereto over about 30 minutes, followed by stirring at room temperature. To the reaction mixture was slowly added a 3% aqueous sodium thiosulfate solution, followed by stirring vigorously and extracting with chloroform twice. The combined organic layer was washed with saturated brine and then dried over anhydrous sodium sulfate. The solvent was evaporated and the residue was purified by silica gel chromatography (elution solvent: HEX-EtOAc) to obtain 490 mg of t-butyl 5-bromo-4-ethyl-3,4,6,7,9,10-hexahydro[1,4]oxazino[2,3-h][3]benzazepine-8(2H)-carboxylate.

Preparation Example 409

Under an argon atmosphere, to a mixed solution of 5.0 g of ethyl 7-hydroxy-1,2,4,5-tetrahydro-3H-3-benzazepine-3-carboxylate in 100 ml of dichloromethane and 20 ml of methanol was added portionwise 8.05 g of N,N,N-trimethylanilinium tribromide under ice-cooling, followed by stirring at the same temperature for 1 hour. The reaction mixture was concentrated under reduced pressure, the residue was extracted by the addition of ethyl acetate and water, and the organic layer was washed with 1 M aqueous hydrochloric acid and saturated brine, dried over anhydrous magnesium sulfate, and then filtered, and the filtrate was concentrated under reduced pressure to obtain 6.67 g of ethyl 7-bromo-8-hydroxy-1,2,4,5-tetrahydro-3H-3-benzazepine-3-carboxylate as a beige solid.

Preparation Example 411

To a solution of 150 mg of t-butyl 1-(3-methoxypropyl)-2-oxo-1,2,3,4,6,7,9,10-octahydro-8H-azepino[4,5-g]quinoline-8-carboxylate in 4.2 ml of acetonitrile were added 107 mg of N-bromosuccinimide and 3.7 mg of ammonium nitrate, followed by stirring at room temperature for 3.5 hours. The reaction mixture was concentrated to about ¼, and ethyl acetate, an aqueous sodium thiosulfate solution, and aqueous sodium bicarbonate was added thereto. The organic layer was washed with saturated brine and then dried over anhydrous magnesium sulfate. The solvent was evaporated to obtain 198 mg of t-butyl 11-bromo-1-(3-methoxypropyl)-2-oxo-1,2,3,4,6,7,9,10-octahydro-8H-azepino[4,5-g]quinoline-8-carboxylate.

Preparation Example 426

To a solution of 16.23 g of ethyl 3-(6-iodo-2-oxo-1,2,3,4-tetrahydroquinolin-7-yl)propanoate in 200 ml of ethanol was added 150 ml of a 1 M aqueous sodium hydroxide solution, followed by stirring at room temperature for 2 hours. The reaction mixture was made weakly acidic by the addition dropwise of concentrated hydrochloric acid and diluted by the addition of water. The precipitated solid was collected by filtration and dried to obtain 8.88 g of 3-(6-iodo-2-oxo-1,2,3,4-tetrahydroquinolin-7-yl)propanoic acid as a pale brown solid.

Preparation Example 427

To 3.421 g of ethyl 8-acetamide-6-bromo-7-(2-ethoxy-2-oxoethoxy)-1,2,4,5-tetrahydro-3H-benzazepine-3-carboxylate were added 30 ml of acetic acid and 30 ml of 8 M hydrochloric acid, followed by stirring at 150° C. for 16 hours. The reaction mixture was concentrated under reduced pressure, and the residue was dissolved in 35 ml of THF, and alkalified by the addition of 35 ml of a 1 M aqueous sodium hydroxide solution. 2 g of di-t-butyl dicarbonate was added thereto, followed by stirring at room temperature for 1 hour. The reaction mixture was extracted with ethyl acetate, the organic layer was dried over anhydrous magnesium sulfate and then filtered, and the filtrate was concentrated under reduced pressure to obtain 1.373 g of t-butyl 11-bromo-3-oxo-3,4,6,7,9,10-hexahydro[1,4]oxazino[2,3-h][3]benzazepine-8(2H)-carboxylate.

Preparation Example 495

To a solution of 590 mg of t-butyl 4-benzyl-3-oxo-3,4,6,7,9,10-hexahydro[1,4]oxazino[2,3-h][3]benzazepine-8 (2H)-carboxylate in 10 ml of tetrahydrofuran was added 3.5 ml of a 1 M solution of a borane-THF complex in THF under ice-cooling, followed by stirring at room temperature for 14 hours. The reaction mixture was cooled, and MeOH and a 1 M aqueous sodium hydroxide solution were added thereto, followed by stirring at room temperature for 3 hours. The reaction mixture was concentrated, to the residue were added ethyl acetate and water, and the organic layer was washed with saturated brine and dried over anhydrous sodium sulfate. The solvent was evaporated, and to a solution of 578 mg of the resulting residue in 10 ml of dichloromethane was added 620 mg of sodium hydrogen carbonate. Further, a solution of 280 mg of bromine in 5 ml of dichloromethane was added dropwise thereto over about 30 minutes, followed by stirring at room temperature. To the reaction mixture was slowly added a 3% aqueous sodium thiosulfate solution, followed by stirring vigorously and extracting with chloroform twice. The combined organic layer was washed with saturated brine, dried over anhydrous sodium sulfate, and then filtered, and the filtrate was concentrated under reduced pressure. The residue was purified by silica gel chromatography (elution solvent: HEX-EtOAc) to obtain 518 mg of t-butyl 4-benzyl-5-bromo-3,4,6,7,9,10-hexahydro[1,4]oxazino[2,3-h][3]benzazepine-8(2H)-carboxylate.

Preparation Example 540

To a solution of 210 mg of 2,4,5-trifluorobenzonitrile and 500 mg of t-butyl 5-cyclopropyl-4-(2-hydroxyethyl)-3,4,6,7,9,10-hexahydro[1,4]oxazino[2,3-h][3]benzazepine-8 (2H)-carboxylate in 15 ml of THF was added portionwise 150 mg of potassium t-butoxide, followed by stirring at −30° C. for 2 hours. Further, to the reaction mixture was added 0.15 ml of MeOH and then 150 mg of potassium t-butoxide was added portionwise thereto, followed by elevating the temperature to −10° C. and stirring for 15 hours. Further, to the reaction mixture were added 0.15 ml of MeOH, and then 150 mg of potassium t-butoxide was added portionwise thereto, followed by elevating the temperature to 0° C. and stirring for additional 14 hours. The reaction mixture was diluted with ethyl acetate, washed with water and saturated brine, dried over anhydrous magnesium sulfate, and then filtered, and the filtrate was concentrated under reduced pressure. The residue was purified by silica gel chromatography (elution solvent: HEX-EtOAc)) to obtain 726 mg of t-butyl 4-[2-(4-cyano-2-fluoro-5-methoxyphenoxy)ethyl]-5-cyclopropyl-3,4,6,7,9,10-hexahydro[1,4]oxazino[2,3-h][3]benzazepine-8(2H)-carboxylate as a colorless viscous substance.

Preparation Example 543

To a solution of 270 mg of t-butyl 5-cyclopropyl-4-[2-(2,6-difluoro-4-formylphenoxy)ethyl]-3,4,6,7,9,10-hexahydro [1,4]oxazino[2,3-h][3]benzazepine-8(2H)-carboxylate in 6 ml of MeOH was added 30 mg of sodium borohydride, followed by stirring at room temperature for 4 hours. The reaction mixture was concentrated under reduced pressure and the residue was purified by silica gel chromatography (elution solvent: HEX-EtOAc)) to obtain 220 mg of t-butyl 5-cyclopropyl-4-{2-[2,6-difluoro-4-(hydroxymethyl) phenoxy]ethyl}-3,4,6,7,9,10-hexahydro[1,4]oxazino[2,3-h][3] benzazepine-8(2H)-carboxylate as a white solid.

Preparation Example 545

To a solution of 400 mg of t-butyl 5-cyclopropyl-4-(2-hydroxyethyl)-3,4,6,7,9,10-hexahydro[1,4]oxazino[2,3-h] [3]benzazepine-8(2H)-carboxylate in 4 ml of dichloromethane were added 217 mg of p-toluenesulfonyl chloride, 0.22 ml of triethylamine, and 125 μl of N-methylimidazole in this order, followed by stirring for 1 hour. The reaction mixture was concentrated under reduced pressure and the residue was purified by silica gel chromatography (elution solvent: HEX-EtOAc) to obtain 541 mg of t-butyl 5-cyclopropyl-4-(2-{[(4-methylphenyl)sulfonyl]oxy}ethyl)-3,4,6,7,9,10-hexahydro[1,4]oxazino[2,3-h][3]benzazepine-8(2H)-carboxylate as a white solid.

Preparation Example 549

To 400 mg of t-butyl 5-cyclopropyl-4-[(2R)-2-methoxy-3-{[(4-methylphenyl)sulfonyl]oxy}propyl]-3,4,6,7,9,10-hexahydro[1,4]oxazino[2,3-h][3]benzazepine-8(2H)-carboxylate was added 7 ml of a 1 M solution of tetrabutylammonium fluoride in THF, followed by heating and stirring at 60° C. for 13 hours under an argon atmosphere. The reaction mixture was cooled to room temperature and a saturated aqueous sodium hydrogen carbonate solution was added thereto, followed by extraction with ethyl acetate twice. The combined organic layer was dried over anhydrous sodium sulfate and then filtered, and the filtrate was concentrated under reduced pressure. The residue was purified by silica gel chromatography (elution solvent: HEX-EtOAc) to obtain 257 mg of t-butyl 5-cyclopropyl-4-[(2R)-3-fluoro-2-methoxypropyl]-3,4,6,7,9,10-hexahydro[1,4]oxazino[2,3-h][3]benzazepine-8(2H)-carboxylate as a white foamed solid.

Preparation Example 565

To a solution of 300 mg of t-butyl 5-cyclopropyl-4-(2-hydroxy-3-methoxypropyl)-3,4,6,7,9,10-hexahydro[1,4]oxazino[2,3-h][3]benzazepine-8(2H)-carboxylate in 3 ml of toluene were added 0.1 ml of o-fluorophenol and 250 mg of cyanomethylenetributylphosphorane, followed by stirring at

47

80° C. for 20 hours. The reaction mixture was concentrated under reduced pressure and the residue was purified by silica gel chromatography (elution solvent: HEX-EtOAc) to obtain 277 mg of t-butyl 5-cyclopropyl-4-[2-(2-fluorophenoxy)-3-methoxypropyl]-3,4,6,7,9,10-hexahydro[1,4]oxazino[2,3-h][3]benzazepine-8(2H)-carboxylate as a pale yellow viscous substance.

In the same manner as in the methods of Preparation Examples above, the compounds of Preparation Examples as shown in the Tables below were prepared. For the compounds of the Preparation Examples, the structures are shown in Tables 2 to 81 and the preparation methods and the physicochemical data are shown in Tables 82 to 96.

Example 1

To 1.865 g of ethyl 11-chloro-2-oxo-1,2,3,4,6,7,9,10-octahydro-8H-azepino[4,5-g]quinoline-8-carboxylate were added 20 mL of ethylene glycol and 20 mL of a 40% aqueous potassium hydroxide solution, followed by heating to 120° C. for 18 hours. The reaction mixture was ice-cooled and adjusted to pH 1 by the addition of concentrated hydrochloric acid, followed by stirring for 1 hour. The reaction mixture was alkalified by the addition of a 1 M aqueous sodium hydroxide solution, followed by extraction with chloroform. The organic layer was dried over anhydrous sodium sulfate and then filtered. The filtrate was concentrated under reduced pressure to obtain 1.451 g of 11-chloro-1,3,4,6,7,8,9,10-octahydro-2H-azepino[4,5-g]quinolin-2-one as a brown solid. To 60 mg of 11-chloro-1,3,4,6,7,8,9,10-octahydro-2H-azepino[4,5-g]quinolin-2-one were added 1 ml of EtOAc and then EtOH, followed by dissolution under heating. The precipitated solid was collected by filtration to obtain 29.5 mg of 11-chloro-1,3,4,6,7,8,9,10-octahydro-2H-azepino[4,5-g]quinolin-2-one as a white solid.

Example 2

To 47 mg of t-butyl 11-chloro-1-isobutyl-1,2,3,4,6,7,9,10-octahydro-8H-azepino[4,5-g]quinoline-8-carboxylate was added 1 ml of a 4 M hydrogen chloride solution in EtOAc, followed by stirring at room temperature for 3 hours. The reaction mixture was concentrated under reduced pressure and the residue was purified by amino-silica gel chromatography (elution solvent: chloroform-MeOH). 26 mg of the resulting pale yellow viscous substance was dissolved in EtOH, followed by addition of 10.3 mg of fumaric acid and stirring. The precipitated solid was collected by filtration to obtain 23.2 mg of 11-chloro-1-isobutyl-2,3,4,6,7,8,9,10-octahydro-1H-azepino[4,5-g]quinoline monofumarate as a white solid.

Example 3

To a solution of 200 mg of t-butyl 2-oxo-1,2,3,4,6,7,9,10-octahydro-8H-azepino[4,5-g]quinoline-8-carboxylate in 2 ml of THF was added 1.9 ml of a 1 M solution of a borane-THF complex in THF under ice-cooling, followed by elevating the temperature to room temperature and stirring for 6 hours, and then elevating the temperature to 45° C. After stirring for 3 hours, 1.9 ml of a 1 M solution of a borane-THF complex in THF was added thereto in an ice-bath. After an additional 2 hours, MeOH was added dropwise thereto, followed by stirring for 20 minutes. The mixed solution was diluted with water, followed by extraction with chloroform. The organic layer was dried over anhydrous sodium sulfate and then filtered, and the filtrate was concentrated under reduced pressure. The residue was dissolved in 1.6 ml of dichloromethane, and 0.4 ml of trifluoroacetic acid was added thereto, followed by stirring at room temperature for 1 hour and then concentrating under reduced pressure. The residue was purified by silica gel chromatography (elution solvent: chloroform-MeOH—aqueous ammonia), and the resulting solid was dissolved in 0.25 ml of hot EtOH, followed by addition of 21 mg of fumaric acid. While stirring, the resultant was cooled to room temperature and the precipitated solid was filtered to obtain 36 mg of 2,3,4,6,7,8,9,10-octahydro-1H-azepino[4,5-g]quinoline monofumarate as a pale yellow solid.

Example 4

To 150 mg of ethyl 1-methyl-2-oxo-1,2,3,4,6,7,9,10-octahydro-8H-azepino[4,5-g]quinoline-8-carboxylate were added 4 ml of ethylene glycol and 2 nil of a 40% aqueous potassium hydroxide solution, followed by heating at 120° C. and stirring for 18 hours. The reaction mixture was ice-cooled and the liquid was made acidic by the addition of concentrated hydrochloric acid, followed by stirring for an additional 1 hour. The reaction mixture was neutralized with a 1 M aqueous sodium hydroxide solution and then extracted with chloroform, the organic layer was dried over anhydrous sodium sulfate and then filtered, and the filtrate was concentrated under reduced pressure. Then, the residue was purified by silica gel chromatography (elution solvent: chloroform-MeOH-aqueous ammonia). To a solution of the resulting residue in 2 ml of EtOAc was added 0.2 ml of a 4 M hydrogen chloride solution in EtOAc, followed by stirring. The solvent was concentrated under reduced pressure and the resulting solid was dissolved in 2 ml of EtOH under heating, followed by stirring at room temperature. The precipitated solid was collected by filtration to obtain 43.7 mg of 1-methyl-1,3,4,6,7,8,9,10-octahydro-2H-azepino[4,5-g]quinolin-2-one monohydrochloride as a pale yellow solid.

Example 5

To a solution of 140 mg of t-butyl 11-cyclopropyl-1-(methoxyacetyl)-1,2,3,4,6,7,9,10-octahydro-8H-azepino[4,5-g]quinoline-8-carboxylate in 1 ml of EtOH was added 2 ml of 4 M hydrogen chloride solution in EtOAc, followed by stirring at room temperature for 3 hours. The reaction mixture was poured into a 1 M aqueous sodium hydroxide solution, the aqueous layer was extracted with chloroform, and the organic layer was dried over sodium sulfate. The solvent was concentrated under reduced pressure and the resulting residue was purified by silica gel chromatography (elution solvent: chloroform-MeOH-aqueous ammonia) to obtain 102 mg of 11-cyclopropyl-1-(methoxyacetyl)-2,3,4,6,7,8,9,10-octahydro-8H-azepino[4,5-g]quinoline as a pale yellow oily substance.

Example 6

To a solution of 200 mg of t-butyl 1,2,3,4,6,7,9,10-octahydro-8H-azepino[4,5-g]quinoline-8-carboxylate in 2.13 ml of dichloroethane were added 0.553 ml of triethylamine and 0.19 ml of ethyl chloroformate, followed by stirring at 60° C. for 2 hours. The reaction mixture was cooled to room temperature, and then the reaction mixture was diluted with EtOAc, washed with 1 M hydrochloric acid, water, a 1 M aqueous sodium hydroxide solution, and saturated brine, and concentrated, and the residue was purified by silica gel column chromatography (elution solvent: HEX-EtOAc). The resulting substance was dissolved in chloroform, followed by adding 0.05 ml of trifluoroacetic acid and stirring for 30 minutes. After concentration under reduced pressure, the resultant was dissolved in EtOH, neutralized by the addition of triethylamine, and then concentrated under reduced pressure. Then, the residue was purified by silica gel column chromatography (elution solvent: chloroform-MeOH-aqueous ammonia). The resulting substance was dissolved in EtOH and 76 mg of fumaric acid was added thereto. The resulting white solid was collected by filtration and dried to obtain 79 mg of ethyl 2,3,4,6,7,8,9,10-octahydro-1H-azepino[4.5-g]quinoline-1-carboxylate hemifumarate.

Example 7

To a solution of 300 mg of t-butyl 1,2,3,4,6,7,9,10-octahydro-8H-azepino[4,5-g]quinoline-8-carboxylate in 5.26 ml of pyridine was added 0.455 ml of N,N-dimethylcarbamoyl chloride, followed by stirring at 80° C. for 3 hours. To the reaction mixture was added 1 M hydrochloric acid, followed by extraction with EtOAc. The organic layer was washed with saturated brine and the solvent was evaporated. The resulting residue was purified by silica gel column chromatography (elution solvent: HEX-EtOAc). The resulting substance was dissolved in 6 ml of chloroform, followed by adding 3 ml of trifluoroacetic acid and stirring for 30 minutes. After concentration under reduced pressure, the resultant was dissolved in 4.5 ml of EtOH, neutralized by the addition of triethylamine, and then concentrated under reduced pressure. Then, the residue was purified by silica gel column chromatography (elution solvent: chloroform-MeOH-aqueous ammonia). The resulting substance was dissolved in 4.5 ml of EtOH and 115 mg of fumaric acid was added thereto. The resulting white solid was collected by filtration and dried to obtain 120 mg of N,N-dimethyl-2,3,4,6,7,8,9,10-octahydro-1H-azepino[4,5-g]quinoline-1-carboxamide fumarate.

Example 8

To a solution of 300 mg of t-butyl 1,2,3,4,6,7,9,10-octahydro-8H-azepino[4,5-g]quinoline-8-carboxylate in 6 ml of toluene was added 1.16 ml of ethyl isocyanate, followed by stirring at 90° C. overnight. The reaction mixture was concentrated under reduced pressure and then purified by silica gel column chromatography (elution solvent: HEX-EtOAc). The resulting substance was dissolved in 7.5 ml of chloroform, followed by adding 3 ml of trifluoroacetic acid and stirring for 30 minutes. After concentration under reduced pressure, the resultant was dissolved in 4.5 ml of EtOH, neutralized by the addition of triethylamine, and then concentrated under reduced pressure. Then, the residue was purified by silica gel column chromatography (elution solvent: chloroform-MeOH-aqueous ammonia). The resulting substance was dissolved in EtOH and 115 mg of fumaric acid was added thereto. The resulting white solid was collected by filtration and dried to obtain 247 mg of N-ethyl-2,3,4,6,7,8,9,10-octahydro-1H-azepino[4,5-g]quinoline-1-carboxamide monofumarate.

Example 9

To a solution of 200 mg of t-butyl 1,2,3,4,6,7,9,10-octahydro-8H-azepino[4,5-g]quinoline-8-carboxylate in 6 ml of dichloromethane were added 0.148 ml of triethylamine, 0.093 ml of ethanesulfonyl chloride, and 54 mg of 1-methylimidazole under ice-cooling, followed by stirring at room temperature overnight. To the reaction mixture were added EtOAc and saturated brine, and the organic layer was washed with saturated brine and then concentrated under reduced pressure. The residue was purified by silica gel chromatography (elution solvent: HEX-EtOAc). The resulting substance was dissolved in 4 ml of chloroform, followed by adding 2 ml of trifluoroacetic acid and stirring for 30 minutes. After concentration under reduced pressure, the resultant was dissolved in 4.5 ml of EtOH, neutralized by the addition of triethylamine, and then concentrated under reduced pressure. Then, the residue was purified by silica gel column chromatography (elution solvent: chloroform-MeOH-aqueous ammonia). The resulting substance was dissolved in EtOH and 76 mg of fumaric acid was added thereto. The resulting white solid was collected by filtration and dried to obtain 61 mg of 1-(ethylsulfonyl)-2,3,4,6,7,8,9,10-octahydro-1H-azepino[4,5-g]quinoline monofumarate.

Example 112

To a solution of 283 mg of t-butyl 4-(3-chlorobenzyl)-3-oxo-3,4,6,7,9,10-hexahydro[1,4]oxazino[2,3-h][3]benzazepine-8(2H)-carboxylate in 1.8 ml of tetrahydrofuran was added 1.46 ml of a 1 M solution of a borane-THF complex in THF, followed by stirring at 50° C. for 4 hours. The reaction mixture was ice-cooled, and MeOH was added thereto, followed by stirring at room temperature for 30 minutes. The reaction mixture was concentrated under reduced pressure and MeOH was added thereto, followed by concentration again. The residue was dissolved in 2.8 ml of EtOH, and 4 M hydrogen chloride-ethyl acetate solution was added thereto, followed by stirring overnight. After concentration under reduced pressure, the resultant was dissolved in EtOH, neutralized by the addition of triethylamine, and concentrated under reduced pressure. Then, the residue was purified by silica gel column chromatography (elution solvent: chloroform-MeOH). The resulting substance was dissolved in ethanol and fumaric acid was added thereto, followed by stirring for a while. The solid was generated, then dissolved by heating once, and stirred at room temperature for 3 hours. The resulting white solid was collected by filtration and dried to obtain 23 mg of 4-(3-chlorobenzyl)-2,3,4,6,7,8,9,10-octahydro[1,4]oxazino[2,3-h][3]benzazepine fumarate.

Example 282

To a solution of 606 mg of t-butyl 11-bromo-1-(2-methoxyethyl)-10-methyl-1,2,3,4,6,7,9,10-octahydro-8H-azepino[4,5-g]quinoline-8-carboxylate in 6 ml of dichloromethane was added 3 ml of trifluoroacetic acid, followed by stirring at room temperature for 1 hour. The reaction mixture was concentrated under reduced pressure and the residue was purified by basic silica gel chromatography (elution solvent: chloroform-MeOH). 150 mg of the resulting residue was collected by separation using DAICEL CHIRALPAK AD-H (2 cmΦ×25 cm) to obtain 51 mg of a low-polarity material and 45 mg of a high-polarity material. Each was dissolved in ethanol and fumaric acid was added thereto to form a salt. The precipitated solid was recrystallized from ethanol to obtain 42 mg and 36 mg of enantiomers of 11-bromo-1-(2-methoxyethyl)-10-methyl-2,3,4,6,7,8,9,10-octahydro-1H-azepino[4,5-g]quinoline fumarate as white solids, respectively.

In this regard, while the products are shown with a single planar structure in the Tables below with respect to the compounds of Example 282, and Example 280 and Example 281 in which preparation was performed as in Example 282, each of two kinds of enantiomers was isolated and obtained similarly as described above but the stereochemistry indentification was not carried out.

In the same manner as in the methods of Examples above, the compounds of Examples shown in the Tables below were prepared. The structure of the compounds of the Examples are shown in Tables 97 to 147 and the preparation methods and the physicochemical data are shown in Tables 148 to 181.

Furthermore, the structures of the other compounds of the present invention are shown in Tables 182 to 190. These can be easily synthesized by the methods described in the preparation methods and Examples above, methods apparent to a person skilled in the art, or modified methods thereof.

TABLE 2

| PEx | Str |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |

TABLE 3

| PEx | Str |
|---|---|
| 9 | (structure) |
| 10 | (structure) |
| 11 | (structure) |
| 12 | (structure) |
| 13 | (structure) |
| 14 | (structure) |

TABLE 3-continued

| PEx | Str |
|---|---|
| 15 | (structure) |
| 16 | (structure) |
| 17 | (structure) |

TABLE 4

| PEx | Str |
|---|---|
| 18 | (structure) |
| 19 | (structure) |
| 20 | (structure) |
| 21 | (structure) |
| 22 | (structure) |

TABLE 4-continued

| PEx | Str |
|---|---|
| 23 | (structure) |
| 24 | (structure) |
| 25 | (structure) |

TABLE 5

| PEx | Str |
|---|---|
| 26 | (structure) |
| 27 | (structure) |
| 28 | (structure) |
| 29 | (structure) |
| 30 | (structure) |

TABLE 5-continued

| PEx | Str |
|---|---|
| 31 | (structure) |
| 32 | (structure) |
| 33 | (structure) |

TABLE 6

| PEx | Str |
|---|---|
| 34 | (structure) |
| 35 | (structure) |
| 36 | (structure) |
| 37 | (structure) |
| 38 | (structure) |

TABLE 6-continued

| PEx | Str |
|---|---|
| 39 | (structure) |
| 40 | (structure) |
| 41 | (structure) |

TABLE 7

| PEx | Str |
|---|---|
| 42 | (structure) |
| 43 | (structure) |
| 44 | (structure) |
| 45 | (structure) |
| 46 | (structure) |
| 47 | (structure) |

TABLE 7-continued

| PEx | Str |
|---|---|
| 48 | (structure: 8-nitro-2,3,4,5-tetrahydro-1H-benzo[d]azepine-3-carboxylic acid ethyl ester) |
| 49 | (structure: 2-oxo-1,2,3,4,7,8-hexahydro-pyrido-benzazepine with ethyl carbamate) |
| 50 | (structure: methyl 2-((3-Boc-nitro-tetrahydrobenzazepinyl)oxy)acetate) |
| 51 | (structure: N-Me, O, Boc-substituted oxazino-benzazepine) |

TABLE 8

| PEx | Str |
|---|---|
| 52 | (structure: N-Me oxazino-benzazepine-N-Boc) |
| 53 | (structure: N-Et, Cl-substituted tetrahydroquinoline-benzazepine-N-Boc) |
| 54 | (structure: NH oxazino-benzazepine-N-Boc) |
| 55 | (structure: N-propionyl (Et-C(O)-), Cl tetrahydroquinoline-benzazepine-N-Boc) |
| 56 | (structure: N-isobutyryl (iPr-C(O)-), Cl tetrahydroquinoline-benzazepine-N-Boc) |

TABLE 8-continued

| PEx | Str |
|---|---|
| 57 | (structure: N-methoxyacetyl, Cl tetrahydroquinoline-benzazepine-N-Boc) |
| 58 | (structure: 3-oxo oxazino-benzazepine-N-Boc) |
| 59 | (structure: N-Me tetrahydroquinoline-benzazepine-N-Boc) |
| 60 | (structure: N-Me, 3-oxo, Me-substituted oxazino-benzazepine-N-Boc) |

TABLE 9

| PEx | Str |
|---|---|
| 61 | (structure: N-nPr, Cl tetrahydroquinoline-benzazepine-N-Boc) |
| 62 | (structure: N-(2-methoxyethyl), Cl tetrahydroquinoline-benzazepine-N-Boc) |
| 63 | (structure: N-iBu, Cl tetrahydroquinoline-benzazepine-N-Boc) |
| 64 | (structure: N-Me, Me-substituted oxazino-benzazepine-N-Boc) |

TABLE 9-continued

| PEx | Str |
|---|---|
| 65 | (structure) |
| 66 | (structure) |
| 67 | (structure) |
| 68 | (structure) |
| 69 | (structure) |

TABLE 10

| PEx | Str |
|---|---|
| 70 | (structure) |
| 71 | (structure) |
| 72 | (structure) |
| 73 | (structure) |

TABLE 10-continued

| PEx | Str |
|---|---|
| 74 | (structure) |
| 75 | (structure) |
| 76 | (structure) |
| 77 | (structure) |
| 78 | (structure) |

TABLE 11

| PEx | Str |
|---|---|
| 79 | (structure) |
| 80 | (structure) |
| 81 | (structure) |

TABLE 11-continued
| PEx | Str |
|---|---|
| 82 | 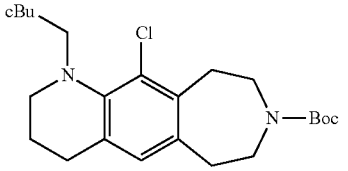 |
| 83 | 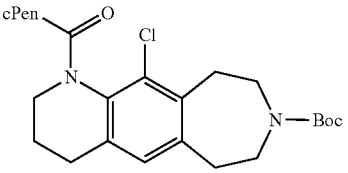 |
| 84 | 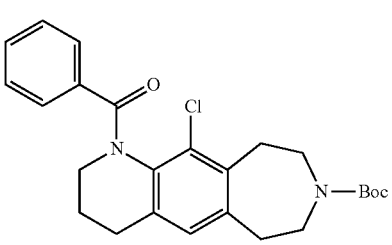 [SMILES: CC(C)(C)OC(=O)N1CCc2cc3c(c(Cl)c2CC1)N(C(=O)c1ccccc1)CCC3] |
| 85 | 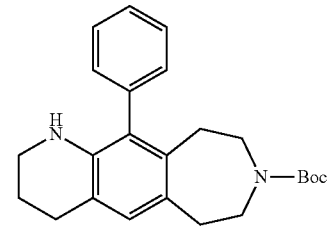 |
| 86 | 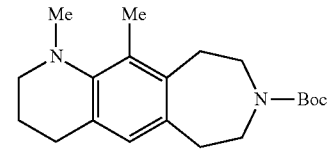 |
TABLE 12
| PEx | Str |
|---|---|
| 87 | 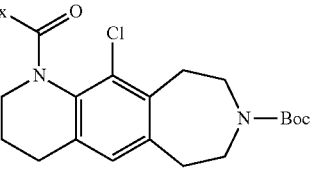 |
| 88 | 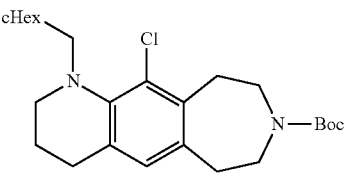 |
TABLE 12-continued
| PEx | Str |
|---|---|
| 89 |  |
| 90 | 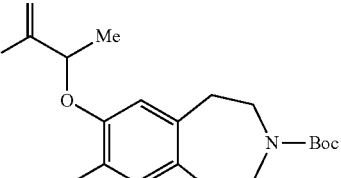 |
| 91 | 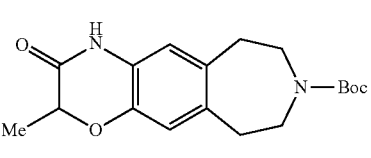 [SMILES: CC1Oc2cc3c(cc2NC1=O)CCN(C(=O)OC(C)(C)C)CC3] |
| 92 | 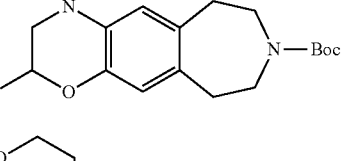 |
| 93 | 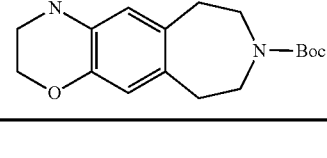 |
| 94 | 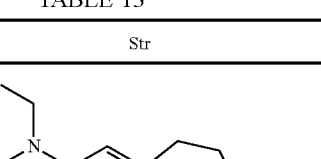 |
TABLE 13
| PEx | Str |
|---|---|
| 95 | 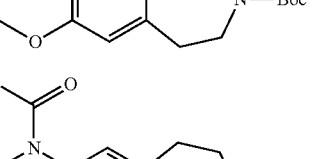 |
| 96 | 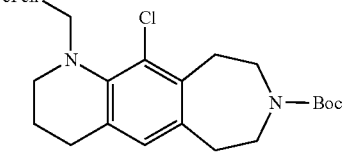 |

TABLE 13-continued
| PEx | Str |
|---|---|
| 97 | 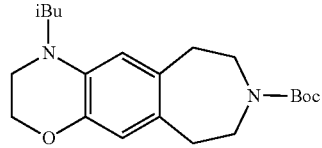 |
| 98 | 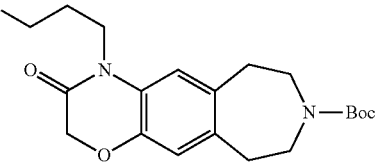 [SMILES: CC(C)OCCN1C(=O)COc2cc3c(cc21)CCN(C(=O)OC(C)(C)C)CC3] |
| 99 | 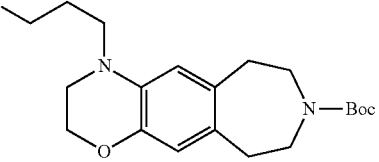 [SMILES: CC(C)OCCN1CCOc2cc3c(cc21)CCN(C(=O)OC(C)(C)C)CC3] |
| 100 | 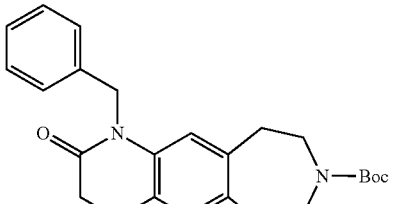 |
| 101 | 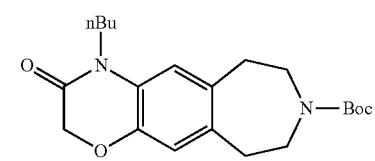 |
| 102 | 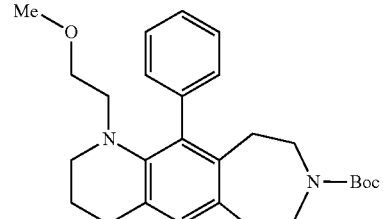 |
TABLE 14
| PEx | Str |
|---|---|
| 103 | 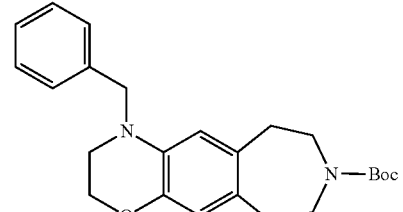 |
TABLE 14-continued
| PEx | Str |
|---|---|
| 104 | 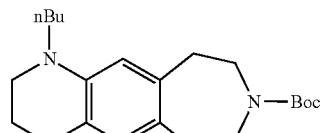 |
| 105 | 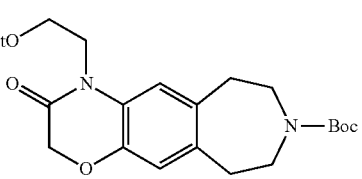 |
| 106 | 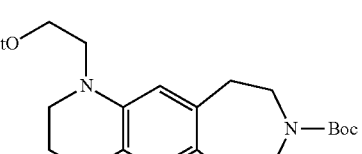 |
| 107 | 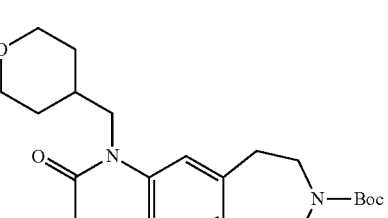 |
| 108 |  |
| 109 | 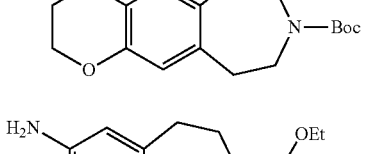 |
TABLE 15
| PEx | Str |
|---|---|
| 110 | 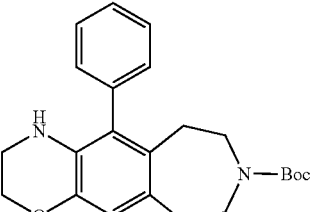 |

TABLE 15-continued

| PEx | Str |
|---|---|
| 111 | (structure) |
| 112 | (structure) |
| 113 | (structure) |
| 114 | (structure) |
| 115 | (structure) |

TABLE 16

| PEx | Str |
|---|---|
| 116 | (structure) |
| 117 | (structure) |
| 118 | (structure) |
| 119 | (structure) |
| 120 | (structure) |
| 121 | (structure) |

TABLE 17

| PEx | Str |
|---|---|
| 122 | (structure) |

TABLE 17-continued

| PEx | Str |
|---|---|
| 123 | |
| 124 | |
| 125 | |
| 126 | |
| 127 | |
| 128 | |
| 129 | |

TABLE 18

| PEx | Str |
|---|---|
| 130 | |
| 131 | |
| 132 | |
| 133 | |
| 134 | |
| 135 | |
| 136 | |

TABLE 19

| PEx | Str |
| --- | --- |
| 137 | |
| 138 | |
| 139 | |
| 140 | |
| 143 | |

TABLE 20

| PEx | Str |
| --- | --- |
| 144 | |
| 145 | |
| 146 | |

TABLE 20-continued

| PEx | Str |
| --- | --- |
| 149 | |
| 150 | |
| 151 | |

TABLE 21

| PEx | Str |
| --- | --- |
| 152 | |
| 153 | |
| 154 | |
| 155 | |

TABLE 21-continued

| PEx | Str |
|---|---|
| 156 | (structure) |
| 157 | (structure) |
| 158 | (structure) |

TABLE 22

| PEx | Str |
|---|---|
| 159 | (structure) |
| 160 | (structure) |
| 161 | (structure) |
| 162 | (structure) |

TABLE 22-continued

| PEx | Str |
|---|---|
| 163 | (structure) |
| 164 | (structure) |
| 165 | (structure) |

TABLE 23

| PEx | Str |
|---|---|
| 166 | (structure) |
| 167 | (structure) |
| 168 | (structure) |
| 169 | (structure) |
| 170 | (structure) |

TABLE 23-continued

| PEx | Str |
|---|---|
| 171 | (structure) |
| 172 | (structure) |
| 173 | (structure) |

TABLE 24

| PEx | Str |
|---|---|
| 175 | (structure) |
| 176 | (structure) |
| 177 | (structure) |
| 178 | (structure) |
| 179 | (structure) |

TABLE 24-continued

| PEx | Str |
|---|---|
| 180 | (structure) |
| 181 | (structure) |

TABLE 25

| PEx | Str |
|---|---|
| 182 | (structure) |
| 183 | (structure) |
| 184 | (structure) |
| 185 | (structure) |
| 186 | (structure) |
| 187 | (structure) |

TABLE 25-continued

| PEx | Str |
|---|---|
| 188 | (structure) |
| 189 | (structure) |

TABLE 26

| PEx | Str |
|---|---|
| 190 | (structure) |
| 192 | (structure) |
| 193 | (structure) |
| 195 | (structure) |
| 196 | (structure) |

TABLE 26-continued

| PEx | Str |
|---|---|
| 197 | (structure) |

TABLE 27

| PEx | Str |
|---|---|
| 198 | (structure) |
| 199 | (structure) |
| 200 | (structure) |
| 201 | (structure) |
| 202 | (structure) |

TABLE 27-continued
| PEx | Str |
|---|---|
| 203 | 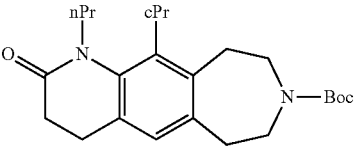 |
| 204 | 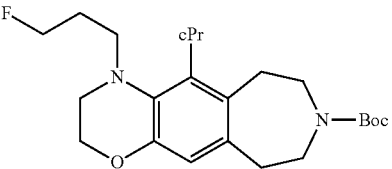 |
TABLE 28
| PEx | Str |
|---|---|
| 205 | 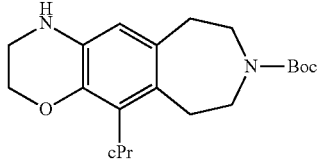 |
| 206 | 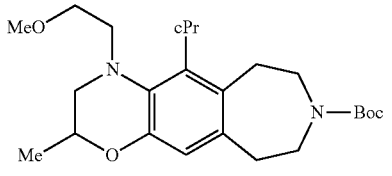 |
| 207 | 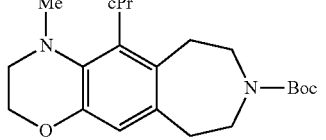 |
| 208 | 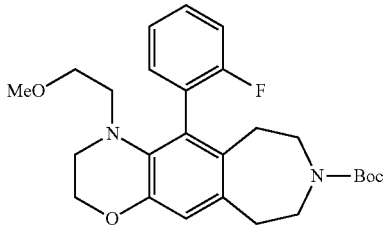 [SMILES: COCCN1CCOc2cc3c(c(-c4ccccc4F)c21)CCN(C(=O)OC(C)(C)C)CC3] |
| 209 | 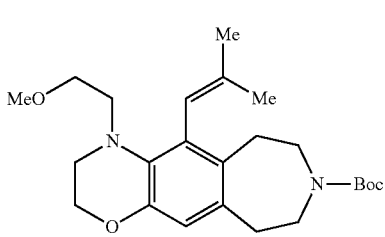 [SMILES: COCCN1CCOc2cc3c(c(C=C(C)C)c21)CCN(C(=O)OC(C)(C)C)CC3] |
TABLE 28-continued
| PEx | Str |
|---|---|
| 210 | 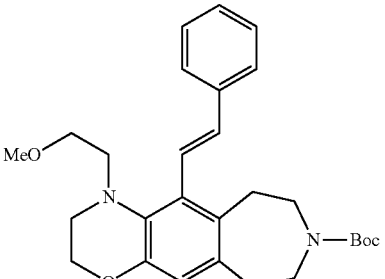 |
| 211 | 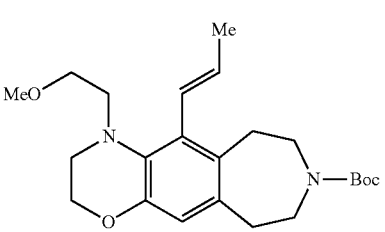 [SMILES: C/C=C/c1c2c(cc3c1N(CCOC)CCO3)CCN(C(=O)OC(C)(C)C)CC2] |
TABLE 29
| PEx | Str |
|---|---|
| 212 | 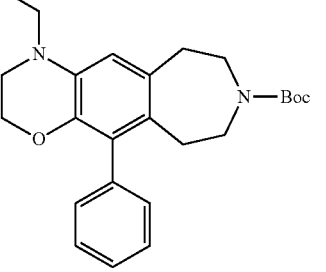 |
| 213 | 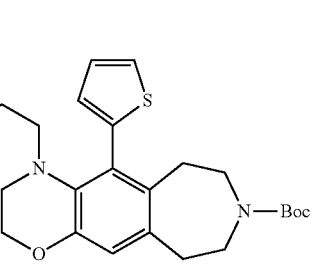 |
| 214 | 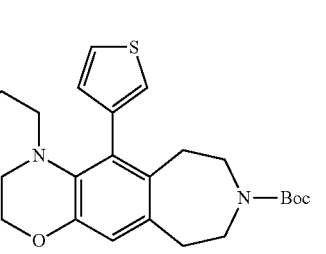 |

TABLE 29-continued
| PEx | Str |
|---|---|
| 215 | 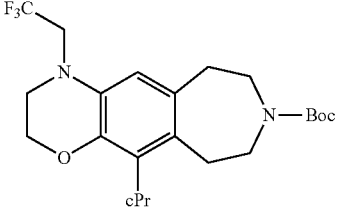 |
| 216 | 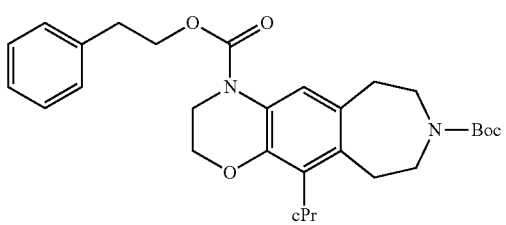 |
| 217 | 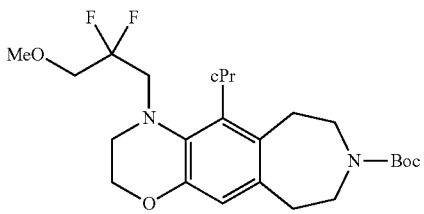 |
TABLE 30
| PEx | Str |
|---|---|
| 218 | 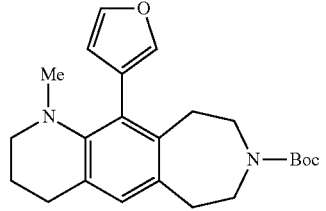 [SMILES: CN1CCCc2cc3c(c(-c4ccoc4)c21)CCN(C(=O)OC(C)(C)C)CC3] |
| 219 | 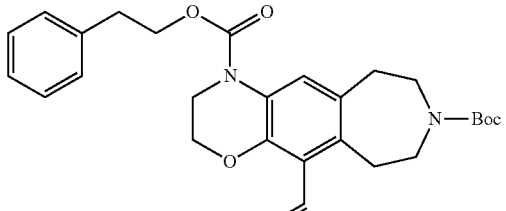 |
| 220 | 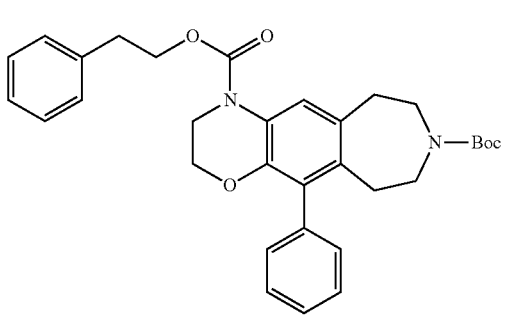 [SMILES: CC(C)(C)OC(=O)N1CCc2cc3c(c(-c4ccccc4)c2CC1)OCCN3C(=O)OCCc1ccccc1] |
TABLE 30-continued
| PEx | Str |
|---|---|
| 221 | 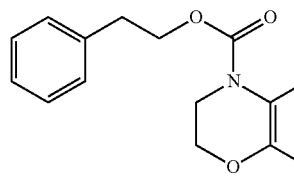 |
| 222 | 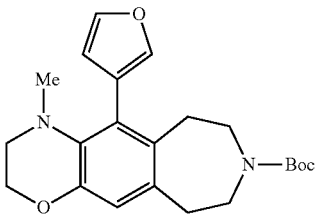 [SMILES: CN1CCOc2cc3c(c(-c4ccoc4)c21)CCN(C(=O)OC(C)(C)C)CC3] |
| 223 | 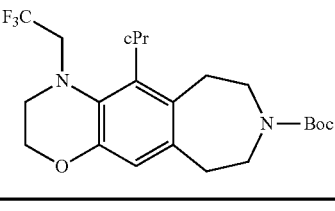 |
TABLE 31
| PEx | Str |
|---|---|
| 224 | 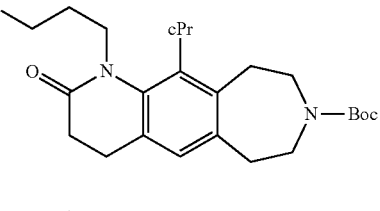 |
| 225 | 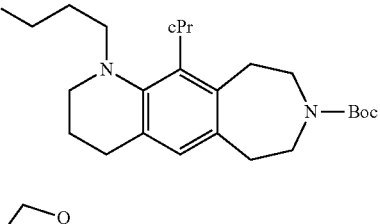 |
| 226 | 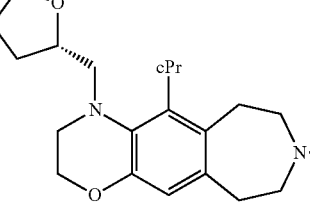 |

TABLE 31-continued

| PEx | Str |
|---|---|
| 227 | (structure) |
| 228 | (structure) |
| 229 | (structure) |
| 230 | (structure) |

TABLE 32

| PEx | Str |
|---|---|
| 231 | (structure) |
| 232 | (structure) |

TABLE 32-continued

| PEx | Str |
|---|---|
| 233 | (structure) |
| 234 | (structure) |
| 235 | (structure) |
| 236 | (structure) |
| 237 | (structure) |

TABLE 33

| PEx | Str |
|---|---|
| 238 | (structure) |
| 239 | (structure) |

TABLE 33-continued

| PEx | Str |
|---|---|
| 240 | (structure) |
| 241 | (structure) |
| 242 | (structure) |
| 243 | (structure) |
| 244 | (structure) |

TABLE 34

| PEx | Str |
|---|---|
| 245 | (structure) |
| 246 | (structure) |
| 247 | (structure) |
| 248 | (structure) |
| 249 | (structure) |
| 250 | (structure) |

TABLE 35

| PEx | Str |
|---|---|
| 251 | (structure) |
| 252 | (structure) |

TABLE 35-continued

| PEx | Str |
|---|---|
| 253 | (structure) |
| 254 | (structure) |
| 255 | (structure) |
| 256 | (structure) |
| 257 | (structure) |

TABLE 36

| PEx | Str |
|---|---|
| 258 | (structure) |
| 259 | (structure) |
| 260 | (structure) |
| 261 | (structure) |
| 262 | (structure) |
| 263 | (structure) |
| 264 | (structure) |

TABLE 37

| PEx | Str |
|---|---|
| 265 | (structure) |
| 266 | (structure) |

TABLE 37-continued

| PEx | Str |
|---|---|
| 267 | |
| 268 | |
| 269 | |
| 270 | |
| 271 | |

TABLE 38

| PEx | Str |
|---|---|
| 272 | |

TABLE 38-continued

| PEx | Str |
|---|---|
| 273 | |
| 274 | |
| 275 | |
| 276 | |
| 277 | |

TABLE 39

| PEx | Str |
|---|---|
| 278 | |

TABLE 39-continued

| PEx | Str |
|---|---|
| 279 | |
| 280 | |
| 281 | |
| 282 | |
| 283 | |

TABLE 40

| PEx | Str |
|---|---|
| 284 | |

TABLE 40-continued

| PEx | Str |
|---|---|
| 285 | |
| 286 | |
| 287 | |
| 288 | |
| 289 | |

TABLE 41

| PEx | Str |
|---|---|
| 290 | |

TABLE 41-continued

| PEx | Str |
|---|---|
| 291 | (structure) |
| 292 | (structure) |
| 293 | (structure) |
| 294 | (structure) |
| 295 | (structure) |
| 296 | (structure) |
| 297 | (structure) |

TABLE 42

| PEx | Str |
|---|---|
| 298 | (structure) |
| 299 | (structure) |
| 300 | (structure) |
| 301 | (structure) |
| 302 | (structure) |
| 303 | (structure) |

TABLE 43

| PEx | Str |
|---|---|
| 304 | (structure) |
| 305 | (structure) |
| 306 | (structure) |
| 307 | (structure) |
| 308 | (structure) |
| 309 | (structure) |
| 310 | (structure) |

TABLE 44

| PEx | Str |
|---|---|
| 311 | (structure) |
| 312 | (structure) |
| 313 | (structure) |
| 314 | (structure) |
| 315 | (structure) |
| 316 | (structure) |

TABLE 45

| PEx | Str |
|---|---|
| 317 | (structure) |
| 318 | (structure) |
| 319 | (structure) |
| 320 | (structure) |
| 321 | (structure) |
| 322 | (structure) |
| 323 | (structure) |

TABLE 46

| PEx | Str |
|---|---|
| 324 | (structure) |
| 325 | (structure) |
| 326 | (structure) |
| 327 | (structure) |
| 328 | (structure) |
| 329 | (structure) |
| 330 | (structure) |

TABLE 47

| PEx | Str |
|---|---|
| 331 | (structure) |
| 332 | (structure) |
| 333 | (structure) |
| 334 | (structure) |
| 335 | (structure) |
| 336 | (structure) |
| 337 | (structure) |

TABLE 48

| PEx | Str |
|---|---|
| 338 | (structure) |
| 339 | (structure) |
| 340 | (structure) |
| 341 | (structure) |
| 342 | (structure) |
| 343 | (structure) |
| 344 | (structure) |
| 345 | (structure) |

TABLE 49
| PEx | Str |
|---|---|
| 346 | 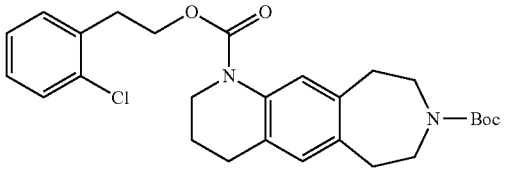 |
| 347 | 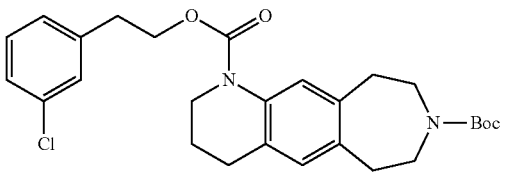 [SMILES: CC(C)(C)OC(=O)N1CCc2cc3c(cc2CC1)N(C(=O)OCCc1cccc(Cl)c1)CCC3] |
| 348 | 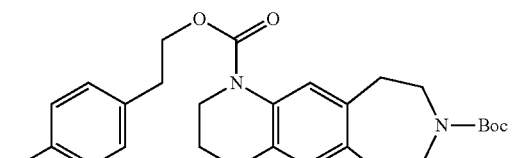 |
| 349 | 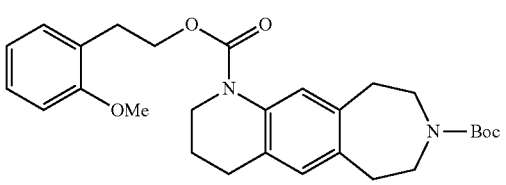 [SMILES: COc1ccccc1CCOC(=O)N1CCCc2cc3c(cc21)CCN(C(=O)OC(C)(C)C)CC3] |
| 350 | 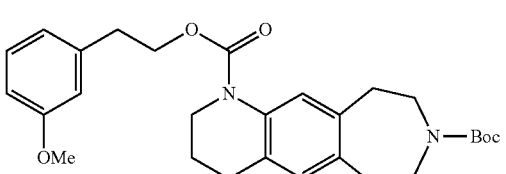 |
| 351 | 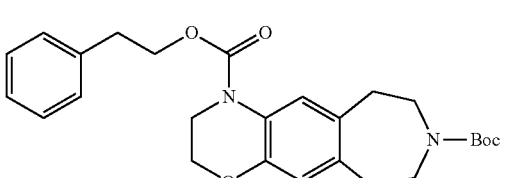 |
| 352 | 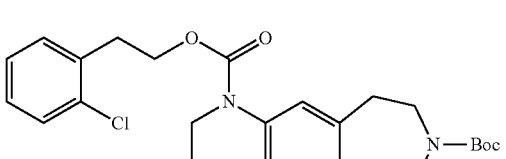 |
| 353 | 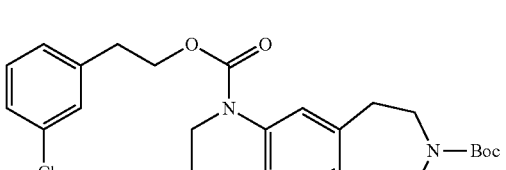 |
TABLE 50
| PEx | Str |
|---|---|
| 354 | 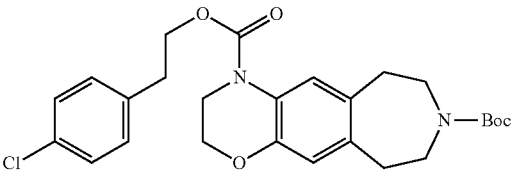 [SMILES: CC(C)(C)OC(=O)N1CCc2cc3c(cc2CC1)N(C(=O)OCCc1ccc(Cl)cc1)CCO3] |
| 355 | 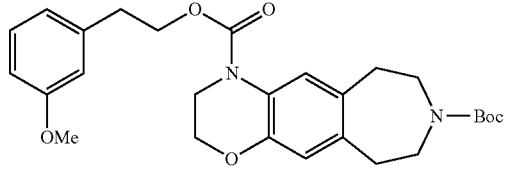 [SMILES: COc1cccc(CCOC(=O)N2CCOc3cc4c(cc32)CCN(C(=O)OC(C)(C)C)CC4)c1] |
| 356 | 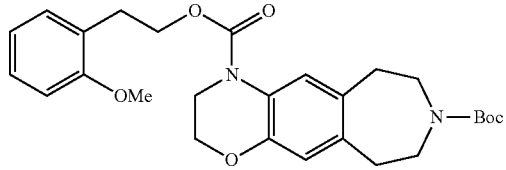 [SMILES: COc1ccccc1CCOC(=O)N1CCOc2cc3c(cc21)CCN(C(=O)OC(C)(C)C)CC3] |
| 357 | 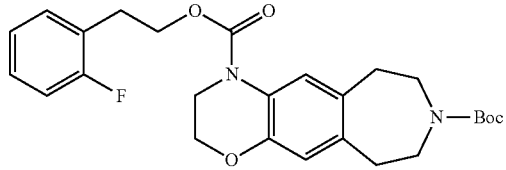 [SMILES: CC(C)(C)OC(=O)N1CCc2cc3c(cc2CC1)N(C(=O)OCCc1ccccc1F)CCO3] |
| 358 | 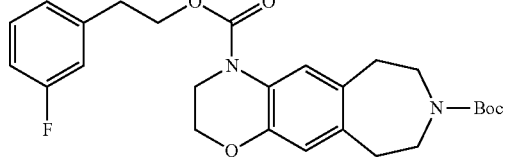 |
| 359 | 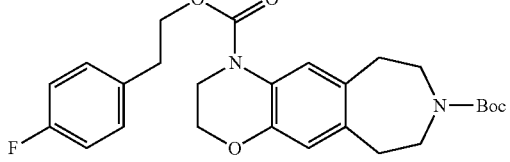 |
| 360 | 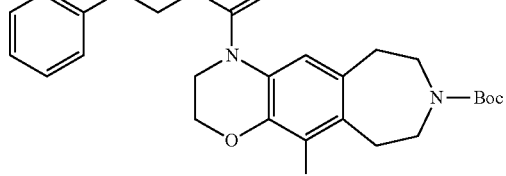 |
| 361 | 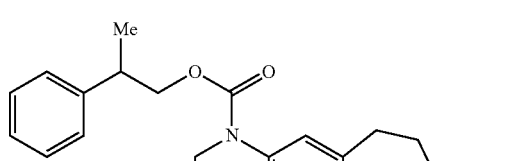 |

TABLE 51

| PEx | Str |
|---|---|
| 362 | (structure) |
| 363 | (structure) |
| 364 | (structure) |
| 365 | (structure) |
| 366 | (structure) |
| 367 | (structure) |
| 368 | (structure) |
| 369 | (structure) |

TABLE 52

| PEx | Str |
|---|---|
| 370 | (structure) |
| 371 | (structure) |
| 372 | (structure) |
| 373 | (structure) |
| 374 | (structure) |
| 375 | (structure) |
| 376 | (structure) |
| 377 | (structure) |

US 9,598,434 B2
TABLE 53
| PEx | Str |
|---|---|
| 378 | 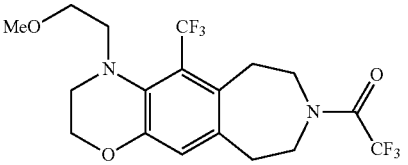 [SMILES: COCCN1CCOc2cc3c(c(C(F)(F)F)c21)CCN(C(=O)C(F)(F)F)CC3] |
| 379 | 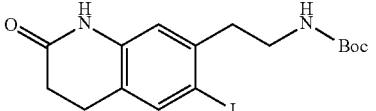 |
| 380 | 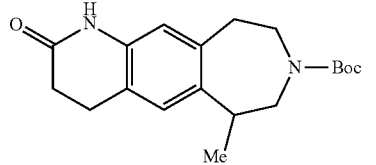 [SMILES: CC1CN(C(=O)OC(C)(C)C)CCc2cc3c(cc21)CCC(=O)N3] |
| 381 | 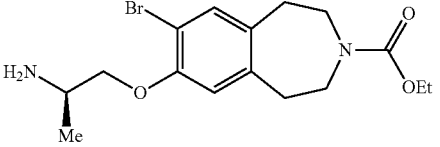 [SMILES: CCOC(=O)N1CCc2cc(Br)c(OC[C@@H](C)N)cc2CC1] |
| 382 | 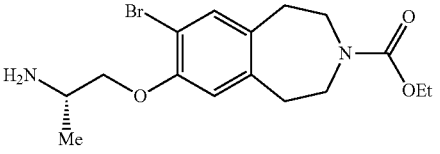 [SMILES: CCOC(=O)N1CCc2cc(Br)c(OC[C@H](C)N)cc2CC1] |
| 383 | 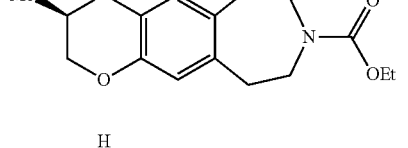 |
| 384 | 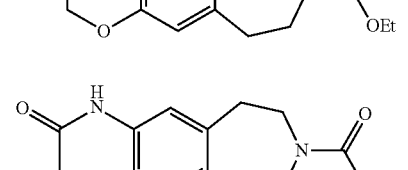 |
| 385 | 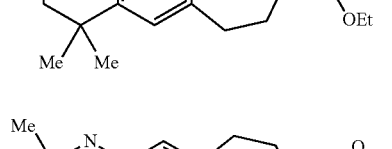 |
| 386 | 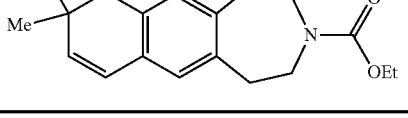 |
TABLE 54
| PEx | Str |
|---|---|
| 387 | 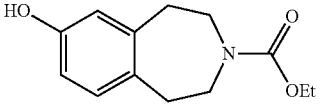 [SMILES: CCOC(=O)N1CCc2ccc(O)cc2CC1] |
| 388 | 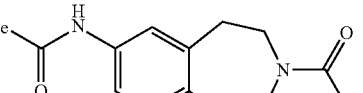 |
| 389 | 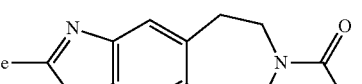 |
| 390 | 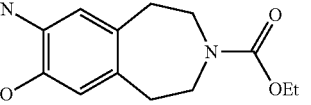 |
| 391 | 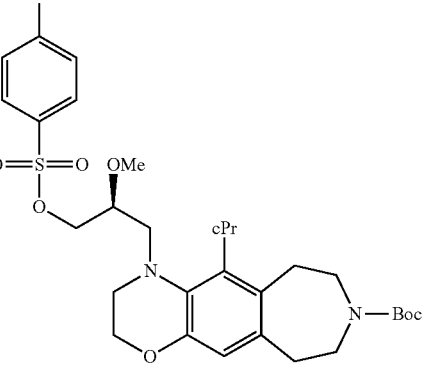 |
| 392 | 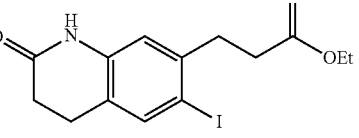 |
| 393 | 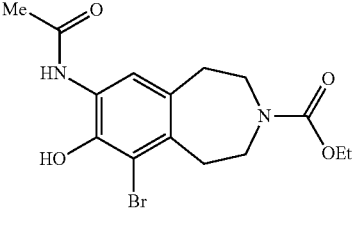 [SMILES: CCOC(=O)N1CCc2cc(NC(C)=O)c(O)c(Br)c2CC1] |

TABLE 55
| PEx | Str |
|---|---|
| 394 | 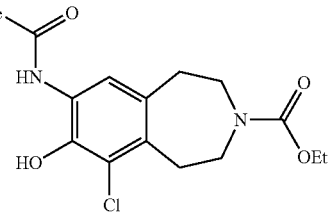 |
| 395 | 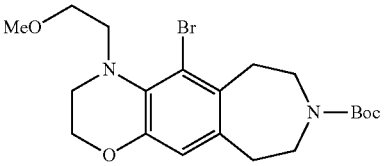 |
| 396 | 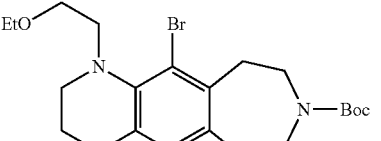 |
| 397 | 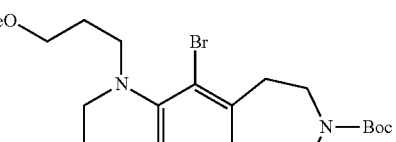 |
| 398 | 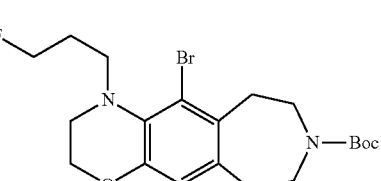 |
| 399 | 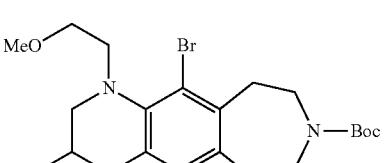 |
| 400 | 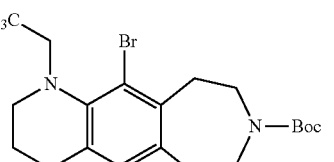 |
| 401 | 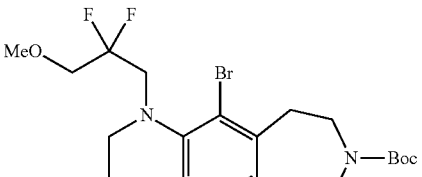 |
TABLE 56
| PEx | Str |
|---|---|
| 402 | 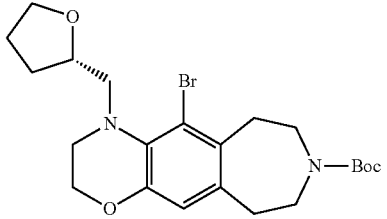 [SMILES: CC(C)(C)OC(=O)N1CCc2cc3c(c(Br)c2CC1)N(C[C@@H]1CCCO1)CCO3] |
| 403 | 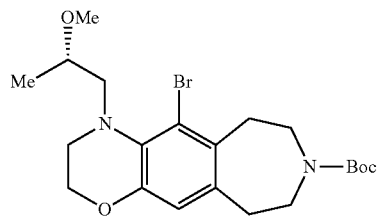 [SMILES: CO[C@@H](C)CN1CCOc2cc3c(c(Br)c21)CCN(C(=O)OC(C)(C)C)CC3] |
| 404 | 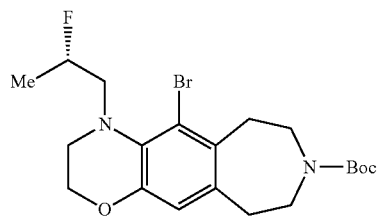 [SMILES: C[C@H](F)CN1CCOc2cc3c(c(Br)c21)CCN(C(=O)OC(C)(C)C)CC3] |
| 405 | 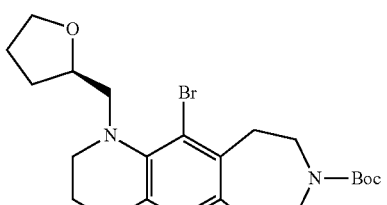 |
| 406 | 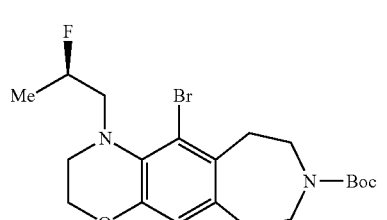 |
| 407 | 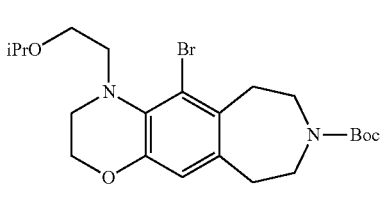 [SMILES: CC(C)OCCN1CCOc2cc3c(c(Br)c21)CCN(C(=O)OC(C)(C)C)CC3] |
| 408 | 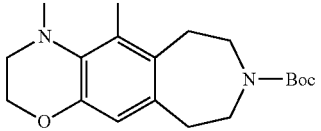 |

TABLE 57

| PEx | Str |
| --- | --- |
| 409 | (structure) |
| 410 | (structure) |
| 411 | (structure) |
| 412 | (structure) |
| 413 | (structure) |
| 414 | (structure) |
| 415 | (structure) |
| 416 | (structure) |

TABLE 58

| PEx | Str |
| --- | --- |
| 417 | (structure) |
| 418 | (structure) |
| 419 | (structure) |
| 420 | (structure) |
| 421 | (structure) |
| 422 | (structure) |
| 423 | (structure) |

TABLE 59
| PEx | Str |
|---|---|
| 424 | 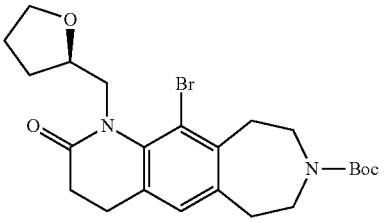 [SMILES: CC(C)(C)OC(=O)N1CCc2cc3c(c(Br)c2CC1)N(C[C@H]1CCCO1)C(=O)CC3] |
| 425 | 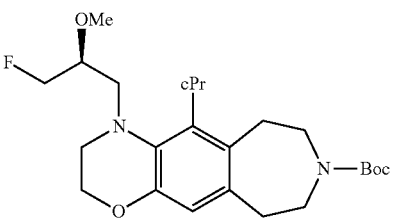 |
| 426 | 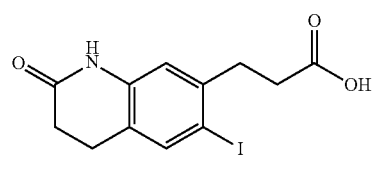 [SMILES: O=C(O)CCc1cc2c(cc1I)CCC(=O)N2] |
| 427 | 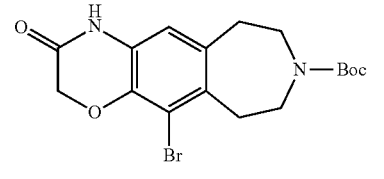 [SMILES: CC(C)(C)OC(=O)N1CCc2cc3c(c(Br)c2CC1)OCC(=O)N3] |
| 428 | 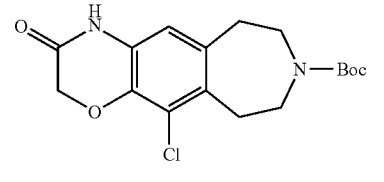 [SMILES: CC(C)(C)OC(=O)N1CCc2cc3c(c(Cl)c2CC1)OCC(=O)N3] |
| 429 | 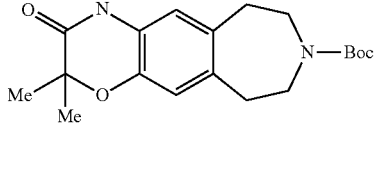 |
| 430 | 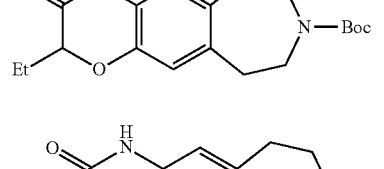 |
| 431 | 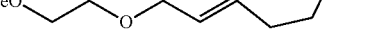 |
TABLE 60
| PEx | Str |
|---|---|
| 432 | 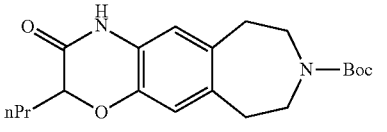 |
| 433 | 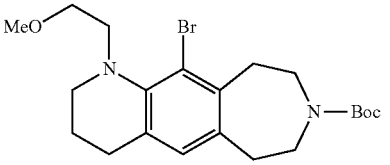 |
| 434 | 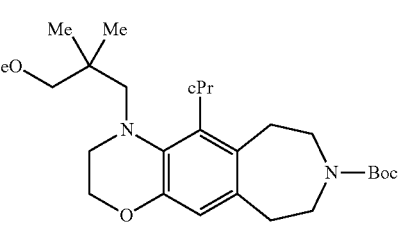 |
| 435 | 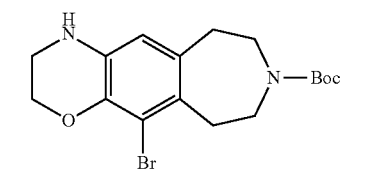 [SMILES: CC(C)(C)OC(=O)N1CCc2cc3c(c(Br)c2CC1)OCCN3] |
| 436 | 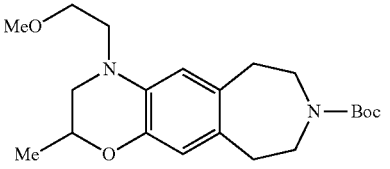 |
| 437 | 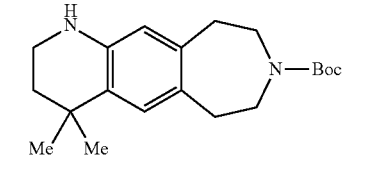 [SMILES: CC(C)(C)OC(=O)N1CCc2cc3c(cc2CC1)C(C)(C)CCN3] |
| 438 | 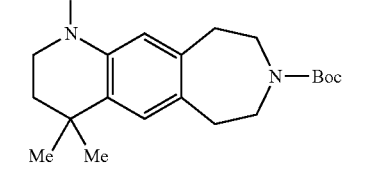 |
| 439 | 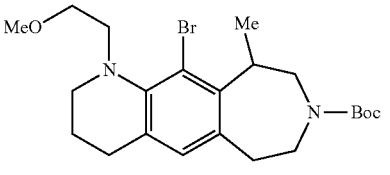 [SMILES: COCCN1CCCc2cc3c(c(Br)c21)C(C)CN(C(=O)OC(C)(C)C)CC3] |

TABLE 61

| PEx | Str |
|---|---|
| 440 | (structure) |
| 441 | (structure) |
| 442 | (structure) |
| 443 | (structure) |
| 444 | (structure) |
| 445 | (structure) |
| 446 | (structure) |

TABLE 62

| PEx | Str |
|---|---|
| 447 | (structure) |
| 448 | (structure) |
| 449 | (structure) |
| 450 | (structure) |
| 451 | (structure) |
| 452 | (structure) |
| 453 | (structure) |

113
TABLE 63
| PEx | Str |
|---|---|
| 454 | |
| 455 | |
| 456 | |
| 457 | |
| 458 | |
| 459 | |
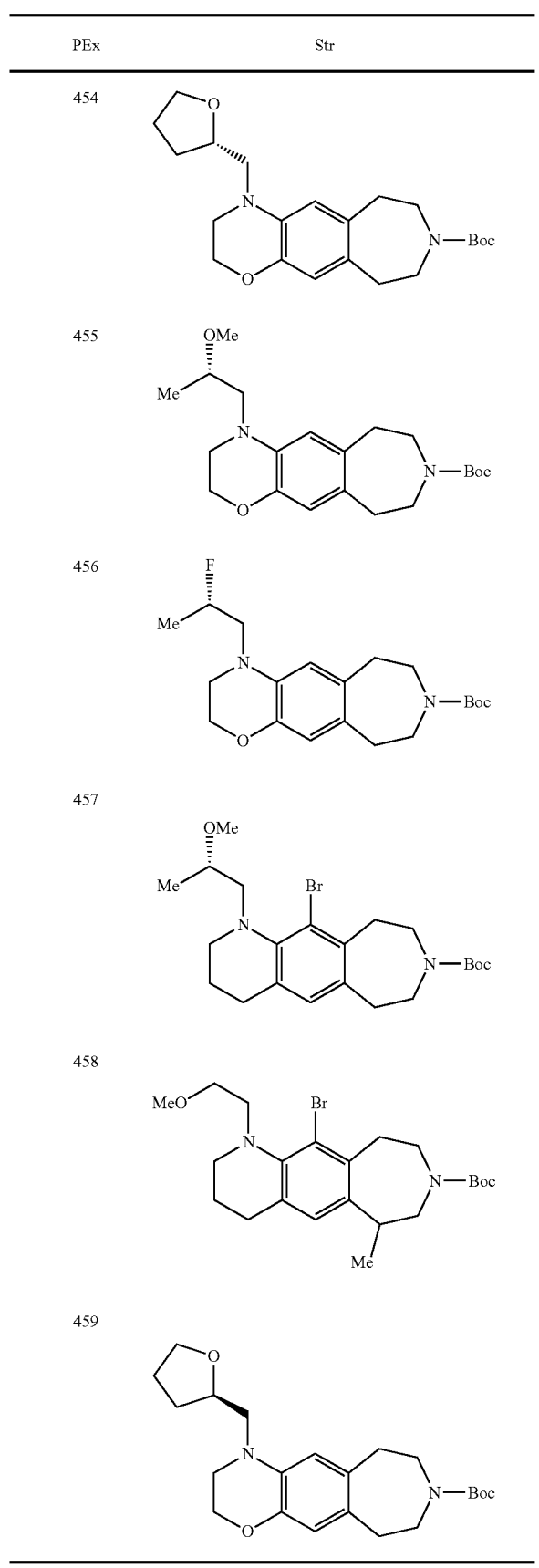
114
TABLE 64
| PEx | Str |
|---|---|
| 460 | |
| 461 | |
| 462 | |
| 463 | |
| 464 | |
| 465 | |
| 466 | |
| 467 | |
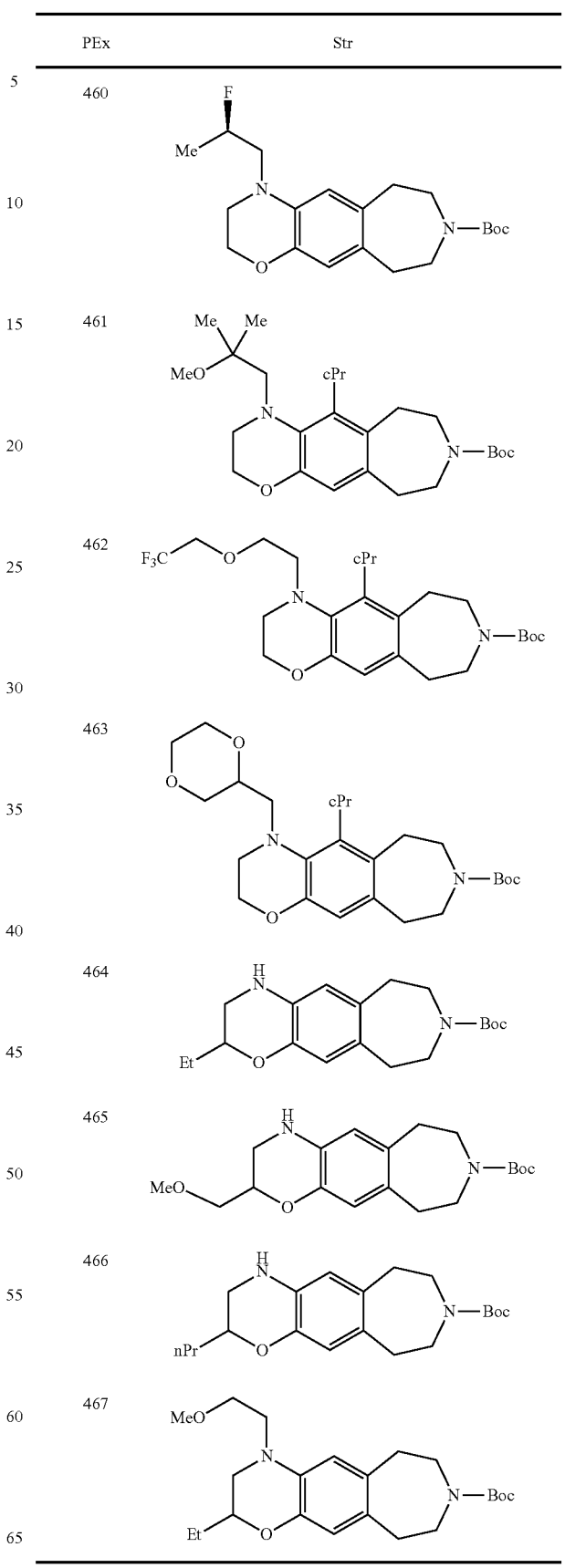

TABLE 65

| PEx | Str |
|-----|-----|
| 468 | (structure) |
| 469 | (structure) |
| 470 | (structure) |
| 471 | (structure) |
| 472 | (structure) |
| 473 | (structure) |
| 474 | (structure) |

TABLE 66

| PEx | Str |
|-----|-----|
| 475 | (structure) |
| 476 | (structure) |
| 477 | (structure) |
| 478 | (structure) |
| 479 | (structure) |
| 480 | (structure) |
| 481 | (structure) |

TABLE 67
| PEx | Str |
|---|---|
| 482 | |
| 483 | |
| 484 | |
| 485 | |
| 486 | |
| 487 | |
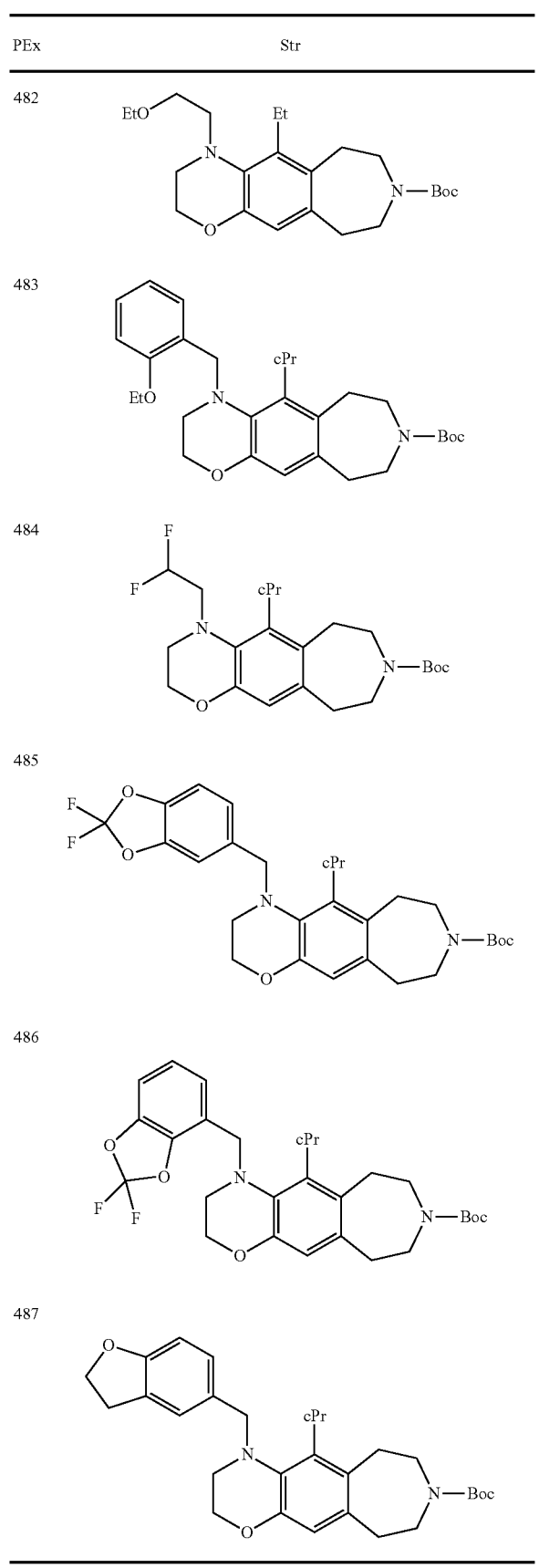
TABLE 68
| PEx | Str |
|---|---|
| 488 | |
| 489 | |
| 490 | |
| 491 | |
| 492 | |
| 493 | |
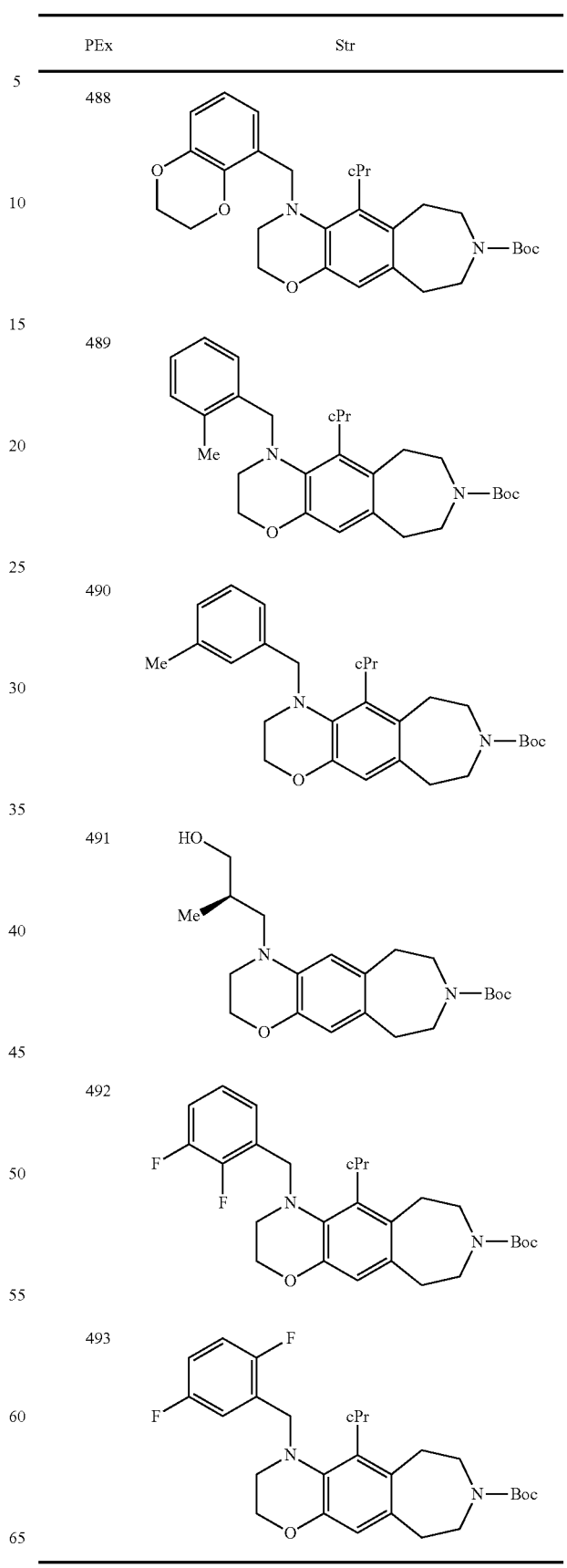

TABLE 69

| PEx | Str |
|---|---|
| 494 | 3-Cl, 2-F-benzyl; cPr substituent; oxazine-fused benzazepine-N-Boc |
| 495 | benzyl; Br substituent; oxazine-fused benzazepine-N-Boc |
| 496 | 3-Cl-benzyl; Br substituent; oxazine-fused benzazepine-N-Boc |
| 497 | 2-Cl-benzyl; Br substituent; oxazine-fused benzazepine-N-Boc |
| 498 | 3-F-benzyl; Br substituent; oxazine-fused benzazepine-N-Boc |
| 499 | 2-F-benzyl; Br substituent; oxazine-fused benzazepine-N-Boc |

TABLE 70

| PEx | Str |
|---|---|
| 500 | 2-Cl-benzyl; oxazine-fused benzazepine-N-Boc |
| 501 | 2-MeO-benzyl; oxazine-fused benzazepine-N-Boc |
| 502 | 3-F-benzyl; oxazine-fused benzazepine-N-Boc |
| 503 | 3-CN-benzyl; oxazine-fused benzazepine-N-Boc |
| 504 | 3-CF$_3$-benzyl; oxazine-fused benzazepine-N-Boc |
| 505 | 3-Me-benzyl; oxazine-fused benzazepine-N-Boc |

TABLE 71
| PEx | Str |
|---|---|
| 506 | 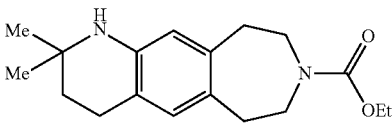 [SMILES: CCOC(=O)N1CCc2cc3c(cc2CC1)NC(C)(C)CC3] |
| 507 | 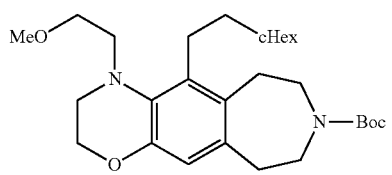 |
| 508 | 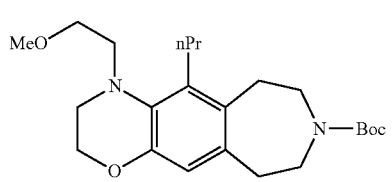 |
| 509 | 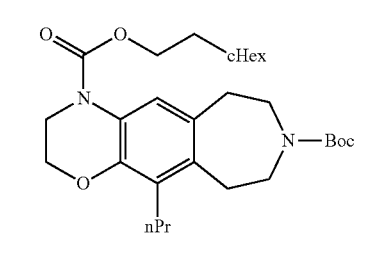 |
| 510 | 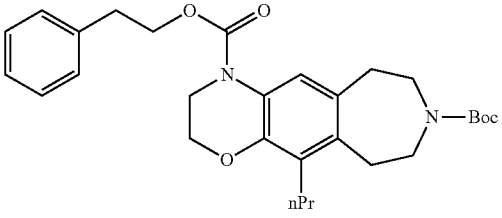 |
| 511 | 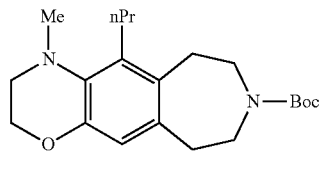 |
| 512 | 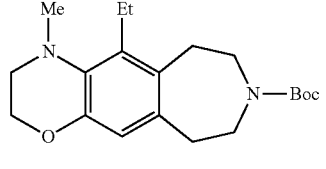 |
| 513 | 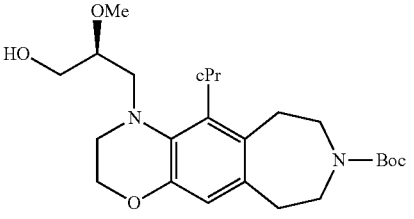 |
TABLE 72
| PEx | Str |
|---|---|
| 514 | 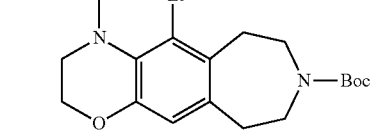 |
| 515 | 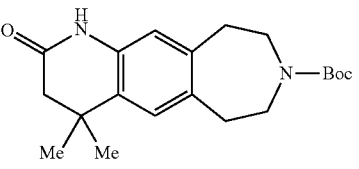 [SMILES: CC(C)(C)OC(=O)N1CCc2cc3c(cc2CC1)C(C)(C)CC(=O)N3] |
| 516 | 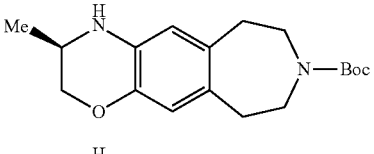 |
| 517 | 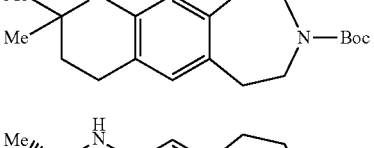 |
| 518 | 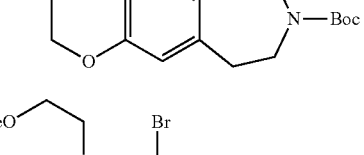 |
| 519 | 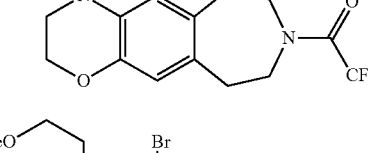 |
| 520 | 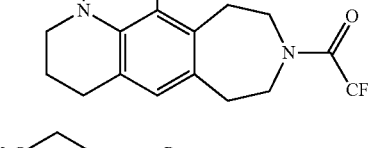 |
| 521 | 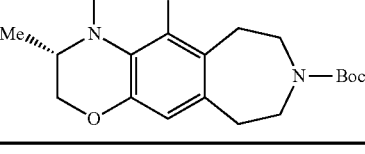 |
TABLE 73
| PEx | Str |
|---|---|
| 522 | 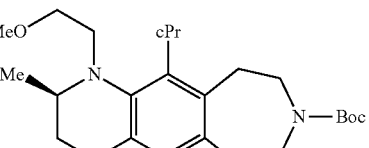 |

TABLE 73-continued

| PEx | Str |
|---|---|
| 523 | (structure) |
| 524 | (structure) |
| 525 | (structure) |
| 526 | (structure) |
| 527 | (structure) |

TABLE 74

| PEx | Str |
|---|---|
| 528 | (structure) |
| 529 | (structure) |
| 530 | (structure) |
| 531 | (structure) |
| 532 | (structure) |
| 533 | (structure) |

TABLE 75

| PEx | Str |
|---|---|
| 534 | (structure) |
| 535 | (structure) |
| 536 | (structure) |
| 537 | (structure) |
| 538 | (structure) |
| 539 | (structure) |

TABLE 76

| PEx | Str |
|---|---|
| 540 | (structure) |
| 541 | (structure) |
| 542 | (structure) |
| 543 | (structure) |
| 544 | (structure) |

TABLE 77

| PEx | Str |
|---|---|
| 545 | (structure: tosylate-O-CH2CH2-N-[cPr-substituted dihydrobenzoxazine-fused azepane-N-Boc]) |
| 546 | (structure: tosylate-O-CH2-CH(OEt)-CH2-N-[cPr-substituted dihydrobenzoxazine-fused azepane-N-Boc]) |
| 547 | (structure: MeO-CH2CH2-N, Me (wedge), Br, on dihydrobenzoxazine-fused azepane-N-Boc) |
| 548 | (structure: MeO-CH2CH2-N, Me (wedge, opposite), Br, on dihydrobenzoxazine-fused azepane-N-Boc) |
| 549 | (structure: F-CH2-CH(OMe)-CH2-N-[cPr-substituted dihydrobenzoxazine-fused azepane-N-Boc]) |
| 550 | (structure: F-CH2-CH(OEt)-CH2-N-[cPr-substituted dihydrobenzoxazine-fused azepane-N-Boc]) |

TABLE 78

| PEx | Str |
|---|---|
| 551 | (structure: 2-MeO-benzyl-N-[cPr-substituted dihydrobenzoxazine-fused azepane-N-Boc]) |
| 552 | (structure: 2,3-dihydrobenzofuran-7-ylmethyl-N-[cPr-substituted dihydrobenzoxazine-fused azepane-N-Boc]) |
| 553 | (structure: 3-MeO-benzyl-N-[cPr-substituted dihydrobenzoxazine-fused azepane-N-Boc]) |
| 554 | (structure: 2,4-difluorobenzyl-N-[cPr-substituted dihydrobenzoxazine-fused azepane-N-Boc]) |
| 555 | (structure: 5-chloro-2-fluorobenzyl-N-[cPr-substituted dihydrobenzoxazine-fused azepane-N-Boc]) |
| 556 | (structure: 2,3-dihydrobenzo[1,4]dioxin-6-ylmethyl-N-[cPr-substituted dihydrobenzoxazine-fused azepane-N-Boc]) |

TABLE 79

| PEx | Str |
|---|---|
| 557 | (structure) |
| 558 | (structure) |
| 559 | (structure) |
| 560 | (structure) |
| 561 | (structure) |
| 562 | (structure) |

TABLE 80

| PEx | Str |
|---|---|
| 563 | (structure) |
| 564 | (structure) |
| 565 | (structure) |
| 566 | (structure) |
| 567 | (structure) |
| 568 | (structure) |

TABLE 81

| PEx | Str |
|---|---|
| 569 | 3,4,5-trifluorophenyl ether with OMe, cPr, N-Boc oxazine-fused azepine |
| 570 | 2,4-difluorophenyl ether with OMe, cPr, N-Boc oxazine-fused azepine |
| 571 | HO-CH2-C(OMe)H-CH2- with cPr, N-Boc oxazine-fused azepine |
| 572 | HO-CH2-C(OEt)H-CH2- with cPr, N-Boc oxazine-fused azepine |
| 573 | Me-C(OH)H-CH2- with N-Boc oxazine-fused azepine |
| 574 | Me-C(OMe)H-CH2- with N-Boc oxazine-fused azepine |

TABLE 82

| PEx | Psyn | Dat |
|---|---|---|
| 1 | 1 | EI: 296, 298, 300 |
| 2 | 2 | EI: 190, 192 |
| 3 | 3 | EI: 209, 211 |
| 4 | 4 | ESI+: 254, 256 |
| 5 | 5 | FAB+: 299, 301 |
| 6 | 6 | EI: 268, 270 |
| 7 | 7 | EI: 346, 348, 350 |
| 8 | 8 | ESI+: 367, 369 |
| 9 | 9 | EI: 322, 324 |
| 10 | 10 | ESI+: 351, 353 |
| 11 | 11 | ESI+: 337, 339 |
| 12 | 12 | ESI+: 351, 353 |
| 13 | 13 | ESI+: 407 |
| 14 | 14 | APCI+: 220 |
| 15 | 15 | ESI+; 303 |
| 16 | 71 | ESI+; 331 |
| 17 | 17 | ESI+; 359 |
| 18 | 18 | ESI+; 317 |
| 19 | 19 | ESI+; 345 |
| 20 | 20 | ESI+; 419 |
| 21 | 21 | ESI+: 403 |
| 22 | 22 | ESI+: 417 ([M + Na]+) |
| 23 | 23 | FAB−: 331 |
| 24 | 24 | ESI+: 333 |
| 25 | 25 | ESI+: 361 |
| 26 | 26 | ESI+: 383, 405 ([M + Na]+) |
| 27 | 27 | ESI+: 448 |
| 28 | 28 | ESI+: 350 |
| 29 | 29 | ESI+: 393 |
| 30 | 30 | ESI+: 349 |
| 31 | 31 | ESI+: 331 |
| 32 | 32 | ESI+: 388 |
| 33 | 33 | ESI+: 389 |
| 34 | 34 | ESI+: 291 |
| 35 | 35 | ESI+: 403 |
| 36 | 36 | FAB+: 537 |
| 37 | 37 | ESI+: 577 |
| 38 | 38 | ESI+: 473 ([M + Na]+) |
| 39 | 39 | EI: 315 |
| 40 | 40 | FAB+: 320 |

TABLE 83

| PEx | Psyn | Dat |
|---|---|---|
| 41 | 41 | FAB+: 333 |
| 42 | 42 | ESI+: 359 |
| 43 | 27 | EI: 181 |
| 44 | 4 | ESI+: 182, 184 |
| 45 | 19 | ESI+: 235 |
| 46 | 7 | EI; 312 |
| 47 | 8 | ESI+; 333 |
| 48 | 5 | EI; 264 |
| 49 | 9 | EI; 288 |
| 50 | 22 | ESI+: 403 ([M + Na]+) |
| 51 | 15 | ESI+: 333 |
| 52 | 11 | ESI+: 319 |
| 53 | 11 | ESI+: 365, 367 |
| 54 | 11 | ESI+: 305 |
| 55 | 13 | ESI+: 393, 395 |
| 56 | 13 | ESI+: 407, 409 |
| 57 | 13 | ESI+: 409, 411 |
| 58 | 23 | FAB−: 317 |
| 59 | 11 | ESI+; 317 |
| 60 | 15 | ESI+: 347, 369 ([M + Na]+) |
| 61 | 11 | ESI+: 379, 381 |
| 62 | 11 | ESI+: 395, 397 |
| 63 | 11 | ESI+: 393, 395 |
| 64 | 11 | ESI+: 333 |
| 65 | 11 | ESI+: 319 |
| 66 | 25 | ESI+: 333 |
| 67 | 7 | ESI+: 383, 385 |
| 68 | 18 | ESI+: 319 |
| 69 | 25 | ESI+: 347 |
| 70 | 24 | APCI+: 333 |
| 71 | 71 | ESI+; 317 |
| 72 | 11 | ESI+; 303 |

TABLE 83-continued

| PEx | Psyn | Dat |
|---|---|---|
| 73 | 7 | ESI+: 381, 383 |
| 74 | 11 | ESI; 331 |
| 75 | 13 | FAB+: 345 |
| 76 | 24 | ESI+: 397, 399 |
| 77 | 13 | ESI+; 373 |
| 78 | 18 | ESI+: 345 |
| 79 | 13 | ESI+: 405, 407 |
| 80 | 13 | ESI+: 419, 421 |

TABLE 84

| PEx | Psyn | Dat |
|---|---|---|
| 81 | 11 | ESI+: 391, 393 |
| 82 | 11 | ESI+: 405, 407 |
| 83 | 13 | ESI+: 433, 435 |
| 84 | 13 | ESI+: 441, 443 |
| 85 | 18 | ESI+; 379 |
| 86 | 15 | ESI+; 331 |
| 87 | 11 | ESI+: 419, 421 |
| 88 | 11 | ESI+: 427, 429 |
| 89 | 13 | ESI+: 447, 449 |
| 90 | 11 | ESI+: 433, 435 |
| 91 | 22 | ESI+: 431 ([M + Na]$^+$) |
| 92 | 23 | FAB−: 331 |
| 93 | 11 | ESI+: 319 |
| 94 | 24 | ESI+: 363 |
| 95 | 24 | ESI+: 359 |
| 96 | 13 | ESI+: 375 |
| 97 | 24 | ESI+: 361 |
| 98 | 15 | ESI+: 391 |
| 99 | 11 | ESI+: 377 |
| 100 | 15 | ESI+: 431 ([M + Na]$^+$) |
| 101 | 15 | ESI+: 375 |
| 102 | 17 | ESI+: 437 |
| 103 | 11 | ESI+: 395 |
| 104 | 11 | ESI+: 361 |
| 105 | 15 | ESI+: 391 |
| 106 | 11 | ESI+: 377 |
| 107 | 15 | ESI+: 417 |
| 108 | 11 | ESI+: 403 |
| 109 | 7 | ESI+: 361 |
| 110 | 18 | ESI+: 381 |
| 111 | 17 | ESI+: 361 |
| 112 | 18 | ESI+: 409 |
| 113 | 18 | ESI; 447, 449 |
| 114 | 18 | ESI; 413, 415 |
| 115 | 17 | ESI; 471, 473 |
| 116 | 17 | ESI; 505, 507 |
| 117 | 18 | ESI; 397 |
| 118 | 17 | ESI; 465 |
| 119 | 12 | ESI+: 363 |
| 120 | 13 | ESI+: 403 |

TABLE 85

| PEx | Psyn | Dat |
|---|---|---|
| 121 | 17 | ESI; 467 |
| 122 | 17 | ESI; 455 |
| 123 | 15 | ESI; 375 |
| 124 | 18 | ESI; 343 |
| 125 | 17 | ESI; 399 |
| 126 | 17 | ESI; 401 |
| 127 | 15 | ESI+: 405 |
| 128 | 11 | ESI+: 391 |
| 129 | 11 | ESI+: 389 |
| 130 | 18 | ESI+: 395 |
| 131 | 13 | ESI+: 467 |
| 132 | 11 | ESI+: 453 |
| 133 | 15 | ESI+: 391 |
| 134 | 15 | ESI+: 405 |
| 135 | 11 | ESI+: 377 |

TABLE 85-continued

| PEx | Psyn | Dat |
|---|---|---|
| 136 | 11 | ESI+: 391 |
| 137 | 18 | ESI; 343 |
| 138 | 13 | ESI+: 439 ([M + Na]$^+$) |
| 139 | 12 | ESI+: 347 |
| 140 | 11 | ESI+: 403 |
| 143 | 11 | ESI+: 389 |
| 144 | 22 | ESI+: 406 |
| 145 | 27 | ESI+: 226 |
| 146 | 27 | EI: 195 |
| 149 | 21 | ESI+: 387 |
| 150 | 17 | ESI; 403 |
| 151 | 28 | ESI+: 392 |
| 152 | 13 | ESI+: 391 |
| 153 | 29 | ESI+: 322 |
| 154 | 41 | ESI+: 421 |
| 155 | 41 | ESI+: 393 |
| 156 | 11 | ESI+: 319 |
| 157 | 42 | ESI+: 397, 399 |
| 158 | 11 | ESI+: 373 |
| 159 | 18 | ESI+: 395, 417 ([M + Na]$^+$) |
| 160 | 13 | ESI+: 431 |

TABLE 86

| PEx | Psyn | Dat |
|---|---|---|
| 161 | 13 | ESI+: 389 |
| 162 | 13 | ESI+: 417 |
| 163 | 11 | ESI+: 417 |
| 164 | 11 | ESI+: 377 |
| 165 | 11 | ESI+: 381 |
| 166 | 12 | ESI+: 351 |
| 167 | 18 | ESI+: 331 |
| 168 | 18 | ESI+: 345 |
| 169 | 19 | ESI+: 333 |
| 170 | 11 | ESI+: 375 |
| 171 | 11 | ESI+: 361 |
| 172 | 18 | ESI+: 329 |
| 173 | 19 | ESI; 331 |
| 175 | 13 | ESI+: 405 |
| 176 | 21 | ESI+: 391 |
| 177 | 17 | ESI; 389 |
| 178 | 18 | ESI; 359 |
| 179 | 11 | ESI+: 391 |
| 180 | 11 | ESI+: 377 |
| 181 | 19 | ESI+: 347 |
| 182 | 13 | FAB+: 419 |
| 183 | 11 | ESI+: 277 |
| 184 | 11 | ESI+: 405 |
| 185 | 15 | FAB+: 379 |
| 186 | 11 | ESI+: 365 |
| 187 | 13 | ESI+: 453([M + Na]$^+$) |
| 188 | 11 | ESI+: 417 |
| 189 | 13 | ESI+: 457, 479([M + Na]$^+$) |
| 190 | 11 | ESI+: 443 |
| 192 | 13 | ESI+: 431, 453([M + Na]$^+$) |
| 193 | 11 | ESI+: 417 |
| 195 | 22 | NMR: 1.19(3H, t, J = 7.1 Hz), 1.38(9H, s), 1.54(6H, s), 2.80-2.93(4H, br), 3.39-3.51(4H, br), 4.20(2H, q, J = 7.1 Hz), 6.79(1H, s), 7.68(1H, s) |
| 196 | 22 | ESI+: 457, 459 |
| 197 | 22 | ESI+: 413, 415 |
| 198 | 22 | ESI+: 431([M + Na]$^+$) |
| 199 | 22 | ESI+: 447([M + Na]$^+$) |
| 200 | 22 | ESI+: 459([M + Na]$^+$) |

TABLE 87

| PEx | Psyn | Dat |
|---|---|---|
| 201 | 18 | ESI+: 439 |
| 202 | 18 | ESI+: 435 |
| 203 | 18 | ESI+: 399 |

TABLE 87-continued

| PEx | Psyn | Dat |
|---|---|---|
| 204 | 18 | ESI+: 405 |
| 205 | 18 | ESI+: 345 |
| 206 | 18 | ESI+: 417 |
| 207 | 18 | ESI+: 359 |
| 208 | 18 | ESI+: 457 |
| 209 | 18 | ESI+: 417 |
| 210 | 18 | ESI+: 465 |
| 211 | 18 | ESI+: 403 |
| 212 | 18 | ESI+: 439 |
| 213 | 18 | ESI+: 445 |
| 214 | 18 | ESI+: 445 |
| 215 | 18 | ESI+: 427 |
| 216 | 18 | ESI+: 493 |
| 217 | 18 | ESI+: 453 |
| 218 | 18 | ESI+: 383 |
| 219 | 18 | ESI+: 493 |
| 220 | 18 | ESI+: 529 |
| 221 | 18 | ESI+: 535 |
| 222 | 18 | ESI+: 385 |
| 223 | 18 | ESI+: 427 |
| 224 | 18 | ESI+: 417 |
| 225 | 18 | ESI+: 403 |
| 226 | 18 | ESI+: 429, 451([M + Na]$^+$) |
| 227 | 18 | ESI+: 417 |
| 228 | 18 | ESI+: 405, 427([M + Na]$^+$) |
| 229 | 18 | ESI+: 401 |
| 230 | 18 | ESI+: 395 |
| 231 | 18 | ESI+: 345 |
| 232 | 18 | ESI+: 359 |
| 233 | 18 | ESI+: 383 |
| 234 | 18 | ESI+: 415 |
| 235 | 18 | ESI+: 415 |
| 236 | 18 | ESI+: 429 |
| 237 | 18 | ESI+: 405 |
| 238 | 18 | ESI+: 431 |
| 239 | 18 | ESI+: 347 |
| 240 | 18 | ESI+: 391 |

TABLE 88

| PEx | Psyn | Dat |
|---|---|---|
| 241 | 18 | ESI+: 401 |
| 242 | 18 | ESI+: 391 |
| 243 | 18 | ESI+: 379 |
| 244 | 18 | ESI+: 427 |
| 245 | 18 | ESI+: 427 |
| 246 | 18 | ESI+: 403 |
| 247 | 18 | ESI+: 403 |
| 248 | 18 | ESI+: 379 |
| 249 | 18 | ESI+: 435 |
| 250 | 18 | ESI+: 469, 471 |
| 251 | 18 | ESI+: 469, 471 |
| 252 | 18 | ESI+: 453 |
| 253 | 18 | ESI+: 391 |
| 254 | 18 | ESI+: 453 |
| 255 | 13 | ESI+: 459, 481([M + Na]$^+$) |
| 256 | 13 | ESI+: 317 |
| 257 | 13 | ESI+: 401 |
| 258 | 13 | ESI+: 403 |
| 259 | 13 | ESI+: 427 |
| 260 | 13 | ESI+: 391 |
| 261 | 13 | ESI+: 391 |
| 262 | 13 | ESI+: 445, 467([M + Na]$^+$) |
| 263 | 13 | ESI+: 485, 507([M + Na]$^+$) |
| 264 | 13 | ESI+: 459, 481([M + Na]$^+$) |
| 265 | 13 | ESI+: 467([M + Na]$^+$) |
| 266 | 13 | ESI+: 457 |
| 267 | 13 | ESI+: 443 |
| 268 | 13 | ESI+: 457, 479([M + Na]$^+$) |
| 269 | 13 | ESI+: 457 |
| 270 | 13 | ESI+: 415, 437([M + Na]$^+$) |
| 271 | 13 | ESI+: 445, 467([M + Na]$^+$) |
| 272 | 13 | ESI+: 507 |
| 273 | 13 | ESI+: 419 |

TABLE 88-continued

| PEx | Psyn | Dat |
|---|---|---|
| 274 | 13 | ESI+: 479 |
| 275 | 13 | ESI+: 493 |
| 276 | 13 | ESI+: 323([M-Boc]$^+$) |
| 277 | 13 | ESI+: 529 |
| 278 | 13 | ESI+: 529 |
| 279 | 13 | ESI+: 491 |
| 280 | 13 | ESI+: 507 |

TABLE 89

| PEx | Psyn | Dat |
|---|---|---|
| 281 | 13 | ESI+: 463 |
| 282 | 13 | ESI+: 463 |
| 283 | 13 | ESI+: 485 |
| 284 | 13 | ESI+: 385([M-Boc]$^+$) |
| 285 | 13 | ESI+: 501 |
| 286 | 13 | ESI+: 491 |
| 287 | 13 | ESI+: 493 |
| 288 | 13 | ESI+: 485 |
| 289 | 13 | ESI+: 501 |
| 290 | 13 | ESI+: 507 |
| 291 | 17 | ESI+: 389 |
| 292 | 17 | ESI+: 387 |
| 293 | 17 | ESI+: 373 |
| 294 | 15 | ESI+: 537 |
| 295 | 15 | ESI+: 361, 383([M + Na]$^+$) |
| 296 | 15 | ESI+: 375 |
| 297 | 15 | ESI+: 447 |
| 298 | 15 | ESI+: 447 |
| 299 | 15 | ESI+: 417 |
| 300 | 15 | ESI+: 523 |
| 301 | 15 | ESI+: 391 |
| 302 | 20 | ESI+: 433, 455([M + Na]$^+$) |
| 303 | 20 | ESI+: 433 |
| 304 | 20 | ESI+: 403 |
| 305 | 20 | ESI+: 509 |
| 306 | 334 | ESI+: 377 |
| 307 | 334 | ESI+: 389 |
| 308 | 334 | ESI+: 373 |
| 309 | 334 | ESI+: 439 |
| 310 | 334 | ESI+: 443, 445 |
| 311 | 334 | ESI+: 391 |
| 312 | 334 | ESI+: 465([M + Na]$^+$), 467([M + Na]$^+$) |
| 313 | 334 | ESI+: 465([M + Na]$^+$), 467([M + Na]$^+$) |
| 314 | 334 | ESI+: 461([M + Na]$^+$) |
| 315 | 334 | ESI+: 416 |
| 316 | 334 | ESI+: 410 |
| 317 | 334 | ESI+: 439 |
| 318 | 334 | ESI+: 437 |
| 319 | 334 | ESI+: 359 |
| 320 | 334 | ESI+: 405, 427([M + Na]$^+$) |

TABLE 90

| PEx | Psyn | Dat |
|---|---|---|
| 321 | 334 | ESI+: 403 |
| 322 | 334 | ESI+: 377 |
| 323 | 334 | ESI+: 405 |
| 324 | 334 | ESI+: 403, 425([M + Na]$^+$) |
| 325 | 334 | ESI+: 391, 413([M + Na]$^+$) |
| 326 | 334 | ESI+: 379, 401([M + Na]$^+$) |
| 327 | 334 | ESI+: 403 |
| 328 | 334 | ESI+: 379, 401([M + Na]$^+$) |
| 329 | 334 | ESI+: 405,427([M + Na]$^+$) |
| 330 | 334 | ESI+: 389 |
| 331 | 334 | ESI+: 419 |
| 332 | 334 | ESI+: 401 |
| 333 | 334 | ESI+: 401 |
| 334 | 334 | ESI+: 416 |
| 335 | 334 | ESI+: 391, 413([M + Na]$^+$) |
| 336 | 334 | ESI+: 427 |

TABLE 90-continued

| PEx | Psyn | Dat |
|---|---|---|
| 337 | 339 | ESI+: 345 |
| 338 | 339 | ESI+: 359 |
| 339 | 339 | ESI+: 407 |
| 340 | 339 | ESI+: 361 |
| 341 | 339 | ESI+: 389 |
| 342 | 339 | ESI+: 411, 413 |
| 343 | 339 | ESI+: 389 |
| 344 | 344 | ESI+: 365, 367 |
| 345 | 345 | ESI+: 451 |
| 346 | 345 | ESI+: 485, 487 |
| 347 | 345 | ESI+: 485, 487 |
| 348 | 349 | ESI+: 485, 487 |
| 349 | 349 | ESI+: 481 |
| 350 | 349 | ESI+: 481 |
| 351 | 349 | ESI+: 453 |
| 352 | 349 | ESI+: 509([M + Na]+), 511([M + Na]+) |
| 353 | 349 | ESI+: 509([M + Na]+), 511([M + Na]+) |
| 354 | 349 | ESI+: 509([M + Na]+), 511([M + Na]+) |
| 355 | 349 | ESI+: 483 |
| 356 | 349 | ESI+: 483 |
| 357 | 349 | ESI+: 471 |
| 358 | 349 | ESI+: 471 |
| 359 | 349 | ESI+: 471 |
| 360 | 349 | ESI+: 531, 533 |

TABLE 91

| PEx | Psyn | Dat |
|---|---|---|
| 361 | 349 | ESI+: 467 |
| 362 | 349 | ESI+: 467 |
| 363 | 367 | ESI+: 437 |
| 364 | 367 | ESI+: 403 |
| 365 | 367 | ESI+: 389 |
| 366 | 367 | ESI+: 375 |
| 367 | 367 | ESI+: 411, 413 |
| 368 | 27 | ESI+: 448 |
| 369 | 38 | ESI+: 451 |
| 370 | 28 | ESI+: 350 |
| 371 | 29 | ESI+: 393 |
| 372 | 30 | ESI+: 349 |
| 373 | 31 | ESI+: 331 |
| 374 | 37 | ESI+: 577 |
| 375 | 375 | ESI+: 383 |
| 376 | 376 | ESI+: 386 |
| 377 | 377 | ESI+: 425 |
| 378 | 377 | ESI+: 427 |
| 379 | 379 | ESI+: 417 |
| 380 | 380 | ESI+: 331 |
| 381 | 381 | NMR-C: 1.19(3H, d, J = 6.6 Hz), 1.28(3H, t, J = 7.1 Hz), 2.75-2.89(4H, m), 3.34-3.44(1H, m), 3.51-3.65(4H, m), 3.69(1H, dd, J = 8.7, 7.6 Hz), 3.93(1H, dd, J = 8.7, 4.1 Hz), 4.18(2H, q, J = 7.1 Hz), 6.66(1H, s), 7.28(1H, s) |
| 382 | 381 | ESI+: 371, 373 |
| 383 | 383 | ESI+: 291 |
| 384 | 383 | ESI+: 291 |
| 385 | 385 | ESI+: 317 |
| 386 | 386 | ESI+: 301 |
| 387 | 387 | ESI+: 236 |
| 388 | 388 | ESI+: 277 |
| 389 | 389 | ESI+: 275 |
| 390 | 390 | ESI+: 293 |
| 391 | 545 | ESI+: 587 |
| 392 | 7 | ESI+: 374 |
| 393 | 7 | ESI+: 371, 373 |
| 394 | 7 | ESI+: 327, 329 |
| 395 | 408 | ESI+: 441, 443 |
| 396 | 408 | ESI+: 455 |
| 397 | 408 | ESI+: 457 |
| 398 | 408 | ESI+: 443, 445 |
| 399 | 408 | ESI+: 455, 457 |
| 400 | 408 | ESI+: 465; 467 |

TABLE 92

| PEx | Psyn | Dat |
|---|---|---|
| 401 | 408 | ESI+: 491; 493 |
| 402 | 408 | ESI+: 467, 469 |
| 403 | 408 | ESI+: 455, 457 |
| 404 | 408 | ESI+: 443, 445 |
| 405 | 408 | ESI+: 467, 469 |
| 406 | 408 | ESI+: 443, 445 |
| 407 | 408 | ESI+: 469, 471 |
| 408 | 408 | ESI+: 413 |
| 409 | 409 | ESI+: 314, 316 |
| 410 | 411 | ESI+: 453; 455 |
| 411 | 411 | ESI+: 467; 469 |
| 412 | 411 | ESI+: 355, 357 |
| 413 | 411 | ESI+: 437; 439 |
| 414 | 411 | ESI+: 455 |
| 415 | 411 | ESI+: 529, 531 |
| 416 | 411 | ESI+: 467, 469 |
| 417 | 411 | ESI+: 455, 457 |
| 418 | 411 | ESI+: 479, 481 |
| 419 | 411 | ESI+: 409, 411 |
| 420 | 411 | ESI+: 455, 457 |
| 421 | 411 | ESI+: 467, 469 |
| 422 | 411 | ESI+: 467, 469 |
| 423 | 411 | ESI+: 479, 481 |
| 424 | 411 | ESI+: 479, 481 |
| 425 | 549 | ESI+: 435 |
| 426 | 426 | ESI+: 346 |
| 427 | 427 | FAB−: 395, 397 |
| 428 | 427 | ESI+: 353, 355 |
| 429 | 23 | ESI+: 369([M + Na]+) |
| 430 | 23 | ESI+: 347, 369([M + Na]+) |
| 431 | 23 | ESI+: 385([M + Na]+) |
| 432 | 23 | ESI+: 361, 383([M + Na]+) |
| 433 | 11 | ESI+: 439, 441 |
| 434 | 11 | NMR-C: 0.44-0.51(2H, m), 0.95(6H, s), 0.97-1.06(2H, m), 1.47(9H, s), 1.58-1.68(1H, m), 2.69-2.78(2H, m), 3.04(2H, s), 3.06-3.18(4H, m), 3.21(3H, s), 3.29-3.36(2H, m), 3.46-3.58(4H, m), 4.15-4.22(2H, m), 6.48(1H, s) |
| 435 | 11 | ESI+: 383, 385 |
| 436 | 11 | ESI+: 377 |
| 437 | 11 | ESI+: 331 |
| 438 | 11 | ESI+: 345 |
| 439 | 11 | ESI+: 453, 455 |
| 440 | 11 | ESI+: 389 |

TABLE 93

| PEx | Psyn | Dat |
|---|---|---|
| 441 | 11 | ESI+: 441, 443 |
| 442 | 11 | ESI+: 391 |
| 443 | 11 | ESI+: 465, 467 |
| 444 | 11 | ESI+: 387 |
| 445 | 11 | ESI+: 389 |
| 446 | 11 | ESI+: 339, 341 |
| 447 | 11 | ESI+: 397, 399 |
| 448 | 11 | ESI+: 413 |
| 449 | 11 | ESI+: 395, 397 |
| 450 | 11 | ESI+: 377 |
| 451 | 11 | ESI+: 377 |
| 452 | 11 | ESI+: 391 |
| 453 | 11 | ESI+: 441, 443 |
| 454 | 11 | ESI+: 389 |
| 455 | 11 | ESI+: 377 |
| 456 | 11 | ESI+: 365 |
| 457 | 11 | ESI+: 453, 455 |
| 458 | 11 | ESI+: 453, 455 |
| 459 | 11 | ESI+: 389 |
| 460 | 11 | ESI+: 365 |
| 461 | 11 | ESI+: 431 |
| 462 | 11 | ESI+: 471 |
| 463 | 11 | ESI+: 445 |
| 464 | 11 | ESI+: 333 |
| 465 | 11 | ESI+: 349 |
| 466 | 11 | ESI+: 347 |
| 467 | 11 | ESI+: 391 |

TABLE 93-continued

| PEx | Psyn | Dat |
|---|---|---|
| 468 | 11 | ESI+: 405 |
| 469 | 11 | ESI+: 347 |
| 470 | 11 | ESI+: 361 |
| 471 | 11 | ESI+: 465, 467 |
| 472 | 11 | ESI+: 465 |
| 473 | 11 | ESI+: 431 |
| 474 | 11 | ESI+: 443 |
| 475 | 11 | ESI+: 429 |
| 476 | 11 | ESI+: 443 |
| 477 | 11 | ESI+: 401 |
| 478 | 11 | ESI+: 443 |
| 479 | 11 | ESI+: 465 |
| 480 | 11 | ESI+: 493 |

TABLE 94

| PEx | Psyn | Dat |
|---|---|---|
| 481 | 11 | ESI+: 431 |
| 482 | 11 | ESI+: 405 |
| 483 | 11 | ESI+: 479 |
| 484 | 11 | ESI+: 309([M-Boc]+) |
| 485 | 11 | ESI+: 515 |
| 486 | 11 | ESI+: 515 |
| 487 | 11 | ESI+: 477 |
| 488 | 11 | ESI+: 493 |
| 489 | 11 | ESI+: 449 |
| 490 | 11 | ESI+: 449 |
| 491 | 11 | ESI+: 377 |
| 492 | 11 | ESI+: 471 |
| 493 | 11 | ESI+: 471 |
| 494 | 11 | ESI+: 487, 489 |
| 495 | 495 | ESI+: 473, 475 |
| 496 | 495 | ESI+: 507, 509 |
| 497 | 495 | ESI+: 507, 509 |
| 498 | 495 | EI: 491, 493 |
| 499 | 495 | ESI+: 492, 493 |
| 500 | 12 | ESI+: 429; 431 |
| 501 | 12 | ESI+: 425 |
| 502 | 12 | ESI+: 413 |
| 503 | 12 | ESI+: 420 |
| 504 | 12 | ESI+: 463 |
| 505 | 12 | ESI+: 409 |
| 506 | 19 | ESI+: 303 |
| 507 | 19 | ESI+: 473 |
| 508 | 19 | ESI+: 405 |
| 509 | 19 | ESI+: 501 |
| 510 | 19 | ESI+: 495 |
| 511 | 19 | ESI+: 361 |
| 512 | 19 | ESI+: 347 |
| 513 | 19 | ESI+: 433 |
| 514 | 19 | ESI+: 393 |
| 515 | 71 | ESI+: 345 |
| 516 | 71 | ESI+: 319 |
| 517 | 71 | ESI+: 331 |
| 518 | 71 | ESI+: 319 |
| 519 | 162 | ESI+: 437, 439 |
| 520 | 162 | ESI+: 435, 437 |

TABLE 95

| PEx | Psyn | Dat |
|---|---|---|
| 521 | 18 | ESI+: 417 |
| 522 | 18 | ESI+: 417 |
| 523 | 13 | ESI+: 479 |
| 524 | 13 | ESI+: 493 |
| 525 | 13 | ESI+: 479 |
| 526 | 13 | ESI+: 533 |
| 527 | 13 | ESI+: 497 |
| 528 | 13 | ESI+: 513 |
| 529 | 13 | ESI+: 493 |
| 530 | 13 | ESI+: 485 |

TABLE 95-continued

| PEx | Psyn | Dat |
|---|---|---|
| 531 | 13 | ESI+: 485 |
| 532 | 15 | ESI+: 523 |
| 533 | 15 | ESI+: 537 |
| 534 | 15 | ESI+: 559 |
| 535 | 15 | ESI+: 431 |
| 536 | 20 | ESI+: 433 |
| 537 | 20 | ESI+: 509 |
| 538 | 339 | ESI+: 486 |
| 539 | 540 | ESI+: 526 |
| 540 | 540 | ESI+: 538 |
| 541 | 540 | ESI+: 467 |
| 542 | 540 | ESI+: 467 |
| 543 | 543 | ESI+: 531 |
| 544 | 545 | ESI+: 587 |
| 545 | 545 | ESI+: 543 |
| 546 | 545 | ESI+: 601 |
| 547 | 408 | ESI+: 455, 457 |
| 548 | 408 | ESI+: 455, 457 |
| 549 | 549 | ESI+: 435 |
| 550 | 549 | ESI+: 449 |
| 551 | 11 | ESI+: 465 |
| 552 | 11 | ESI+: 477 |
| 553 | 11 | ESI+: 479 |
| 554 | 11 | ESI+: 471 |
| 555 | 11 | ESI+: 487, 489 |
| 556 | 11 | ESI+: 493 |
| 557 | 11 | ESI+: 479 |
| 558 | 11 | ESI+: 465 |
| 559 | 11 | ESI+: 519 |
| 560 | 11 | ESI+: 479 |

TABLE 96

| PEx | Psyn | Dat |
|---|---|---|
| 561 | 11 | ESI+: 483 |
| 562 | 11 | ESI+: 499, 501 |
| 563 | 11 | ESI+: 471 |
| 564 | 11 | ESI+: 471 |
| 565 | 565 | ESI+: 527 |
| 566 | 565 | ESI+: 527 |
| 567 | 565 | ESI+: 527 |
| 568 | 565 | ESI+: 561, 563 |
| 569 | 565 | ESI+: 563 |
| 570 | 565 | ESI+: 545 |
| 571 | 19 | ESI+: 433 |
| 572 | 19 | ESI+: 447 |
| 573 | 20 | ESI+: 363 |
| 574 | 15 | ESI+: 377 |

TABLE 97

| Ex | Str |
|---|---|
| 1 | (structure) |
| 2M | (structure) |

TABLE 97-continued

| Ex | Str |
|---|---|
| 3M | (structure) fumaric acid |
| 4 | (structure) HCl |
| 5 | (structure) |
| 6H | (structure) fumaric acid |
| 7M | (structure) fumaric acid |
| 8M | (structure) fumaric acid |

TABLE 98

| Ex | Str |
|---|---|
| 9M | (structure) fumaric acid |
| 10M | (structure) fumaric acid |
| 11 | (structure) |
| 12M | (structure) fumaric acid |
| 13H | (structure) fumaric acid |
| 14M | (structure) fumaric acid |
| 15 | (structure) HCl |
| 16 | (structure) HCl |

TABLE 99

| Ex | Str |
|---|---|
| 17 | (structure) HCl |

TABLE 99-continued

| Ex | Str |
|---|---|
| 18 | (structure) HCl |
| 19M | (structure) fumaric acid |
| 20M | (structure) fumaric acid |
| 21 | (structure) HCl |
| 22H | (structure) fumaric acid |
| 23H | (structure) fumaric acid |
| 24M | (structure) fumaric acid |

TABLE 100

| Ex | Str |
|---|---|
| 25H | (structure) fumaric acid |
| 26M | (structure) fumaric acid |
| 27M | (structure) fumaric acid |
| 28H | (structure) fumaric acid |
| 29 | (structure) HCl |
| 30 | (structure) 2HCl |
| 31M | (structure) fumaric acid |
| 32M | (structure) fumaric acid |

TABLE 101

| Ex | Str |
|---|---|
| 33M | Acetyl-tetrahydro-pyrido-benzazepine; fumarate |
| 34M | N-Ethyl-tetrahydro-pyrido-benzazepine; fumarate |
| 35M | N-Methyl, Br-substituted tetrahydro-pyrido-benzoxazine-benzazepine; fumarate |
| 36 | cPr-substituted pyrido-benzoxazine-benzazepine; 2HCl |
| 37M | iPr-C(O)-tetrahydro-pyrido-benzazepine; fumarate |
| 38M | N-iBu-tetrahydro-pyrido-benzazepine; fumarate |
| 39M | cPr-C(O)-, Cl-substituted tetrahydro-pyrido-benzazepine; fumarate |
| 40M | cBu-C(O)-, Cl-substituted tetrahydro-pyrido-benzazepine; fumarate |

TABLE 102

| Ex | Str |
|---|---|
| 41H | cPr-CH2-, Cl-substituted tetrahydro-pyrido-benzazepine; fumarate |
| 42M | cBu-CH2-, Cl-substituted tetrahydro-pyrido-benzazepine; fumarate |
| 43M | cPen-C(O)-, Cl-substituted tetrahydro-pyrido-benzazepine; fumarate |
| 44M | Benzoyl-, Cl-substituted tetrahydro-pyrido-benzazepine; fumarate |
| 45M | cPen-CH2-, Cl-substituted tetrahydro-pyrido-benzazepine; fumarate |
| 46 | Benzyl-, Cl-substituted tetrahydro-pyrido-benzazepine; HCl |
| 47M | cHex-C(O)-, Cl-substituted tetrahydro-pyrido-benzazepine; fumarate |

TABLE 103
| Ex | Str |
|---|---|
| 48M | 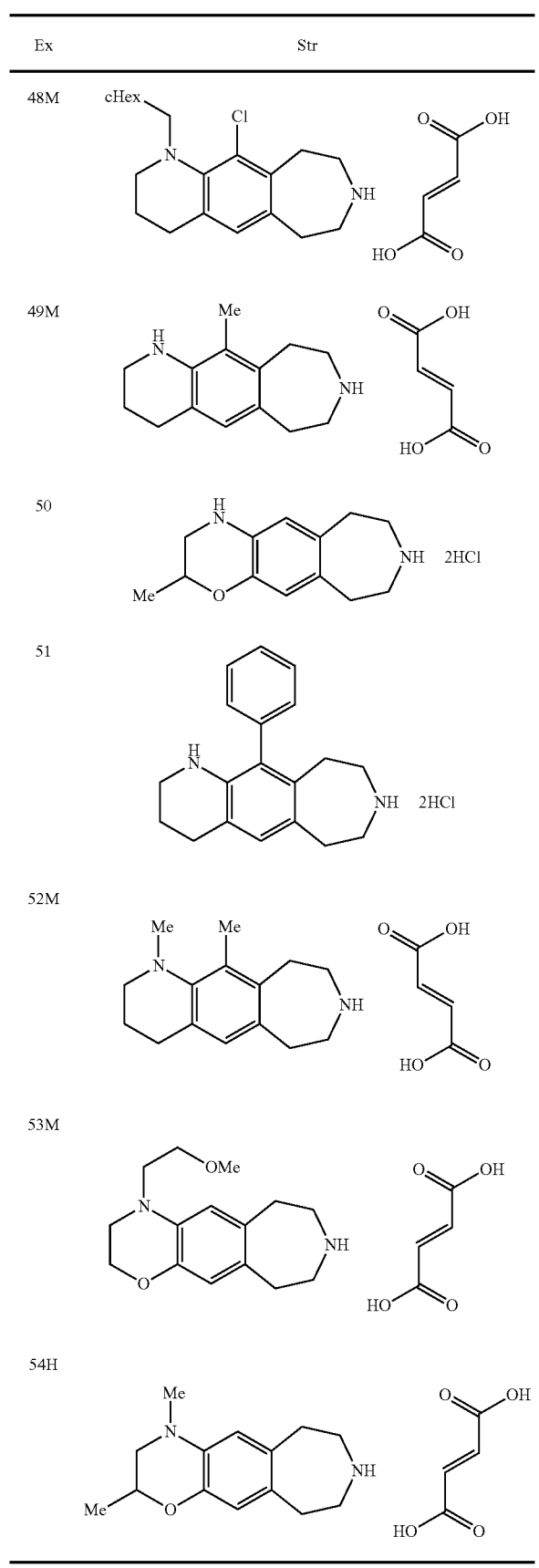 |
| 49M | |
| 50 | |
| 51 | |
| 52M | |
| 53M | |
| 54H | |
TABLE 104
| Ex | Str |
|---|---|
| 55M | 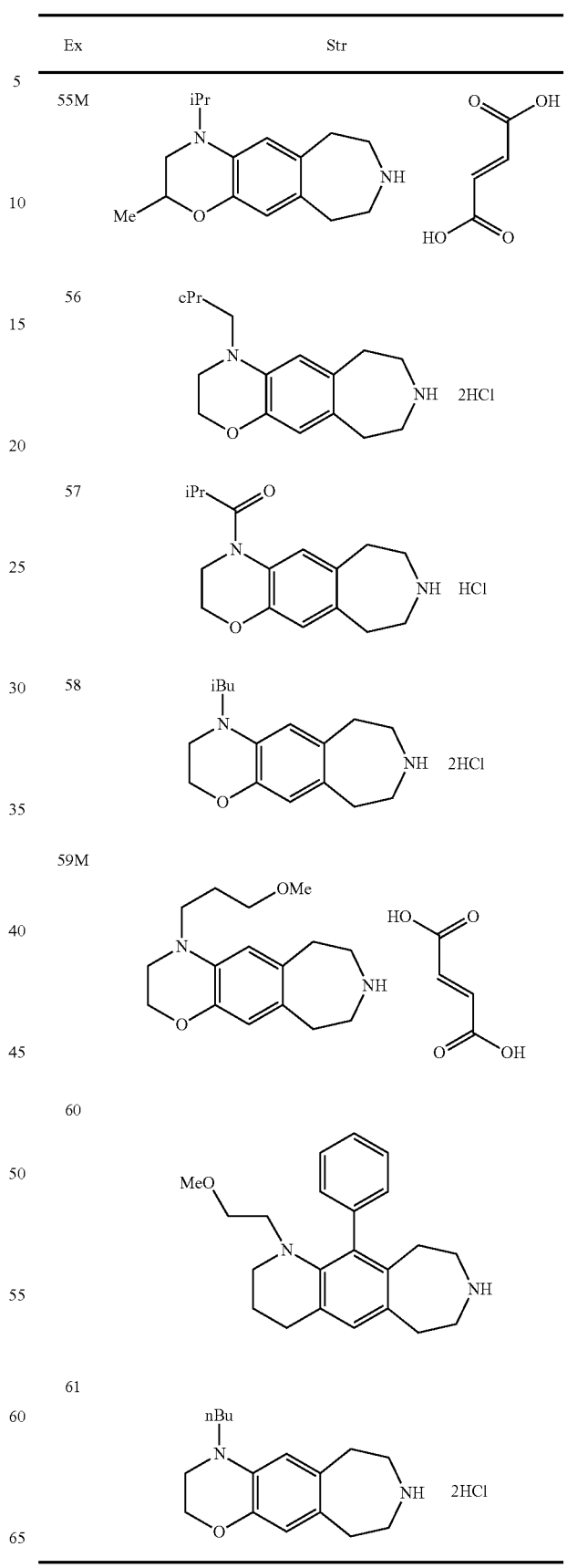 |
| 56 | |
| 57 | |
| 58 | |
| 59M | |
| 60 | |
| 61 | |

TABLE 105

| Ex | Str |
|---|---|
| 62H | (benzyl-substituted dihydrobenzoxazine fused benzazepine) · fumarate |
| 63M | (2-ethoxyethyl-substituted dihydrobenzoxazine fused benzazepine) · fumarate |
| 64 | ((tetrahydropyran-4-yl)methyl-substituted dihydrobenzoxazine fused benzazepine) · 2HCl |
| 65 | (5-phenyl dihydrobenzoxazine fused benzazepine) · 2HCl |
| 66M | (5-(3-methoxyphenyl)-tetrahydroquinoline fused benzazepine) · fumarate |
| 67M | (5-(3-chlorophenyl)-tetrahydroquinoline fused benzazepine) · fumarate |

TABLE 106

| Ex | Str |
|---|---|
| 68H | (5-(3,4-dichlorophenyl)-tetrahydroquinoline fused benzazepine) · fumarate |
| 69H | (N-(2-methoxyethyl)-5-(3-chlorophenyl)-tetrahydroquinoline fused benzazepine) · fumarate |
| 70M | (N-(2-methoxyethyl)-5-(3,4-dichlorophenyl)-tetrahydroquinoline fused benzazepine) · fumarate |
| 71M | (N-(2-methoxyethyl)-2-oxo-tetrahydroquinoline fused benzazepine) · fumarate |
| 72M | (N-isobutyl-5-(3-methoxyphenyl)-tetrahydroquinoline fused benzazepine) · fumarate |
| 73H | (N-(2-methoxyethyl)-5-(3-methoxyphenyl)-tetrahydroquinoline fused benzazepine) · fumarate |

TABLE 107
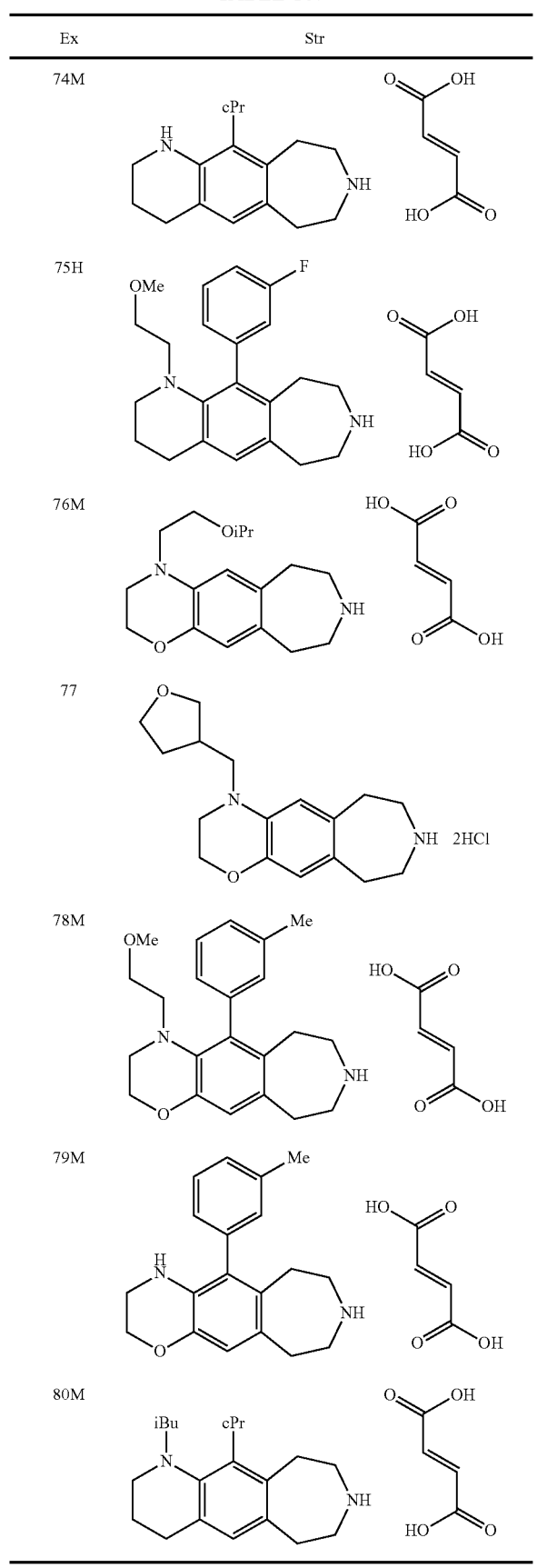
TABLE 108
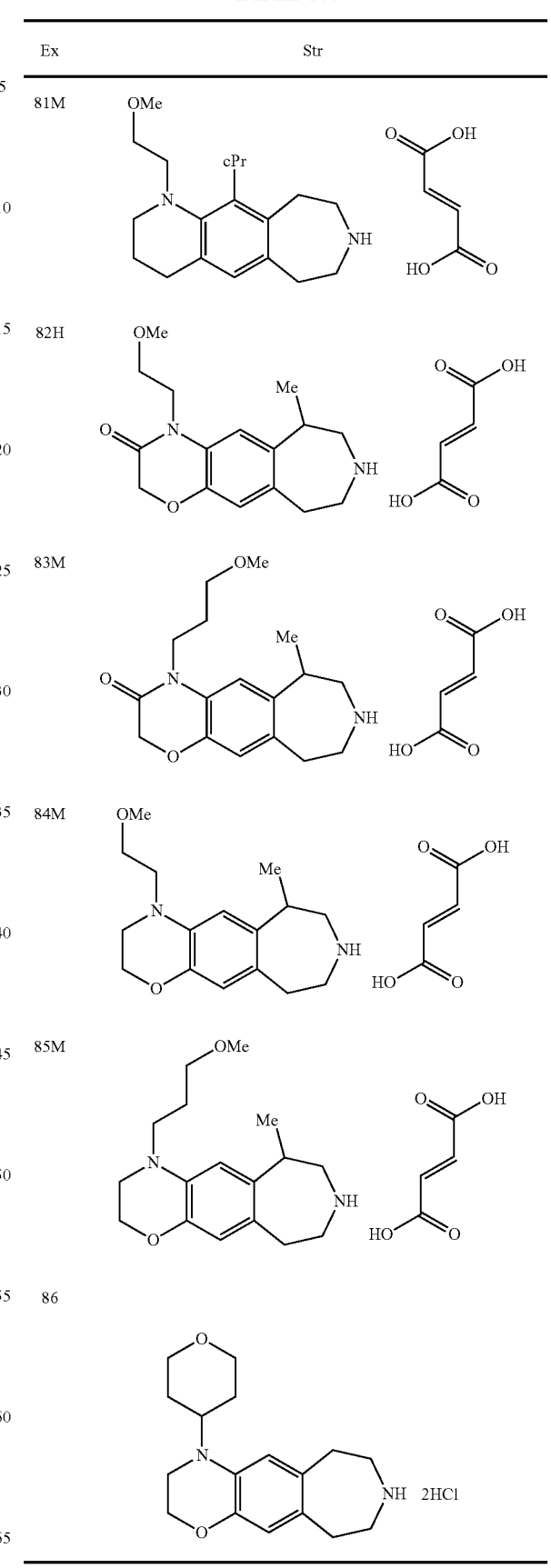

TABLE 109
| Ex | Str |
|----|-----|
| 87 | 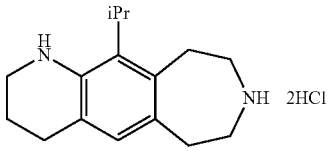 |
| 88H | 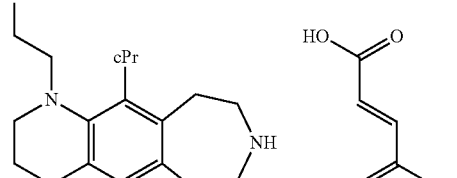 |
| 89M | 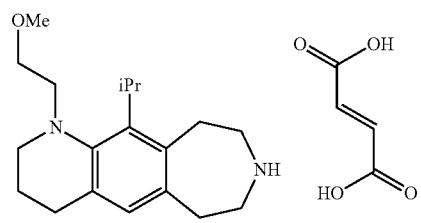 [SMILES: COCCN1CCCc2cc3c(c(C(C)C)c21)CCNCC3 ; O=C(O)/C=C/C(=O)O] |
| 90M | 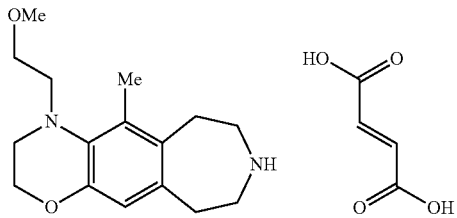 [SMILES: COCCN1CCOc2cc3c(c(C)c21)CCNCC3 ; O=C(O)/C=C/C(=O)O] |
| 91M | 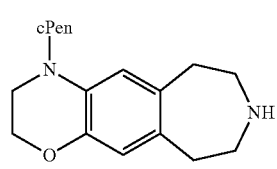 |
| 92H | 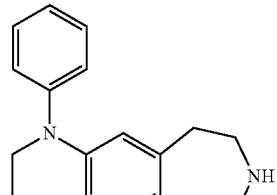 |
| 93M | 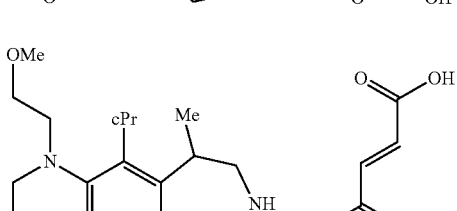 |
TABLE 110
| Ex | Str |
|----|-----|
| 94H | 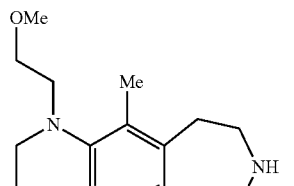 |
| 95M | 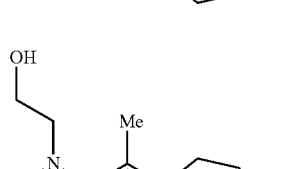 |
| 96 | 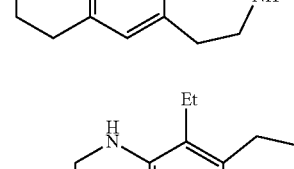 |
| 97M | 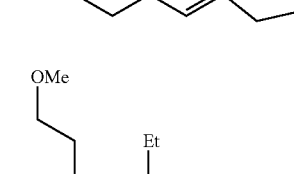 |
| 98M | 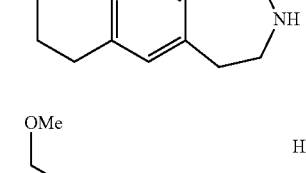 |
| 99M | 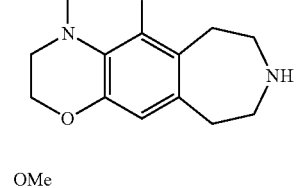 |
| 100 | 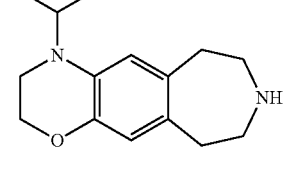 |

TABLE 111

| Ex | Str |
|---|---|
| 101 M | (structure with OMe, iPr substituents on oxazine-fused azepine; fumaric acid) |
| 102 M | (structure with MeO, HO, Et substituents on tetrahydroquinoline-fused azepine; fumaric acid) |
| 103 | (structure with 3-fluoropropyl on oxazine-fused azepine; 2HCl) |
| 104 M | (structure with OEt, cPr substituents on oxazine-fused azepine; fumaric acid) |
| 105 | (structure with MeO-methyl-cyclopropyl-methyl, cPr on oxazine-fused azepine; 2HCl) |
| 106 H | (structure with OMe-propyl, cPr substituents on oxazine-fused azepine; fumaric acid) |

TABLE 112

| Ex | Str |
|---|---|
| 107 M | (structure with BzO-carbonyl on tetrahydroquinoline-fused azepine, Me substituent; fumaric acid) |
| 108 M | (structure with EtO-carbonyl, Me on tetrahydroquinoline-fused azepine; oxalic acid) |
| 109 M | (structure with Et-NH-C(=O), Me on tetrahydroquinoline-fused azepine; oxalic acid) |
| 110 | (structure with benzyl on tetrahydroquinoline-fused azepine; fumaric acid) |
| 111 | (structure with 3-methoxybenzyl on oxazine-fused azepine; 2HCl) |
| 112 M | (structure with 3-chlorobenzyl on oxazine-fused azepine; fumaric acid) |

TABLE 113

| Ex | Str |
|---|---|
| 113 | 4-methoxybenzyl substituted 2,3,4,5-tetrahydro-[1,4]oxazino[2,3-g][3]benzazepine, 2HCl |
| 114 M | 4-chlorobenzyl substituted 2,3,4,5-tetrahydro-[1,4]oxazino[2,3-g][3]benzazepine, succinic acid |
| 115 M | 2-phenoxyethyl substituted 2,3,4,5-tetrahydro-[1,4]oxazino[2,3-g][3]benzazepine, succinic acid |
| 116 M | pyridin-2-ylmethyl substituted 2,3,4,5-tetrahydro-[1,4]oxazino[2,3-g][3]benzazepine, fumaric acid |
| 117 M | thiazol-4-ylmethyl substituted 2,3,4,5-tetrahydro-[1,4]oxazino[2,3-g][3]benzazepine, fumaric acid |
| 118 H | 2-methoxyethyl, phenyl substituted 2,3,4,5-tetrahydro-[1,4]oxazino[2,3-g][3]benzazepine, fumaric acid |

TABLE 114

| Ex | Str |
|---|---|
| 119 | 2-hydroxyethyl substituted 2,3,4,5-tetrahydro-[1,4]oxazino[2,3-g][3]benzazepine, 2HCl |
| 120 M | 3-fluoropropyl, cPr substituted tetrahydroquinoline-benzazepine, succinic acid |
| 121 H | 2-methoxyethyl, Br substituted oxo-tetrahydroquinoline-benzazepine, fumaric acid |
| 122 | BzO-C(O)- substituted tetrahydroquinoline-benzazepine, HCl |
| 123 | iBuO-C(O)- substituted tetrahydroquinoline-benzazepine, HCl |
| 124 | Et, oxo substituted tetrahydroquinoline-benzazepine, HCl |
| 125 | nPr, oxo substituted tetrahydroquinoline-benzazepine, HCl |

TABLE 115

| Ex | Str |
|---|---|
| 126 | (benzyl-substituted dihydroquinolinone fused azepane) · HCl |
| 127 M | (iBu-substituted dihydroquinolinone fused azepane) · succinic acid |
| 128 M | (iPrO-C(=O)-N dihydroquinoline fused azepane) · succinic acid |
| 129 M | (3-methoxypropyl, Br-substituted dihydroquinolinone fused azepane) · fumaric acid |
| 130 M | (2-methoxyethyl, CF₃-substituted benzoxazine fused azepane) · fumaric acid |
| 131 M | (2-methoxyethyl, CF₃-substituted dihydroquinoline fused azepane) · fumaric acid |
| 132 M | (nPr-substituted benzoxazinone fused azepane) · fumaric acid |

TABLE 116

| Ex | Str |
|---|---|
| 133 | (benzyl-substituted benzoxazinone fused azepane) · HCl |
| 134 M | (phenethyloxy-C(=O)-N dihydroquinoline fused azepane) · succinic acid |
| 135 M | (2-methoxyethyl, Br-substituted benzoxazine fused azepane) · fumaric acid |
| 136 M | (nPr, Br-substituted dihydroquinolinone fused azepane) · fumaric acid |
| 137 M | (nPr, phenyl-substituted dihydroquinolinone fused azepane) · succinic acid |
| 138 M | (3-methoxybenzyl-substituted benzoxazinone fused azepane) · succinic acid |

TABLE 117

| Ex | Str |
|---|---|
| 139 M | (structure) |
| 140 M | (structure) |
| 141 H | (structure) |
| 142 H | (structure) |
| 143 H | (structure) |
| 144 M | (structure) |

TABLE 118

| Ex | Str |
|---|---|
| 145 M | (structure) |
| 146 M | (structure) |
| 147 M | (structure) |
| 148 M | (structure) |
| 149 | (structure) |
| 150 H | (structure) |

TABLE 119

| Ex | Str |
|---|---|
| 151 M | (Et, cPr substituted dihydrobenzoxazine-benzazepine) · fumaric acid |
| 152 H | (nPr, cPr substituted dihydrobenzoxazine-benzazepine) · fumaric acid |
| 153 H | (hydroxyethyl, cPr substituted dihydrobenzoxazine-benzazepine) · fumaric acid |
| 154 H | (methoxyethyl-N, Me substituted dihydrobenzoxazine-benzazepine) · fumaric acid |
| 155 M | (2-chlorobenzyl substituted dihydrobenzoxazine-benzazepine) · fumaric acid |
| 156 M | (methoxyethyl, cPr, Me substituted dihydrobenzoxazine-benzazepine) · fumaric acid |
| 157 M | (Me, cPr substituted dihydrobenzoxazine-benzazepine) · fumaric acid |

TABLE 120

| Ex | Str |
|---|---|
| 158 M | (EtO-C(O)-N, Br substituted tetrahydroquinoline-benzazepine) · oxalic acid |
| 159 | (dimethyl tetrahydroquinoline-benzazepine) · 2HCl |
| 160 M | (phenethyl carbamate, Br substituted tetrahydroquinoline-benzazepine) · oxalic acid |
| 161 M | (Me-N, Me,Me substituted tetrahydroquinoline-benzazepine) · fumaric acid |
| 162 M | (3-chlorophenethyl carbamate tetrahydroquinoline-benzazepine) · fumaric acid |
| 163 M | (2-methoxyphenethyl carbamate tetrahydroquinoline-benzazepine) · fumaric acid |

TABLE 121
| Ex | Str |
|---|---|
| 164 M | 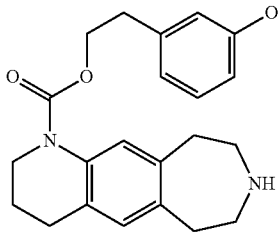 |
| 165 | 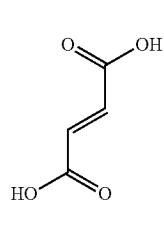 |
| 166 | 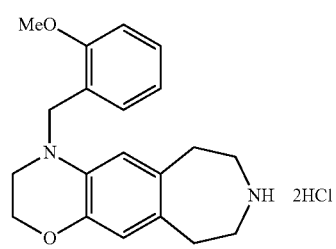 [SMILES: COc1ccccc1CN1CCOc2cc3c(cc21)CCNCC3 ; "2HCl"] |
| 167 | 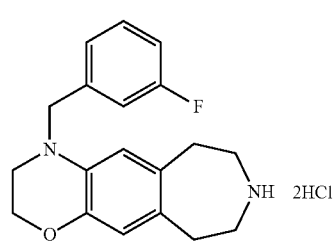 [SMILES: Fc1cccc(CN2CCOc3cc4c(cc32)CCNCC4)c1 ; "2HCl"] |
| 168 | 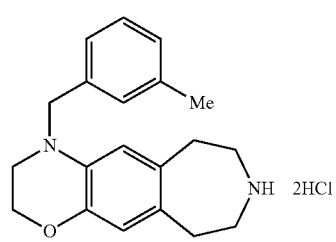 [SMILES: N#Cc1cccc(CN2CCOc3cc4c(cc32)CCNCC4)c1 ; "2HCl"] |
| 169 M | 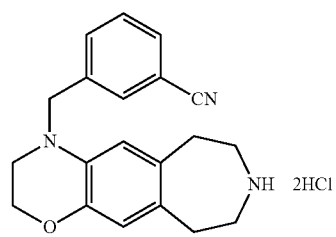 |
TABLE 122
| Ex | Str |
|---|---|
| 170 M | 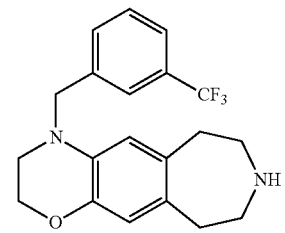 |
| 171 M | 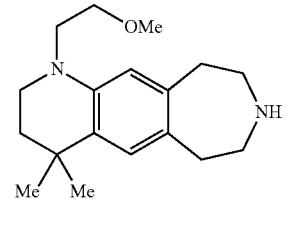 |
| 172 M | 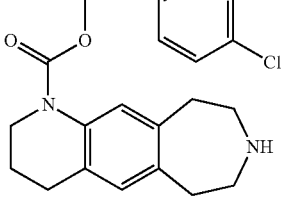 |
| 173 M | 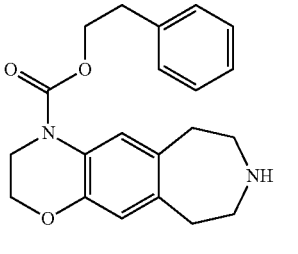 |
| 174 H | 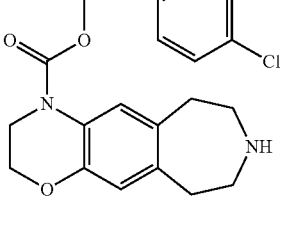 |
| 175 | 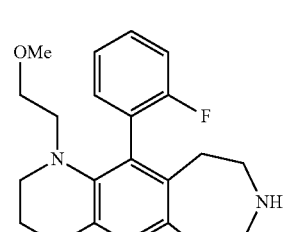 |

TABLE 123

| Ex | Str |
|---|---|
| 176 | (structure: methoxyethyl-substituted dihydrobenzoxazine-fused azepine with Br; 2HCl) |
| 177 M | (structure: 2-chlorophenethyl carbamate of dihydrobenzoxazine-fused azepine; with fumaric acid) |
| 178 M | (structure: 3-chlorophenethyl carbamate of dihydrobenzoxazine-fused azepine; with succinic/fumaric acid) |
| 179 M | (structure: 2-methoxyphenethyl carbamate of dihydrobenzoxazine-fused azepine; with diacid) |
| 180 M | (structure: 3-methoxyphenethyl carbamate of dihydrobenzoxazine-fused azepine; with diacid) |
| 181 H | (structure: methoxyethyl-N with 2-methylprop-1-enyl substituted dihydrobenzoxazine-fused azepine; with fumaric acid) |

TABLE 124

| Ex | Str |
|---|---|
| 182 H | (structure: methoxyethyl-N, phenethyl-substituted dihydrobenzoxazine-fused azepine; with fumaric acid) |
| 183 M | (structure: methoxyethyl-N, nPr-substituted dihydrobenzoxazine-fused azepine; with fumaric acid) |
| 184 M | (structure: methoxyethyl-N, phenyl-substituted dihydrobenzoxazine-fused azepine; with fumaric acid) |
| 185 M | (structure: 2-fluorophenethyl carbamate of dihydrobenzoxazine-fused azepine; with succinic acid) |
| 186 M | (structure: 3-fluorophenethyl carbamate of dihydrobenzoxazine-fused azepine; with succinic acid) |

TABLE 125

| Ex | Str |
|---|---|
| 187 M | [structure: 4-fluorophenethyl carbamate of oxazine-fused benzazepine; with succinic acid] |
| 188 H | [structure: 2-methoxyethyl-N, gem-dimethyl oxazinone-fused benzazepine; with fumaric acid] |
| 189 | [structure: N-CH2CF3 oxazine-fused benzazepine; HCl] |
| 190 | [structure: N-CH2CF3 oxazine-fused benzazepine with Br; HCl] |
| 191 | [structure: N-CH2CF3 oxazine-fused benzazepine with Br; HCl] |
| 192 H | [structure: N-(2-methoxyethyl) oxazine-fused benzazepine with 3-thienyl; with fumaric acid] |
| 193 H | [structure: N-(2-methoxyethyl) oxazine-fused benzazepine with 2-thienyl; with fumaric acid] |

TABLE 126

| Ex | Str |
|---|---|
| 194 H | [structure: N-CH2CF3 oxazine-fused benzazepine with cPr; with fumaric acid] |
| 195 M | [structure: N-(2-methoxyethyl), gem-dimethyl tetrahydroquinoline-fused benzazepine; with fumaric acid] |
| 196 M | [structure: 2-phenylpropyl carbamate of oxazine-fused benzazepine; with succinic acid] |
| 197 M | [structure: 1-methyl-2-phenylethyl carbamate of oxazine-fused benzazepine; with succinic acid] |
| 198 M | [structure: phenethyl carbamate of oxazine-fused benzazepine with Br; with succinic acid] |
| 199 M | [structure: N-(2-methoxyethyl) oxazine-fused benzazepine with Cl; with succinic acid] |

TABLE 127

| Ex | Str |
|---|---|
| 200 H | Ethyl carbamate of chloro-dihydro-benzoxazine fused tetrahydroazepine; succinic acid |
| 201 M | Phenethyl carbamate of cPr-substituted dihydro-benzoxazine fused tetrahydroazepine; succinic acid |
| 202 | 2,2-difluoro-3-methoxypropyl dihydro-benzoxazine fused tetrahydroazepine; HCl |
| 203 M | 2,2-difluoro-3-methoxypropyl, cPr-substituted dihydro-benzoxazine fused tetrahydroazepine; fumaric acid |
| 204 H | N-(2-methoxyethyl)-, Me,Me-substituted dihydro-benzoxazine fused tetrahydroazepine; fumaric acid |
| 205 H | N-Me, 3-furyl-substituted tetrahydroquinoline fused tetrahydroazepine; fumaric acid |

TABLE 128

| Ex | Str |
|---|---|
| 206 M | N-(2-methoxyethyl)-, (R)-Me dihydro-benzoxazine fused tetrahydroazepine; fumaric acid |
| 207 M | N-(2-methoxyethyl)-, (S)-Me dihydro-benzoxazine fused tetrahydroazepine; fumaric acid |
| 208 H | Phenethyl carbamate of phenyl-substituted dihydro-benzoxazine fused tetrahydroazepine; fumaric acid |
| 209 H | N-Me, pyrazolyl-substituted tetrahydroquinoline fused tetrahydroazepine; fumaric acid |
| 210 M | N-Me, 3-furyl-substituted dihydro-benzoxazine fused tetrahydroazepine; fumaric acid |
| 211 M | N-(2,2,2-trifluoroethyl), cPr-substituted dihydro-benzoxazine fused tetrahydroazepine; fumaric acid |

TABLE 129
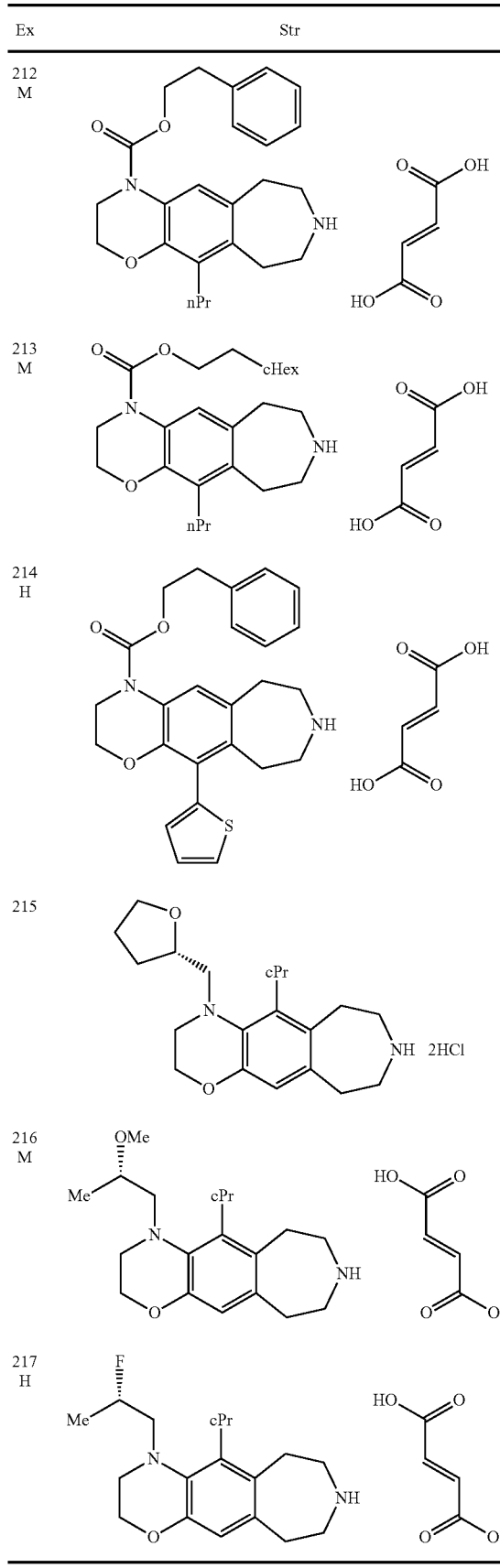
TABLE 130
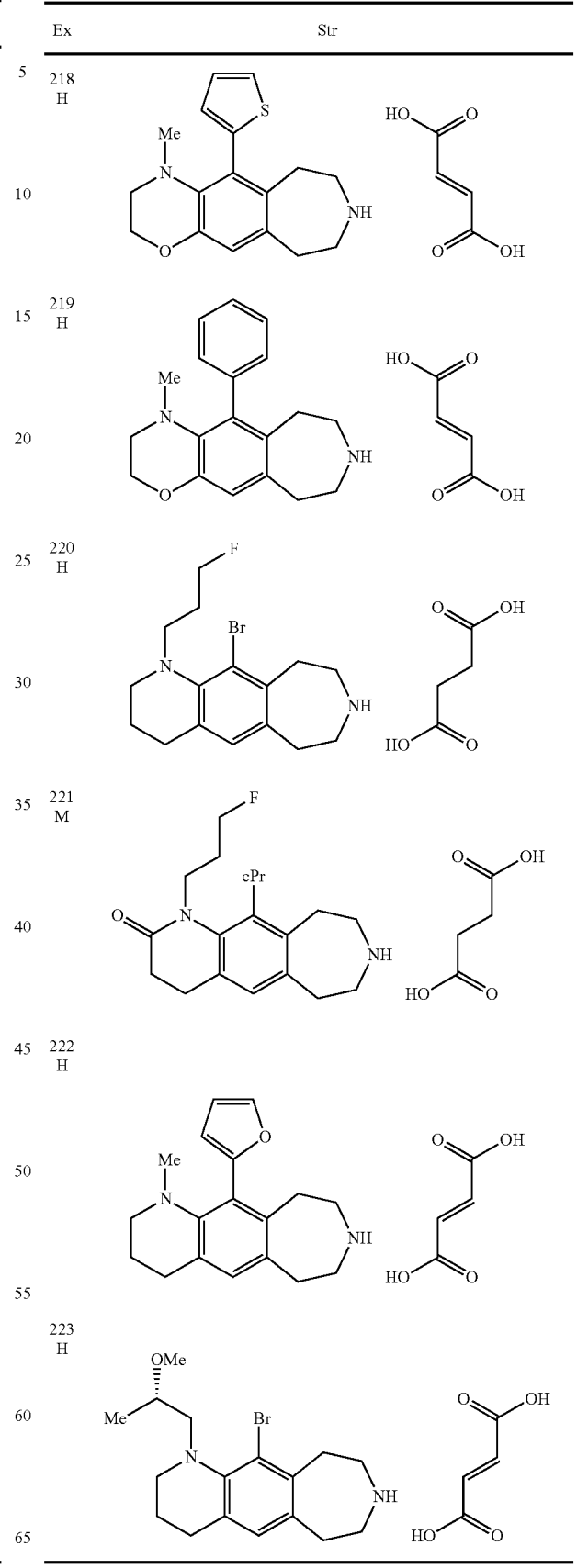

TABLE 131
| Ex | Str |
|---|---|
| 224 M | 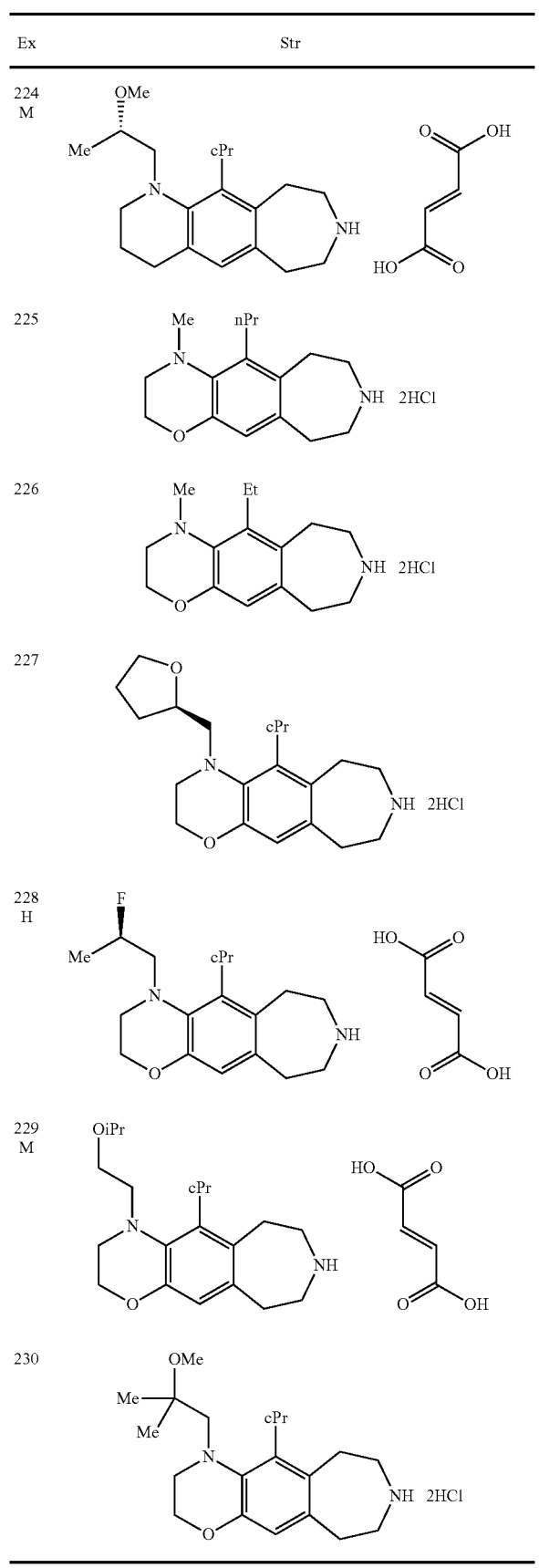 |
| 225 | |
| 226 | |
| 227 | |
| 228 H | |
| 229 M | |
| 230 | |
TABLE 132
| Ex | Str |
|---|---|
| 231 | 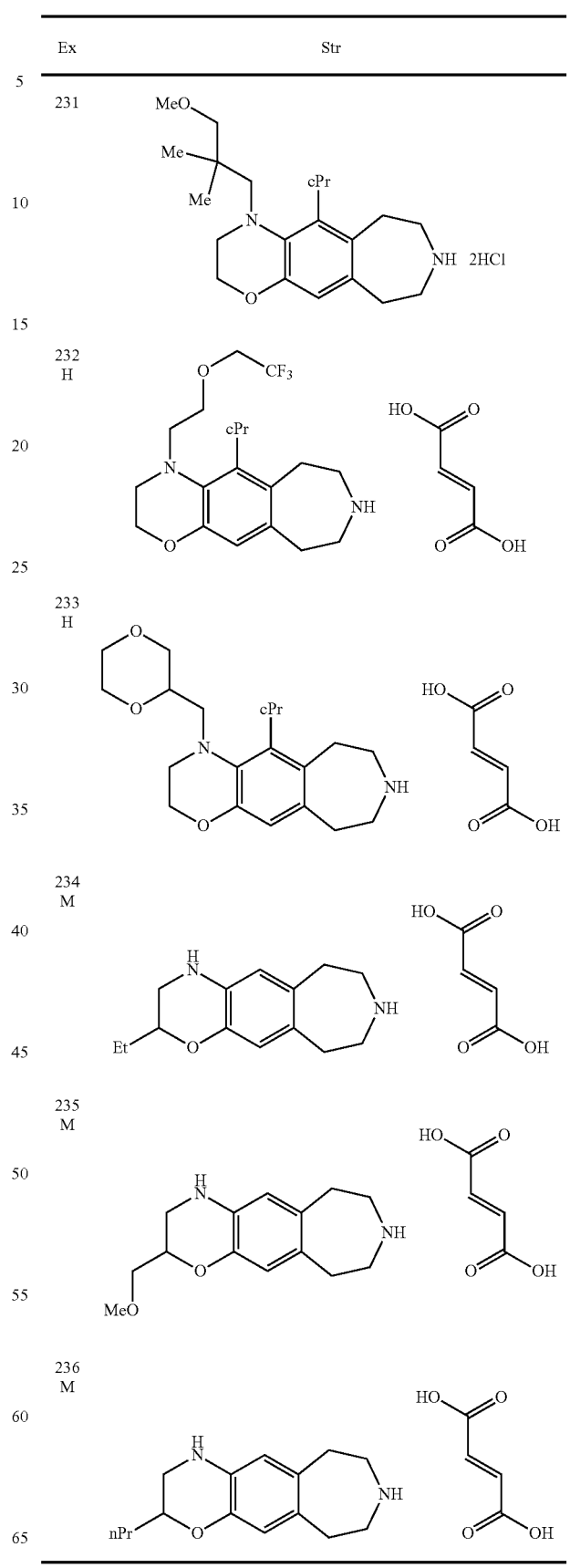 |
| 232 H | |
| 233 H | |
| 234 M | |
| 235 M | |
| 236 M | |

TABLE 133

| Ex | Str |
|---|---|
| 237 M | (structure with MeO, MeO, cPr substituents on oxazine-fused benzazepine) · fumaric acid |
| 238 M | (structure with MeO-ethyl on N, Et on oxazine) · fumaric acid |
| 239 M | (structure with MeO-ethyl on N, nPr on oxazine) · fumaric acid |
| 240 M | (structure with Me on N, Et on oxazine) · fumaric acid |
| 241 M | (structure with Me on N, nPr on oxazine) · fumaric acid |
| 242 M | (structure with MeO, MeO, cPr substituents) · fumaric acid |
| 243 M | (structure with OMe, Me, cPr substituents) · fumaric acid |

TABLE 134

| Ex | Str |
|---|---|
| 244 M | (structure with Et on N, Me on ring) · fumaric acid |
| 245 M | (structure with OMe-propyl on N, Me on ring) · fumaric acid |
| 246 M | (structure with OEt-ethyl on N, Me on ring) · fumaric acid |
| 247 M | (structure with F-propyl on N, Me on ring) · fumaric acid |
| 248 M | (structure with tetrahydrofuranylmethyl on N, cPr on ring) · fumaric acid |
| 249 M | (structure with tetrahydrofuranylmethyl on N, cPr on ring) · fumaric acid |

TABLE 135
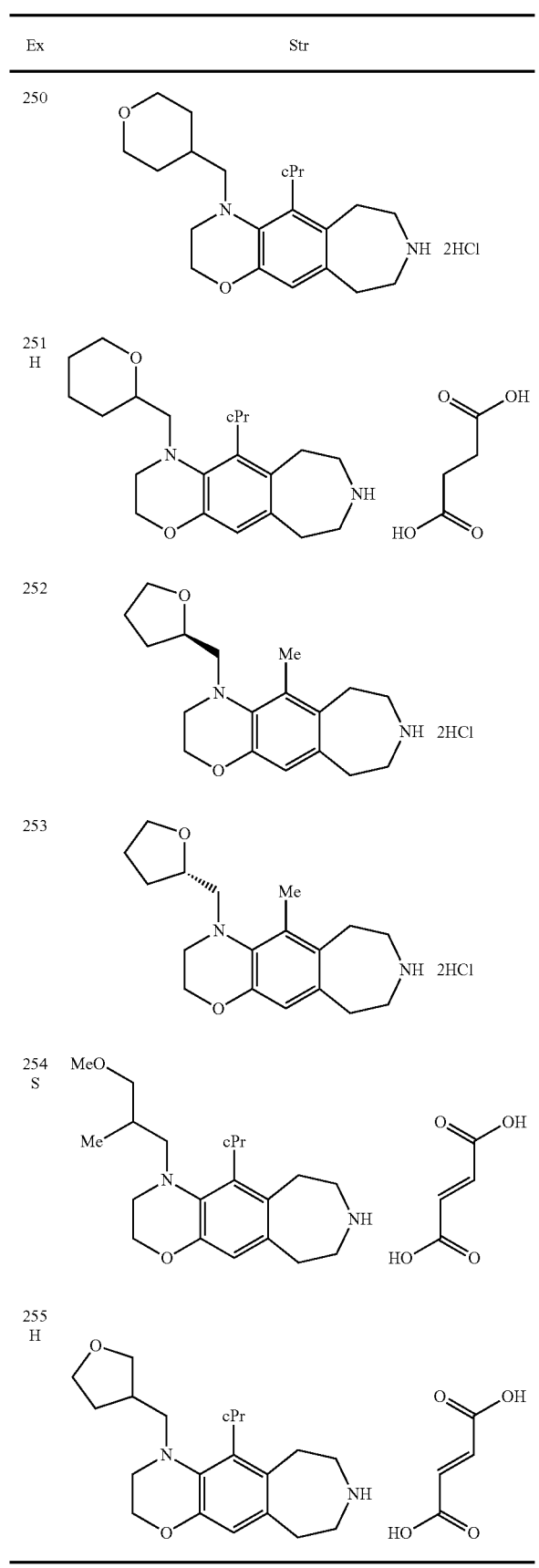
TABLE 136
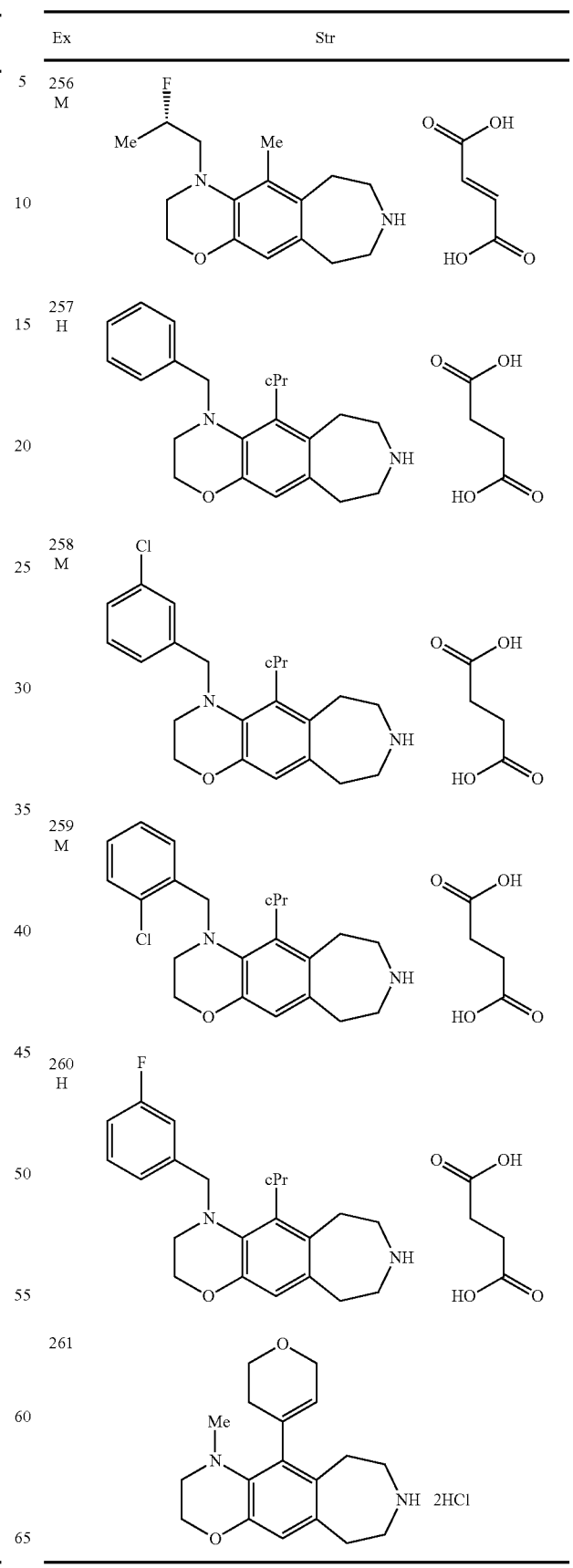

TABLE 137
| Ex | Str |
|---|---|
| 262 | 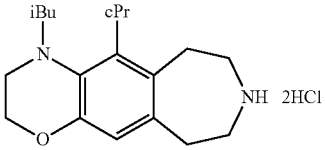 |
| 263 H | 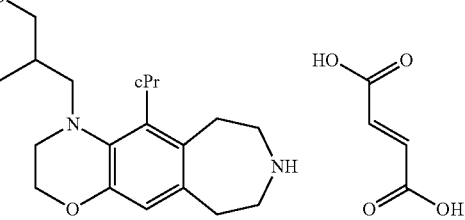 |
| 264 | 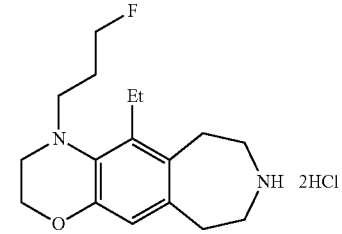 [SMILES: CCc1c2c(cc3c1N(CCCF)CCO3)CCNCC2 ; "2HCl"] |
| 265 H | 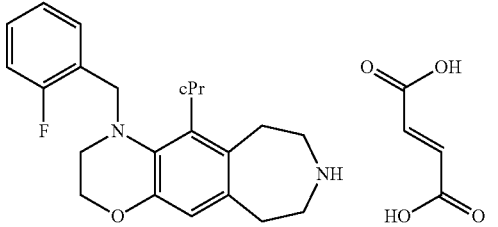 |
| 266 M | 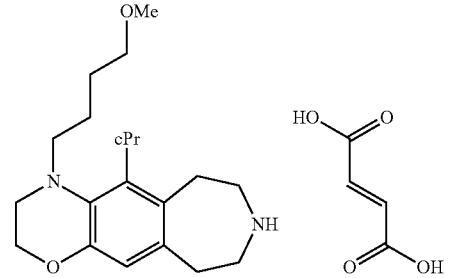 |
| 267 T | 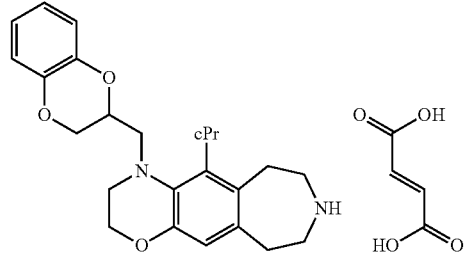 |
TABLE 138
| Ex | Str |
|---|---|
| 268 M | 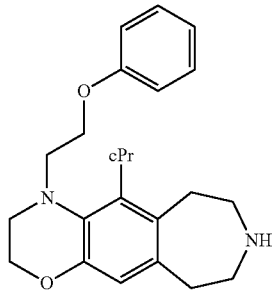 |
| 269 H |  |
| 270 M |  |
| 271 M |  |
| 272 M |  |

TABLE 139

| Ex | Str |
|---|---|
| 273 M | (structure) |
| 274 M | (structure) |
| 275 M | (structure) |
| 276 M | (structure) |
| 277 M | (structure) |

TABLE 140

| Ex | Str |
|---|---|
| 278 | (structure) HCl |
| 279 | (structure) 2HCl |
| 280 M | (structure) |
| 281 M | (structure) |
| 282 M | (structure) |
| 283 H | (structure) |

TABLE 141
| Ex | Str |
|---|---|
| 284 H | 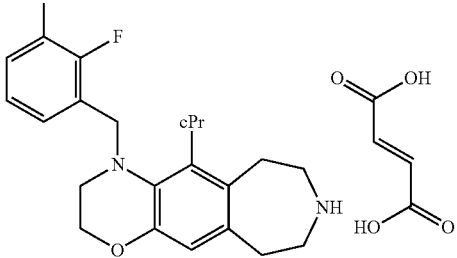 |
| 285 H | 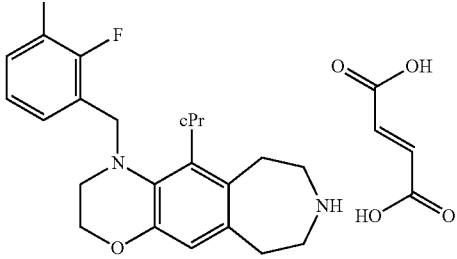 |
| 286 M | 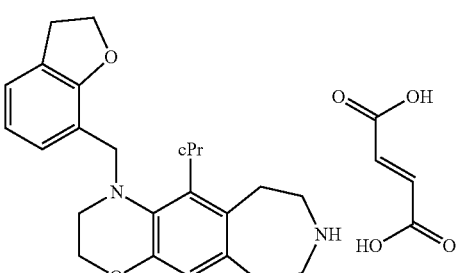 |
| 287 M | 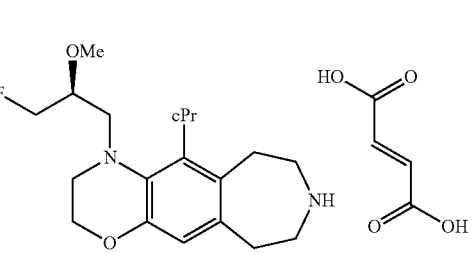 |
| 288 M | 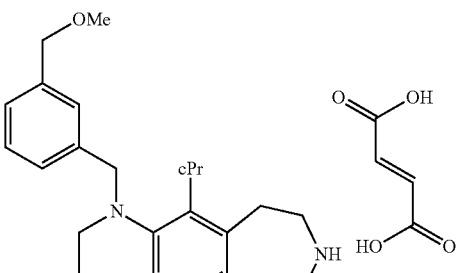 |
TABLE 142
| Ex | Str |
|---|---|
| 289 H | 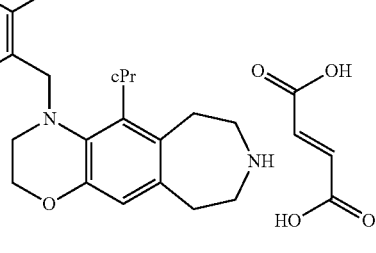 |
| 290 M | 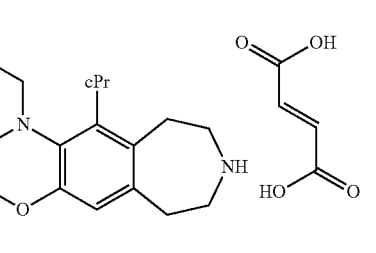 |
| 291 H | 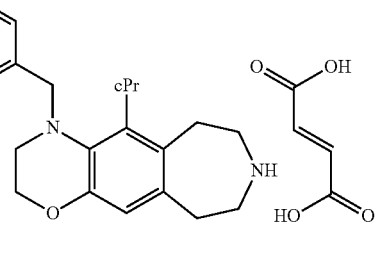 |
| 292 M | 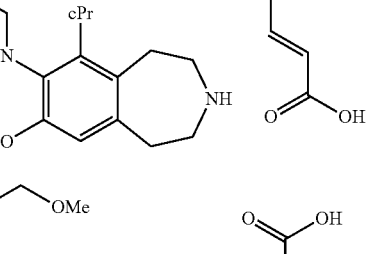 |
| 293 M | 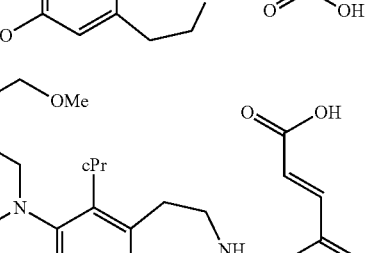 |
| 294 M | 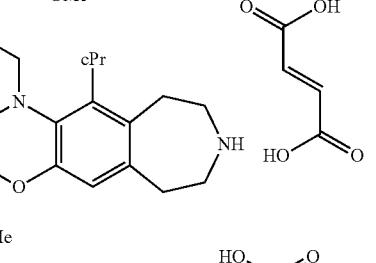 |

TABLE 143
| Ex | Str |
|---|---|
| 295 M | 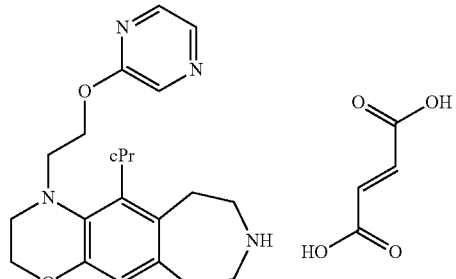 |
| 296 M | 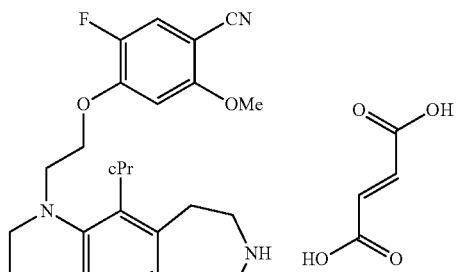 |
| 297 M | 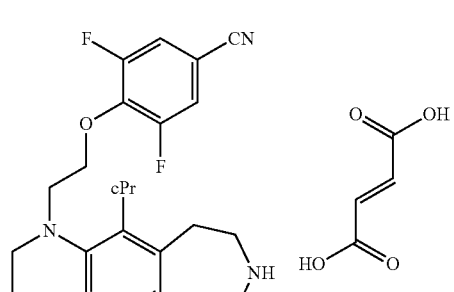 |
| 298 M | 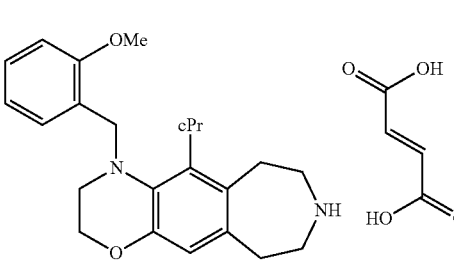 |
| 299 M | 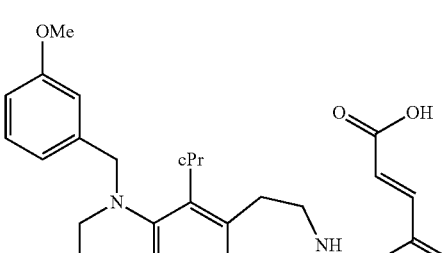 |
TABLE 144
| Ex | Str |
|---|---|
| 300 M | 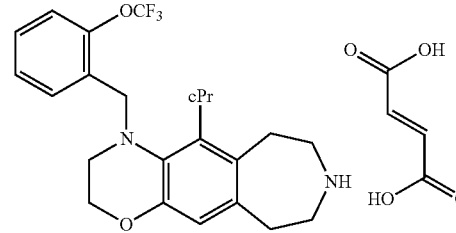 |
| 301 M | 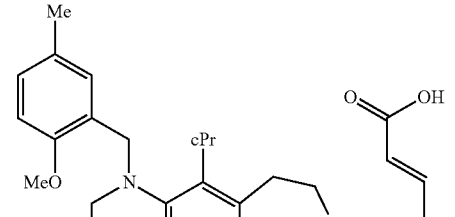 |
| 302 M | 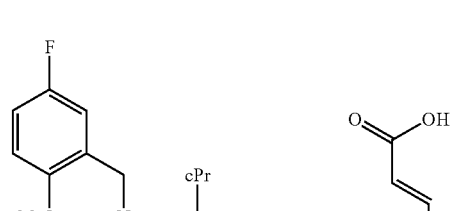 |
| 303 M | 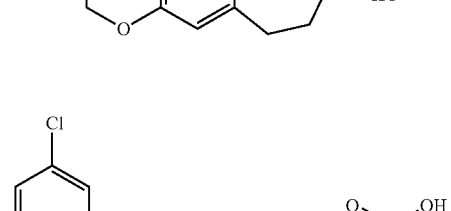 |
| 304 M | 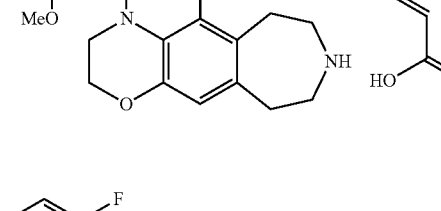 |

TABLE 145
| Ex | Str |
|---|---|
| 305 M | 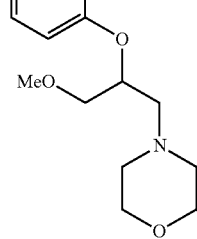 |
| 306 M | 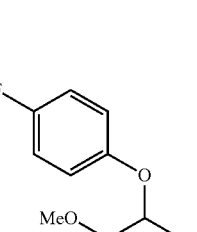 |
| 307 M | 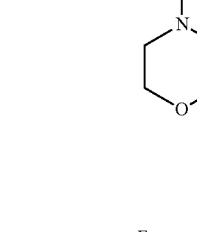 |
| 308 M | 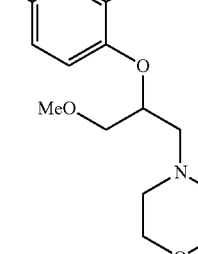 |
TABLE 146
| Ex | Str |
|---|---|
| 309 M | 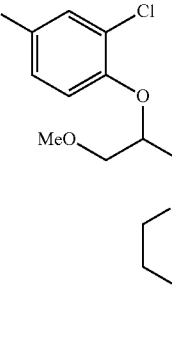 |
| 310 M | 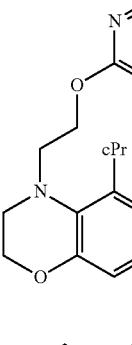 |
| 311 S | 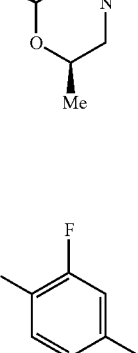 |
| 312 H |  |
| 313 H | 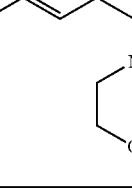 |

TABLE 147

| Ex | Str |
|---|---|
| 314 M | [structure: difluorophenyl-OEt with ethoxy linker to oxazine-fused benzazepine, cPr substituent; fumaric acid] |
| 315 M | [structure: (S)-2-ethoxypropyl on N of oxazine-fused benzazepine with cPr; fumaric acid] |
| 316 M | [structure: 2-methoxyethyl with Me-substituted oxazine fused benzazepine, cPr; fumaric acid] |
| 317 M | [structure: fluoromethyl-ethoxy propyl on oxazine-fused benzazepine with cPr; fumaric acid] |
| 318 | [structure: MeO-CH2-CH(Me)-CH2- on oxazine-fused benzazepine; 2HCl] |
| 319 | [structure: (S)-2-methoxypropyl on oxazine-fused benzazepine; 2HCl] |

TABLE 148

| Ex | Syn | Dat |
|---|---|---|
| 1 | 1 | ESI+: 251, 253<br>NMR: 2.44-2.53(3H, m), 2.72-2.74(4H, m), 2.79-2.85(4H, m), 3.02-3.04(2H, m), 6.93 (1H, s), 9.20(1H, s)<br>mp: 165-167 |
| 2 | 2 | ESI+: 293, 295<br>NMR: 0.96(6H, d, J = 6.5 Hz), 1.69-1.75(2H, m), 1.98-2.07(1H, m), 2.67-2.70(4H, m), 2.90-2.95(2H, m), 2.97-3.04(6H, m), 3.10-3.65(5H, m), 6.46(2H, s), 6.81(1H, s)<br>mp: 159-163 |
| 3 | 3 | ESI+: 203<br>NMR: 1.69-1.81(2H, m), 2.57(2H, t, J = 6.2 Hz), 2.75-2.86(4H, m), 2.94-3.06(4H, m), 3.08-3.15(2H, m), 6.23(1H, s), 6.44(2H, s), 6.62(1H, s) |
| 4 | 4 | ESI+: 231<br>NMR: 2.49-2.56(2H, m), 2.76-2.83(2H, m), 2.98-3.20(8H, m), 3.23(3H, s), 6.97(1H, s), 7.05(1H, s), 9.14(2H, s) |
| 5 | 5 | ESI+: 315<br>NMR: 0.22-0.32(1H, m), 0.38-0.49(1H, m), 0.97-1.07(2H, m), 1.50-1.70(2H, m), 2.17-2.30(1H, m), 2.31-2.43(1H, m), 2.51-2.61(1H, m), 2.74-3.18(8H, m), 3.30-3.42(1H, m), 3.34(3H, s), 3.73(1H, d, J = 14.3 Hz), 4.14(1H, d, J = 14.3 Hz), 4.70-4.81(1H, m), 6.85(1H, s) |
| 6 | 6 | ESI+: 275<br>NMR: 1.23(3H, t, J = 7.1 Hz), 1.78-1.86(2H, m), 2.66(2H, t, J = 6.6 Hz), 2.83-2.91(4H, m), 2.91-2.99(4H, m), 3.61-3.67(2H, m), 4.13(2H, q, J = 7.1 Hz), 6.40(1H, s), 6.88(1H, s), 7.43(1H, s)<br>mp: 178(decomp.) |
| 7 | 7 | ESI+: 274<br>NMR: 1.78-1.86(2H, m), 2.65(2H, t, J = 6.7 Hz), 2.76-2.86(10H, m), 2.86-2.94(4H, m), 3.36-3.41(2H, m), 6.39(1H, s), 6.56(1H, s), 6.83(1H, s)<br>mp: 230(decomp.) |
| 8 | 8 | ESI+: 274<br>NMR: 1.05(3H, t, J = 7.1 Hz), 1.74-1.82(2H, m), 2.62(2H, t, J = 6.5 Hz), 2.89-2.97(4H, m), 3.01-3.15(6H, m), 3.52(2H, m), 6.45(2H, s), 6.65(1H, t, J = 5.4 Hz), 6.89(1H, s), 7.25(1H, s)<br>mp: 174-176 |
| 9 | 9 | ESI+: 295<br>NMR: 1.20(3H, t, J = 7.3 Hz), 1.85-1.94(2H, m), 2.73(2H, t, J = 6.7 Hz), 2.91-3.00(4H, m), 3.00-3.10(4H, m), 3.23(2H, q, J = 7.3 Hz), 3.62-3.69(2H, m), 6.45(2H, s), 6.96(1H, s), 7.30(1H, s)<br>mp: 176(decomp.) |
| 10 | 2 | ESI+: 261<br>NMR: 1.75-1.83(2H, m), 2.55-2.62(2H, m), 2.78-2.84(2H, m), 2.84-2.90(2H, m), 2.94-3.06(4H, m), 3.20-3.28(2H, m), 3.26(3H, s), 3.34-3.41(2H, m), 3.44-3.50(2H, m), 6.40 (1H, s), 6.43(2H, s), 6.65(1H, s) |

TABLE 149

| Ex | Syn | Dat |
|---|---|---|
| 11 | 5 | ESI+: 313<br>NMR: 0.26-0.33(1H, m), 0.36-0.43(1H, m), 0.82(3H, d, J = 6.6 Hz), 0.92-1.05(2H, m), 1.15(3H, d, J = 6.9 Hz), 1.48-1.70(2H, m), 2.13-2.29(1H, m), 2.32-2.45(1H, m), 2.50-2.59 (1H, m), 2.62-3.13(9H, m), 3.35-3.45(1H, m), 4.67-4.78(1H, m), 6.84(1H, s) |
| 12 | 2 | ESI+: 237, 239<br>NMR: 1.73-1.79(2H, m), 2.64(2H, t, J = 6.2 Hz), 2.74-4.34(13H, m), 5.40(1H, m), 6.44(2H, s), 6.67(1H, s) |
| 13 | 2 | ESI+: 251, 253<br>NMR: 1.72-1.78(2H, m), 2.67-2.70(5H, m), 2.85-2.92(6H, m), 2.96-2.99(2H, m), 3.13-3.76(4H, m), 6.40(1H, s), 6.79(1H, s) |
| 14 | 2 | ESI+: 219<br>NMR: 2.78(3H, s), 2.81-2.87(2H, m), 2.87-2.93(2H, m), 2.98-3.09(4H, m), 3.13-3.19(2H, m), 4.15-4.21(2H, m), 6.44(2H, s), 6.50(1H, s), 6.54(1H, s) |
| 15 | 2 | ESI+: 279, 281<br>NMR: 1.58-3.32(16H, m), 4.05-4.12(0.35H, m), 4.51-4.58(0.65H, m), 7.04(0.35H, s), 7.16(0.65H, s), 9.06-9.18(2H, br) |

TABLE 149-continued

| Ex | Syn | Dat |
|----|-----|-----|
| 16 | 2 | ESI+: 265, 267<br>NMR: 1.19(3H, t, J = 6.9 Hz), 1.68-1.74(2H, m), 2.69(2H, t, J = 6.6 Hz), 2.85(2H, q, J = 6.9 Hz), 2.95-2.98(2H, m), 3.00-3.02(2H, m), 3.13-3.18(4H, m), 3.29-3.32(2H, m), 6.86(1H, s), 9.01-9.20(2H, br)<br>mp: 221-223 |
| 17 | 2 | ESI+: 219<br>NMR: 2.96-3.04(4H, m), 3.05-3.14(4H, m), 4.52(2H, s), 6.72(1H, s), 6.82(1H, s), 9.26-9.42(2H, br), 10.71(1H, s) |
| 18 | 2 | ESI+: 233<br>NMR: 3.01-3.19(8H, m), 3.25(3H, s), 4.61(2H, s), 6.88(1H, s), 7.05(1H, s), 9.33-9.47(2H, br) |
| 19 | 2 | FAB+: 233<br>NMR: 2.04(3H, s), 2.78(3H, s), 2.85-3.09(8H, br), 3.12-3.23(2H, m), 4.17-4.28(2H, m), 6.42(1H, s), 6.44(2H, s) |
| 20 | 2 | FAB+: 205<br>NMR: 2.75-2.89(4H, br), 2.93-3.08(4H, br), 3.15-3.31(2H, m), 3.99-4.13(2H, m), 5.17-5.93(0.7H, br), 6.36(1H, s), 6.44(1.8H, s), 6.46(1H, s)<br>mp: 192-195 |
| 21 | 2 | ESI+: 307, 309<br>NMR: 0.73(3H, d, J = 6.3 Hz), 1.07-1.19(4H, m), 1.54-2.19(2H, m), 2.38-2.75(6H, m), 3.07-3.39(6H, m), 4.14-4.27(0.15H, br), 4.49-4.55(0.85H, br), 7.01-7.20(1H, m), 9.00-9.27(2H, br)<br>mp: 245-249 |
| 22 | 2 | ESI+: 279, 281<br>NMR: 0.87(3H, t, J = 7.3 Hz), 1.64-1.73(4H, m), 2.65-2.68(2H, m), 2.72-2.76(2H, m), 2.84-2.91(6H, m), 2.96-2.98(2H, m), 3.02-3.70(4H, m), 6.41(1H, s), 6.77(1H, s) |
| 23 | 2 | ESI+: 295, 297<br>NMR: 1.69-1.75(2H, m), 2.67(2H, t, J = 6.4 Hz), 2.85-2.91(6H, m), 2.98(2H, t, J = 6.4 Hz), 3.02-3.04(2H, m), 3.10-3.60(6H, m), 3.67(2H, t, J = 6.4 Hz), 6.41(1H, s), 6.78(1H, s) |

TABLE 150

| Ex | Syn | Dat |
|----|-----|-----|
| 24 | 2 | ESI+: 217<br>NMR: 1.79-1.90(2H, m), 2.61(2H, t, J = 6.2 Hz), 2.79(3H, s), 2.74-2.93(4H, m), 2.94-3.07 (4H, m), 3.07-3.15(2H, m), 6.40(1H, s), 6.43(2H, s), 6.67(1H, s) |
| 25 | 2 | FAB+: 219<br>NMR: 2.02(3H, s), 2.65-2.95(8H, m), 3.15-3.28(2H, m), 4.05-4.14(2H, m), 5.32-5.54(1H, br), 6.21(1H, s), 6.37(1H, s) |
| 26 | 2 | FAB+: 233<br>NMR: 1.04(3H, t, J = 7.0 Hz), 2.78-2.94(4H, br), 2.95-3.08(4H, br), 3.15-3.24(2H, m), 3.28(2H, q, J = 7.0 Hz), 4.06-4.18(2H, m), 6.44(2H, s), 6.49(1H, s), 6.55(1H, s) |
| 27 | 2 | FAB+: 283, 285<br>NMR: 2.81-2.90(2H, m), 2.90-3.00(4H, m), 3.11-3.20(2H, m), 3.29-3.37(2H, m), 4.02-4.10(2H, m), 5.31-5.39(1H, br), 6.43(1.3H, s), 6.57(1H, s) |
| 28 | 2 | ESI+: 219<br>NMR: 1.99(3H, s), 2.74-2.83(2H, m), 2.86-2.97(6H, m), 3.24-3.31(2H, m), 3.98-4.06(2H, m), 4.86-5.09(1H, br), 6.37(1H, s), 6.38(1H, s) |
| 29 | 2 | ESI+: 283<br>NMR: 2.97-3.06(4H, m), 3.07-3.18(7H, m), 3.74-3.81(2H, m), 4.20-4.28(2H, m), 6.80 (1H, s), 7.40(1H, s), 9.28-9.42(2H, br) |
| 30 | 2 | ESI+: 247<br>NMR: 1.12(6H, d, J = 6.6 Hz), 2.87-3.14(8H, br), 3.15-3.25(2H, br), 4.02-4.20(3H, m), 6.57(1H, s), 6.75(1H, s), 9.31-9.52(2H, br) |
| 31 | 2 | ESI+: 233<br>NMR: 2.19(3H, s), 2.56(3H, s), 2.88-2.94(2H, m), 2.95-3.08(8H, m), 4.04-4.11(2H, m), 6.44(2H, s), 6.51(1H, s) |
| 32 | 2 | ESI+: 281, 283<br>NMR: 1.69-1.80(2H, m), 2.64(2H, t, J = 6.2 Hz), 2.80-2.89(2H, m), 2.89-3.01(4H, m), 3.13-3.21(2H, m), 3.21-3.29(2H, m), 6.42(1.4H, s), 6.69(1H, s) |

TABLE 150-continued

| Ex | Syn | Dat |
|----|-----|-----|
| 33 | 2 | ESI+: 245<br>NMR: 1.78-1.89(2H, m), 2.15(3H, s), 2.64(2H, t, J = 6.6 Hz), 2.88-3.08(8H, m), 3.64(2H, t, J = 6.2 Hz), 6.44(2H, s), 6.96(1H, s)<br>mp: 159-162 |
| 34 | 2 | ESI+: 231<br>NMR: 1.03(3H, t, J = 7.0 Hz), 1.78-1.87(2H, m), 2.59(2H, t, J = 6.2 Hz), 2.79-2.84(2H, m), 2.86-2.92(2H, m), 2.96-3.06(4H, m), 3.16(2H, t, J = 5.5 Hz), 3.28(2H, q, J = 7.0 Hz), 6.41(1H, s), 6.43(2H, s), 6.65(1H, s) |
| 35 | 2 | ESI+: 297, 299<br>NMR: 2.72(3H, s), 2.93-3.12(8H, m), 3.23-3.33(2H, m), 4.08-4.20(2H, m), 6.46(2H, s), 6.72(1H, s)<br>mp: 200-204 |
| 36 | 2 | ESI+: 245<br>NMR: 0.50-0.64(2H, m), 0.99-1.12(2H, m), 1.57-1.68(1H, m), 2.90-3.01(2H, m), 3.04-3.17(4H, m), 3.23-3.34(2H, m), 3.36-3.47(2H, m), 4.20-4.33(2H, br), 6.62(1H, s), 9.19-9.38(2H, br)<br>mp: 193-197 |

TABLE 151

| Ex | Syn | Dat |
|----|-----|-----|
| 37 | 2 | ESI+: 273<br>NMR: 1.01(6H, d, J = 6.6 Hz), 1.78-1.90(2H, m), 2.64(2H, t, J = 6.8 Hz), 2.91-3.14(9H, m), 3.64(2H, t, J = 6.2 Hz), 6.46(2H, s), 7.00(1H, s), 7.09-7.24(1H, br) |
| 38 | 2 | ESI+: 259<br>NMR: 0.89(6H, d, J = 6.5 Hz), 1.76-1.84(2H, m), 1.92-2.04(1H, m), 2.60(2H, t, J = 6.3 Hz), 2.77-2.84(2H, m), 2.85-2.91(2H, m), 2.97(2H, d, J = 7.4 Hz), 2.97-3.06(4H, m), 3.16-3.25(2H, m), 6.33(1H, s), 6.44(2H, s), 6.65(1H, s) |
| 39 | 2 | ESI+: 305, 307<br>NMR: 0.52-0.98(4H, m), 1.43-2.77(6H, m), 2.89-4.33(11H,), 4.42-4.54(1H, m), 6.48(2H, s), 6.97-7.11(1H, m) |
| 40 | 2 | ESI+: 319, 321<br>NMR: 1.39-4.80(24H, m), 6.48(2H, s), 6.99(0.4H, s), 7.08(0.6H, s) |
| 41 | 2 | ESI+: 291, 293<br>NMR: 0.17-0.20(2H, m), 0.47-0.52(2H, m), 1.04-1.15(1H, m), 1.69-1.75(2H, m), 2.67 (2H, t, J = 6.7 Hz), 2.74(2H, d, J = 6.4 Hz), 2.85-2.91(6H, m), 3.05-3.80(6H, m), 6.41(1H, s), 6.78(1H, s) |
| 42 | 2 | ESI+: 305, 307<br>NMR: 1.69-1.92(6H, m), 1.99-2.05(2H, m), 2.65-2.75(3H, m), 2.82-3.95(15H, m), 6.46 (2H, s), 6.80(1H, s)<br>mp: 141-143 |
| 43 | 2 | ESI+: 333, 335<br>NMR: 1.18-2.12(10H, m), 2.32-2.75(4H, m), 2.92-4.18(11H, m), 4.18-4.29(0.25H, br), 4.48-4.59(0.75H, br), 6.48(2H, s), 6.99(0.25H, s), 7.11(0.75H, s) |
| 44 | 2 | ESI+: 341, 343<br>NMR: 11.68-1.83(1H, br), 2.64-2.82(2H, m), 2.82-4.02(14H, m), 6.48(2H, s), 7.08(1H, s), 7.14-7.71(5H, br) |
| 45 | 2 | ESI+: 319, 321<br>NMR: 1.30-1.38(2H, m), 1.47-1.63(4H, m), 1.70-1.77(4H, m), 2.28(1H, quint, J = 7.5 Hz), 2.68(2H, t, J = 6.7 Hz), 2.82(2H, d, J = 7.3 Hz), 2.91-2.94(2H, m), 2.99-3.05(6H, m), 3.11-3.71(5H, m), 6.46(2H, s), 6.81(1H, s)<br>mp: 151-153 |
| 46 | 2 | ESI+: 327, 329<br>NMR: 1.72-1.78(2H, m), 2.74(2H, t, J = 6.6 Hz), 2.81-2.84(2H, m), 3.05-3.07(2H, m), 3.15-3.20(4H, m), 3.32-3.35(2H, m), 4.09(2H, s), 6.93(1H, s), 7.28(1H, t, J = 7.4 Hz), 7.37(2H, t, J = 7.4 Hz), 7.54(2H, d, J = 7.4 Hz), 9.0-9.30(2H, br) |

TABLE 151-continued

| Ex | Syn | Dat |
|---|---|---|
| 47 | 2 | ESI+: 347, 348<br>NMR: 0.73-3.85(26H, m), 4.13-4.24(0.2H, br), 4.46-4.55(0.8H, br), 6.45(1H, s), 6.93-7.00(0.2H, br), 7.08(0.8H, s) |
| 48 | 2 | ESI+: 333, 335<br>NMR: 0.94-1.04(2H, m), 1.13-1.27(3H, m), 1.62-1.75(6H, m), 1.83(2H, d, J = 12.8 Hz), 2.66-2.72(4H, m), 2.91-2.94(2H, m), 2.99-3.03(6H, m), 3.11-3.74(5H, m), 6.46(2H, s), 6.81(1H, s) |
| 49 | 2 | ESI+: 217<br>NMR: 1.69-1.79(2H, m), 1.95(3H, s), 2.61(2H, t, J = 6.2 Hz), 2.79-2.87(2H, m), 2.93-3.05 (6H, m), 3.21(2H, t, J = 5.3 Hz), 6.44(2H, s), 6.54(1H, s) |

TABLE 152

| Ex | Syn | Dat |
|---|---|---|
| 50 | 2 | ESI+: 219<br>NMR: 1.33(3H, d, J = 6.4 Hz), 2.91-3.22(9H, m), 3.44-3.54(1H, m), 4.26-4.37(1H, m), 6.75(1H, s), 6.87(1H, s), 9.36-9.58(2H, br)<br>mp: 193-194 |
| 51 | 2 | ESI+: 279<br>NMR: 1.79-1.97(2H, m), 2.58-2.69(2H, m), 2.69-2.80(2H, m), 2.93-3.08(4H, m), 3.08-3.23(4H, m), 6.95(1H, s), 7.15-7.29(2H, m), 7.37-7.56(3H, m), 9.11-9.33(2H, m) |
| 52 | 2 | FAB+; 231<br>NMR: 1.67-1.79(2H, m), 2.18(3H, s), 2.53(3H, s), 2.66(2H, t, J = 6.6 Hz), 2.85-2.93(2H, m), 2.93-3.06(8H, m), 6.43(2H, s), 6.67(1H, s) |
| 53 | 2 | ESI+: 263<br>NMR: 2.80-2.94(4H, m), 2.96-3.09(4H, m), 3.26(3H, s), 3.29-3.34(2H, m), 3.38(2H, t, J = 5.4 Hz), 3.50(2H, t, J = 5.4 Hz), 4.04-4.12(2H, m), 6.44(1.8H, s), 6.50(1H, s), 6.54(1H, s) |
| 54 | 2 | ESI+: 233<br>NMR-A: 1.26(3H, d, J = 6.3 Hz), 2.74-2.98(8H, m), 3.06-3.18(4H, br), 3.19-3.26(1H, m), 4.18-4.28(1H, m), 6.54(1H, s), 6.56(1H, s), 6.64(1H, s), 8.65-8.98(2H, br) |
| 55 | 2 | ESI+: 261<br>NMR: 1.05(3H, d, J = 6.5 Hz), 1.12(3H, d, J = 6.5 Hz), 1.26(3H, d, J = 6.2 Hz), 2.63-2.73(1H, m), 2.76-3.12(8H, m), 3.19-3.30(1H, m), 3.98-4.13(2H, m), 6.44(1.7H, s), 6.50(1H, s), 6.62(1H, s) |
| 56 | 2 | ESI+: 259<br>NMR: 0.18-0.32(2H, m), 0.41-0.57(2H, m), 0.92-1.08(1H, m), 2.83-3.22(10H, m), 3.30-3.48(2H, m), 4.10-4.24(2H, m), 6.57(1H, s), 6.73(1H, s), 9.27-9.55(2H, br)<br>mp: 179-182 |
| 57 | 2 | ESI+: 275<br>NMR: 1.06(6H, d, J = 6.6 Hz), 2.94-3.04(4H, m), 3.08-3.19(5H, m), 3.80-3.90(2H, m), 4.16-4.28(2H, m), 6.76(1H, s), 7.25-7.86(1H, br), 9.10-9.36(2H, br) |
| 58 | 2 | ESI+: 261<br>NMR: 0.90(6H, d, J = 6.7 Hz), 1.91-2.05(1H, m), 2.82-2.99(6H, m), 3.05-3.15(4H, br), 3.24-3.30(2H, m), 4.07-4.12(2H, m), 6.50(1H, s), 6.52(1H, s), 8.80-8.96(2H, br)<br>mp: 157 |
| 59 | 2 | ESI+: 277<br>NMR: 1.68-1.80(2H, m), 2.77-2.92(4H, m), 2.96-3.09(4H, m), 3.17-3.30(7H, m), 3.36 (2H, t, J = 6.1 Hz), 4.05-4.15 (2H, m), 6.44(2H, s), 6.49(1H, s), 6.51(1H, s)<br>mp: 141-145 |
| 60 | 1 | ESI+: 337<br>NMR: 1.70-1.80(2H, m), 2.36-2.42(2H, m), 2.66-2.80(4H, m), 2.86-2.93(2H, m), 2.97-3.07(4H, m), 3.02(3H, s), 3.11-3.17(2H, m), 3.21-3.28(2H, m), 6.82(1H, s), 7.07-7.13(2H, m), 7.28-7.34(1H, m), 7.36-7.42(2H, m) |
| 61 | 2 | ESI+: 261<br>NMR: 0.92(3H, t, J = 7.3 Hz), 1.26-1.40(2H, m), 1.45-1.58(2H, m), 2.85-3.14(8H, m), 3.16-3.34(4H, m), 4.08-4.23(2H, m), 6.54(1H, s), 6.60(1H, s), 9.30-9.54(2H, br) |
| 62 | 2 | ESI+: 295<br>NMR: 2.70-2.97(8H, m), 3.22-3.31(2H, m), 4.10-4.20(2H, m), |

TABLE 152-continued

| Ex | Syn | Dat |
|---|---|---|
| | | 4.42(2H, s), 6.39(1H, s), 6.51(1H, s), 6.55(1H, s), 7.21-7.40(5H, m) |

TABLE 153

| Ex | Syn | Dat |
|---|---|---|
| 63 | 2 | ESI+: 277<br>NMR: 1.10(3H, t, J = 6.9 Hz), 2.78-2.95(4H, m), 2.97-3.10(4H, m), 3.29-3.48(6H, m), 3.53 (2H, t, J = 5.7 Hz), 4.04-4.12(2H, m), 6.44(1.8H, s), 6.50(1H, s), 6.55(1H, s) |
| 64 | 2 | ESI+: 303<br>NMR: 1.17-1.32(2H, m), 1.52-1.64(2H, br), 1.85-2.00(1H, m), 2.81-3.18(10H, m), 3.21-3.36(4H, m), 3.79-3.92(2H, m), 4.02-4.17(2H, m), 6.51(1H, s), 6.54(1H, s), 9.30-9.52(2H, br) |
| 65 | 2 | ESI+: 281<br>NMR: 2.59-2.70(2H, m), 2.90-3.17(6H, m), 3.20-3.32(2H, m), 4.14-4.24(2H, m), 6.73(1H, s), 7.19-7.30(2H, m), 7.39-7.54(3H, m), 9.29-9.49(2H, br) |
| 66 | 2 | ESI+: 309<br>NMR: 1.66-1.78(2H, m), 2.51-2.58(2H, m), 2.61-2.70(2H, m), 2.82-2.95(4H, m), 2.97-3.12(4H, m), 3.76(3H, s), 6.43(2H, s), 6.65(1H, d, J = 2.0 Hz), 6.67(1H, d, J = 7.7 Hz), 6.72(1H, s), 6.94(1H, dd, J = 2.0, 7.8 Hz), 7.38(1H, dd, J = 7.7, 7.8 Hz) |
| 67 | 2 | ESI+: 313, 315<br>NMR: 1.64-1.80(2H, m), 2.46-2.56(2H, m), 2.66(2H, t, J = 6.2 Hz), 2.79-2.93(3H, m), 2.94-3.02(2H, m), 3.03-3.13(2H, m), 3.88-3.99(1H, br), 6.40(1.5H, s), 6.73(1H, s), 7.03-7.10 (1H, m), 7.12-7.16(1H, m) 7.40-7.46(1H, m) 7.49(1H, dd, J = 7.6, 7.9 Hz)<br>mp: 159-162 |
| 68 | 2 | ESI+: 347, 349<br>NMR: 1.66-1.78(2H, m), 2.41-2.47(2H, m), 2.65(2H, t, J = 6.2 Hz), 2.72-2.84(4H, m), 2.84-2.94(2H, m), 3.01-3.11(2H, m), 4.08-4.15(1H, br), 6.37(1H, s), 6.71(1H, s), 7.07(1H, dd, J = 1.8, 8.2 Hz), 7.32(1H, d, J = 1.8 Hz), 7.68(1H, d, J = 8.2 Hz) |
| 69 | 2 | ESI+: 371, 373<br>NMR: 1.62-1.73(2H, m), 2.38-2.45(2H, m), 2.52-2.65(4H, m), 2.66-2.73(2H, m), 2.74-2.83(2H, m), 2.84-2.99(6H, m), 2.95 (3H, s), 6.38(1H, s), 6.84(1H, s), 7.07-7.12(1H, m), 7.17-7.21(1H, m), 7.38-7.50(2H, m) |
| 70 | 2 | ESI+: 405, 407<br>NMR: 1.61-1.73(2H, m), 2.39-2.74(8H, m), 2.77-2.99(8H, m), 2.96(3H, s), 6.40(0.8H, s), 6.87(1H, s), 7.13(1H, dd), 7.41(1H, d, J = 1.8 Hz), 7.70(1H, d, J = 8.2 Hz) |
| 71 | 2 | ESI+: 275<br>NMR: 2.47-2.53(2H, m), 2.71-2.80(2H, m), 2.88-3.08(8H, m), 3.24(3H, s), 3.48(2H, t, J = 6.1 Hz), 4.02(2H, t, J = 6.1 Hz), 6.44(1.7H, s), 6.99(1H, s), 7.01(1H, s)<br>mp: 164-166 |
| 72 | 2 | ESI+: 365<br>NMR: 0.34(3H, d, J = 6.8 Hz), 0.35(3H, d, J = 6.8 Hz), 1.13-1.29(1H, m), 1.58-1.78(2H, m), 2.18-2.36(2H, m), 2.56-2.66 (2H, m), 2.71(2H, t, J = 6.6 Hz), 2.81-3.09(8H, m), 3.74(3H, s), 6.42(2H, s), 6.63-6.73(2H, m), 6.85(1H, s), 6.88(1H, dd, J = 1.8, 7.8 Hz), 7.30(1H, dd, J = 7.7, 7.8 Hz) |
| 73 | 2 | ESI+: 367<br>NMR: 1.61-1.73(2H, m), 2.30-2.50(4H, m), 2.53-2.60(2H, m), 2.60-2.73(4H, m), 2.73-2.81(2H, m), 2.82-2.97(4H, m), 2.93 (3H, s), 3.75(3H, s), 6.37(1H, s), 6.66-6.70(2H, m), 6.80 (1H, s), 6.88-6.93(1H, m), 7.33(1H, dd, J = 7.9, 8.2 Hz) |
| 74 | 2 | ESI+: 243<br>NMR: 0.23-0.33(2H, m), 0.98-1.08(2H, m), 1.29-1.39(1H, m), 1.70-1.81(2H, m), 2.60(2H, t, J = 6.2 Hz), 2.76-2.85(2H, m), 2.92-3.08(4H, m), 3.13-3.23(2H, m), 3.23-3.29(2H, m), 4.97(1H, s), 6.42(2H, s), 6.57(1H, s) |

TABLE 154

| Ex | Syn | Dat |
|---|---|---|
| 75 | 2 | ESI+: 355<br>NMR: 1.70-1.81(2H, m), 2.47-2.53(2H, m), 2.61-2.66(2H, m), 2.66-2.74(2H, m), 2.79 (2H, t, J = 6.6 Hz), 2.82-2.89(2H, m), 2.90-3.05(6H, m), 3.04(3H, s), 6.47 (1H, s), 6.92(1H, s), 7.01-7.10(2H, m), 7.21-7.31(1H, m), 7.51-7.60(1H, dd, J = 7.1, 14.4 Hz) |
| 76 | 2 | ESI+: 291<br>NMR: 1.07(6H, d, J = 6.1 Hz), 2.79-2.94(4H, m), 2.96-3.10(4H, m), 3.28-3.41(4H, m), 3.48-3.59(3H, m), 4.04-4.13(2H, m), 6.44(1.8H, s), 6.50(1H, s), 6.54(1H, s)<br>mp: 135 |
| 77 | 2 | ESI+: 289<br>NMR: 1.51-1.64(1H, m), 1.92-2.04(1H, m), 2.54-2.65 (1H, m), 2.84-3.35(12H, m),3.38-3.49(1H, m), 3.58-3.68 (1H, m), 3.69-3.84(2H, m), 4.06-4.15(2H, m), 6.53(1H, s), 6.59(1H, s), 9.28-9.54(2H, br) |
| 78 | 2 | ESI+: 353<br>NMR: 2.34(3H, s), 2.39-2.48(2H, m), 2.54-2.65(4H, m), 2.77-3.09(11H, m), 3.96-4.08(2H, m), 6.40(1.5H, s), 6.67(1H, s), 6.93(1H, d, J = 7.6 Hz), 6.98(1H, d, J = 7.6 Hz), 7.33(1H, t, J = 7.6 Hz)<br>mp: 173-176 |
| 79 | 2 | ESI+: 295<br>NMR: 2.35(3H, s), 2.52-2.61(2H, m), 2.81-2.97(4H, m), 2.97-3.12(2H, m), 3.12-3.25(2H, m), 3.92-4.12(3H, m), 6.42(1.8H, s), 6.57(1H, s), 6.92(1H, d, J = 7.7 Hz), 6.95(1H, s), 7.19(1H, d, J = 7.7 Hz), 7.36(1H, t, J = 7.7 Hz) |
| 80 | 2 | ESI+: 299<br>NMR: 0.29-0.38(2H, m), 0.81(6H, d, J = 6.7 Hz), 0.89-1.00(2H, m), 1.54-1.66(1H, m), 1.66-1.77(2H, m), 1.84-1.99(1H, m), 2.58(2H, t, J = 6.3 Hz), 2.78-2.85(4H, m), 2.92(2H, d, J = 7.3 Hz), 2.94-3.05(4H, m), 3.07-3.17(2H, m), 3.17-3.25(2H, m), 6.40(1H, s), 6.62(1H, s) |
| 81 | 2 | ESI+: 301<br>NMR: 0.30-0.42(2H, m), 0.93-1.04(2H, m), 1.57-1.74(3H, m), 2.61(2H, t, J = 6.4 Hz), 2.83-2.94(2H, m), 2.98-3.32(13H, m), 3.56(2H, t, J = 6.2 Hz), 6.43(2H, s), 6.65(1H, s) |
| 82 | 2 | ESI+: 291<br>NMR: 1.29(3H, d, J = 7.3 Hz), 2.73(1H, dd, J = 12.0, 7.3 Hz), 2.80-3.00(5H, m), 3.11-3.18 (1H, m), 3.25(3H, s), 3.53(2H, t, J = 5.6 Hz), 4.01-4.12(2H, m), 4.58(2H, s), 6.44(1H, s), 6.79(1H, s), 7.04(1H, s) |
| 83 | 2 | ESI+: 305<br>NMR: 1.32(3H, d, J = 7.4 Hz), 1.79(2H, quint, J = 6.6 Hz), 2.80(1H, dd, J = 13.0, 7.4 Hz), 2.85-3.09(5H, m), 3.20-3.28(4H, m), 3.36(2H, t, J = 6.6 Hz), 3.94(2H, t, J = 6.6 Hz), 4.57(2H, s), 6.48(1H, s), 6.83(1H, s), 6.96(1H, s) |
| 84 | 2 | ESI+: 277<br>NMR: 1.27(3H, d, J = 7.2 Hz), 2.77-2.88(4H, m), 3.02-3.14(3H, m), 3.26(3H, s), 3.31-3.33(2H, m), 3.38-3.41(2H, m), 3.51(2H, t, J = 5.5 Hz), 4.07-4.09(2H, m), 6.45(2H, s), 6.48(1H, s), 6.51(1H, s) |
| 85 | 2 | ESI+: 291<br>NMR: 1.28(3H, d, J = 7.2 Hz), 1.74(2H, quint, J = 6.3 Hz), 2.76-2.89(4H, m), 3.04-3.16(3H, m), 3.22-3.29(7H, m), 3.37(2H, t, J = 6.3 Hz), 4.10-4.12(2H, m), 6.45(2H, s), 6.48(1H, s), 6.50(1H, s) |

TABLE 155

| Ex | Syn | Dat |
|---|---|---|
| 86 | 2 | ESI+: 289<br>NMR: 1.53-1.62(2H, br), 1.62-1.77(2H, m), 2.84-3.15(8H, m), 3.16-3.26(2H, m), 3.45 (2H, t, J = 11.2 Hz), 3.80-3.97(3H, m), 4.05-4.14(2H, m), 6.54(1H, s), 6.75(1H, s), 9.24-9.48(1.8H, br) |
| 87 | 2 | ESI+: 245<br>NMR: 1.31(6H, d, J = 7.1 Hz), 1.83-1.95(2H, m), 2.68-2.80(2H, m), 2.97-3.27(8H, m), 3.27-3.45(3H, m), 6.94 (1H, s), 9.27(2H, s) |
| 88 | 2 | ESI+: 303<br>NMR: 0.41-0.48(2H, m), 0.96-1.03(2H, m), 1.56-1.64 (1H, m), 2.75-2.85(2H, m), 2.85-2.97(4H, m), 3.08-3.18(6H, m), 3.25(3H, s), 3.62(2H, t, J = 6.0 Hz), 3.97-4.03(2H, m), 6.38(1H, s), 6.47(1H, s) |
| 89 | 2 | ESI+: 303<br>NMR: 1.23(6H, d, J = 7.1 Hz), 1.65-1.81(2H, m), 2.63-2.70(2H, m), 2.76-2.91(4H, m), 2.93-3.15(8H, m), 3.29(3H, s), 3.58(2H, t, J = 6.2 Hz), 3.85-3.99(1H, m), 6.43(2H, s), 6.68(1H, s) |
| 90 | 2 | ESI+: 277<br>NMR: 2.18(3H, s), 2.80-2.86(2H, m), 2.87-2.93(2H, m), 2.94-3.10(8H, m), 3.30(3H, s), 3.61(2H, t, J = 5.8 Hz), 4.02-4.08(2H, m), 6.42(1.7H, s), 6.49(1H, s)<br>mp: 166-170 |
| 91 | 2 | ESI+: 273<br>NMR: 1.46-1.84(8H, m), 2.79-2.94(4H, m), 2.95-3.07 (4H, m), 3.12-3.19(2H, m), 4.08-4.22(3H, m), 6.43(1.7H, s), 6.49(1H, s), 6.67(1H, s) |
| 92 | 2 | ESI+: 281<br>NMR: 2.66-2.74(2H, m), 2.77-2.97(6H, m), 3.60-3.70(2H, m), 4.15-4.22(2H, m), 6.38(1H, s), 6.62-6.66(2H, br), 7.02-7.09(1H, m), 7.18-7.25(2H, m), 7.31-7.39(2H, m)<br>mp: 220-222 |
| 93 | 2 | ESI+: 317<br>NMR: 0.43-0.49(1H, m), 0.61-0.66(1H, m), 0.98-1.05(2H, m), 1.28(3H, d, J = 7.4 Hz), 1.60-1.67(1H, m), 2.61-2.67(2H, m), 2.90-2.93(1H, m), 3.04-3.25(8H, m), 3.32(2H, dd, J = 13.2, 4.8 Hz), 3.62(2H, t, J = 5.9 Hz), 3.97-4.03(2H, m), 4.14-4.20(1H, m), 6.44-6.46(3H, m) |
| 94 | 2 | ESI+: 275<br>NMR: 1.67-1.73(2H, m), 2.15(3H, s), 2.64(2H, t, J = 6.7 Hz), 2.79-2.84(4H, m), 2.88-2.93(6H, m), 3.02-3.04(2H, m), 3.28(3H, s), 3.59(2H, t, J = 6.2 Hz), 6.37(1H, s), 6.62(1H, s) |
| 95 | 2 | ESI+: 261<br>NMR: 1.67-1.73(2H, m), 2.17(3H, s), 2.65(2H, t, J = 6.7 Hz), 2.72(2H, t, J = 6.7 Hz), 2.89-2.91(2H, m), 2.99-3.04(8H, m), 3.66(2H, t, J = 6.7 Hz), 6.43(2H, s), 6.66(1H, s) |
| 96 | 2 | ESI+: 231<br>NMR: 1.08(3H, t, J = 7.3 Hz), 1.88-1.98(2H, m), 2.62-2.79 (4H, m), 2.98-3.18(8H, m), 3.27-3.37(2H, m), 6.92(1H, s), 9.33(2H, s) |
| 97 | 2 | ESI+: 289<br>NMR: 1.03(3H, t, J = 7.4 Hz), 1.68-1.78(2H, m), 2.66(2H, t, J = 6.9 Hz), 2.72(2H, q, J = 7.4 Hz), 2.86(2H, t, J = 6.3 Hz), 2.90-2.95(2H, m), 2.95-3.05(4H, m), 3.06-3.13(4H, m), 3.30(3H, s), 3.59(2H, t, J = 6.3 Hz), 6.52(2H, s), 6.69(1H, s) |

TABLE 156

| Ex | Syn | Dat |
|---|---|---|
| 98 | 2 | ESI+: 291<br>NMR: 1.04(3H, t, J = 7.4 Hz), 2.71(2H, q, J = 7.4 Hz), 2.84-2.93(4H, m), 2.94-3.08(8H, m), 3.31(3H, s), 3.61 (2H, t, J = 5.9 Hz), 4.06-4.12(2H, m), 6.44(2H, s), 6.50 (1H, s)<br>mp: 159-163 |
| 99 | 2 | ESI+: 277<br>NMR: 1.07(3H, d, J = 6.7 Hz), 2.79-2.94(4H, m), 2.97-3.09(4H, m), 3.14-3.22(2H, m), 3.24(3H, s), 3.32-3.39 (1H, m), 3.41-3.48(1H, m), 4.01-4.11(3H, m), 6.44(2H, s), 6.50(1H, s), 6.63(1H, s) |
| 100 | 2 | ESI+: 259<br>NMR: 0.88(6H, d, J = 6.6 Hz), 1.77-1.98(3H, m), 2.54-2.78(4H, m), 2.91-3.17(8H, m), 3.26-3.33(2H, m), 6.88 (1H, s), 9.34(2H, s) |
| 101 | 2 | ESI+: 305<br>NMR: 1.24(6H, d, J = 7.4 Hz), 2.80-2.92(4H, m), 2.98-3.13(8H, m), 3.30(3H, s), 3.60(2H, t, J = 5.9 Hz), 3.80-3.97(1H, m), 4.04-4.12(2H, m), 6.43(1.8H, s), 6.51(1H, s) |

TABLE 156-continued

| Ex | Syn | Dat |
|---|---|---|
| 102 | 2 | ESI+: 319<br>NMR: 1.01(3H, t, J = 7.2 Hz), 1.62-1.87(2H, m), 2.62-2.82(6H, m), 2.85-3.07(8H, m), 3.16-3.28(2H, m), 3.26(3H, s), 3.30(2H, d, J = 5.5 Hz), 3.91-3.99(1H, m), 6.43(2H, s), 6.67(1H, s) |
| 103 | 2 | ESI+: 265<br>NMR: 1.83-1.98(2H, m), 2.85-3.00(4H, m), 3.01-3.14(4H, br), 3.22-3.29(2H, m), 3.29-3.37(2H, m), 4.09-4.18(2H, m), 4.53(2H, dt, J = 47.4, 5.8 Hz), 6.54(1H, s), 6.57(1H, s), 9.30-9.46(2H, br) |
| 104 | 2 | ESI+: 317<br>NMR: 0.40-0.50(2H, m), 0.96-1.05(2H, m), 1.10(3H, t, J = 7.0 Hz), 1.58-1.67(1H, m), 2.84-2.92(2H, m), 2.99-3.18(8H, m), 3.18-3.27(2H, m), 3.43(2H, q, J = 7.0 Hz), 3.65(2H, t, J = 6.0 Hz), 3.98-4.05(2H, m), 6.44(1.8H, s), 6.52 (1H, s)<br>mp: 140-145 |
| 105 | 2 | ESI+: 343<br>NMR: 0.35-0.56(6H, m), 0.97-1.08(2H, m), 1.64-1.75(1H, m), 2.90-2.98(2H, m), 3.00-3.36(15H, m), 4.04-4.13(2H, m), 6.54(1H, s), 9.24-9.38(1.8H, br)<br>mp: 166-167 |
| 106 | 2 | ESI+: 317<br>NMR: 0.39-0.47(2H, m), 0.95-1.03(2H, m), 1.56-1.65(1H, m), 1.82-1.92(2H, m), 2.78-2.85(2H, m), 2.87-3.00(6H, m), 3.02-3.08(2H, m), 3.13-3.23(5H, m), 3.34(2H, t, J = 6.2 Hz), 3.95-4.01(2H, m), 6.37(1H, s), 6.48(1H, s)<br>mp: 169-171 |
| 107 | 2 | ESI+: 351<br>NMR: 1.29(3H, d, J = 7.2 Hz), 1.84(2H, quint, J = 6.3 Hz), 2.70(2H, t, J = 6.3 Hz), 2.72-2.88(3H, m), 2.97-3.23(4H, m), 3.69(2H, t, J = 6.3 Hz), 5.17(2H, s), 6.47(2H, s), 6.92(1H, s), 7.31-7.42(5H, m), 7.45(1H, s) |
| 108 | 2 | ESI+: 289<br>NMR: 1.06-1.23(3H, br), 161-1.74(1H, br), 1.96-2.08(4H, br), 2.62-2.70(1H, m), 2.91-3.13(7H, m), 3.16-3.27(2H, m), 3.52-4.29(7H, m), 6.87(1H, s)<br>mp: 185-186 |

TABLE 157

| Ex | Syn | Dat |
|---|---|---|
| 109 | 2 | ESI+: 288<br>NMR: 0.98(3H, t, J = 7.1 Hz), 1.73-1.84(2H, br), 2.05(3H, s), 2.56(2H, t, J = 6.8 Hz), 2.99-3.08(6H, m), 3.11-3.18(4H, m), 3.29-4.63(5H, br), 5.88-6.09(1H, br), 6.87(1H, s)<br>mp: 170-171 |
| 110 | 112 | ESI+: 293<br>NMR: 1.82-1.95(2H, m), 2.61-2.71(2H, m), 2.74-2.87(4H, m), 2.91-3.07(4H, m), 3.22-3.32(2H, m), 4.45(2H, s), 6.36(1H, s), 6.42(2H, s), 6.70(1H, s), 7.17-7.37(5H, m)<br>mp: 148(decomp.) |
| 111 | 112 | ESI+: 325<br>NMR: 2.85-2.94(4H, m), 3.00-3.12(4H, m), 3.24-3.28(2H, m), 3.73(3H, s), 4.12-4.19(2H, m), 4.41(2H, s), 6.56(1H, s), 6.60(1H, s), 6.79-6.89(3H, m), 7.22-7.28(1H, m), 9.23-9.44(2H, br) |
| 112 | 112 | ESI+: 329, 331<br>NMR: 2.78-2.88(4H, m), 2.96-3.08(4H, m), 3.27-3.34(2H, m), 4.12-4.21(2H, m), 4.44(2H, s), 6.47(2H, s), 6.54(1H, s), 6.56(1H, s), 7.23-7.42(4H, m)<br>mp: 151(decomp.) |
| 113 | 112 | ESI+: 325<br>NMR: 2.85-2.96(4H, m), 3.01-3.11(4H, m), 3.20-3.27(2H, m), 3.73(3H, s), 4.11-4.17(2H, m), 4.36(2H, s), 6.55(1H, s), 6.68(1H, s), 6.87-6.92(2H, m), 7.20-7.27(2H, m), 9.30-9.49(2H, br) |

TABLE 157-continued

| Ex | Syn | Dat |
|---|---|---|
| 114 | 112 | ESI+: 329, 331<br>NMR: 2.28(4H, s), 2.72-2.82(4H, m), 2.92-3.04(4H, m), 3.24-3.33(2H, m), 4.10-4.20(2H, m), 4.42(2H, s), 6.52(1H, s), 6.54(1H, s), 7.29-7.35(2H, m), 7.37-7.42(2H, m)<br>mp: 178(decomp.) |
| 115 | 112 | ESI+: 325<br>NMR: 2.28(4H, s), 2.73-2.88(4H, m), 2.94-3.05(4H, m), 3.37-3.46(2H, m), 3.63(2H, t, J = 5.6 Hz), 4.07-4.18(4H, m), 6.51(1H, s), 6.61(1H, s), 6.89-6.98(3H, m), 7.23-7.33(2H, m)<br>mp: 132-134 |
| 116 | 112 | ESI+: 296<br>NMR: 2.73-2.86(4H, m), 2.90-3.04(4H, m), 3.40-3.48(2H, m), 4.14-4.22(2H, m), 4.52(2H, s), 6.43(2H, s), 6.46(1H, s), 6.54(1H, s), 7.23-7.35(2H, m), 7.70-7.79(1H, m), 8.50-8.57(1H, m) |
| 117 | 112 | ESI+: 302<br>NMR: 2.78-2.90(4H, m), 2.95-3.06(4H, m), 3.38-3.45(2H, m), 4.11-4.17(2H, m), 4.57(2H, s), 6.44(2H, s), 6.51(1H, s), 6.66(1H, s), 7.53(1H, d, J = 2 Hz), 9.06(1H, d, J = 2 Hz)<br>mp: 134-138 |
| 118 | 2 | ESI+: 339<br>NMR-A: 2.41-2.47(2H, m), 2.54-2.67(4H, m), 2.94(3H, s), 2.96-3.03(6H, m), 3.13-3.20(2H, m), 4.00-4.07(2H, m), 6.63(1H, s), 6.74(1H, s), 7.15-7.21(2H, m), 7.36-7.42(1H, m), 7.44-7.50(2H, m)<br>mp: 199-201 |

TABLE 158

| Ex | Syn | Dat |
|---|---|---|
| 119 | 2 | ESI+: 249<br>NMR: 2.85-2.98(4H, m), 3.03-3.12(4H, m), 3.29(2H, t, J = 6.1 Hz), 3.32-3.38(2H, m), 3.57(2H, t, J = 6.1 Hz), 4.02-4.17(2H, m), 5.33-5.89(2H, br), 6.52(1H, s), 6.56(1H, s), 9.17-9.42(2H, br) |
| 120 | 2 | ESI+: 303<br>NMR: 0.35-0.39(2H, m), 0.97-1.01(2H, m), 1.59-1.72(3H, m), 1.90-2.03(2H, m), 2.27(4H, s), 2.61(2H, t, J = 6.4 Hz), 2.82-2.84(2H, m), 3.00-3.03(2H, m), 3.05-3.09(6H, m), 3.19-3.22(2H, m), 4.40(1H, t, J = 5.8 Hz), 4.52(1H, t, J = 5.8 Hz), 6.66(1H, s) |
| 121 | 2 | ESI+: 353, 355<br>NMR: 2.42-2.48(2H, m), 2.69-2.76(2H, m), 2.92-3.01(6H, m), 3.03(3H, s), 3.23-3.35(4H, m), 4.19(2H, t, J = 5.4 Hz), 6.42(1H, s), 7.09(1H, s)<br>mp: 99-104 |
| 122 | 2 | ESI+: 337<br>NMR: 1.78-1.88(2H, m), 2.67(2H, t, J = 6.5 Hz), 2.95-3.05(4H, m), 3.08-3.17(4H, m), 3.66-3.73(2H, m), 5.17(2H, s), 6.95(1H, s), 7.28-7.44(5H, m), 7.50(1H, s), 9.20-9.43(2H, br)<br>mp: 185-188 |
| 123 | 2 | ESI+: 303<br>NMR: 0.92(6H, d, J = 6.8 Hz), 1.77-1.97(3H, m), 2.68 (2H, t, J = 6.5 Hz), 2.95-3.04(4H, m), 3.10-3.18(4H, m), 3.63-3.70(2H, m), 3.90(2H, d, J = 6.4 Hz), 6.96(1H, s), 7.48(1H, s), 9.06-9.26(2H, br)<br>mp: 202-207 |
| 124 | 2 | ESI+: 245<br>NMR: 1.12(3H, t, J = 7.0 Hz), 2.46-2.52(2H, m), 2.72-2.82(2H, m), 3.00-3.24(8H, m), 3.88(2H, q, J = 7.0 Hz), 6.99(1H, s), 7.04(1H, s), 9.26-9.50(2H, br)<br>mp: 241(decomp.) |
| 125 | 2 | ESI+: 259<br>NMR: 0.87(3H, t, J = 7.4 Hz), 1.47-1.61(2H, m), 2.46-2.52(2H, m), 2.73-2.82(2H, m), 3.00-3.21(8H, m), 3.81 (2H, t, J = 7.5 Hz), 6.98(1H, s), 7.04(1H, s), 9.23-9.49(2H, br)<br>mp: 125-129 |
| 126 | 2 | ESI+: 307<br>NMR: 2.61-2.70(2H, m), 2.82-3.16(10H, m), 5.11(2H, s), 6.83(1H, s), 7.06(1H, s), 7.18-7.35(5H, m), 9.21-9.40(2H, |

TABLE 158-continued

| Ex | Syn | Dat |
|---|---|---|
| | | br) |
| | | mp: 177-180 |
| 127 | 2 | ESI+: 273 |
| | | NMR: 0.83(6H, d, J = 6.7 Hz), 1.84-1.97(1H, m), 2.30 (4H, s), 2.45-2.54(2H, m), 2.73-2.81(2H, m), 2.86-3.07(8H, m), 3.72-3.80(2H, m), 6.96(1H, s), 7.01(1H, s) |
| | | mp: 142-144 |

TABLE 159

| Ex | Syn | Dat |
|---|---|---|
| 128 | 2 | ESI+: 289 |
| | | NMR: 1.24(6H, d, J = 6.2 Hz), 1.78-1.84(2H, m), 2.29(4H, s), 2.66(2H, t, J = 6.5 Hz), 2.87-2.89(4H, br), 2.99-3.01(4H, br), 3.61-3.64(2H, m), 4.87(1H, quint, J = 6.2 Hz), 6.90(1H, s), 7.44(1H, s) |
| 129 | 2 | ESI+: 367, 369 |
| | | NMR: 1.52-1.67(2H, m), 2.38-2.47(2H, m), 2.71-2.82(2H, m), 3.01-3.10(9H, m), 3.15(2H, t, J = 6 Hz), 3.30-3.39(2H, m), 4.06(2H, t, J = 7.1 Hz), 6.47(2H, s), 7.13(1H, s) |
| | | mp: 153-155 |
| 130 | 2 | ESI+: 331 |
| | | NMR: 2.93-3.10(10H, m), 3.13-3.21(2H, m), 3.24(3H, s), 3.58(2H, t, J = 5.9 Hz), 4.12(2H, t, J = 4.4 Hz), 6.46(2H, s), 6.91(1H, s) |
| | | mp: 180(decomp.) |
| 131 | 2 | ESI+: 329 |
| | | NMR: 1.66-1.81(2H, m), 2.68(2H, t, J = 6.4 Hz), 2.90-3.18(12H, m), 3.20(3H, s), 3.52(2H, t, J = 6.0 Hz), 6.45(2H, s), 7.02(1H, s) |
| | | mp: 175(decomp.) |
| 132 | 2 | ESI+: 261 |
| | | NMR: 0.88(3H, t, J = 7.4 Hz), 1.49-1.63(2H, m), 2.86-3.07(8H, m), 3.77-3.88(2H, m), 4.57(2H, s), 6.43(2H, s), 6.84(1H, s), 7.03(1H, s) |
| | | mp: 183(decomp.) |
| 133 | 2 | ESI+: 309 |
| | | NMR: 2.89-3.18(8H, m), 3.32(3H, s), 4.75(2H, s), 5.12(2H, s), 6.90(1H, s), 6.94(1H, s), 7.21-7.36(5H, m), 9.19-9.37(2H, br) |
| | | mp: 233(decomp.) |
| 134 | 2 | ESI+: 351 |
| | | NMR: 1.74-1.80(2H, m), 2.30(4H, s), 2.64(2H, t, J = 6.6 Hz), 2.76-2.79(2H, m), 2.84-2.87(2H, br), 2.93-2.99(6H, m), 3.57-3.60(2H, m), 4.33(2H, t, J = 6.6 Hz), 6.88(1H, s), 7.21-7.33(6H, m) |
| 135 | 2 | ESI+: 341, 343 |
| | | NMR-A: 2.98-3.05(4H, m), 3.07-3.13(2H, m), 3.14-3.23(4H, m), 3.28-3.35(5H, m), 3.74(2H, t, J = 6.18 Hz), 4.10-4.16(2H, m), 6.64(2H, s), 6.77(1H, s), 8.89(2H, s) |
| | | mp: 183(decomp.) |
| 136 | 2 | ESI+: 337, 339 |
| | | NMR: 0.70(3H, t, J = 7.4 Hz), 1.29-1.45(2H, m), 2.41-2.48(2H, m), 2.72-2.80(2H, m), 3.00-3.11(6H, m), 3.28-3.40(2H, m), 3.98(2H, t, J = 7.3 Hz), 6.47(2H, s), 6.98(1H, s) |
| | | mp: 187(decomp.) |
| 137 | 2 | ESI+: 335 |
| | | NMR: 0.46(3H, t, J = 7.4 Hz), 0.91-1.03(2H, m), 2.30(4H, s), 2.45-2.52(2H, m), 2.71-2.84 (6H, m), 2.89-3.11(6H, m), 7.13(1H, s), 7.16-7.23(2H, m), 7.38-7.52(3H, m) |
| | | mp: 196-200 |

TABLE 160

| Ex | Syn | Dat |
|---|---|---|
| 138 | 2 | ESI+: 339 |
| | | NMR: 2.28(3H, s), 2.74-2.96(8H, m), 3.72(3H, s), 4.73(2H, s), 5.08(2H, s), 6.79-6.89(5H, m), 7.18-7.29 (1H, m) |
| | | mp: 188-189 |
| 139 | 2 | ESI+: 343, 345 |
| | | NMR: 2.29(3H, s), 2.74-2.98(8H, m), 4.75(2H, s), 5.12(2H, s), 6.83-6.89(2H, m), 7.21-7.26(1H, m), 7.30-7.40(3H, m) |
| | | mp: 192-194 |
| 140 | 2 | ESI+: 299 |
| | | NMR: 0.25-0.36(2H, m), 0.66(3H, t, J = 7.4 Hz), 0.95-1.04(2H, m), 1.24-1.36(2H, m), 1.81-1.99(1H, m), 2.27-2.45(8H, m), 2.60-2.74(2H, m), 2.87-3.87(8H, m), 6.94(1H, s) |
| | | mp: 170-171 |
| 141 | 2 | ESI+: 305 |
| | | NMR: 0.37-0.50(2H, m), 0.95-1.04(2H, m), 1.57-1.67(1H, m), 1.95-2.11(2H, m), 2.78-2.85(2H, m), 2.86-3.03(6H, m), 3.03-3.10(2H, m), 3.11-3.21(2H, m), 3.99(2H, t, J = 4.3 Hz), 4.50(2H, dt, J = 47.5, 5.8 Hz), 6.37(1H, s), 6.49(1H, s) |
| | | mp: 144-147 |
| 142 | 2 | ESI+: 245 |
| | | NMR: 0.33-0.42(2H, m), 0.81-0.95(2H, m), 1.38-1.48(1H, m), 2.70-2.79(2H, m), 2.84-2.98(4H, m), 3.05-3.15(2H, m), 3.17-3.26(2H, m), 4.03-4.11(2H, m), 5.32-5.62(1H, br), 6.24(1H, s), 6.36(1H, s) |
| 143 | 2 | ESI+: 286 |
| | | NMR: 1.71-1.77(2H, m), 2.29(2H, s), 2.64(2H, t, J = 6.4 Hz), 2.79-2.85(4H, m), 2.90-2.92(2H, m), 3.04-3.07(2H, m), 3.14-3.17(2H, m), 3.27(3H, s), 3.38(2H, t, J = 6.3 Hz), 3.69(2H, t, J = 6.3 Hz), 7.02(1H, s) |
| 144 | 2 | ESI+: 339 |
| | | NMR: 2.30(4H, s), 2.78-2.99(8H, m), 3.71(3H, s), 4.71(2H, m), 5.04(2H, s), 6.84(1H, s), 6.85-6.91(2H, m), 6.92(1H, s), 7.19-7.24(2H, m) |
| | | mp: 173-176 |
| 145 | 2 | ESI+: 343, 345 |
| | | NMR: 2.81-3.03(8H, m), 4.74(2H, s), 5.11(2H, s), 6.44(2H, s), 6.86(1H, s), 6.88(1H, s), 7.27-7.34(2H, m), 7.36-7.43(2H, m) |
| | | mp: 207(decomp.) |
| 146 | 2 | ESI+: 343, 345 |
| | | NMR: 2.28(3H, s), 2.71-2.96(8H, m), 4.77(2H, s), 5.11(2H, s), 6.86(1H, s), 6.88(1H, s), 7.04-7.09(1H, m), 7.24-7.35(2H, m), 7.50-7.54(1H, m) |
| | | mp: 119-127 |

TABLE 161

| Ex | Syn | Dat |
|---|---|---|
| 147 | 2 | ESI+: 385, 387 |
| | | NMR: 1.74-1.80(2H, m), 2.30(4H, s), 2.64(2H, t, J = 6.5 Hz), 2.78-2.81(2H, br), 2.85-2.87(2H, br), 2.96-2.99(4H, br), 3.09(2H, t, J = 6.5 Hz), 3.57-3.60(2H, m), 4.36(2H, t, J = 6.5 Hz), 6.88(1H, s), 7.26-7.33(3H, m), 7.39-7.46(2H, m) |
| | | mp: 187-188 |
| 148 | 2 | ESI+: 337 |
| | | NMR: 1.78-1.94(2H, m), 2.65(2H, t, J = 7.6 Hz), 2.89-3.12(8H, m), 3.87(2H, t, J = 7.5 Hz), 4.58(2H, s), 6.46(2H, s), 6.85(1H, s), 6.87(1H, s), 7.15-7.35(5H, m) |
| | | mp: 218(decomp.) |
| 149 | 2 | ESI+: 339 |
| | | NMR: 2.97-3.20(8H, m), 4.12-4.32(4H, m), 4.62(2H, s), 6.83-6.98(4H, m), 7.18-7.34(3H, m), 9.22-9.41(2H, br) |
| | | mp: 246(decomp.) |
| 150 | 2 | ESI+: 291 |
| | | NMR: 1.39(3H, d, J = 6.7 Hz), 2.83-3.07(8H, m), 3.24(3H, s), 3.46-3.55(2H, m), 3.97-4.10(2H, m), 4.63(1H, q, J = 6.7 Hz), 6.41(1H, s), 6.82(1H, s), 7.06(1H, s) |
| | | mp: 189(decomp.) |
| 151 | 2 | ESI+: 273 |
| | | NMR: 0.42-0.50(2H, m), 0.96-1.05(2H, m), 1.17(3H, t, J = 7.0 Hz), 1.61-1.70(1H, m), 2.85-2.99(4H, m), 3.00-3.13 |

TABLE 161-continued

| Ex | Syn | Dat |
|---|---|---|
| | | (6H, m), 3.19-3.28(2H, m), 3.94-4.01(2H, m), 6.45(2H, s), 6.53(1H, s)<br>mp: 174-177 |
| 152 | 2 | ESI+: 287<br>NMR: 0.41-0.48(2H, m), 0.86(3H, t, J = 7.4 Hz), 0.95-1.03(2H, m), 1.57-1.72(3H, m), 2.76-2.88(4H, m), 2.88-2.98(4H, m), 3.02-3.09(2H, m), 3.11-3.20(2H, m), 3.95-4.01(2H, m), 6.37(1H, s), 6.47(1H, s)<br>mp: 138-141 |
| 153 | 2 | ESI+: 289<br>NMR: 0.39-0.47(2H, m), 0.94-1.03(2H, m), 1.55-1.65(1H, m), 2.77-2.84(2H, m), 2.87-2.99(4H, m), 3.03(2H, t, J = 6.5 Hz), 3.10-3.20(4H, m), 3.69(2H, t, J = 6.5 Hz), 3.97-4.05(2H, m), 6.37(1H, s), 6.47(1H, s)<br>mp: 146-150 |
| 154 | 2 | ESI+: 277<br>NMR: 1.23(3H, d, J = 6.3 Hz), 2.75-2.81(2H, m), 2.81-2.87(2H, m), 2.90-3.03(5H, m), 3.25(3H, s), 3.28-3.37(2H, m), 3.38-3.55(3H, m), 4.02-4.12(1H, m), 6.39(1H, s), 6.48(1H, s), 6.51(1H, s)<br>mp: 170(decomp.) |
| 155 | 2 | ESI+: 329, 331<br>NMR: 2.75-2.87(4H, m), 2.91-3.06(4H, m), 3.30-3.38(2H, m), 4.16-4.24(2H, m), 4.48(2H, s), 6.36(1H, s), 6.43(2H, s), 6.57(1H, s), 7.26-7.35(3H, m), 7.45-7.52(1H, m)<br>mp: 184(decomp.) |

TABLE 162

| Ex | Syn | Dat |
|---|---|---|
| 156 | 2 | ESI+: 317<br>NMR: 0.17-0.26(1H, m), 0.59-0.69(1H, m), 0.93-1.07(2H, m), 1.23(3H, d, J = 6.1 Hz), 1.58-1.69(1H, m), 2.52-2.58(1H, m), 2.75-2.87(1H, m), 2.89-3.05(3H, m), 3.05-3.21(5H, m), 3.25(3H, s), 3.29-3.43(2H, m), 3.54-3.67(2H, m), 3.96-4.07(1H, m), 6.44(2H, s), 6.51(1H, s)<br>mp: 102-103 |
| 157 | 2 | ESI+: 259<br>NMR: 0.49-0.56(2H, m), 0.96-1.05(2H, m), 1.62-1.71(1H, m), 2.77(3H, s), 2.85-2.93(2H, m), 2.99-3.12(6H, m), 3.20-3.28(2H, m), 3.97-4.03(2H, m), 6.43(2H, s), 6.53(1H, s)<br>mp: 211(decomp.) |
| 158 | 2 | ESI+: 353, 355<br>NMR: 1.07-1.29(3H, br), 1.62-1.77(1H, br), 1.95-2.11(1H, br), 2.63-2.77(2H, br), 2.86-3.42(9H, m), 3.94-4.27(3H, m), 7.08(1H, s)<br>mp: 187-189 |
| 159 | 2 | ESI+: 231<br>NMR: 1.27(6H, s), 1.84-1.91(2H, m), 3.05-3.20(8H, m), 3.26-3.32(2H, m), 6.99(1H, s), 7.37(1H, s), 9.36-9.59(1.9H, br)<br>mp: 288-290 |
| 160 | 2 | ESI+: 429, 431<br>NMR: 1.60-2.08(2H, m), 2.65-3.38(12H, m), 3.93-4.41(4H, m), 6.94-7.39(6H, m)<br>mp: 176-177 |
| 161 | 2 | ESI+: 245<br>NMR: 1.19(6H, s), 1.64-1.70(2H, m), 2.81(3H, s), 2.86-2.94(4H, m), 2.99-3.15(6H, m), 6.39(1H, s), 6.44(1.8H, s), 6.93(1H, s)<br>mp: 197-200 |
| 162 | 2 | ESI+: 385, 387<br>NMR: 1.74-1.81(2H, m), 2.64(2H, t, J = 6.6 Hz), 2.81-2.83(2H, br), 2.88-2.90(2H, br), 2.95-3.01(6H, m), 3.57-3.60(2H, m), 4.34(2H, t, J = 6.4 Hz), 6.45(2H, s), 6.89(1H, s), 7.23-7.36(5H, m)<br>mp: 201(decomp.) |
| 163 | 2 | ESI+: 381<br>NMR: 1.74-1.81(2H, m), 2.64(2H, t, J = 6.6 Hz), 2.82-2.84(2H, br), 2.89-2.94(4H, m), 2.98-3.02(4H, br), 3.57- |

TABLE 162-continued

| Ex | Syn | Dat |
|---|---|---|
| | | 3.60(2H, m), 3.78(3H, s), 4.28(2H, t, J = 6.6 Hz), 6.45(2H, s), 6.86-6.90(2H, m), 6.98(1H, d, J = 7.9 Hz), 7.16-7.19(1H, m), 7.21-7.25(1H, m), 7.30(1H, br)<br>mp: 190(decomp.) |
| 164 | 2 | ESI+: 381<br>NMR: 1.75-1.81(2H, m), 2.64(2H, t, J = 6.6 Hz), 2.81-2.83(2H, br), 2.89-2.93(4H, m), 2.98-3.02(4H, br), 3.58-3.61(2H, m), 3.72(3H, s), 4.33(2H, t, J = 6.5 Hz), 6.45(2H, s), 6.79-6.84(3H, m), 6.89(1H, s), 7.22(1H, t, J = 8.1 Hz), 7.26(1H, br)<br>mp: 196(decomp.) |

TABLE 163

| Ex | Syn | Dat |
|---|---|---|
| 165 | 2 | ESI+: 325<br>NMR: 2.81-2.94(4H, m), 2.97-3.11(4H, m), 3.28-3.37(2H, m), 3.83(3H, s), 4.09-4.20(2H, m), 4.37(2H, s), 6.45(1H, s), 6.56(1H, s), 6.85-6.93(1H, m), 7.00-7.06(1H, m), 7.11-7.16(1H, m), 7.21-7.30(1H, m), 9.12-9.41(2H, br) |
| 166 | 2 | ESI+: 313<br>NMR: 2.81-2.94(4H, m), 2.98-3.15(4H, m), 3.22-3.38(2H, m), 4.09-4.24(2H, m), 4.46(2H, s), 6.55(1H, s), 6.57(1H, s), 7.01-7.20(3H, m), 7.32-7.45(1H, m), 9.13-9.41(2H, br) |
| 167 | 2 | ESI+: 309<br>NMR: 2.29(3H, s), 2.84-2.95(4H, m), 2.99-3.11(4H, m), 3.23-3.31(2H, m), 4.11-4.19(2H, m), 4.39(2H, s), 6.56(1H, s), 6.60(1H, s), 7.05-7.14(3H, m), 7.22(1H, t, J = 7.5 Hz), 9.28-9.54(2H, br) |
| 168 | 2 | ESI+: 320<br>NMR: 2.83-2.95(4H, m), 2.99-3.13(4H, m), 3.28-3.37(2H, m), 4.14-4.24(2H, m), 4.49(2H, s), 6.54(1H, s), 6.58(1H, s), 7.52-7.60(1H, m), 7.63-7.69(1H, m), 7.71-7.80(2H, m), 9.17-9.53(2H, br) |
| 169 | 2 | ESI+: 363<br>NMR: 2.76-2.88(4H, m), 2.94-3.07(4H, m), 3.2-3.34(2H, m), 4.13-4.21(2H, m), 4.53(2H, s), 6.44(2H, s), 6.56(1H, s), 6.58(1H, s), 7.54-7.70(4H, m)<br>mp: 141-146 |
| 170 | 2 | ESI+: 289<br>NMR: 1.18(6H, s), 1.58-1.64(2H, m), 2.85-2.93(4H, m), 3.00-3.10(4H, m), 3.24-3.30(5H, m), 3.37-3.45(2H, m), 3.46-3.52(2H, m), 6.40(1H, s), 6.44(2H, s), 6.92(1H, s)<br>mp: 172-175 |
| 171 | 2 | ESI+: 385, 387<br>NMR: 1.74-1.81(2H, m), 2.64(2H, t, J = 6.5 Hz), 2.81-2.83(2H, br), 2.89-2.92(2H, br), 2.95(2H, t, J = 6.4 Hz), 2.99-3.03(4H, m), 3.57-3.60(2H, m), 4.33(2H, t, J = 6.4 Hz), 6.45(2H, s), 6.89(1H, s), 7.22(1H, br), 7.30(2H, d, J = 8.5 Hz), 7.37(2H, d, J = 8.5 Hz) |
| 172 | 2 | ESI+: 353<br>NMR: 2.29(4H, s), 2.73-2.75(2H, br), 2.81-2.83(2H, m), 2.93-2.98(6H, m), 3.74(2H, t, J = 4.5 Hz), 4.14(2H, t, J = 4.5 Hz), 4.37(2H, t, J = 6.5 Hz), 6.67(1H, s), 7.21-7.34(5H, m), 7.36-7.44(1H, br)<br>mp: 185-187 |
| 173 | 2 | ESI+: 387, 389<br>NMR: 2.30(4H, s), 2.73-2.75(2H, br), 2.82-2.84(2H, br), 2.94-2.98(6H, m), 3.73(2H, t, J = 4.5 Hz), 4.14(2H, t, J = 4.5 Hz), 4.37(2H, t, J = 6.4 Hz), 6.67(1H, s), 7.30-7.38(5H, m)<br>mp: 186(decomp.) |
| 174 | 2 | ESI+: 357<br>NMR: 2.52-3.04(17H, m), 3.97-4.12(2H, m), 6.36(1H, s), 6.71(1H, s), 7.16-7.24(1H, m), 7.26-7.34(2H, m), 7.41-7.50(1H, m)<br>mp: 179-182 |

TABLE 164

| Ex | Syn | Dat |
|---|---|---|
| 175 | 2 | ESI+: 355, 357<br>NMR: 3.13-3.21(6H, m), 3.23(3H, s), 3.30-3.37(2H, m), 3.52(2H, t, J = 5.7 Hz), 4.09(2H, t, J = 5.7 Hz), 4.73(2H, s), 7.22(1H, s), 9.19-9.38(2H, br)<br>mp: 244(decomp.) |
| 176 | 2 | ESI+: 341, 343<br>NMR: 3.00-3.06(2H, m), 3.07-3.15(4H, m), 3.21-3.27(5H, m), 3.35-3.40(2H, m), 3.42-3.53(4H, m), 4.10-4.24(2H, m), 6.64(1H, s), 9.20-9.42(2H, br)<br>mp: 107-110 |
| 177 | 2 | ESI+: 387, 389<br>NMR: 2.30(4H, s), 2.75-2.77(2H, br), 2.81-2.83(2H, br), 2.93-2.97(4H, br), 3.11(2H, t, J = 6.4 Hz), 3.74(2H, t, J = 4.5 Hz), 4.14(2H, t, J = 4.5 Hz), 4.40(2H, t, J = 6.4 Hz), 6.67(1H, s), 7.26-7.33(2H, m), 7.41-7.46(3H, m)<br>mp: 169-170 |
| 178 | 2 | ESI+: 387, 389<br>NMR: 2.30(4H, s), 2.74-2.76(2H, br), 2.81-2.84(2H, br), 2.93-3.00(6H, m), 3.74(2H, t, J = 4.5 Hz), 4.14(2H, t, J = 4.5 Hz), 4.39(2H, t, J = 6.4 Hz), 6.67(1H, s), 7.25-7.38(5H, m)<br>mp: 160-162 |
| 179 | 2 | ESI+: 383<br>NMR: 2.30(4H, s), 2.75-2.77(2H, br), 2.81-2.84(2H, br), 2.92-2.98(6H, m), 3.73(2H, t, J = 4.5 Hz), 3.78(3H, s), 4.14(2H, t, J = 4.5 Hz), 4.32(2H, t, J = 6.6 Hz), 6.67(1H, s), 6.87-6.90 (1H, m), 6.97-6.99(1H, m), 7.18-7.25(2H, m), 7.39-7.51(1H, br)<br>mp: 158-160 |
| 180 | 2 | ESI+: 383<br>NMR: 2.30(4H, s), 2.73-2.75(2H, br), 2.81-2.84(2H, br), 2.92-2.98(6H, m), 3.72(3H, s), 3.74(2H, t, J = 4.5 Hz), 4.14(2H, t, J = 4.5 Hz), 4.37(2H, t, J = 6.5 Hz), 6.67(1H, s), 6.79-6.82(1H, m), 6.84-6.86(2H, m), 7.22(1H, t, J = 8.1 Hz), 7.35-7.44(1H, br)<br>mp: 134-136 |
| 181 | 2 | ESI+: 317<br>NMR: 1.41(3H, s), 1.88(3H, s), 2.61-3.16(12H, m), 3.25 (3H, s), 3.37-3.52(2H, m), 3.92-4.09(2H, m), 5.06(1H, s), 6.38(1H, s), 6.55(1H, s)<br>mp: 173-176 |
| 182 | 2 | ESI+: 367<br>NMR: 2.57-2.68(2H, m), 2.83-3.10(14H, m), 3.26(3H, s), 3.58(2H, t, J = 5.8 Hz), 4.11-4.14(2H, m), 6.44(1H, s), 6.54 (1H, s), 7.15-7.34(5H, m) |
| 183 | 2 | ESI+: 305<br>NMR: 0.96(3H, t, J = 7.7 Hz), 1.28-1.45(2H, m), 2.58-2.68 (2H, m), 2.78-3.09(12H, m), 3.31(3H, s), 3.61(2H, t, J = 6.3 Hz), 4.03-4.21(2H, m), 6.40(1H, s), 6.48(1H, s) |
| 184 | 2 | ESI+: 339<br>NMR: 2.52-2.60(2H, m), 2.85-2.99(4H, m), 3.03-3.10(2H, m), 3.28(3H, s), 3.29-3.35(2H, m), 3.41-3.58(4H, m), 3.92-4.01(2H, m), 6.42(2H, s), 6.62(1H, s), 7.05-7.14(2H, m), 7.27-7.33(1H, m), 7.35-7.41(2H, m)<br>mp: 169(decomp.) |

TABLE 165

| Ex | Syn | Dat |
|---|---|---|
| 185 | 2 | ESI+: 371<br>NMR: 2.30(4H, s), 2.75-2.77(2H, br), 2.81-2.84(2H, br), 2.94-2.98(4H, br), 3.01(2H, t, J = 6.4 Hz), 3.73 (2H, t, J = 4.5 Hz), 4.14(2H, t, J = 4.5 Hz), 4.37(2H, t, J = 6.4 Hz), 6.67(1H, s), 7.14-7.20(1H, m), 7.27-7.33(1H, m), 7.36-7.47(2H, m)<br>mp: 186-187 |
| 186 | 2 | ESI+: 371<br>NMR: 2.30(4H, s), 2.73-2.75(2H, br), 2.81-2.83(2H, br), 2.93-2.98(4H, br), 3.00(2H, t, J = 6.4 Hz), 3.73 (2H, t, J = 4.5 Hz), 4.14(2H, t, J = 4.5 Hz), 4.39(2H, t, J = 6.4 Hz), 6.67(1H, s), 7.03-7.08(1H, m), 7.12-7.17(2H, m), 7.32-7.43(2H, m)<br>mp: 162-164 |
| 187 | 2 | ESI+: 371<br>NMR: 2.30(4H, s), 2.74-2.76(2H, br), 2.82-2.84(2H, br), 2.94-2.98(6H, m), 3.74(2H, t, J = 4.5 Hz), 4.14 (2H, t, J = 4.5 Hz), 4.36(2H, t, J = 6.5 Hz), 6.67(1H, s), 7.10-7.16(2H, m), 7.29-7.35(2H, m), 7.35-7.44(1H, br)<br>mp: 179-181 |
| 188 | 2 | ESI+: 305<br>NMR: 1.36(6H, s), 2.81-3.02(8H, m), 3.24(3H, s), 3.50(2H, t, J = 6.0 Hz), 4.04(2H, t, J = 5.9 Hz), 6.40 (1H, s), 6.78(1H, s), 7.02(1H, s)<br>mp: 175-176 |
| 189 | 2 | ESI+: 287<br>NMR: 2.85-3.00(4H, m), 3.04-3.15(4H, m), 3.37-3.48(2H, m), 4.03-4.20(4H, m), 6.59 (1H, s), 6.73 (1H, s), 9.09-9.33(2H, br)<br>mp: 221-222 |
| 190 | 2 | ESI+: 365, 367<br>NMR: 3.04-3.19(8H, m), 3.33-3.39(2H, m), 3.72(2H, q, J = 9.3 Hz), 4.20-4.27(2H, m), 6.81(1H, s), 9.17-9.38(2H, br)<br>mp: 214-215 |
| 191 | 2 | ESI+: 365, 367<br>NMR: 2.99-3.17(6H, m), 3.21-3.29(2H, m), 3.46(2H, t, J = 4.2 Hz), 4.13-4.26(4H, m), 6.83(1H, s), 9.10-9.33(2H, br)<br>mp: 216-221 |
| 192 | 2 | ESI+: 345<br>NMR-A: 2.57-2.68(6H, m), 2.95-3.22(11H, m), 4.00-4.08(2H, m), 6.63(1H, s), 6.72(1H, s), 6.98(1H, dd, J = 4.9, 1.2 Hz), 7.33(1H, dd, J = 2.8, 1.2 Hz), 7.66(1H, dd, J = 4.9, 2.8 Hz)<br>mp: 200(decomp.) |
| 193 | 2 | ESI+: 345<br>NMR: 2.65-2.79(6H, m), 2.94-3.22(11H, m), 4.02-4.10(2H, m), 6.64(1H, s), 6.78(1H, s), 6.97(1H, dd, J = 3.5, 1.2 Hz), 7.18(1H, dd, J = 5.3, 3.5 Hz), 7.69(1H, dd, J = 5.3, 1.2 Hz)<br>mp: 200(decomp.) |

TABLE 166

| Ex | Syn | Dat |
|---|---|---|
| 194 | 2 | ESI+: 327<br>NMR: 0.35-0.43(2H, m), 0.86-0.96(2H, m), 1.40-1.52(1H, m), 2.77-2.86(2H, m), 2.86-2.98(4H, m), 3.05-3.18(2H, m), 3.36-3.42(2H, m), 4.00-4.16(4H, m), 6.37(1H, s), 6.57(1H, s)<br>mp: 177(decomp.) |
| 195 | 2 | ESI+: 289<br>NMR: 1.16(6H, s), 1.66(2H, t, J = 6.6 Hz), 2.61 (2H, t, J = 6.6 Hz), 2.81-2.95(4H, m), 2.98-3.10 (4H, m), 3.30(3H, s), 3.31-3.37(2H, m), 3.38-3.44(2H, m), 6.35(1H, s), 6.44(1.8H, s), 6.71(1H, s)<br>mp: 156-158 |
| 196 | 2 | ESI+: 367<br>NMR: 1.26(3H, d, J = 7.0 Hz), 2.30(4H, s), 2.71-2.72(2H, br), 2.81-2.83(2H, m), 2.93-2.97(4H, m), 3.10-3.19(1H, m), 3.69-3.71(2H, m), 4.09-4.12(2H, m), 4.26(2H, d, J = 7.1 Hz), 6.66(1H, s), 7.21-7.35(6H, m)<br>mp: 177-179 |
| 197 | 2 | ESI+: 367<br>NMR: 1.26(3H, d, J = 6.3 Hz), 2.29(4H, s), 2.80-2.85(4H, m), 2.91(2H, d, J = 6.4 Hz), 2.96-2.98(4H, m), 3.64-3.69(1H, m), 3.77-3.83(1H, m), 3.99-4.04(1H, m), 4.12-4.17(1H, m), 5.00-5.08(1H, m), 6.67(1H, s), 7.19-7.23(3H, m), 7.27-7.31(2H, m), 7.48(1H, brs)<br>mp: 85-87 |
| 198 | 2 | ESI+: 431, 433<br>NMR: 2.31(4H, s), 2.79-2.82(2H, m), 2.91-2.99(6H, |

TABLE 166-continued

| Ex | Syn | Dat |
|---|---|---|
|  |  | m), 3.15-3.18(2H, m), 3.76(2H, t, J = 4.4 Hz), 4.26(2H, t, J = 4.4 Hz), 4.39(2H, t, J = 6.5 Hz), 7.21-7.33(5H, m), 7.39-7.45(1H, br) mp: 142-143 |
| 199 | 2 | ESI+: 297, 299 NMR: 2.29(4H, s), 2.85-2.88(2H, m), 2.95-2.99(4H, m), 3.02-3.05(2H, m), 3.25(3H, s), 3.35-3.38(2H, m), 3.41-3.44(2H, m), 3.49-3.51(2H, m), 4.16-4.18(2H, m), 6.56(1H, s) mp: 139-141 |
| 200 | 2 | ESI+: 311, 313 NMR: 1.26(3H, t, J = 7.1 Hz), 2.28(2H, s), 2.86-2.91 (6H, m), 3.08-3.11(2H, m), 3.82-3.84(2H, m), 4.18 (2H, q, J = 7.1 Hz), 4.29-4.31(2H, m), 7.61(1H, brs); mp: 145-147 |
| 201 | 2 | ESI+: 393 NMR: 0.38-0.43(2H, m), 0.92-0.97(2H, m), 1.46-1.53 (1H, m), 2.28(4H, s), 2.74-2.77(2H, m), 2.94-2.97(4H, m), 3.01-3.03(2H, m), 3.17-3.19(2H, m), 3.70-3.72(2H, m), 4.16-4.18(2H, m), 4.36(2H, t, J = 6.5 Hz), 7.21-7.34(6H, m) mp: 142-144 |

TABLE 167

| Ex | Syn | Dat |
|---|---|---|
| 202 | 2 | ESI+: 313 NMR: 2.84-2.99(4H, m), 3.02-3.15(4H, m), 3.34-3.40(5H, m), 3.56-3.76(4H, m), 4.03-4.14(2H, m), 6.57(1H, s), 6.63(1H, s), 9.06-9.25(2H, br) mp: 172-173 |
| 203 | 2 | ESI+: 353 NMR: 0.35-0.46(2H, m), 0.97-1.06(2H, m), 1.59-1.70(1H, m), 2.83-2.91(2H, m), 2.96-3.10(4H, m), 3.16-3.23(5H, m), 3.24-3.31(2H, m), 3.51(2H, t, J = 13.3 Hz), 3.70(2H, t, J = 16 Hz), 4.08-4.16(2H, m), 6.43(2H, s), 6.52(1H, s) mp: 163-165 |
| 204 | 2 | ESI+: 291 NMR: 1.20(6H, s), 2.71-2.77(2H, m), 2.78-2.84(2H, m), 2.87-2.96(4H, m), 3.05(2H, s), 3.25(3H, s), 3.39-3.45(2H, m), 3.47-3.53(2H, m), 6.37(1H, s), 6.44(1H, s), 6.50(1H, s) mp: 194(decomp.) |
| 205 | 2 | ESI+: 283 NMR-A: 1.81-2.00(2H, m), 2.46-2.63(3H, br), 2.75-2.90(4H, m), 2.97-3.26(8H, m), 6.48-6.59(1H, br), 6.63(1H, s), 6.98-7.13(1H, br), 7.63-7.78(1H, br), 7.82-7.94(1H, br) mp: 203(decomp.) |
| 206 | 2 | ESI+: 277 NMR: 1.07(3H, d, J = 6.5 Hz), 2.79-2.91(4H, m), 2.98-3.07(4H, m), 3.25-3.34(4H, m), 3.40-3.54(4H, m), 3.86(1H, dd, J = 10.4, 2.3 Hz), 3.93(1H, dd, J = 10.4, 3.1 Hz), 6.43(1.8H, s), 6.50(1H, s), 6.53(1H, s) mp: 133-136 |
| 207 | 2 | ESI+: 277 NMR: 1.07(3H, d, J = 6.5 Hz), 2.79-2.93(4H, m), 2.98-3.07(4H, m), 3.25-3.34(4H, m), 3.39-3.54(4H, m), 3.86 (1H, dd, J = 10.4, 2.3 Hz), 3.93(1H, dd, J = 10.4, 3.0 Hz), 6.44(1.8H, s), 6.50(1H, s), 6.53(1H, s) mp.131-134 |
| 208 | 2 | ESI+: 429 NMR: 2.26(2H, s), 2.49-2.53(2H, m), 2.77-2.79(4H, m), 2.89-2.91(2H, m), 2.98(2H, t, J = 6.5 Hz), 3.70-3.72(2H, m), 4.01-4.03(2H, m), 4.39(2H, t, J = 6.5 Hz), 7.08-7.11 (2H, m), 7.22-7.35(6H, m), 7.37-7.41(3H, m) mp: 169-171 |
| 209 | 2 | ESI+: 283 NMR: 1.68-1.83(2H, m), 2.03(3H, s), 2.33-2.42(2H, m), 2.71(2H, t, J = 6.4 Hz), 2.93-3.10(6H, m), 3.11-3.24(2H, |

TABLE 167-continued

| Ex | Syn | Dat |
|---|---|---|
|  |  | m), 6.50(1H, t, J = 2.1 Hz), 6.63(1H, s), 7.00(1H, s), 8.65-8.95(2H, m) mp: 206(decomp.) |

TABLE 168

| Ex | Syn | Dat |
|---|---|---|
| 210 | 2 | ESI+: 285 NMR: 2.33(3H, s), 2.82-2.89(2H, m), 2.95-3.12(6H, m), 3.12-3.22(2H, m), 4.07-4.13(2H, m), 6.51-6.52(1H, m), 6.64(1H, s), 6.75(1H, s), 7.63-7.65(1H, m), 7.81 (1H, t, J = 1.7 Hz), 8.66-8.91(2H, br) mp: 226(decomp.) |
| 211 | 2 | ESI+: 327 NMR: 0.35-0.48(2H, m), 0.97-1.08(2H, m), 1.64-1.78(1H, m), 2.84-2.94(2H, m), 2.98-3.11(4H, m), 3.17-3.30(4H, m), 3.93(2H, q, J = 10 Hz), 4.12(2H, t, J = 4.5 Hz), 6.44(2H, s), 6.55(1H, s) mp: 174(decomp.) |
| 212 | 2 | ESI+: 395 NMR: 0.90(3H, t, J = 7.3 Hz), 1.30-1.39(2H, m), 2.53-2.57(2H, m), 2.80-2.82(2H, m), 2.95-3.01(8H, m), 3.71-3.73(2H, m), 4.16-4.18(2H, m), 4.37(2H, t, J = 6.5 Hz), 6.45(2H, s), 7.21-7.34(6H, m) mp: 134-136 |
| 213 | 2 | ESI+: 401 NMR: 0.87-0.97(5H, m), 1.10-1.25(3H, m), 1.31-1.41 (3H, m), 1.53(2H, q, J = 6.6 Hz), 1.59-1.71(5H, m), 2.55-2.59(2H, m), 2.88-2.91(2H, m), 2.95-3.02(6H, m), 3.76-3.78(2H, m), 4.16(2H, t, J = 6.6 Hz), 4.20-4.22(2H, m), 6.44(2H, s), 7.46(1H, brs) mp: 139-141 |
| 214 | 2 | ESI+: 435 NMR: 2.63-2.66(2H, m), 2.77-2.82(4H, m), 2.88-2.91 (2H, m), 2.96-2.99(2H, m), 3.71-3.73(2H, m), 4.07-4.09(2H, m), 4.39(2H, t, J = 6.5 Hz), 6.40(1H, s), 6.84 (1H, dd, J = 3.4, 1.1 Hz), 7.10(1H, dd, J = 5.2, 3.4 Hz), 7.21-7.34(5H, m), 7.40-7.47(1H, br), 7.59(1H, dd, J = 5.2, 1.1 Hz) mp: 215-216 |
| 215 | 2 | ESI+: 329 NMR: 0.32-0.39(1H, m), 0.54-0.62(1H, m), 0.96-1.07 (2H, m), 1.33-1.44(1H, m), 1.58-1.67(1H, m), 1.69-1.85 (2H, m), 1.91-2.01(1H, m), 2.86-3.38(11H, m), 3.46-3.55(1H, m), 3.60-3.69(1H, m), 3.72-3.80(1H, m), 3.94-4.18(3H, m), 6.53(1H, s), 9.18-9.44(2H, br) mp: 154-156 |
| 216 | 2 | ESI+: 317 NMR: 0.32-0.41(1H, m), 0.48-0.57(1H, m), 0.96-1.10 (5H, m), 1.55-1.65(1H, m), 2.81-3.30(14H, m), 3.34-3.42(1H, m), 3.64-3.73(1H, m), 3.96-4.08(2H, m), 6.43 (2H, s), 6.50(1H, s) mp: 135-138 |
| 217 | 2 | ESI+: 305 NMR: 0.31-0.41(1H, m), 0.46-0.57(1H, m), 0.95-1.04 (2H, m), 1.27(3H, dd, J = 23.9, 6.3 Hz), 1.55-1.65(1H, m), 2.74-3.02(6H, m), 3.04-3.31(6H, m), 3.97-4.09(2H, m), 4.96-5.22(1H, m), 6.37(1H, s), 6.49(1H, s) mp: 171-173 |

TABLE 169

| Ex | Syn | Dat |
|---|---|---|
| 218 | 2 | ESI+: 301 NMR-A: 2.24(3H, s), 2.76-2.85(2H, m), 2.93-3.11(6H, m), 3.12-3.23(2H, br), 4.03-4.11(2H, m), 6.63(1H, s), 6.79(1H, s), 6.98(1H, dd, J = 3.4, 1.1 Hz), 7.16(1H, dd, J = 5.1, 3.5 Hz), 7.68(1H, dd, J = 5.1, 1.1 Hz), 8.71-8.96(2H, br) mp: 248-252 |

TABLE 169-continued

| Ex | Syn | Dat |
|---|---|---|
| 219 | 2 | ESI+: 295<br>NMR-A: 2.09(3H, s), 2.63-2.71(2H, m), 2.95-3.09 (6H, m), 3.14-3.23(2H, br), 4.04-4.11(2H, m), 6.64 (1H, s), 6.76(1H, s), 7.19-7.24(2H, m), 7.34-7.40 (1H, m), 7.43-7.49(2H, m), 6.80(2H, s)<br>mp: 250(decomp.) |
| 220 | 2 | ESI+: 341, 343<br>NMR: 1.69-1.75(2H, m), 2.04-2.17(2H, m), 2.27 (2H, s), 2.70(2H, t, J = 6.7 Hz), 2.85-2.91(8H, m), 2.96-2.99(2H, m), 3.20-3.22(2H, m), 4.46(1H, t, J = 5.9 Hz), 4.58(1H, t, J = 5.9 Hz), 6.83(1H, s) |
| 221 | 2 | ESI+: 317<br>NMR: 0.29-0.35(2H, br), 0.98-1.05(2H, br), 1.62-1.75(2H, m), 1.86-1.93(1H, m), 2.29(4H, s), 2.36-2.39(2H, m), 2.65-2.69(2H, m), 2.90-2.94(2H, br), 3.01-3.10(4H, br), 3.21-3.28(2H, br), 4.06-4.29 (2H, br), 4.23(1H, t, J = 5.8 Hz), 4.34(1H, t, J = 5.8 Hz), 6.94(1H, s)<br>mp: 182(decomp.) |
| 222 | 2 | ESI+: 283<br>NMR-A: 1.76-1.88(2H, m), 2.38(3H, s), 2.61-2.68 (2H, m), 2.73(2H, t, J = 6.4 Hz), 2.95-3.22(8H, m), 6.44(1H, d, J = 2.9 Hz), 6.60-6.65(2H, m), 7.02(1H, s), 7.78-7.84(1H, m)<br>mp: 180(decomp.) |
| 223 | 2 | ESI+: 353, 355<br>NMR: 1.12(3H, d, J = 6.3 Hz), 1.60-1.68(1H, m), 1.76-1.86(1H, m), 2.66-2.70(2H, m), 2.81(1H, dd, J = 14.1, 3.4 Hz), 2.86-2.96(7H, m), 3.22-3.25(2H, m), 3.27(3H, s), 3.36-3.41(2H, m), 3.81-3.89(1H, m), 6.41 (2H, s), 6.82(1H, s)<br>mp: 161(decomp.) |
| 224 | 2 | ESI+: 315<br>NMR: 0.28-0.35(1H, m), 0.38-0.44(1H, m), 0.95-1.00 (5H, m), 1.55-1.62(1H, m), 1.65-1.76(2H, m), 2.57-2.60(2H, m), 2.83-2.85(2H, m), 2.99-3.13(8H, m), 3.17(3H, s), 3.19-3.23(2H, m), 3.52-3.59(2H, m), 6.41 (2H, s), 6.63(1H, s) |
| 225 | 2 | ESI+: 261<br>NMR: 1.00(3H, t, J = 7.2 Hz), 1.33-1.47(2H, m), 2.62-2.73(2H, m), 2.81(3H, s), 2.94-3.15(8H, m), 3.16-3.31 (2H, br), 4.21-4.35(2H, br), 6.64(1H, s), 9.42(2H, s)<br>mp: 151-152 |
| 226 | 2 | ESI+: 247<br>NMR: 1.09(3H, t, J = 7.4 Hz), 2.70-2.95(5H, m), 2.97-3.17(8H, m), 3.18-3.39(2H, br), 4.23-4.39(2H, m), 6.67(1H, s), 9.48(2H, s)<br>mp: 184-185 |

TABLE 170

| Ex | Syn | Dat |
|---|---|---|
| 227 | 2 | ESI+: 329<br>NMR: 0.30-0.40(1H, m), 0.54-0.64(1H, m), 0.96-1.06(2H, m), 1.33-1.45(1H, m), 1.58-1.67(1H, m), 1.70-1.85(2H, m), 1.92-2.01(1H, m), 2.85-3.37(11H, m), 3.46-3.55(1H, m), 3.61-3.69(1H, m), 3.72-3.80 (1H, m), 3.95-4.03(1H, m), 4.05-4.18(2H, m), 6.53 (1H, s), 9.19-9.37(2H, br)<br>mp: 156-158 |
| 228 | 2 | ESI+: 305<br>NMR: 0.32-0.41(1H, m), 0.48-0.55(1H, m), 0.95-1.04(2H, m), 1.27(3H, dd, J = 23.9, 6.3 Hz), 1.56-1.65(1H, m), 2.72-3.01(6H, m), 3.04-3.31(6H, m), 3.97-4.09(2H, m), 4.97-5.01(1H, m), 6.38(1H, s), 6.48(1H, m)<br>mp: 117(decomp.) |
| 229 | 2 | ESI+: 331<br>NMR: 0.41-0.48(2H, m), 0.97-1.04(2H, m), 1.07(6H, d, J = 6.1 Hz), 1.58-1.66(1H, m), 2.85-2.92(2H, m), 2.99-3.18(8H, m), 3.18-3.27(2H, m), 3.47-3.57(1H, m), 3.63(2H, t, J = 5.9 Hz), 3.99-4.05(2H, m), 6.43 (2H, s), 6.51(1H, s)<br>mp: 117(decomp.) |

TABLE 170-continued

| Ex | Syn | Dat |
|---|---|---|
| 230 | 2 | ESI+: 331<br>NMR: 0.37-0.44(2H, m), 0.96-1.03(2H, m), 1.11(6H, s), 1.63-1.72(1H, m), 2.87-2.94(2H, m), 3.04-3.16(9H, m), 3.21-3.33(4H, m), 4.10-4.17(2H, m), 6.51(1H, s), 8.99-9.17(2H, br)<br>mp: 155-156 |
| 231 | 2 | ESI+: 345<br>NMR: 0.33-0.41(2H, m), 0.90(6H, m), 0.96-1.03(2H, m), 1.65-1.74(1H, m), 2.88-2.95(2H, m), 3.00(2H, s), 3.03-3.17(9H, m), 3.22-3.30(4H, m), 4.09-4.16(2H, m), 6.50(1H, s), 9.22-9.35(2H, br)<br>mp: 141-145 |
| 232 | 2 | ESI+: 371<br>NMR: 0.39-0.46(2H, m), 0.97-1.04(2H, m), 1.57-1.66 (1H, m), 2.76-2.82(2H, m), 2.84-2.97(4H, m), 3.07-3.19(6H, m), 3.88(2H, t, J = 6.0 Hz), 3.99-4.12(4H, m), 6.37(1H, s), 6.48(1H, s)<br>mp: 187(decomp.) |
| 233 | 2 | ESI+: 345<br>NMR: 0.29-0.38(1H, m), 0.51-0.60(1H, m), 0.93-1.05 (2H, m), 1.57-1.66(1H, m), 2.72-3.25(12H, m), 3.32-3.47(2H, m), 3.55-3.74(4H, m), 3.85-3.93(1H, m), 3.95-4.08(2H, m), 6.38(1H, s), 6.47(1H, s)<br>mp: 204(decomp.) |
| 234 | 2 | ESI+: 233<br>NMR: 0.96(3H, t, J = 7.6 Hz), 1.48-1.66(2H, m), 2.76-2.86(4H, m), 2.89(1H, dd, J = 11.8, 7.7 Hz), 2.94-3.09 (4H, m), 3.27(1H, dd, J = 11.8, 2.4 Hz), 3.77-3.86(1H, m), 5.32-5.87(1H, br), 6.37(1H, s), 6.43(2H, s), 6.48 (1H, s)<br>mp: 193(decomp.) |

TABLE 171

| Ex | Syn | Dat |
|---|---|---|
| 235 | 2 | ESI+: 249<br>NMR: 2.76-2.87(4H, m), 2.94-3.07(5H, m), 3.25 (1H, dd, J = 11.9, 2.6 Hz), 3.30(3H, s), 3.41-3.52(2H, m), 4.07-4.14(1H, m), 5.40-5.83(1H, br), 6.38(1H, s), 6.43(2H, s), 6.50(1H, s) |
| 236 | 2 | ESI+: 247<br>NMR: 0.87-0.97(3H, m), 1.32-1.63(4H, m), 2.75-2.86(4H, m), 2.90(1H, dd, J = 11.8, 7.7 Hz), 2.94-3.09 (4H, m), 3.26(1H, dd, J = 11.8, 2.4 Hz), 3.86-3.94(1H, m), 5.31-5.86(1H, br), 6.36(1H, s), 6.43(2H, s), 6.47 (1H, s)<br>mp: 191(decomp.) |
| 237 | 2 | ESI+: 347<br>NMR: 0.33-0.41(1H, m), 0.46-0.54(1H, m), 0.97-1.08 (2H, m), 1.54-1.62(1H, m), 2.84-2.98(3H, m), 2.98-3.12(5H, m), 3.14-3.25(6H, m), 3.27-3.41(6H, m), 3.61-3.70(1H, m), 3.96-4.08(2H, m), 6.43(2H, s), 6.51(1H, s)<br>mp: 150-154 |
| 238 | 2 | ESI+: 291<br>NMR: 0.96(3H, t, J = 7.5 Hz), 1.48-1.64(2H, m), 2.79-2.93(4H, m), 2.97-3.10(5H, m), 3.25(3H, s), 3.27-3.39 (2H, m), 3.40-3.55(3H, m), 3.80-3.89(1H, m), 6.44(2H, s), 6.52(1H, s), 6.53(1H, s)<br>mp: 147(decomp.) |
| 239 | 2 | ESI+: 305<br>NMR: 0.88-0.96(3H, m), 1.34-1.60(4H, m), 2.79-2.93 (4H, m), 2.95-3.10(5H, m), 3.25(3H, s), 3.29-3.38(2H, m), 3.39-3.55(3H, m), 3.89-3.97(1H, m), 6.44(2H, s), 6.51(1H, s), 6.53(1H, s)<br>mp: 151(decomp.) |
| 240 | 2 | ESI+: 247<br>NMR: 0.97(3H, t, J = 7.5 Hz), 1.50-1.67(2H, m), 2.78 (3H, s), 2.80-2.92(5H, m), 2.97-3.07(4H, m), 3.22(1H, dd, J = 11.6, 2.4 Hz), 3.97-4.05(1H, m), 6.43(2H, s), 6.51(1H, s), 6.53(1H, s)<br>mp: 166(decomp.) |
| 241 | 2 | ESI+: 261<br>NMR: 0.88-0.97(3H, m), 1.33-1.63(4H, m), 2.78(3H, s), 2.80-2.93(5H, m), 2.96-3.09(4H, m), 3.21(1H, dd, |

TABLE 171-continued

| Ex | Syn | Dat |
|---|---|---|
|  |  | J = 11.6, 2.3 Hz), 4.04-4.14(1H, m), 6.44(2H, s), 6.50 (1H, s), 6.53(1H, s)<br>mp: 152-153 |
| 242 | 2 | ESI+: 347<br>NMR: 0.31-0.42(1H, m), 0.44-0.57(1H, m), 0.95-1.11 (2H, m), 1.53-1.64(1H, m), 2.80-2.97(3H, m), 2.98-3.13 (5H, m), 3.13-3.26(6H, m), 3.27-3.42(6H, m), 3.62-3.70 (1H, m), 3.96-4.09(2H, m), 6.43(2H, s), 6.51(1H, s)<br>mp: 156-158 |

TABLE 172

| Ex | Syn | Dat |
|---|---|---|
| 243 | 2 | ESI+: 317<br>NMR: 0.30-0.42(1H, m), 0.46-0.59(1H, m), 0.95-1.09(5H, m), 1.55-1.67(1H, m), 2.80-3.30(14H, m), 3.33-3.43(1H, m), 3.62-3.75(1H, m), 3.95-4.09(2H, m), 6.42(2H, s), 6.50(1H, s)<br>mp: 133-136 |
| 244 | 2 | ESI+: 247<br>NMR: 1.17(3H, t, J = 7.3 Hz), 2.16(3H, s), 2.66(2H, q, J = 7.3 Hz), 2.87-3.09(10H, m), 3.98-4.04(2H, m), 6.44(2H, s), 6.50(1H, s)<br>mp: 200(decomp.) |
| 245 | 2 | ESI+: 291<br>NMR: 1.82-1.92(2H, m), 2.15(3H, s), 2.63-2.71(2H, m), 2.79-3.03(10H, m), 3.23(3H, s), 3.40(2H, t, J = 5.2 Hz), 3.99-4.06(2H, m), 6.37(1H, s), 6.46(1H, s)<br>mp: 160-163 |
| 246 | 2 | ESI+: 291<br>NMR: 1.13(3H, t, J = 6.9 Hz), 2.19(3H, s), 2.83(2H, t, J = 6.2 Hz), 2.87-3.12(10H, m), 3.48(2H, q, J = 6.9 Hz), 3.65(2H, t, J = 6.2 Hz), 3.99-4.09(2H, m), 6.44 (2H, s), 6.50(1H, s)<br>mp: 152-155 |
| 247 | 2 | ESI+: 279<br>NMR: 1.94-2.11(2H, m), 2.16(3H, s), 2.69-2.79(2H, m), 2.88-3.10(10H, m), 4.01-4.08(2H, m), 4.55(2H, dt, J = 48.1, 6.9 Hz), 6.44(2H, s), 6.51(1H, s)<br>mp: 187-190 |
| 248 | 2 | ESI+: 327<br>NMR: 0.28-0.32(1H, m), 0.44-0.48(1H, m), 0.97-0.99 (2H, m), 1.30-1.39(1H, m), 1.56-1.79(5H, m), 1.87-1.94(1H, m), 2.58-2.61(2H, m), 2.85-2.86(2H, m), 2.99-3.08(6H, m), 3.17-3.47(4H, m), 3.58-3.64(1H, m), 3.70-3.76(1H, m), 4.02-4.09(1H, m), 6.42(2H, s), 6.64(1H, s) |
| 249 | 2 | ESI+: 327<br>NMR: 0.28-0.32(1H, m), 0.44-0.48(1H, m), 0.97-0.99(2H, m), 1.30-1.39(1H, m), 1.56-1.79(5H, m), 1.87-1.94(1H, m), 2.58-2.61(2H, m), 2.85-2.87(2H, m), 2.99-3.08(6H, m), 3.17-3.47(4H, m), 3.58-3.64(1H, m), 3.70-3.76(1H, m), 4.02-4.09(1H, m), 6.42(2H, s), 6.64(1H, s) |
| 250 | 2 | ESI+: 343<br>NMR: 0.36-0.50(2H, m), 0.97-1.06(2H, m), 1.13-1.29 (2H, m), 1.56-1.74(3H, m), 1.90-2.06(1H, m), 2.84(2H, d, J = 7.3 Hz), 2.89-2.98(2H, m), 3.03-3.18(6H, m), 3.23-3.35(4H, m), 3.79-3.87(2H, m), 4.00-4.08(2H, m), 6.53 (1H, s), 9.13-9.41(2H, br)<br>mp: 153-155 |

TABLE 173

| Ex | Syn | Dat |
|---|---|---|
| 251 | 2 | ESI+: 343<br>NMR: 0.28-0.40(1H, m), 0.50-0.62(1H, m), 0.94-1.03(2H, m), 1.10-1.25(1H, m), 1.33-1.62(5H, m), 1.71-1.80(1H, m), 2.24(3H, s), 2.70-3.10(10H, m), 3.10-3.21(1H, m), 3.30-3.48(2H, m), 3.63-3.70(1H, |

TABLE 173-continued

| Ex | Syn | Dat |
|---|---|---|
|  |  | m), 3.82-3.89(1H, m), 3.93-4.07(2H, m), 6.46(1H, s)<br>mp: 171(decomp.) |
| 252 | 2 | ESI+: 303<br>NMR: 1.43-1.54(1H, m), 1.73-1.90(2H, m), 2.00-2.06(1H, m), 2.25(3H, s), 2.83-3.23(11H, m), 3.35-3.45(1H, m), 3.66-3.84(2H, m), 4.10-4.30(3H, m), 6.57(1H, s), 9.57(2H, br) |
| 253 | 2 | ESI+: 303<br>NMR: 1.41-1.53(1H, m), 1.70-1.88(2H, m), 1.94-2.05(1H, m), 2.23(3H, s), 1.77-2.85(2H, m), 2.93-3.16(9H, m), 3.31-3.42(1H, m), 3.65-3.89(2H, m), 4.06-4.25(3H, m), 6.54(1H, s), 9.40(2H, s) |
| 254 | 2 | ESI+: 331<br>NMR: 0.34-0.49(2H, m), 0.92(3H, d, J = 6.7 Hz), 0.96-1.03(2H, m), 1.57-1.69(1H, m), 2.08-2.23(1H, m), 2.80(1H, dd, J = 13.4, 7.8 Hz), 2.86-2.99(3H, m), 3.02-3.14(6H, m), 3.14-3.21(4H, m), 3.21-3.26(2H, m), 3.30(1H, dd, J = 9.2, 5.0 Hz), 3.95-4.08(2H, m), 6.48(3H, m), 6.52(1H, s) |
| 255 | 2 | ESI+: 329<br>NMR: 0.37-0.50(2H, m), 0.93-1.05(2H, m), 1.50-1.68(2H, m), 1.92-2.04(1H, m), 2.53-2.65(1H, m), 2.76-2.85(2H, m), 2.86-3.22(10H, m), 3.37-3.47 (1H, m), 3.57-3.79(3H, m), 3.97-4.09(2H, m), 6.37 (1H, s), 6.48(1H, s)<br>mp: 117-118 |
| 256 | 2 | ESI+: 279<br>NMR: 1.31(3H, dd, J = 5.87, 24.2 Hz), 2.19(3H, s), 2.70-3.17(12H, m), 4.03-4.12(2H, m), 4.96-5.19 (1H, m), 6.44(2H, s), 6.51(1H, s)<br>mp: 165-168 |
| 257 | 2 | ESI+: 335<br>NMR: 0.46-0.62(2H, m), 0.89-1.01(2H, m), 1.64-1.76(1H, m), 2.25(3H, s), 2.75-2.85(2H, m), 2.88-3.02(6H, m), 3.11-3.22(2H, m), 3.86-3.98(2H, m), 4.19(2H, s), 6.54(1H, s), 7.24-7.31(1H, m), 7.33-7.40(2H, m), 7.42-7.49(2H, m)<br>mp: 107-110 |
| 258 | 2 | ESI+: 369, 371<br>NMR: 0.47-0.62(2H, m), 0.87-1.00(2H, m), 1.65-1.78(1H, m), 2.28(4H, s), 2.82-2.92(2H, m), 2.94-3.13(6H, m), 3.17-3.29(2H, m), 3.90-4.01(2H, m), 4.20(2H, s), 6.58(1H, s), 7.32-7.45(3H, m), 7.50-7.54(1H, m)<br>mp: 139-141 |

TABLE 174

| Ex | Syn | Dat |
|---|---|---|
| 259 | 2 | ESI+: 369, 371<br>0.41-0.56(2H, m), 0.72-0.85(2H, m), 1.52-1.63 (1H, m), 2.28(4H, s), 2.81-2.93(2H, m), 2.98-3.12 (6H, m), 3.16-3.27(2H, m), 3.94-4.04(2H, m), 4.23 (2H, s), 6.60(1H, s), 7.33(1H, dt, J = 1.61, 7.48 Hz), 7.40-7.49(2H, m), 7.80-7.88(1H, m)<br>mp: 106-109 |
| 260 | 2 | ESI+: 353<br>0.47-0.63(2H, m), 0.83-1.00(2H, m), 1.60-1.74(1H, m), 2.25(4H, s), 2.76-2.85(2H, m), 2.88-3.05(6H, m), 3.11-3.26(2H, m), 3.87-3.99(2H, m), 4.21(2H, s), 6.55(1H, s), 7.07-7.14(1H, m), 7.24-7.32(2H, m), 7.38-7.45(1H, m)<br>mp: 102-105 |
| 261 | 2 | ESI+: 301<br>NMR: 1.85-2.01(1H, m), 2.80(3H, s), 2.94-3.26 (11H, m), 3.74-3.92(2H, m), 4.10-4.31(4H, m), 5.66 (1H, s), 6.69(1H, s), 9.38-9.62(2H, br) |
| 262 | 2 | ESI+: 301<br>NMR: 0.37-0.51(2H, m), 0.91(6H, d, J = 6.6 Hz), 0.96-1.04(2H, m), 1.58-1.71(1H, m), 1.92-2.08(1H, m), 2.72-2.83(2H, m), 2.89-2.99(2H, m), 3.03-3.19(6H, m), 3.23-3.34(2H, m), 3.99-4.07(2H, m), 6.53(1H, s), 9.24-9.42(2H, br)<br>mp: 160-162 |

TABLE 174-continued

| Ex | Syn | Dat |
|---|---|---|
| 263 | 2 | ESI+: 343<br>NMR: 0.30-0.49(2H, m), 0.90-1.05(2H, m), 1.12-1.27 (1H, m), 1.41-1.67(3H, m), 1.73-1.85(1H, m), 1.91-2.05(1H, m), 2.66-2.99(8H, m), 3.00-3.21(5H, m), 3.22-3.32(1H, m), 3.71-3.78(1H, m), 3.82-3.90(1H, m), 3.96-4.08(2H, m), 6.37(1H, s), 6.47(1H, s)<br>mp: 186-189 |
| 264 | 2 | ESI+: 293<br>NMR: 1.07(3H, t, J = 7.3 Hz), 1.95-2.15(2H, m), 2.68 (2H, q, J = 7.3 Hz), 2.80-2.92(2H, m), 2.93-3.18(10H, m), 4.07-4.19(2H, m), 4.56(2H, dt, J = 47.4, 5.7 Hz), 6.55(1H, s), 9.24-9.52(2H, br)<br>mp: 153-154 |
| 265 | 2 | ESI+: 353<br>NMR: 0.46-0.57(2H, m), 0.84-0.96(2H, m), 1.64-1.74(1H, m), 2.80-3.07(8H, m), 3.14-3.25(2H, m), 3.88-3.97(2H, m), 4.24(2H, s), 6.38(1H, s), 6.54(1H, s), 7.13-7.28(2H, m), 7.30-7.39(1H, m), 7.66(1H, dt, J = 1.66, 7.68 Hz)<br>mp: 133-136 |
| 266 | 2 | ESI+: 331<br>NMR: 0.37-0.52(2H, m), 0.95-1.06(2H, m), 1.43-1.55(2H, m), 1.58-1.74(3H, m), 2.82-2.95(4H, m), 2.98-3.12(6H, m), 3.16-3.27(5H, m), 3.33(2H, t, J = 6.4 Hz), 3.94-4.02(2H, m), 6.43(2H, s), 6.51(1H, s) |

TABLE 175

| Ex | Syn | Dat |
|---|---|---|
| 267 | 2 | ESI+: 393<br>NMR: 0.28-0.43(1H, m), 0.44-0.58(1H, m), 0.94-1.10(2H, m), 1.52-1.64(1H, m), 2.81-3.09(6H, m), 3.09-3.25(3H, m), 3.25-3.34(2H, m), 3.34-3.46 (1H, m), 3.94-4.17(3H, m), 4.29(1H, dd, J = 11.5, 2.4 Hz), 4.53-4.63(1H, m), 6.42(1.5H, s), 6.52(1H, s), 6.69-6.76(1H, m), 6.77-6.87(3H, m)<br>mp: 179-182 |
| 268 | 2 | ESI+: 365<br>NMR: 0.40-0.52(2H, m), 0.98-1.10(2H, m), 1.61-1.71(1H, m), 2.85-2.93(2H, m), 2.98-3.12(4H, m), 3.17-3.29(4H, m), 3.33-3.41(2H, m), 4.02-4.10(2H, m), 4.25(2H, t, J = 5.9 Hz), 6.44(2H, s), 6.53(1H, s), 6.90-6.97(3H, m), 7.24-7.32(2H, m) |
| 269 | 2 | ESI+: 305<br>NMR: 1.04(3H, t, J = 7.4 Hz), 1.14(3H, t, J = 7.0 Hz), 2.71(2H, q, J = 7.4 Hz), 2.76-2.95(10H, m), 2.98-3.07(2H, m), 3.49(2H, q, J = 7.0 Hz), 3.64(2H, t, J = 5.9 Hz), 4.04-4.11(2H, m), 6.38(1H, s), 6.45(1H, s)<br>mp: 179-181 |
| 270 | 2 | ESI+: 379<br>NMR: 0.46-0.57(2H, m), 0.84-0.97(2H, m), 1.25 (3H, t, J = 7.09 Hz), 1.60-1.72(1H, m), 2.87-2.95(2H, m), 2.97-3.15(6H, m), 3.20-3.33(2H, m), 3.85-3.93 (2H, m), 3.97(2H, q, J = 7.09 Hz), 4.16(2H, s), 6.45 (2H, s), 6.56(1H, s), 6.93-6.00(2H, m), 7.24(1H, dt, J = 1.42, 7.34 Hz), 7.55(1H, dd, J = 1.42, 8.22 Hz)<br>mp: 215(decomp.) |
| 271 | 2 | ESI+: 309<br>NMR: 0.38-0.49(2H, m), 1.01-1.15(2H, m), 1.62-1.75(1H, m), 2.87-2.94(2H, m), 2.99-3.10(4H, m), 3.11-3.17(2H, m), 3.20-3.27(2H, m), 3.35(2H, dt, J = 4.3, 15.2 Hz), 4.04-4.12(2H, m), 6.22-6.40(1H, m), 6.44(2H, s), 6.55(1H, s)<br>mp: 198-201 |
| 272 | 2 | ESI+: 415<br>NMR: 0.48-0.59(2H, m), 0.88-0.98(2H, m), 1.69-1.80 (1H, m), 2.89-2.97(2H, m), 3.01-3.17(6H, m), 3.23-3.32(2H, m), 3.91-4.00(2H, m), 4.30(2H, s), 6.48(2H, s), 6.58(1H, s), 7.22-7.27(1H, m), 7.30-7.35(1H, m), 7.38-7.42(1H, m)<br>mp: 200(decomp.) |
| 273 | 2 | ESI+: 415<br>NMR: 0.48-0.64(2H, m), 0.91-1.01(2H, m), 1.64-1.80 (1H, m), 2.86-3.17(8H, m), 3.21-3.33(2H, m), 3.88- |

TABLE 175-continued

| Ex | Syn | Dat |
|---|---|---|
| | | 3.99(2H, m), 4.21(2H, s), 6.45(2H, s), 6.59(1H, s), 7.28(1H, dd, J = 1.22, 8.36 Hz), 7.41(1H, d, J = 8.36 Hz), 7.46(1H, d, J = 1.22 Hz)<br>mp: 161-164 |
| 274 | 2 | ESI+: 377<br>NMR: 0.46-0.64(2H, m), 0.93-1.10(2H, m), 1.67-1.81(1H, m), 2.87-3.00(4H, m), 3.01-3.35(8H, m), 3.88-3.99(2H, m), 4.09(2H, s), 4.46-4.59(2H, m), 6.45(2H, s), 6.57(1H, s), 6.73(1H, d, J = 8:17 Hz), 7.11-7.16(1H, m), 7.29(1H, s)<br>mp: 215(decomp.) |

TABLE 176

| Ex | Syn | Dat |
|---|---|---|
| 275 | 2 | ESI+: 393<br>NMR: 0.40-0.63(2H, m), 0.78-1.00(2H, m), 1.56-1.77(1H, m), 2.83-2.96(2H, m), 2.99-3.17(6H, m), 3.20-3.34(2H, m), 3.84-3.93(2H, m), 4.14(2H, s), 4.17-4.25(4H, m), 6.44(2H, s), 6.56(1H, s), 6.76 (1H, dd, J = 1.37, 8.27 Hz), 6.84(1H, t, J = 8.27 Hz), 7.10(1H, dd, J = 1.37, 8.27 Hz)<br>mp: 184-187 |
| 276 | 2 | ESI+: 349<br>NMR: 0.45-0.58(2H, m), 0.75-0.88(2H, m), 1.55-1.66(1H, m), 2.17(3H, s), 2.84-2.96(2H, m), 2.99-3.14(6H, m), 3.19-3.29(2H, m), 3.93-4.01(2H, m), 4.14(2H, s), 6.42(2H, s), 6.59(1H, s), 7.14-7.17(2H, m), 7.21-7.28(1H, m), 7.68-7.75(1H, m)<br>mp: 163-166 |
| 277 | 2 | ESI+: 349<br>NMR: 0.50-0.63(2H, m), 0.92-1.03(2H, m), 1.67-1.78 (1H, m), 2.31(3H, s), 2.88-2.99(4H, m), 3.03-3.15 (4H, m), 3.24-3.33(2H, m), 3.91-3.99(2H, m), 4.16 (2H, s), 6.45(2H, s), 6.58(1H, s), 7.05-7.11(1H, m), 7.22-7.29(3H, m)<br>mp: 192-195 |
| 278 | 4 | ESI+: 245<br>NMR: 1.20(6H, s), 2.31(2H, s), 2.95-3.18(8H, m), 6.69(1H, s), 7.12(1H, s), 9.24-9.38(1.8H, br), 10.12 (1H, s)<br>mp: 270-272 |
| 279 | 4 | ESI+: 231<br>NMR: 1.32(6H, s), 1.78-1.89(2H, m), 2.72-2.81(2H, m), 3.00-3.21(8H, m), 6.90-7.16(2H, m), 9.29-9.48 (2H, br)<br>mp: 270-273 |
| 280 | 282 | ESI+: 353, 355<br>NMR: 1.27(3H, d, J = 7.2 Hz), 1.69-1.79(2H, m), 2.61-2.77(4H, m), 2.93-3.46(9H, m), 3.28(3H, s), 3.72(2H, t, J = 6.5 Hz), 6.47(2H, s), 6.85(1H, s)<br>mp: 188(decomp.) |
| 281 | 282 | ESI+: 315<br>NMR: 0.32-0.43(2H, m), 0.97-1.01(2H, m), 1.27(3H, d, J = 7.2 Hz), 1.59-1.77(3H, m), 2.62-2.70(2H, m), 2.77-2.84(1H, br), 3.03-3.28(8H, m), 3.23(3H, s), 3.43-3.58(2H, m), 3.56(2H, t, J = 6.3 Hz), 6.43(2H, s), 6.67(1H, s)<br>mp: 195(decomp.) |
| 282 | 282 | ESI+: 353, 355<br>NMR: 1.24(3H, d, J = 7.4 Hz), 1.69-1.76(2H, m), 2.62-2.75(4H, m), 2.90-3.31(8H, m), 3.28(3H, s), 3.72(2H, t, J = 6.5 Hz), 3.84-3.89(1H, m), 6.49(2H, s), 6.79(1H, s)<br>mp: 184(decomp.) |
| 283 | 2 | ESI+: 371<br>NMR: 0.46-0.60(2H, m), 0.81-0.95(2H, m), 1.61-1.75 (1H, m), 2.78-2.89(2H, m), 2.91-3.01(4H, m), 3.01-3.08(2H, m), 3.14-3.25(2H, m), 3.91-3.99(2H, m), 4.22(2H, s), 6.40(1H, s), 6.55(1H, s), 7.12-7.30(2H, m), 7.41-7.52(1H, m)<br>mp: 195(decomp.) |

TABLE 177

| Ex | Syn | Dat |
|---|---|---|
| 284 | 2 | ESI+: 371<br>NMR: 0.46-0.55(2H, m), 0.84-0.94(2H, m), 1.64-1.75(1H, m), 2.81-3.09(8H, m), 3.14-3.25(2H, m), 3.88-3.99(2H, m), 4.28(2H, s), 6.38(1H, s), 6.55(1H, s), 7.20-7.29(1H, m), 7.30-7.40(1H, m), 7.44-7.52(1H, m)<br>mp: 157-159 |
| 285 | 2 | ESI+: 387, 389<br>NMR: 0.41-0.56(2H, m), 0.79-0.93(2H, m), 1.61-1.75(1H, m), 2.78-3.09(8H, m), 3.15-3.24(2H, m), 3.92-3.98(2H, m), 4.27(2H, s), 6.39(1H, s), 6.55(1H, s), 7.25-7.32(1H, m), 7.47-7.55(1H, m), 7.62-7.70(1H, m)<br>mp: 181-184 |
| 286 | 2 | ESI+: 377<br>NMR: 0.44-0.62(2H, m), 0.85-1.02(2H, m), 1.62-1.79(1H, m), 2.83-3.38(12H, m), 3.83-3.99(2H, m), 4.10(2H, s), 4.49(2H, t, J = 8.51 Hz), 6.47(2H, s), 6.57(1H, s), 6.81-6.90(1H, m), 7.14(1H, d, J = 6.8 Hz), 7.30(1H, d, J = 8.1 Hz)<br>mp: 190(decomp.) |
| 287 | 2 | ESI+: 335<br>NMR: 0.29-0.43(1H, m), 0.43-0.57(1H, m), 0.92-1.10(2H, m), 1.56-1.68(1H, m), 2.82-2.92(2H, m), 2.95-3.39(13H, m), 3.69-3.86(1H, m), 3.96-4.11(2H, m), 4.32-4.65(2H, m), 6.43(2H, s), 6.52(1H, s) |
| 288 | 2 | ESI+: 379<br>NMR: 0.54-0.62(2H, m), 0.94-1.04(2H, m), 1.68-1.79(1H, m), 2.90-3.17(8H, m), 3.24-3.34(5H, m), 3.90-3.98(2H, m), 4.20(2H, s), 4.41(2H, s), 6.44(2H, s), 6.58(1H, s), 7.15-7.24(1H, m), 7.29-7.42(3H, m)<br>mp: 190-193 |
| 289 | 2 | ESI+: 371<br>NMR: 0.44-0.56(2H, m), 0.85-0.96(2H, m), 1.65-1.75(1H, m), 2.80-3.08(8H, m), 3.14-3.26(2H, m), 3.88-3.98(2H, m), 4.20(2H, s), 6.38(1H, s), 6.54(1H, s), 7.13(1H, dt, J = 2.5, 8.5 Hz), 7.18-7.26(1H, m), 7.64-7.72(1H, m)<br>mp: 220(decomp.) |
| 290 | 2 | ESI+: 387, 389<br>NMR: 0.44-0.58(2H, m), 0.82-0.96(2H, m), 1.64-1.75(1H, m), 2.89-2.97(2H, m), 3.00-3.16(6H, m), 3.21-3.32(2H, m), 3.90-4.01(2H, m), 4.22(2H, s), 6.45(2H, s), 6.58(1H, s), 7.22-7.29(1H, m), 7.38-7.44(1H, m), 7.69(1H, dd, J = 6.7, 3.0 Hz)<br>mp: 165-168 |
| 291 | 2 | ESI+: 393<br>NMR: 0.47-0.60(2H, m), 0.92-1.02(2H, m), 1.65-1.76(1H, m), 2.81-3.04(8H, m), 3.17-3.27(2H, m), 3.86-3.95(2H, m), 4.06(2H, s), 4.22(4H, s), 6.38(1H, s), 6.54(1H, s), 6.79-6.89(2H, m), 6.91-6.95(1H, m)<br>mp: 165-168 |

TABLE 178

| Ex | Syn | Dat |
|---|---|---|
| 292 | 2 | ESI+: 317<br>NMR: 0.14-0.25(1H, m), 0.58-0.68(1H, m), 0.91(3H, d, J = 6.9 Hz), 0.97-1.09(2H, m), 1.55-1.68(1H, m), 2.75-3.19(8H, m), 3.25(3H, s), 3.28-3.48(3H, m), 3.61(2H, t, J = 6.1 Hz), 3.86(1H, dd, J = 10.5, 1.6 Hz), 3.92(1H, dd, J = 10.6, 2.3 Hz), 6.43(2H, s), 6.52(1H, s)<br>mp: 183(decomp.) |
| 293 | 2 | ESI+: 379<br>NMR: 0.43-0.55(2H, m), 0.76-0.87(2H, m), 1.53-1.65(1H, m), 2.86-3.12(8H, m), 3.18-3.29(5H, m), 3.88-3.97(2H, m), 4.23(2H, s), 4.36(2H, s), 6.44(2H, s), 6.60(1H, s), 7.20-7.29(1H, m), 7.31-7.43(2H, m), 7.82(1H, d, J = 7.8 Hz)<br>mp: 180(decomp.) |

TABLE 178-continued

| Ex | Syn | Dat |
|---|---|---|
| 294 | 2 | ESI+: 335<br>NMR: 0.31-0.43(1H, m), 0.44-0.54(1H, m), 0.94-1.10(2H, m), 1.55-1.67(1H, m), 2.82-2.93(2H, m), 2.95-3.40(13H, m), 3.68-3.86(1H, m), 3.97-4.12(2H, m), 4.33-4.65(2H, m), 6.43(2H, s), 6.52(1H, s) |
| 295 | 2 | ESI+: 367<br>NMR: 0.43-0.46(2H, m), 1.00-1.06(2H, m), 1.60-1.67(1H, m), 2.82-2.85(2H, m), 2.98-3.03(4H, m), 3.15-3.17(2H, m), 3.20-3.23(2H, m), 3.38-3.41(2H, m), 4.05-4.07(2H, m), 4.60(2H, t, J = 6.1 Hz), 6.42(2H, s), 6.51(1H, s), 8.20(2H, s), 8.22(1H, s)<br>mp: 170(decomp.) |
| 296 | 2 | ESI+: 438<br>NMR: 0.44-0.48(2H, m), 1.05-1.10(2H, m), 1.63-1.70(1H, m), 2.84-2.86(2H, m), 2.98-3.04(4H, m), 3.18-3.23(4H, m), 3.41-3.44(2H, m), 3.94(3H, s), 4.06-4.09(2H, m), 4.46-4.49(2H, m), 6.42(2H, s), 6.52(1H, s), 6.99(1H, d, J = 7.1 Hz), 7.71(1H, d, J = 10.9 Hz)<br>mp: 125-128 |
| 297 | 2 | ESI+: 426<br>NMR: 0.42-0.46(2H, m), 0.97-1.02(2H, m), 1.57-1.64(1H, m), 2.83-2.85(2H, m), 2.98-3.03(4H, m), 3.16-3.21(4H, m), 3.34-3.37(2H, m), 4.05-4.07(2H, m), 4.56-4.59(2H, m), 6.41(2H, s), 6.52(1H, s), 7.82-7.90(2H, m)<br>mp: 178(decomp.) |
| 298 | 2 | ESI+: 365<br>NMR: 0.42-0.56(2H, m), 0.78-0.91(2H, m), 1.57-1.68(1H, m), 2.83-3.14(8H, m), 3.21-3.33(2H, m), 3.72(3H, s), 3.85-3.96(2H, m), 4.15(2H, s), 6.45(2H, s), 6.57(1H, s), 6.93-7.04(2H, m), 7.22-7.30(1H, m), 7.53-7.61(1H, m)<br>mp: 195(decomp.) |
| 299 | 2 | ESI+: 365<br>NMR: 0.51-0.64(2H, m), 0.93-1.03(2H, m), 1.68-1.78(1H, m), 2.84-3.15(8H, m), 3.22-3.33(2H, m), 3.74(3H, s), 3.86-3.97(2H, m), 4.18(2H, s), 6.44(2H, s), 6.57(1H, s), 6.81-6.88(1H, m), 6.96-7.04(2H, m), 7.24-7.31(1H, m)<br>mp: 220(decomp.) |

TABLE 179

| Ex | Syn | Dat |
|---|---|---|
| 300 | 2 | ESI+: 419<br>NMR: 0.44-0.58(2H, m), 0.78-0.91(2H, m), 1.55-1.67(1H, m), 2.87-3.15(8H, m), 3.21-3.33(2H, m), 3.87-3.98(2H, m), 4.27(2H, s), 6.45(2H, s), 6.66(1H, s), 7.33-7.39(1H, m), 7.41-7.52(2H, m), 7.84-7.91(1H, m)<br>mp: 210(decomp.) |
| 301 | 2 | ESI+: 379<br>NMR: 0.45-0.56(2H, m), 0.82-0.95(2H, m), 1.58-1.69(1H, m), 2.27(3H, s), 2.86-3.15(8H, m), 3.22-3.32(2H, m), 3.68(3H, s), 3.78-3.96(2H, m), 4.10(2H, s), 6.45(2H, s), 6.56(1H, s), 6.86(1H, d, J = 8.3 Hz), 7.05(1H, dd, J = 1.8, 8.3 Hz), 7.38(1H, d, J = 1.8 Hz)<br>mp: 205(decomp.) |
| 302 | 2 | ESI+: 383<br>NMR: 0.44-0.60(2H, m), 0.76-0.89(2H, m), 1.55-1.66(1H, m), 2.89-2.96(2H, m), 3.00-3.12(6H, m), 3.21-3.30(2H, m), 3.72(3H, s), 3.91-3.97(2H, m), 4.11(2H, s), 6.45(2H, s), 6.58(1H, s), 6.95-7.01(1H, m), 7.04-7.11(1H, m), 7.35-7.42(1H, m)<br>mp: 189-192 |
| 303 | 2 | ESI+: 399, 401<br>NMR: 0.39-0.57(2H, m), 0.74-0.89(2H, m), 1.53-1.68(1H, m), 2.81-3.15(8H, m), 3.20-3.32(2H, m), 3.73(3H, s), 3.88-3.99(2H, m), 4.10(2H, s), |

TABLE 179-continued

| Ex | Syn | Dat |
|---|---|---|
|  |  | 6.45(2H, s), 6.58(1H, s), 7.01(1H, d, J = 8.7 Hz), 7.31(1H, dd, J = 2.6, 8.7 Hz), 7.59(1H, d, J = 2.59 Hz) <br> mp: 193-196 |
| 304 | 2 | ESI+: 427 <br> NMR: 0.34-0.50(2H, m), 0.97-1.07(2H, m), 1.60-1.67(1H, m), 2.82-2.85(2H, m), 2.96-3.05(4H, m), 3.09-3.46(6H, m), 3.22(3H, s), 3.46-3.53(2H, m), 4.03-4.05(2H, m), 4.83-4.86(1H, m), 6.42(2H, s), 6.47(1H, s), 6.92-6.97(1H, m), 7.08-7.22(3H, m) <br> mp: 132-133 |
| 305 | 2 | ESI+: 427 <br> NMR: 0.34-0.49(2H, m), 0.99-1.11(2H, m), 1.61-1.68(1H, m), 2.82-2.86(2H, m), 2.89-3.43(10H, m), 3.22(3H, s), 3.44-3.52(2H, m), 3.97-4.06(2H, m), 4.81-4.87(1H, m), 6.42(2H, s), 6.45(1H, s), 6.73-6.78(3H, m), 7.25-7.31(1H, m) <br> mp: 174(decomp.) |
| 306 | 2 | ESI+: 427 <br> NMR: 0.35-0.51(2H, m), 0.97-1.09(2H, m), 1.60-1.67(1H, m), 2.80-3.51(14H, m), 3.21(3H, s), 3.97-4.06(2H, m), 4.71-4.76(1H, m), 6.43(2H, s), 6.47(1H, s), 6.91-6.95(2H, m), 7.07-7.11(2H, m) <br> mp: 138-140 |
| 307 | 2 | ESI+: 445 <br> NMR: 0.35-0.50(2H, m), 0.97-1.08(2H, m), 1.59-1.66(1H, m), 2.79-2.86(2H, m), 2.89-3.43(10H, m), 3.21(3H, s), 3.44-3.52(2H, m), 4.03-4.05(2H, m), 4.75-4.80(1H, m), 6.43(2H, s), 6.47(1H, s), 6.95-7.00(1H, m), 7.17(1H, td, J = 9.3, 5.6 Hz), 7.26(1H, ddd, J = 11.5, 8.7, 2.9 Hz) <br> mp: 150-151 |

TABLE 180

| Ex | Syn | Dat |
|---|---|---|
| 308 | 2 | ESI+: 463 <br> NMR: 0.35-0.46(2H, m), 0.97-1.12(2H, m), 1.61-1.68(1H, m), 2.78-3.58(14H, m), 3.21(3H, s), 3.96-4.05(2H, m), 4.77-4.82(1H, m), 6.43(3H, s), 6.84-6.88(2H, m) <br> mp: 155(decomp.) |
| 309 | 2 | ESI+: 461, 463 <br> NMR: 0.34-0.39(1H, m), 0.46-0.51(1H, m), 0.98-1.10(2H, m), 1.61-1.68(1H, m), 2.80-3.42(12H, m), 3.21(3H, s), 3.45-3.53(2H, m), 4.02-4.07(2H, m), 4.83-4.88(1H, m), 6.43(2H, s), 6.48(1H, s), 7.12-7.21(2H, m), 7.41(1H, dd, J = 8.3, 3.0 Hz) <br> mp: 149(decomp.) |
| 310 | 2 | ESI+: 367 <br> NMR: 0.43-0.47(2H, m), 1.03-1.07(2H, m), 1.63-1.70(1H, m), 2.83-2.86(2H, m), 2.99-3.05(4H, m), 3.18-3.22(4H, m), 3.35-3.38(2H, m), 4.05-4.07(2H, m), 4.58(2H, t, J = 6.1 Hz), 6.42(2H, s), 6.52(1H, s), 7.14(1H, t, J = 4.8 Hz), 8.60(2H, d, J = 4.8 Hz) <br> mp: 188(decomp.) |
| 311 | 2 | ESI+: 386 <br> NMR: 0.42-0.46(2H, m), 1.01(6H, d, J = 6.3 Hz), 1.60-1.69(3H, m), 2.57-2.61(2H, m), 2.71-2.74(2H, m), 2.88-2.90(2H, m), 3.03-3.11(8H, m), 3.23-3.24(2H, m), 3.41-3.50(4H, m), 4.01-4.03(2H, m), 6.48(3H, s), 6.52(1H, s) <br> mp: 129(decomp.) |
| 312 | 2 | ESI+: 371 <br> NMR: 0.49-0.60(2H, m), 0.85-1.00(2H, m), 1.61-1.74(1H, m), 2.78-3.07(8H, m), 3.13-3.27(2H, m), 3.87-4.00(2H, m), 4.17(2H, s), 6.38(1H, s), 6.55(1H, s), 7.25-7.51(3H, m) <br> mp: 230(decomp.) |
| 313 | 2 | ESI+: 371 <br> NMR: 0.49-0.60(2H, m), 0.85-0.95(2H, m), 1.62-1.72(1H, m), 2.81-3.06(8H, m), 3.17-3.25(2H, m), 3.92-4.01(2H, m), 4.21(2H, s), 6.38(1H, s), 6.56(1H, s), 7.09-7.22(3H, m) <br> mp: 191-194 |
| 314 | 2 | ESI+: 459 <br> NMR: 0.43-0.47(2H, m), 0.95-1.00(2H, m), 1.15(3H, t, J = 7.0 Hz), 1.53-1.60(1H, m), 2.85-2.87(2H, m), 3.00-3.05(4H, m), 3.17-3.22(4H, m), 3.31-3.34(2H, m), 3.47(2H, q, J = 7.0 Hz), 4.05-4.07(2H, m), 4.38-4.40(4H, m), 6.42(2H, s), 6.53(1H, s), 7.06-7.12(2H, m) <br> mp: 138-139 |
| 315 | 2 | ESI+: 331 <br> NMR: 0.30-0.42(1H, m), 0.46-0.59(1H, m), 0.93-1.12(8H, m), 1.53-1.65(1H, m), 2.79-3.58(14H, m), 3.71-3.83(1H, m), 3.94-4.12(2H, m), 6.42(2H, s), 6.50(1H, s) <br> mp: 157-160 |
| 316 | 2 | ESI+: 317 <br> NMR: 0.14-0.27(1H, m), 0.57-0.68(1H, m), 0.91(3H, d, J = 6.9 Hz), 0.96-1.09(2H, m), 1.55-1.68(1H, m), 2.76-3.19(9H, m), 3.25(3H, s), 3.28-3.48(2H, m), 3.61(2H, t, J = 6.1 Hz), 3.80-3.97(2H, m), 6.43(2H, s), 6.52(1H, s) <br> mp: 186(decomp) |

TABLE 181

| Ex | Syn | Dat |
|---|---|---|
| 317 | 2 | ESI+: 349 <br> NMR: 0.32-0.43(1H, m), 0.44-0.55(1H, m), 0.93-1.15(5H, m), 1.55-1.67(1H, m), 2.82-2.92(2H, m), 2.94-3.30(9H, m), 3.33-3.48(2H, m), 3.57-3.67(1H, m), 3.79-3.94(1H, m), 3.98-4.13(2H, m), 4.31-4.60(2H, m), 6.43(2H, s), 6.52(1H, s) |
| 318 | 2 | ESI+: 291 <br> NMR: 0.91(3H, d, J = 6.8 Hz), 2.01-2.15(1H, m), 2.83-3.31(17H, m), 4.05-4.14(2H, m), 6.51(1H, s), 6.52(1H, s), 9.24-9.50(2H, br) mp: 129-132 |
| 319 | 2 | ESI+: 277 <br> NMR: 1.1(3H, t, J = 6.2 Hz), 2.85-2.93(2H, m), 2.93-3.00(2H, m), 3.01-3.12(4H, m), 3.12-3.46(7H, m), 3.53-3.64(1H, m), 4.02-4.13(2H, m), 6.52(1H, s), 6.54(1H, s), 9.32-9.48(2H, br) |

TABLE 182

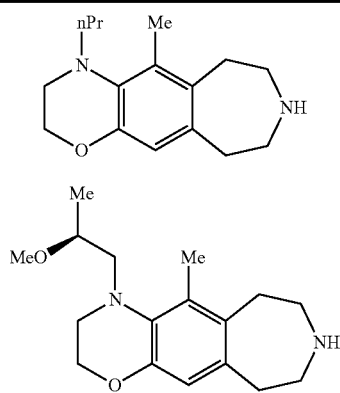

TABLE 182-continued
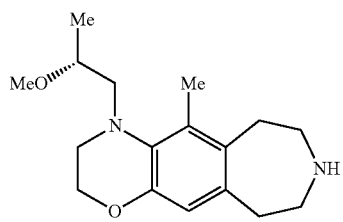 [SMILES: CO[C@H](C)CN1CCOc2cc3c(c(C)c21)CCNCC3]
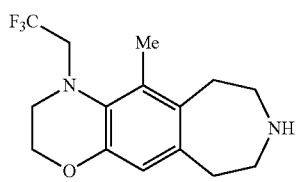 [SMILES: Cc1c2c(cc3c1N(CC(F)(F)F)CCO3)CCNCC2]
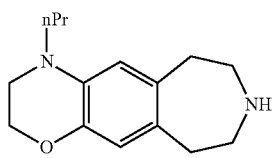
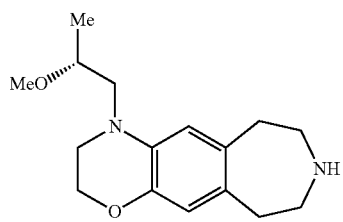 [SMILES: CO[C@H](C)CN1CCOc2cc3c(cc21)CCNCC3]
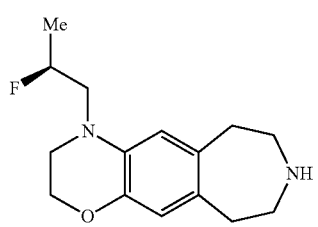 [SMILES: C[C@H](F)CN1CCOc2cc3c(cc21)CCNCC3]
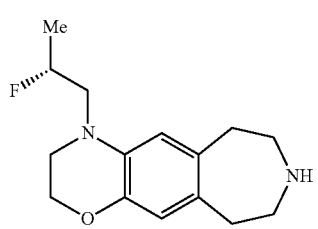 [SMILES: C[C@@H](F)CN1CCOc2cc3c(cc21)CCNCC3]
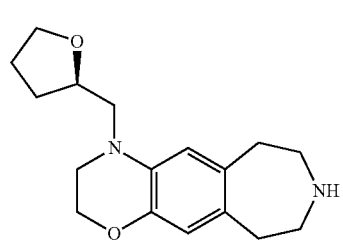 [SMILES: c1c2c(cc3c1OCCN3C[C@H]1CCCO1)CCNCC2]
TABLE 182-continued
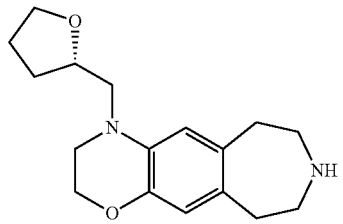 [SMILES: c1c2c(cc3c1OCCN3C[C@@H]1CCCO1)CCNCC2]
TABLE 183
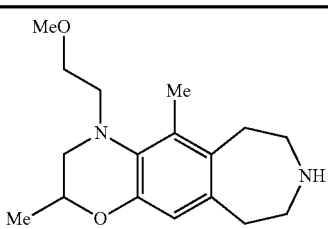
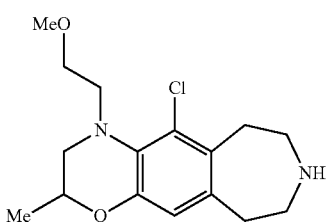 [SMILES: COCCN1CC(C)Oc2cc3c(c(Cl)c21)CCNCC3]
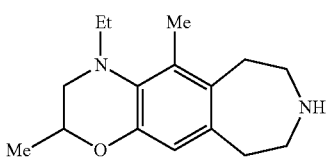 [SMILES: CCN1CC(C)Oc2cc3c(c(C)c21)CCNCC3]
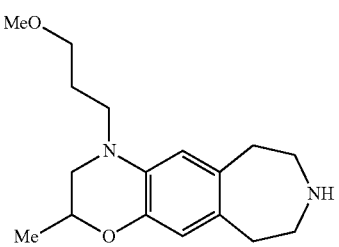 [SMILES: COCCCN1CC(C)Oc2cc3c(cc21)CCNCC3]
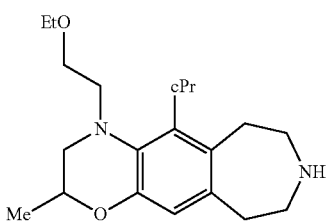
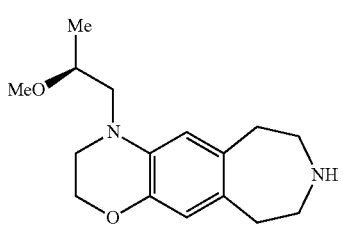 [SMILES: CO[C@@H](C)CN1CCOc2cc3c(cc21)CCNCC3]

TABLE 183-continued
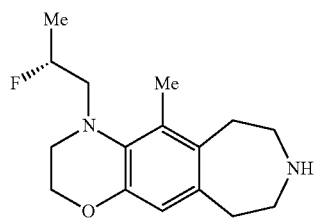 [SMILES: Cc1c2c(cc3c1N(C[C@@H](C)F)CCO3)CCNCC2]
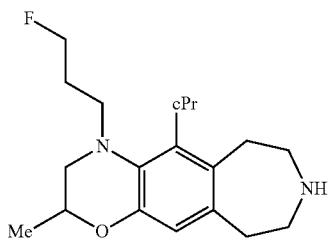
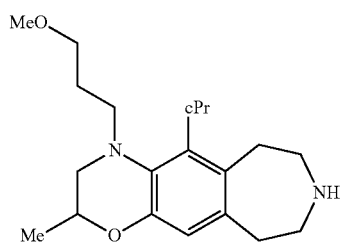
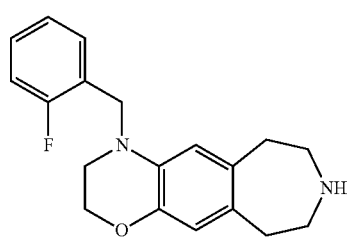 [SMILES: Fc1ccccc1CN1CCOc2cc3c(cc21)CCNCC3]
TABLE 184
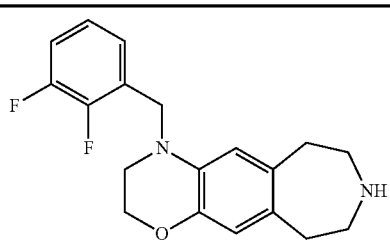
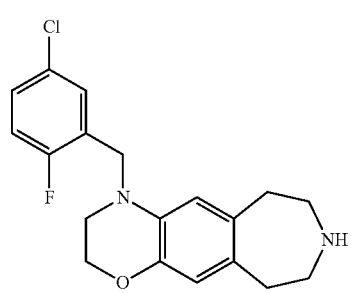 [SMILES: Fc1ccc(Cl)cc1CN1CCOc2cc3c(cc21)CCNCC3]
TABLE 184-continued
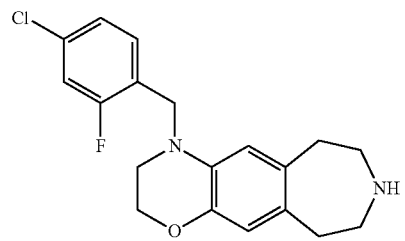 [SMILES: Fc1cc(Cl)ccc1CN1CCOc2cc3c(cc21)CCNCC3]
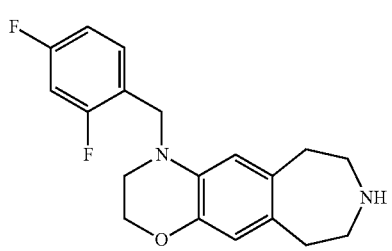 [SMILES: Fc1ccc(CN2CCOc3cc4c(cc32)CCNCC4)c(F)c1]
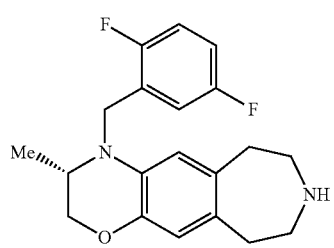 [SMILES: C[C@H]1COc2cc3c(cc2N1Cc1cc(F)ccc1F)CCNCC3]
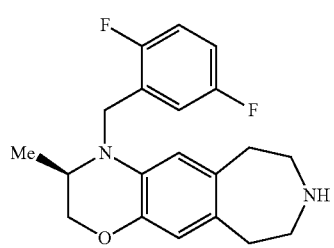 [SMILES: C[C@@H]1COc2cc3c(cc2N1Cc1cc(F)ccc1F)CCNCC3]
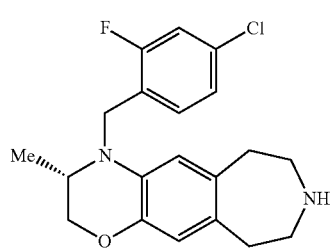
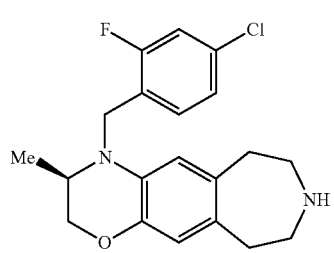 [SMILES: C[C@@H]1COc2cc3c(cc2N1Cc1ccc(Cl)cc1F)CCNCC3]

TABLE 184-continued
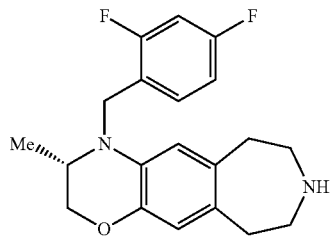 [SMILES: C[C@H]1COc2cc3c(cc2N1Cc1ccc(F)cc1F)CCNCC3]
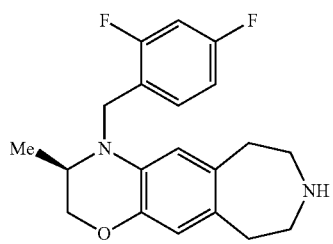 [SMILES: C[C@@H]1COc2cc3c(cc2N1Cc1ccc(F)cc1F)CCNCC3]
TABLE 185
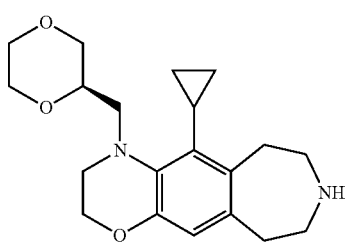 [SMILES: c1c2c(c(C3CC3)c3c1OCCN3C[C@@H]1COCCO1)CCNCC2]
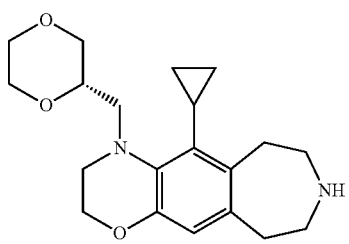 [SMILES: c1c2c(c(C3CC3)c3c1OCCN3C[C@H]1COCCO1)CCNCC2]
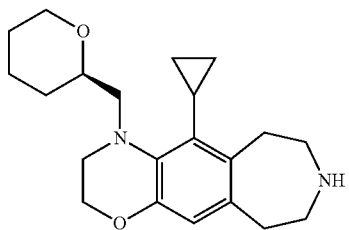 [SMILES: c1c2c(c(C3CC3)c3c1OCCN3C[C@H]1CCCCO1)CCNCC2]
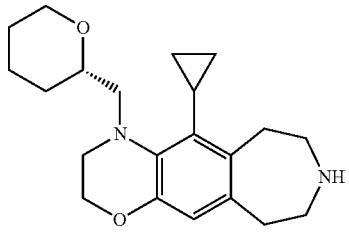 [SMILES: c1c2c(c(C3CC3)c3c1OCCN3C[C@@H]1CCCCO1)CCNCC2]
TABLE 185-continued
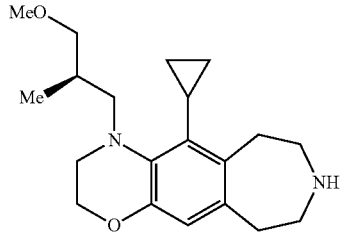
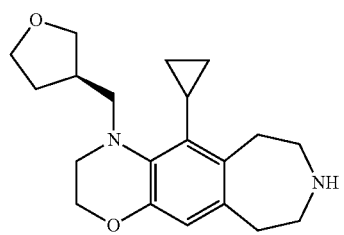 [SMILES: c1c2c(c(C3CC3)c3c1OCCN3C[C@H]1CCOC1)CCNCC2]
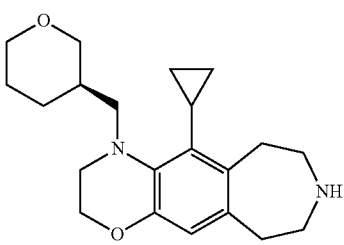 [SMILES: c1c2c(c(C3CC3)c3c1OCCN3C[C@H]1CCCOC1)CCNCC2]
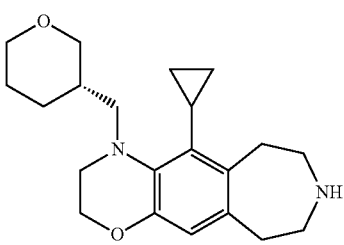 [SMILES: c1c2c(c(C3CC3)c3c1OCCN3C[C@@H]1CCCOC1)CCNCC2]

TABLE 186
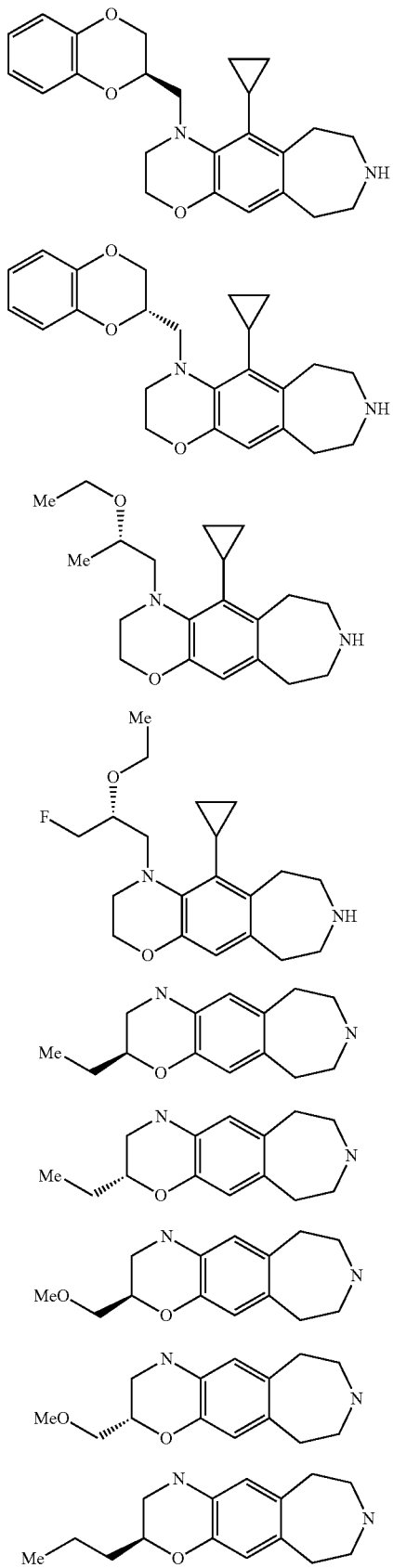
TABLE 186-continued
TABLE 187
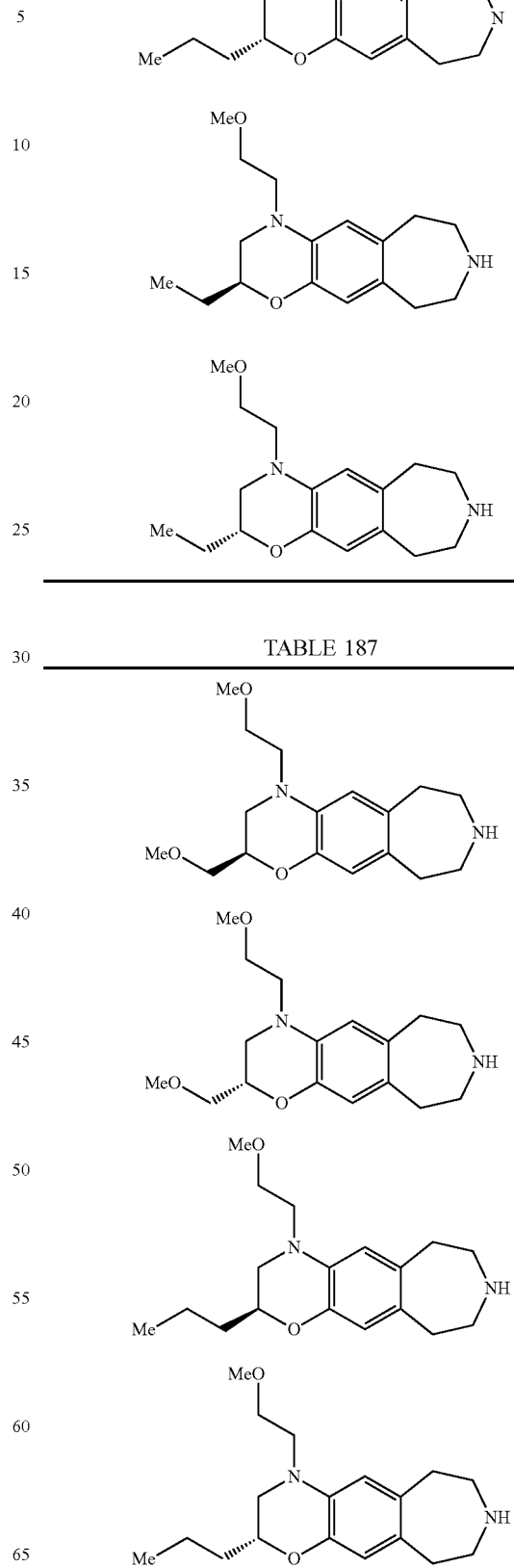

TABLE 187-continued
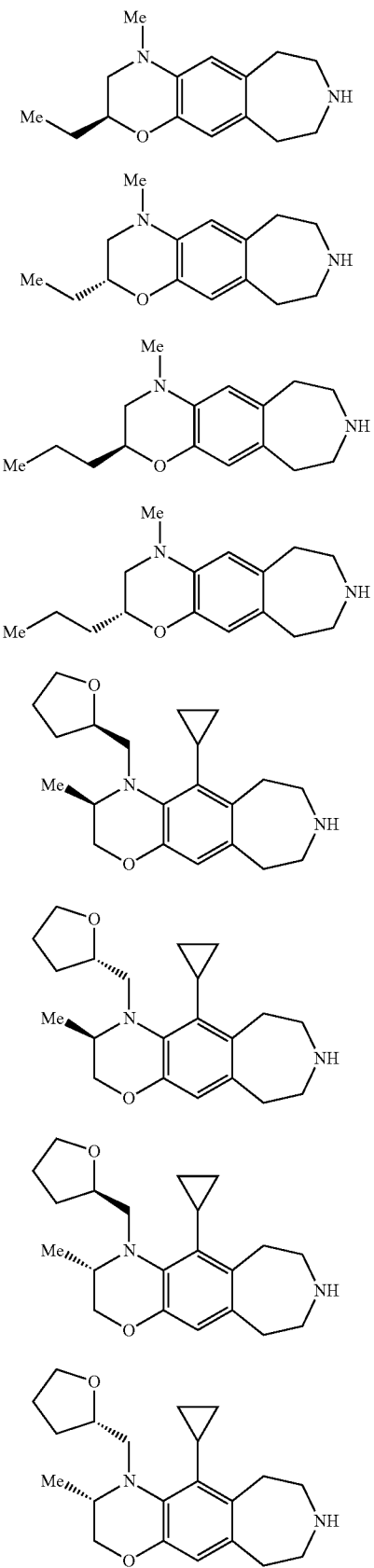
TABLE 188
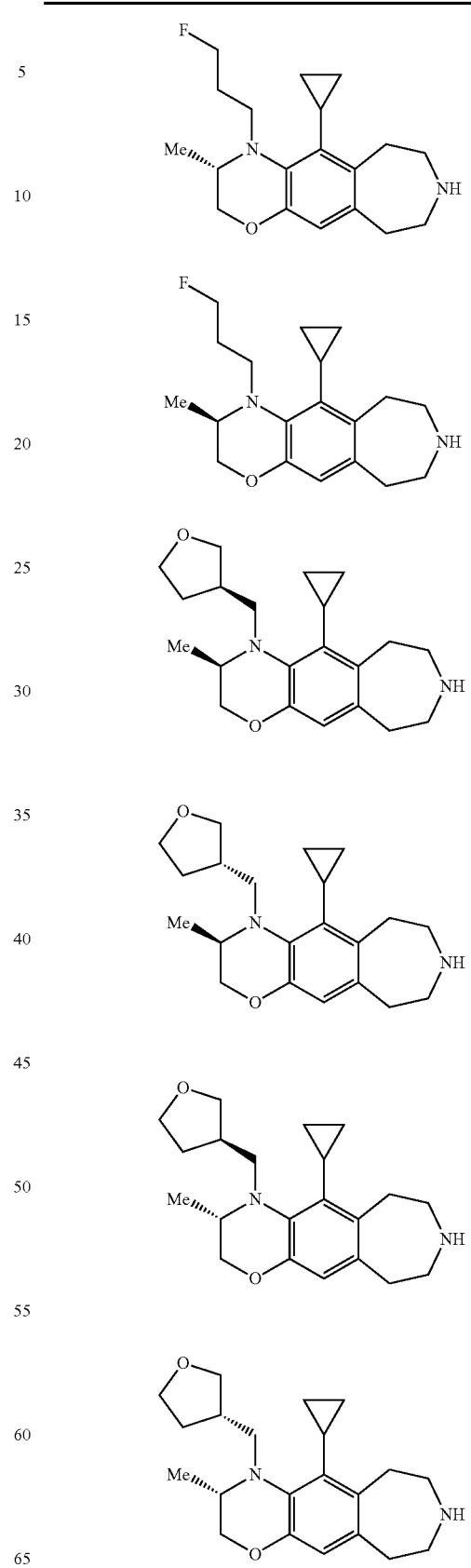

TABLE 188-continued
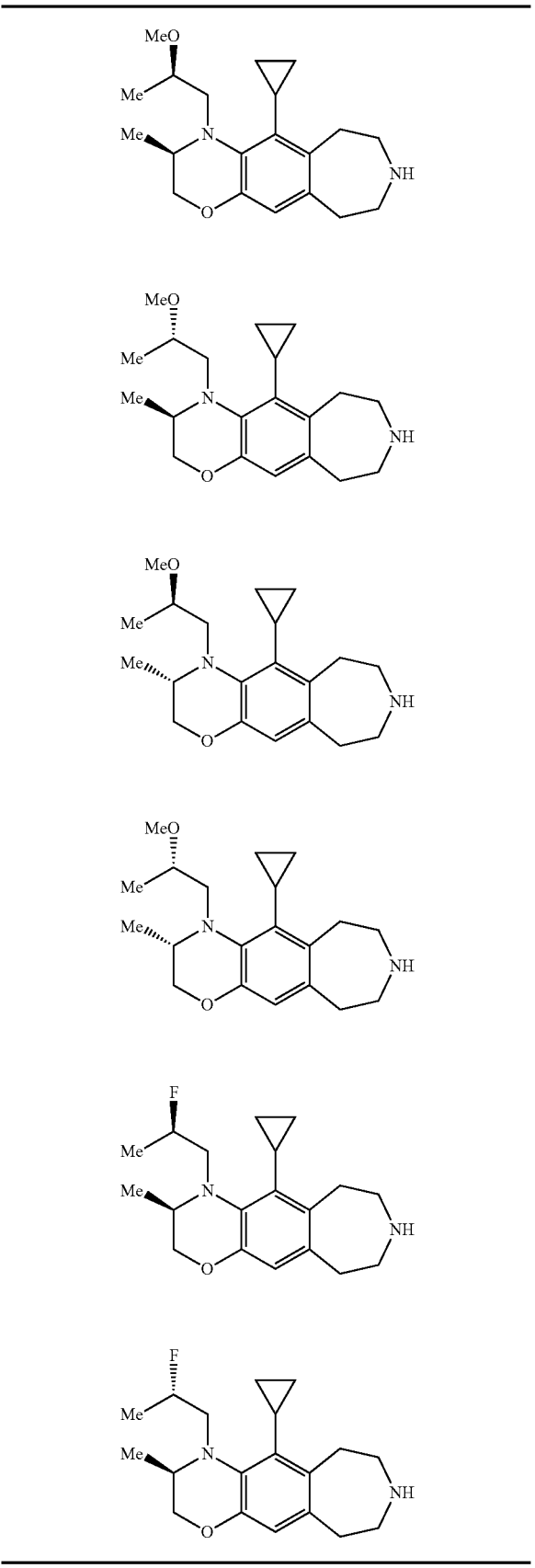
TABLE 189
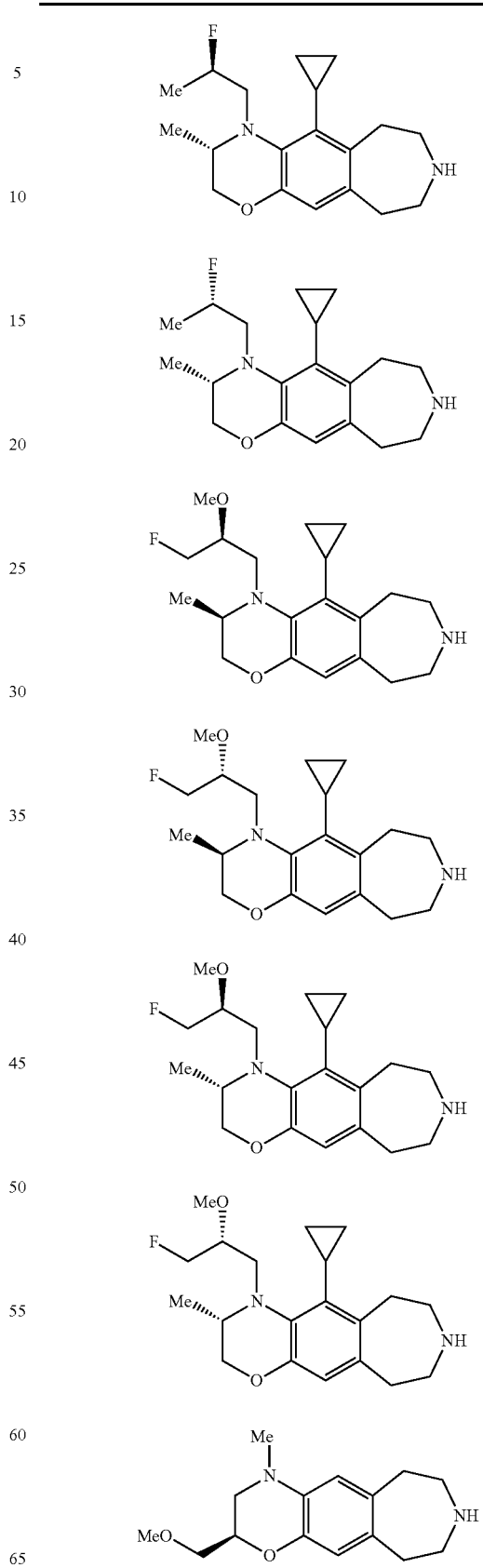

TABLE 189-continued

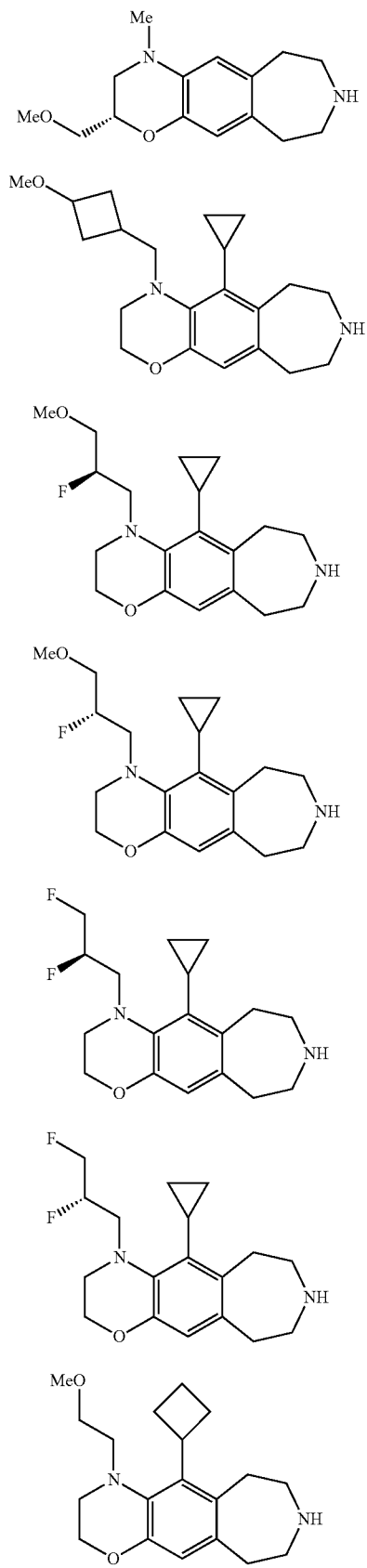

TABLE 190

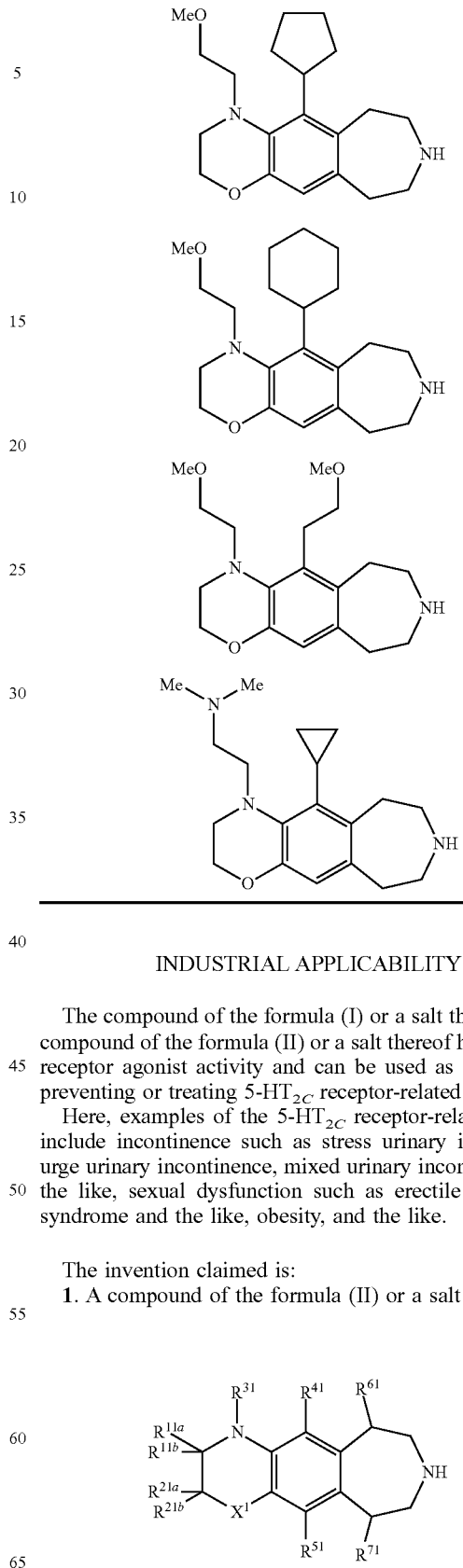

INDUSTRIAL APPLICABILITY

The compound of the formula (I) or a salt thereof, or the compound of the formula (II) or a salt thereof has a 5-HT$_{2C}$ receptor agonist activity and can be used as an agent for preventing or treating 5-HT$_{2C}$ receptor-related diseases.

Here, examples of the 5-HT$_{2C}$ receptor-related diseases include incontinence such as stress urinary incontinence, urge urinary incontinence, mixed urinary incontinence, and the like, sexual dysfunction such as erectile dysfunction syndrome and the like, obesity, and the like.

The invention claimed is:
1. A compound of the formula (II) or a salt thereof:

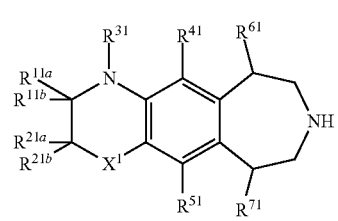

(II)

(wherein

R$^{11a}$ and R$^{11b}$ are respectively the same or different and each represents —H or C$_{1-6}$ alkyl, or are combined to form oxo, R$^{21a}$ and R$^{21b}$ are respectively the same or different and each represents —H or C$_{1-6}$ alkyl which may be substituted with —O—C$_{1-6}$ alkyl, R$^{31}$ represents —H, C$_{1-6}$ alkyl which may be substituted, C$_{3-8}$ cycloalkyl, aryl which may be substituted, —SO$_2$—C$_{1-6}$ alkyl, or a hetero ring which may be substituted, R$^{41}$ represents —H, halogen, cyano, C$_{1-6}$ alkyl which may be substituted, C$_{2-6}$ alkenyl, aryl which may be substituted, C$_{3-8}$ cycloalkyl which may be substituted, an aromatic hetero ring, or an oxygen-containing hetero ring, R$^{51}$ represents —H, halogen, C$_{1-6}$ alkyl, C$_{3-8}$ cycloalkyl, aryl, or an aromatic hetero ring, R$^{61}$ and R$^{71}$ are the same or different and each represents —H or C$_{1-6}$ alkyl, X$^1$ represents —C(R$^{A1}$)(R$^{B1}$)— or —O—, and R$^{A1}$ and R$^{B1}$ are the same or different and each represents —H or C$_{1-6}$ alkyl, provided that (i) in the case where R$^{11a}$, R$^{11b}$, R$^{21a}$, R$^{21b}$, R$^{41}$, R$^{51}$, R$^{61}$, and R$^{71}$ are respectively —H and X$^1$ is —O—, R$^{31}$ is a group other than —H, —CO-methyl, or —SO$_2$-methyl, and (ii) in the case where R$^{11a}$ and R$^{11b}$ are combined to form oxo, R$^{21a}$, R$^{21b}$, R$^{41}$, R$^{51}$, R$^{61}$, and R$^{71}$ are respectively —H, and X$^1$ is —O—, R$^{31}$ is a group other than —H or methyl).

2. A compound or a salt thereof as described in claim 1, wherein R$^{31}$ is —H, C$_{1-6}$ alkyl which may be substituted, C$_{3-8}$ cycloalkyl, aryl which may be substituted, —SO$_2$—C$_{1-6}$ alkyl, or an oxygen-containing hetero ring, and R$^{41}$ is —H, halogen, cyano, C$_{1-6}$ alkyl which may be substituted, C$_{2-6}$ alkenyl, aryl which may be substituted, C$_{3-8}$ cycloalkyl, an aromatic hetero ring, or an oxygen-containing hetero ring.

3. A compound or a salt thereof as described in claim 2, wherein R$^{31}$ is a group other than —H, methyl, —CO-methyl, or —SO$_2$-methyl.

4. A compound or a salt thereof as described in claim 3, wherein R$^{11a}$ is —H or methyl, and R$^{11b}$, R$^{21a}$, R$^{21b}$, R$^{51}$, R$^{61}$, and R$^{71}$ are respectively —H.

5. A compound or a salt thereof as described in claim 4, wherein R$^{41}$ is —H, halogen, or C$_{3-8}$ cycloalkyl.

6. A compound or a salt thereof as described in claim 5, wherein R$^{41}$ is cyclopropyl.

7. A compound or a salt thereof as described in claim 6, wherein R$^{31}$ is C$_{1-6}$ alkyl which may be substituted and wherein the substitutions to the C$_{1-6}$ alkyl are selected from the group consisting of (a) halogen, (b) —O—C$_{1-6}$ alkyl, (c) phenoxy which may be substituted with one or more groups selected from the group consisting of halogen and cyano, (d) an oxygen-containing hetero ring, and (e) phenyl which may be substituted with one or more groups selected from the group consisting of C$_{1-6}$ alkyl which may be substituted with —O—C$_{1-6}$ alkyl, halogen, and —O—C$_{1-6}$ alkyl.

8. A pharmaceutical composition comprising a compound or a salt thereof as described in claim 1 and a pharmaceutically acceptable excipient.

9. A method for treating incontinence, comprising administering to a subject an effective amount of a compound or a salt thereof as described in claim 1.

* * * * *